US008541406B2

(12) United States Patent
Griffioen et al.

(10) Patent No.: US 8,541,406 B2
(45) Date of Patent: Sep. 24, 2013

(54) THIADIAZOLE DERIVATIVES FOR THE TREATMENT OF NEURODEGENERATIVE DISEASES

(75) Inventors: Gerard Griffioen, Linden (BE); Kristel Marie Edith Coupet, Dilbeek (BE); Hein Roger Duhamel, Kessel-Lo (BE); Stefaan Wera, Bierbeek (BE); Ellen Gommé, Kortenberg (BE); Nele Van Damme, Kessel-Lo (BE); Ingrid Van Der Auwera, Langdorp (BE); Marleen Lox, Tienen (BE); Tom Van Dooren, Berchem (BE); Tine Decruy, Moerkerke-Damme (BE)

(73) Assignee: NV reMYND, Heverlee (BE)

( * ) Notice: Subject to any disclaimer, the term of this patent is extended or adjusted under 35 U.S.C. 154(b) by 1449 days.

(21) Appl. No.: 12/187,115

(22) Filed: Aug. 6, 2008

(65) Prior Publication Data

US 2009/0054410 A1   Feb. 26, 2009
US 2009/0233911 A2   Sep. 17, 2009
US 2010/0261707 A9   Oct. 14, 2010

Related U.S. Application Data

(63) Continuation-in-part of application No. PCT/EP2007/001022, filed on Feb. 7, 2007.

(30) Foreign Application Priority Data

Feb. 7, 2006  (GB) .................................. 0602335.2
Aug. 6, 2007  (GB) .................................. 0715255.6
Aug. 6, 2007  (GB) .................................. 0715260.6
Aug. 7, 2007  (GB) .................................. 0715192.1

(51) Int. Cl.
*A61K 31/55* (2006.01)
*C07D 241/02* (2006.01)

(52) U.S. Cl.
USPC .................. 514/218; 514/254.03; 544/357

(58) Field of Classification Search
USPC .............................. 514/218, 254.03; 544/357
See application file for complete search history.

(56) References Cited

U.S. PATENT DOCUMENTS 6,060,472 A * 5/2000 Karimian et al. ........... 514/253.1
7,799,782 B2 * 9/2010 Munson et al. ............. 514/234.5
2007/0112011 A1 5/2007 Kuhnert et al.

FOREIGN PATENT DOCUMENTS

| CA | 2572685 | 1/2006 |
|---|---|---|
| CH | GB 1400287 | 7/1975 |
| WO | WO-02/083863 A2 | 10/2002 |
| WO | WO-02083863 A2 | 10/2002 |
| WO | WO 2005/020991 | 3/2005 |
| WO | WO 2005/095368 | 10/2005 |
| WO | WO 2006/002981 | 1/2006 |
| WO | WO-2006/002981 A1 | 1/2006 |
| WO | WO 2006/002981 A1 | 1/2006 |
| WO | WO-2006002981 A1 | 1/2006 |

OTHER PUBLICATIONS

Office Action for Chinese Patent Application No. 200780004583.3, dated Feb. 17, 2012 (3 pages).
English Translation Office Action for Chinese Patent Application No. 200780004583.3, dated Feb. 17, 2012 (5 pages).
Office Action for Chinese Patent Application No. 200780004583.3, dated Apr. 23, 2010. English translation provided.
Office Action for European Patent Application No. EP 07 711 455.1, dated Mar. 10, 2010.
Notice of Reasons for Rejection issued in Japanese Patent Application No. 2008-553672, dated Jul. 24, 2012 (English Language Translation Provided) (7 pages).
Office Action for Eurasian Patent Application No. 200870233, dated Feb. 16, 2010. English trnaslation provided.
Office Action for Japanese Patent Application No. 2008-553672, dated Dec. 27, 2011 (4 pages).
Office Action for Chinese Patent Application No. 200780004583.3, dated Mar. 30, 2011. (English translation provided.).
Communication Dated Jun. 8, 2009 and Issued by European Patent Office for European Patent Application No. EP 07 711 455.1.
Notice of Grounds of Rejection issued in Japanese Patent Application No. 2008-553672, dated Feb. 5, 2013 (5 pages) (English Language Translation Provided).
Database Chemcats [Online] Comgenex, Product List, Apr. 15, 2005 (Abstract).
Office Action for Canadian Patent Application No. 2641453, mailed Jul. 18, 2011.
Office Action for Eurasian Patent Application No. 200870233, mailed Sep. 1, 2011.
English Translation for Office Action for Eurasian Patent Application No. 200870233, mailed Sep. 1, 2011.
Office Action for Eurasian Patent Application No. 200870233, dated Aug. 18, 2010. English translation provided.
International Search Report for International Application PCT/EP2007/001022, mailed Dec. 5, 2007.
International Written Opinion for International Application PCT/EP2007/001022, mailed Dec. 5, 2007.
Examiner's first report on Australian patent application No. 2007213954, dated Jul. 20, 2011. Examiner's Report for Canadian Application No. 2,641,453, dated Dec. 20, 2010.
Communication dated Oct. 23, 2009, and Issued by the European Patent Office for European Patent Application No. EP07711455.1.
Office Action for Chinese Patent Application No. 200780004583.3, dated Nov. 10, 2010.
English translation of Office Action for Chinese Patent Application No. 200780004583.3, dated Nov. 10, 2010.
Examiner's Report for Canadian Patent Application No. 2,641,453, dated Mar. 8, 2013 (2 pages).

* cited by examiner

*Primary Examiner* — Rei-tsang Shiao
(74) *Attorney, Agent, or Firm* — Clark & Elbing LLP

(57) ABSTRACT

This invention provides specifically substituted 1,2,4-thiadiazole derivatives for use in the treatment of an α-synucleopathy such as Parkinson's disease, diffuse Lewy body disease, traumatic brain injury, amyotrophic lateral sclerosis, Niemann-Pick disease, Hallervorden-Spatz syndrome, Down syndrome, neuroaxonal dystrophy, multiple system atrophy and Alzheimer's disease. This invention also provides various methods for producing such substituted 1,2,4-thiadiazole derivatives.

28 Claims, 3 Drawing Sheets

THIADIAZOLE DERIVATIVES FOR THE TREATMENT OF NEURODEGENERATIVE DISEASES

CROSS REFERENCE TO RELATED APPLICATIONS

This application is a continuation-in-part of the International Application No. PCT/EP2007/001022, filed Feb. 7, 2007, which claims the benefit of British patent application No. 0602335.2, filed Feb. 7, 2006. This application also claims the benefit of British patent application No. 0715260.6 filed Aug. 6, 2007, British patent application No. 0715192.1 filed Aug. 7, 2007, and British patent application No. 0715255.6 filed Aug. 6, 2007. The disclosures of each of the aforementioned applications is incorporated by reference in its entirety.

FIELD OF THE INVENTION

The present invention relates to novel thiadiazole derivatives useful for treating certain neurological disorders characterised by cytotoxic α-synuclein amyloidogenesis. The invention further relates to methods of treatment or prevention of such neurological disorders by the administration of a pharmaceutical composition, comprising one or more thiadiazole derivatives in an amount which alleviates or prevents the cytotoxic properties of α-synuclein. The invention further relates to methods of preparing novel thiadiazole derivatives, as well as certain classes of intermediates useful in such preparation.

BACKGROUND OF THE INVENTION

α-Synuclein is a neuronal protein which originally has been associated with neuronal plasticity during Zebra finch song learning. Although its role at the molecular level is at present largely elusive it appears to have lipid bi-layer (or membrane) with binding properties important for preserving proper transport of neurotransmitter vesicles to the axonal ends of neurons presumably to ensure proper signalling at the synapse. Apart from its physiological role in brain cells, human α-synuclein also possesses pathological features that underlies a plethora of neurodegenerative diseases including Parkinson's disease, diffuse Lewy body disease, traumatic brain injury, amyotrophic lateral sclerosis, Niemann-Pick disease, Hallervorden-Spatz syndrome, Down syndrome, neuroaxonal dystrophy, multiple system atrophy and Alzheimer's disease. These neurological disorders are characterised by the presence of insoluble α-synuclein polymers or aggregates usually residing within neuronal cells, although in the case of Alzheimer's disease α-synuclein (or proteolytic fragments thereof) constitutes the non-amyloid component of extracellular "amyloid-β plaques". It is widely believed that the amyloidogenic properties α-synuclein disrupt cellular integrity leading to dysfunctioning or death of affected neurons resulting in cognitive and/or motoric decline as it is found in patients suffering from such diseases. The aggregation of α-synuclein is at present very poorly defined, but constitutes most likely a multi-step process wherein self-polymerization of α-synuclein into insoluble aggregates is preceded by the formation of soluble protofibrils of α-synuclein monomers. Self-association may be triggered by the formation of alternative conformations of α-synuclein monomers with high propensity to polymerize. Several studies using neuronal cell lines or whole animals have shown that formation of reactive oxygen species (hereinafter abbreviated as ROS) appear to stimulate noxious α-synuclein amyloidogenesis. For instance paraquat (an agent stimulating ROS formation within the cell) has been recognized as a stimulator of α-synuclein aggregation. Like in animals, exposure to paraquat is believed to induce the formation of synuclein inclusions, and consequently neurodegeneration, especially of dopaminergic neurons in humans. Dopaminergic neurons appear to be particularly sensitive because the concurrent dopamine metabolism may on the one hand contribute significantly to the oxidative stress load but may on the other hand result in kinetic stabilisation of highly toxic protofibrillar α-synuclein species by dopamine (or its metabolic derivatives). Parkinson's disease is characterised by a selective loss of dopaminergic substantia nigra cells and therefore treatment of animals (or neuronal cells) with paraquat is a common well-accepted experimental set-up for studying synucleopathies, in particular Parkinson's disease.

Apart from ROS, mutations in the coding region of the α-synuclein gene have also been identified as stimulators of self-polymerization resulting in early disease onset as it is observed in families afflicted by such mutations. Finally, increased expression of α-synuclein also promotes early disease onset as evidenced by a duplication or triplication of the α-synuclein gene in the genome of some individuals. The molecular mechanism by which α-synuclein self-association triggers cellular degeneration is at present largely unknown. Although it has been speculated that insoluble aggregates affect cellular integrity, it has recently been suggested that soluble protofibrillar intermediates of the aggregation process are particularly toxic for the cell as opposed to mature insoluble fibrils which may be inert end-products or may even serve as cytoprotective reservoirs of otherwise harmful soluble species. Therapeutic attempts to inhibit formation of insoluble aggregates may therefore be conceptually wrong, possibly even promoting disease progress.

While the identification of pathological α-synuclein mutations unequivocally revealed a causative factor of a plethora of neurodegenerative disorders, treatments ensuring suppression of toxic α-synuclein amyloidogenesis are presently not available. Only symptomatic treatments of Parkinson's disease exist, which aim e.g. at increasing dopamine levels in order to replenish its lowered level due to degeneration of dopaminergic neurons, for instance by administrating L-DOPA or inhibitors of dopamine breakdown. Although such treatments suppress disease symptoms to some extent, they are only temporarily effective and certainly do not slow down ongoing neuronal degeneration.

Thus there is a need in the art for designing new drugs for therapeutic treatments that target the underlying molecular mechanism of α-synuclein related pathologies in order to reduce neuronal cell death and/or degeneration.

WO 99/51584 discloses 5-piperazinyl-1,2,4-thiadiazoles as inhibitors of proton pump $H^+/K^+$-ATPase and therefor useful in the treatment of peptic ulcer. However these compounds are not suggested for use in the prevention or treatment of neuro-degenerative disorders.

SUMMARY OF THE INVENTION

The present invention relates to several classes of 1,2,4-thiadiazole derivatives that have been shown to effectively counteract or inhibit the toxic properties of α-synuclein. Administration of these compounds to patients suffering from a neurodegenerative disease characterised by noxious α-synuclein amyloidogenesis therefore constitutes an effective therapeutic and/or prophylactic method of treatment.

According to a first aspect, the present invention provides a class of novel 1,2,4-thiadiazole derivatives which are capable of inhibiting or significantly reducing α-synuclein-instigated loss of neuronal cell integrity, said derivatives being represented by the structural formula (A)

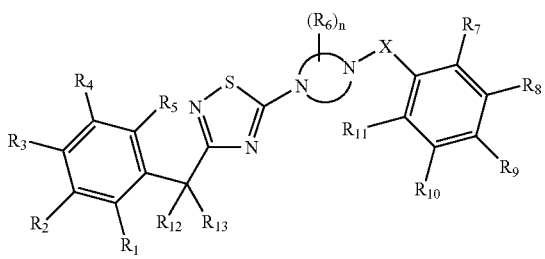

wherein the divalent group schematically represented by the structural formula (A')

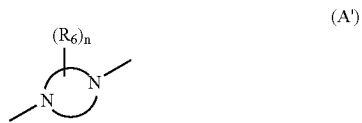

(A')

includes an optionally mono-substituted or poly-substituted, saturated or partly unsaturated heterocyclic ring with at least two nitrogen atoms in the said heterocyclic ring and with a total of 5 to 7 atoms in the said heterocyclic ring, and further wherein:

$R_6$ is a substituent independently selected from the group consisting of oxo and $C_{1-4}$ alkyl;

n is selected from the group consisting of 0, 1, 2 and 3;

$R_1$, $R_2$, $R_3$, $R_4$ and $R_5$ are each independently selected from the group consisting of hydrogen, $C_{1-4}$ alkyl, $C_{1-4}$ alkoxy, aryl, aryloxy, aryl-$C_{1-4}$ alkyloxy, heteroaryloxy, benzenesulfonate, amino, hydroxy, nitro, trifluoromethyl, trifluoromethoxy and halogen, or any two adjacent substituents selected from the group consisting of $R_1$, $R_2$, $R_3$, $R_4$ and $R_5$ form, together with the phenyl ring carbon atoms to which they are attached, a saturated or unsaturated ring fused to said phenyl ring and having from 5 to 7 ring members, said saturated or unsaturated ring optionally comprising one or two oxygen atoms and being optionally substituted with one or more halogen atoms;

$R_7$, $R_8$, $R_9$, $R_{10}$ and $R_{11}$ are each independently selected from the group consisting of hydrogen, $C_{1-10}$ alkyl, $C_{2-4}$ alkenyl, $C_{3-8}$ cycloalkyl, $C_{1-6}$ alkoxy, $C_{1-4}$ alkylthio, aryl, hydroxy, acetyl, nitro, trifluoromethyl and halogen; or any two adjacent substituents selected from the group consisting of $R_7$, $R_8$, $R_9$, $R_{10}$ and $R_{11}$ form, together with the phenyl ring carbon atoms to which they are attached, a saturated or unsaturated ring fused to said phenyl ring and having from 5 to 7 ring members, said saturated or unsaturated ring optionally comprising one or two heteroatoms independently selected from the group consisting of oxygen, sulfur and nitrogen (e.g. methylenedioxy); and each of said $C_{1-6}$ alkyl, $C_{1-6}$ alkoxy, $C_{1-4}$ alkylthio, aryl or fused ring is optionally substituted with one or more halogen atoms;

$R_{12}$ and $R_{13}$ are each independently selected from the group consisting of hydrogen, $C_{1-6}$ alkyl, aryl-$C_{1-4}$ alkyl, aryl and N-containing heterocyclic rings, or $R_{12}$ and $R_{13}$ together form a $C_{3-6}$ cycloalkyl or heterocyclic group; and X is a linking moiety selected from the group consisting of a single bond; —C(=O)—; —S(=O)$_2$—; divalent saturated or unsaturated (e.g. ethylenically unsaturated) non-cyclic hydrocarbon groups comprising from 1 to 6 atoms in the main chain, each atom in the main chain being independently selected from the group consisting of carbon, nitrogen and sulfur, each carbon atom in the main chain being optionally substituted with one or more substituents independently selected from the group consisting of oxo, thioxo, $C_{1-4}$ alkyl and halogen, and each sulfur atom in the main chain being optionally substituted with oxo provided that the number of heteroatoms in the main chain of said divalent saturated or unsaturated non-cyclic hydrocarbon group is 0, 1 or 2; and divalent saturated or unsaturated heterocyclic groups comprising from 2 to 6 carbon atoms and from 1 to 3 heteroatoms independently selected from the group consisting of oxygen, sulfur and nitrogen in the said heterocyclic group; or X together with one of $R_7$ and $R_{11}$ forms a saturated or unsaturated ring having from 5 to 7 ring members and being fused to the phenyl ring bearing said one of $R_7$ and $R_{11}$, said saturated or unsaturated ring optionally comprising one or two heteroatoms independently selected from the group consisting of oxygen, sulfur and nitrogen, and said saturated or unsaturated ring optionally comprising one or more substituents independently selected from the group consisting of $C_{1-4}$ alkyl and trifluoromethyl;

or a stereoisomer or a solvate thereof, or a pharmaceutically acceptable salt thereof. In particular, 1,2,4-thiadiazole derivatives of the first aspect of the invention may be selected from the group consisting of:

1-[3-methoxyphenylsulfonyl]-4-[3-(4-fluorobenzyl)-1,2,4-thiadiazol-5-yl]piperazine;

1-[4-methoxyphenylsulfonyl]-4-[3-(3-methoxybenzyl)-1,2,4-thiadiazol-5-yl]piperazine;

1-[4-methoxyphenylsulfonyl]-4-[3-(3-fluorobenzyl)-1,2,4-thiadiazol-5-yl]piperazine;

1-[4-methoxyphenylsulfonyl]-4-[3-(2-fluorobenzyl)-1,2,4-thiadiazol-5-yl]piperazine;

1-[2-methoxyphenylsulfonyl]-4-[3-(4-fluorobenzyl)-1,2,4-thiadiazol-5-yl]piperazine;

1-[4-ethoxyphenylsulfonyl]-4-[3-(4-fluorobenzyl)-1,2,4-thiadiazol-5-yl]piperazine;

1-[4-ethylphenylsulfonyl]-4-[3-(4-fluorobenzyl)-1,2,4-thiadiazol-5-yl]piperazine;

1-phenylsulfonyl-4-[3-(4-fluorobenzyl)-1,2,4-thiadiazol-5-yl]piperazine;

1-[4-methoxyphenylsulfonyl]-4-[3-benzyl-1,2,4-thiadiazol-5-yl]piperazine;

1-(4-propionyloxy)benzene-sulfonyl-4-[3-(4-fluorobenzyl)-1,2,4-thiadiazol-5-yl]piperazine;

1-[4-methoxyphenylsulfonyl]-4-[3-(3-methylbenzyl-1,2,4-thiadiazol-5-yl]piperazine;

1-[4-methoxyphenylsulfonyl]-4-[3-(2-methylbenzyl-1,2,4-thiadiazol-5-yl]piperazine;

1-[4-methoxyphenylsulfonyl]-4-[3-(2-methoxybenzyl-1,2,4-thiadiazol-5-yl]piperazine;

1-[4-methoxyphenylsulfonyl]-4-[3-(3-methyl-4-fluorobenzyl-1,2,4-thia-diazol-5-yl] piperazine;

1-[4-methoxyphenylsulfonyl]-4-[3-(4-methoxybenzyl-1,2,4-thiadiazol-5-yl]piperazine;

1-[4-bromophenylsulfonyl]-4-[3-(3-methoxybenzyl-1,2,4-thiadiazol-5-yl]piperazine;

1-[4-methoxyphenylsulfonyl]-4-[3-(3-methoxybenzyl)-1,2,
4-thia-diazol-5-yl]-2-methyl-piperazine; and
1-(4-hydroxybenzenesulfonyl)-4-[3-(4-fluorobenzyl)-1,2,4-
thiadiazol-5-yl]piperazine.

According to a second aspect, the present invention provides pharmaceutical compositions comprising an effective amount of one or more 1,2,4-thiadiazole derivatives represented by the structural formula (A), said compositions being useful for the prevention and/or treatment of an α-synucleopathy such as, but not limited to, Parkinson's disease, diffuse Lewy body disease, multiple system atrophy and Alzheimer's disease. Accordingly, the present invention also relates to a method of preventing or treating an α-synucleopathy, comprising the administration of a therapeutic effective amount of a 1,2,4-thiadiazole derivative represented by the structural formula (A) to a patient in need thereof, optionally in combination with one or more pharmaceutically acceptable carriers, and optionally in combination with a therapeutic amount of one or more drugs selected from the group consisting of neuro-protective agents and α-synuclein deposition inhibitors. In a third aspect, the present invention provides a method for preparing the novel 1,2,4-thiadiazole derivatives represented by the structural formula (A) in a limited number of steps and starting from commercially available materials or easily obtainable analogues thereof.

According to a fourth aspect, the present invention provides a class of novel 1,2,4-thiadiazole derivatives which are capable of inhibiting or significantly reducing α-synuclein-instigated loss of neuronal cell integrity, said derivatives being represented by the structural formula (B)

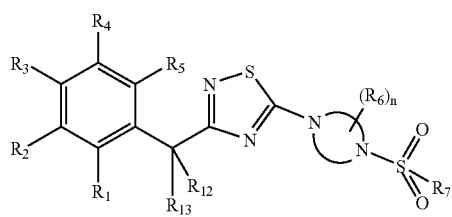

(B)

wherein the divalent group schematically represented by the structural formula (A')

(A')

includes an optionally mono-substituted or poly-substituted, saturated or partly unsaturated heterocyclic ring with at least two nitrogen atoms in the said heterocyclic ring and with a total of 5 to 7 atoms in the said heterocyclic ring, and further wherein:

$R_6$ is a substituent independently selected from the group consisting of oxo and $C_{1-4}$ alkyl;

n is selected from the group consisting of 0, 1, 2 and 3;

$R_1$, $R_2$, $R_3$, $R_4$ and $R_5$ are each independently selected from the group consisting of hydrogen, $C_{1-4}$ alkyl, $C_{1-4}$ alkoxy, aryl, aryloxy, aryl-$C_{1-4}$ alkyloxy, heteroaryloxy, benzenesulfonate, amino, hydroxy, nitro, halo $C_{1-6}$ alkyl, halo $C_{1-6}$ alkoxy and halogen, or any two adjacent substituents selected from the group consisting of $R_1$, $R_2$, $R_3$, $R_4$ and $R_5$ form, together with the phenyl ring carbon atoms to which they are attached, a saturated or unsaturated ring fused to said phenyl ring and having from 5 to 7 ring members, said saturated or unsaturated ring optionally comprising one or two oxygen atoms and being optionally substituted with one or more halogen atoms;

$R_7$ is selected from the group consisting of $C_{1-20}$ alkyl, $C_{3-10}$ cycloalkyl, aryl$C_{1-4}$ alkyl, aryl-$C_{2-4}$ alkenyl, and $C_{3-10}$ cycloalkyl-$C_{1-6}$ alkyl, wherein said $C_{1-20}$ alkyl, $C_{3-10}$ cycloalkyl or aryl-$C_{1-4}$ alkyl is optionally substituted by one or more substituents independently selected from the group consisting of halogen, cyano, nitro, aryloxy, carboxylic acid ($CO_2H$) and $C_{1-4}$alkyl esters thereof;

$R_{12}$ and $R_{13}$ are each independently selected from the group consisting of hydrogen, hydroxy, $C_{1-6}$ alkyl, aryl-$C_{1-4}$ alkyl, aryl and N-containing heterocyclic rings, wherein said aryl and aryl-$C_{1-4}$ alkyl are optionally substituted with di-$C_{1-6}$alkylamine; or $R_{12}$ and $R_{13}$ together form a $C_{3-6}$ cycloalkyl or heterocyclic group, wherein said $C_{3-6}$ cycloalkyl is optionally substituted with oxo;

including stereoisomers thereof, enantiomers thereof, solvates thereof, pharmaceutically acceptable salts thereof. Optionally the following compounds are disclaimed:
1-(butylsulfonyl)-4-[3-(4-chlorobenzyl)-1,2,4-thiadiazol-5-yl]piperazine,
1-(octylsulfonyl)-4-[3-(4-methylbenzyl)-1,2,4-thiadiazol-5-yl]piperazine,
1-(butylsulfonyl)-4-[3-(4-methylbenzyl)-1,2,4-thiadiazol-5-yl]piperazine,
1-(ethylsulfonyl)-4-[3-(4-chlorobenzyl)-1,2,4-thiadiazol-5-yl]piperazine,
1-(isopropylsulfonyl)-4-[3-(4-methylbenzyl)-1,2,4-thiadiazol-5-yl]piperazine,
1-(benzylsulfonyl)-4-[3-(4-chlorobenzyl)-1,2,4-thiadiazol-5-yl]piperazine,
1-(benzylsulfonyl)-4-[3-(4-methylbenzyl)-1,2,4-thiadiazol-5-yl]piperazine,
1-(phenylprop-2-ensulfonyl)-4-[3-(4-fluorobenzyl)-1,2,4-thiadiazol-5-yl]piperazine,
1-(phenylprop-2-ensulfonyl)-4-[3-(4-methylbenzyl)-1,2,4-thiadiazol-5-yl]-2-methylpiperazine, or
1-(phenylprop-2-ensulfonyl)-4-[3-(4-methylbenzyl)-1,2,4-thiadiazol-5-yl]piperazine.

According to another aspect, the present invention provides pharmaceutical compositions comprising an effective amount of one or more 1,2,4-thiadiazole derivatives represented by the structural formula (B), said compositions being useful for the prevention and/or treatment of an α-synucleopathy such as, but not limited to, Parkinson's disease, diffuse Lewy body disease, multiple system atrophy and Alzheimer's disease. Accordingly, the present invention also relates to a method of preventing or treating an α-synucleopathy, comprising the administration of a therapeutic effective amount of a 1,2,4-thiadiazole derivative represented by the structural formula (B) to a patient in need thereof, optionally in combination with one or more pharmaceutically acceptable carriers, and optionally in combination with a therapeutic amount of one or more drugs selected from the group consisting of neuro-protective agents and α-synuclein deposition inhibitors. In a third aspect, the present invention provides a method for preparing the novel 1,2,4-thiadiazole derivatives represented by the structural formula (B) in a limited number of steps and starting from commercially available materials or easily obtainable analogues thereof.

According to a fifth aspect, the present invention provides a class of novel 1,2,4-thiadiazole derivatives which are capable of inhibiting or significantly reducing α-synuclein-instigated loss of neuronal cell integrity, said derivatives being represented by the structural formula (C)

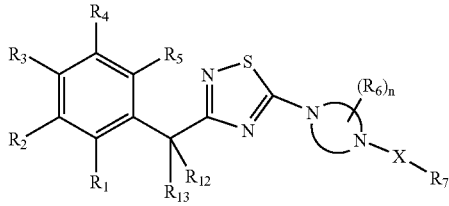
(C)

wherein the divalent group scematically represented by the structural formula (A')

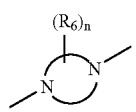
(A')

includes an optionally mono-substituted or poly-substituted, saturated or partly unsaturated heterocyclic ring with at least two nitrogen atoms in the said heterocyclic ring and with a total of 5 to 7 atoms in the said heterocyclic ring, and further wherein:

$R_6$ is a substituent independently selected from the group consisting of oxo and $C_{1-4}$ alkyl;

n is selected from the group consisting of 0, 1, 2 and 3;

$R_1, R_2, R_3, R_4$ and $R_5$ are each independently selected from the group consisting of hydrogen, $C_{1-4}$ alkyl, $C_{1-4}$ alkoxy, aryl, aryloxy, aryl-$C_{1-4}$ alkyloxy, heteroaryloxy, benzenesulfonate, amino, hydroxy, nitro, halo $C_{1-6}$ alkyl, halo $C_{1-6}$ alkoxy and halogen, or any two adjacent substituents selected from the group consisting of $R_1, R_2, R_3, R_4$ and $R_5$ form, together with the phenyl ring carbon atoms to which they are attached, a saturated or unsaturated ring fused to said phenyl ring and having from 5 to 7 ring members, said saturated or unsaturated ring optionally comprising one or two oxygen atoms and being optionally substituted with one or more halogen atoms;

X is a linking moiety selected from the group consisting of a single bond; C(=O); S(=O)$_2$; divalent saturated or unsaturated (e.g. ethylenically unsaturated) non-cyclic hydrocarbon groups comprising from 1 to 6 atoms in the main chain, each of said atoms in the main chain being independently selected from the group consisting of carbon, nitrogen and sulfur, and each sulfur atom in the main chain being optionally substituted with one or two double bonded oxygen atoms, and each of said carbon atoms in the main chain being optionally substituted with one or more substituents independently selected from the group consisting of oxo, thioxo, $C_{1-4}$ alkyl, aryl (in particular phenyl) and halogen, provided that the number of heteroatoms in the main chain of said divalent saturated or unsaturated non-cyclic hydrocarbon group is 0, 1 or 2; and divalent saturated or unsaturated heterocyclic groups comprising from 2 to 6 carbon atoms and from 1 to 3 heteroatoms independently selected from the group consisting of oxygen, sulfur and nitrogen in the said heterocyclic group;

$R_7$ is a heterocyclyl optionally substituted with one or more substituents independently selected from $R_8$ and $R_9$, provided that $R_7$ is not 2-pyrazinyl or an optionally substituted pyridyl when X is a single bond;

each $R^8$ is independently selected from the group consisting of $C_{1-10}$ alkyl, $C_{2-6}$ alkenyl, $C_{2-6}$ alkynyl, $C_{1-6}$ alkoxy, aryl, aryloxy, aryl-$C_{1-6}$alkyl, heterocyclyl, heterocyclyl-$C_{1-6}$alkyl, heterocyclyl oxy, $C_{1-6}$ alkanoyl wherein each of said $R_8$ is optionally substituted with one or more substituents independently selected from the group consisting of halogen, oxo, thioxo, $C_{1-6}$alkyl, $C_{1-6}$alkoxy, amino, $C_{1-6}$ alkyl-amino, di-$C_{1-6}$alkyl-amino, $C_{1-6}$alkylthio, —CN, —NO, —C(O)—NR$_{14}$R$_{15}$, —C(O)—R$_{15}$, —NH—C(O)—R$_{14}$, —O—C(O)—R$_{14}$, —C(O)—O—R$_{14}$, —S(O)—R$_{14}$, —S(O)$_2$—R$_{14}$, —S(O)$_2$—NR$_{14}$R$_{15}$;

each $R_9$ is independently selected from the group consisting of OH, NO$_2$, halogen, NH$_2$, $C_{1-6}$alkyl-amino, di-$C_{1-6}$ alkyl-amino, —CN, —NO, —C(O)—NR$_{14}$R$_{15}$, —C(O)—R$_{15}$, —NH—C(O)—R$_{14}$, —O—C(O)—R$_{14}$, —C(O)—O—R$_{14}$, —S(O)—R$_{14}$, —S(O)$_2$—R$_{14}$, —S(O)$_2$—NR$_{14}$R$_{15}$, and $C_{1-6}$alkylthio;

$R_{12}$ and $R_{13}$ are each independently selected from the group consisting of hydrogen, hydroxy, $C_{1-6}$ alkyl, aryl-$C_{1-4}$ alkyl, aryl and N-containing heterocyclic rings, wherein said aryl and aryl-$C_{1-4}$ alkyl are optionally substituted with di-$C_{1-6}$alkylamino; or $R_{12}$ and $R_{13}$ together form a $C_{3-6}$ cycloalkyl or heterocyclic group, wherein said $C_{3-6}$ cycloalkyl is optionally substituted with oxo;

each $R_{14}$ is independently selected from the group consisting of hydrogen, $C_{1-6}$ alkyl, $C_{2-6}$ alkenyl, $C_{2-6}$ alkynyl, aryl, aryl $C_{1-6}$ alkyl, $C_{3-10}$ cycloalkyl and heterocyclyl;

each $R_{15}$ is independently selected from the group consisting of hydrogen and $C_{1-6}$ alkyl;

or a stereoisomer thereof, or an enantiomer thereof, or a solvate thereof, or a N-oxide thereof, or a pharmaceutically acceptable salt thereof. Optionally said 1,2,4-thiadiazole derivative is not 1-[2-thienylsulfonyl]-4-[3-(2-methyl-benzyl-1,2,4-thiadiazol-5-yl]piperazine.

According to another aspect, the present invention provides pharmaceutical compositions comprising an effective amount of one or more 1,2,4-thiadiazole derivatives represented by the structural formula (C), said compositions being useful for the prevention and/or treatment of an α-synucleopathy such as, but not limited to, Parkinson's disease, diffuse Lewy body disease, multiple system atrophy and Alzheimer's disease. Accordingly, the present invention also relates to a method of preventing or treating an α-synucleopathy, comprising the administration of a therapeutic effective amount of a 1,2,4-thiadiazole derivative represented by the structural formula (C) to a patient in need thereof, optionally in combination with one or more pharmaceutically acceptable carriers, and optionally in combination with a therapeutic amount of one or more drugs selected from the group consisting of neuro-protective agents and α-synuclein deposition inhibitors. In a third aspect, the present invention provides a method for preparing the novel 1,2,4-thiadiazole derivatives represented by the structural formula (C) in a limited number of steps and starting from commercially available materials or easily obtainable analogues thereof.

According to a sixth aspect, the present invention provides a class of novel 1,2,4-thiadiazole derivatives which are capable of inhibiting or significantly reducing α-synuclein-instigated loss of neuronal cell integrity, said derivatives being represented by the structural formula (D)

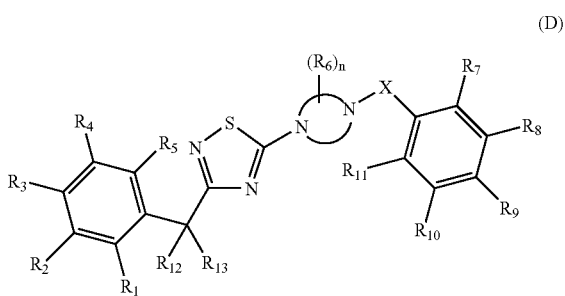

(D)

wherein the divalent group schematically represented by the structural formula

(A')

includes an optionally mono-substituted or poly-substituted, saturated or partly unsaturated heterocyclic ring with at least two nitrogen atoms in the said heterocyclic ring and with a total of 5 to 7 atoms in the said heterocyclic ring, and further wherein:

$R_6$ is a substituent independently selected from the group consisting of oxo and $C_{1-4}$ alkyl;

n is an integer selected from the group consisting of 0, 1, 2 and 3;

$R_1$, $R_2$, $R_3$, $R_4$ and $R_5$ are each independently selected from the group consisting of hydrogen, $C_{1-4}$ alkyl, $C_{1-4}$ alkoxy, aryl, aryloxy, aryl-$C_{1-4}$ alkyloxy, heteroaryloxy, benzenesulfonate, amino, hydroxy, nitro, halo $C_{1-6}$ alkyl, halo $C_{1-6}$ alkoxy and halogen, or any two adjacent substituents selected from the group consisting of $R_1$, $R_2$, $R_3$, $R_4$ and $R_5$ form, together with the phenyl ring carbon atoms to which they are attached, a saturated or unsaturated ring fused to said phenyl ring and having from 5 to 7 ring members, said saturated or unsaturated ring optionally comprising one or two oxygen atoms and being optionally substituted with one or more halogen atoms;

at least one of $R_7$, $R_8$, $R_9$, $R_{10}$ and $R_{11}$ is R'; and the remaining of $R_7$, $R_8$, $R_9$, $R_{10}$ and $R_{11}$ are independently selected from R' and R";

each R' is independently selected from the group consisting of CN, trifluoromethoxy, NO, —C(O)—$NR_{14}R_{15}$, —NH—C(O)—$R_{14}$, —O—C(O)—$R_{14}$, —C(O)—O—$R_{14}$, —S(O)—$R_{14}$, —S(O)$_2$—$R_{14}$, —S(O)$_2$—$NR_{14}R_{15}$, $C_{1-6}$ alkylthio, $C_{3-10}$ cycloalkyloxy, aryl (in particular phenyl), benzyloxy, aryloxy and heterocyclyl (in particular heteroaryl); wherein said heterocyclyl is optionally substituted with one or more substituents independently selected from the group consisting of oxo, halogen, $C_{1-6}$ alkyl and halo $C_{1-6}$ alkyl; and wherein said aryloxy is optionally substituted with $C_{1-6}$ alkoxy;

each R" is independently selected from the group consisting of hydrogen, $C_{1-10}$ alkyl, $C_{1-7}$ alkoxy, aryl, hydroxy, acetyl, nitro, trifluoromethyl and halogen, or two R" form, together with the phenyl ring carbon atoms to which they are attached, a saturated or unsaturated ring fused to said phenyl ring and having from 5 to 7 ring members, said saturated or unsaturated ring optionally comprising one, two or three heteroatoms independently selected from the group consisting of oxygen, sulfur and nitrogen; and each of said $C_{1-10}$ alkyl, $C_{1-6}$ alkoxy aryl or fused ring is optionally substituted with one or more halogen atoms;

$R_{12}$ and $R_{13}$ are each independently selected from the group consisting of hydrogen, hydroxy, $C_{1-6}$ alkyl, aryl-$C_{1-14}$ alkyl, aryl and N-containing heterocyclic rings, wherein said aryl and aryl-$C_{1-4}$ alkyl are optionally substituted with di-$C_{1-6}$alkylamine; or $R_{12}$ and $R_{13}$ together form a $C_{3-6}$ cycloalkyl or heterocyclic group, wherein said $C_{3-6}$ cycloalkyl is optionally substituted with oxo;

each $R_{14}$ is independently selected from the group consisting of $C_{1-6}$ alkyl, aryl, aryl $C_{1-6}$ alkyl, $C_{3-10}$ cycloalkyl and heterocyclyl;

each $R_{15}$ is independently selected from the group consisting of hydrogen and $C_{1-6}$ alkyl; and X is a linking moiety selected from the group consisting of a single bond; C(=O); S(=O)$_2$; divalent saturated or unsaturated (e.g. ethylenically unsaturated) non-cyclic hydrocarbon groups comprising from 1 to 6 atoms in the main chain, each of said atoms in the main chain being independently selected from the group consisting of carbon, nitrogen and sulfur, and each sulfur atom in the main chain being optionally substituted with one or two double bonded oxygen atoms, and each of said carbon atoms in the main chain being optionally substituted with one or more substituents independently selected from the group consisting of oxo, thioxo, $C_{1-4}$ alkyl, aryl (in particular phenyl) and halogen, provided that the number of heteroatoms in the main chain of said divalent saturated or unsaturated non-cyclic hydrocarbon group is 0, 1 or 2; and divalent saturated or unsaturated heterocyclic groups comprising from 2 to 6 carbon atoms and from 1 to 3 heteroatoms independently selected from the group consisting of oxygen, sulfur and nitrogen in the said heterocyclic group; or X together with one of $R_7$ and $R_{11}$ forms a saturated or unsaturated ring having from 5 to 7 ring members and being fused to the phenyl ring bearing said one of $R_7$ and $R_{11}$, said saturated or unsaturated ring optionally comprising one or two heteroatoms independently selected from the group consisting of oxygen, sulfur and nitrogen, and said saturated or unsaturated ring optionally comprising one or more substituents independently selected from the group consisting of $C_{1-4}$ alkyl and trifluoromethyl;

or a stereoisomer or solvate thereof, or a pharmaceutically acceptable salt thereof. Optionally said 1,2,4-thiadiazole derivative is not:

1-[4-acetamidophenylsulfonyl]-4-[3-(4-methylbenzyl)-1,2,4-thiadiazol-5-yl]piperazine, 1-[4-acetamidophenylsulfonyl]-4-[3-(4-methylbenzyl)-1,2,4-thiadiazol-5-yl]-2-methylpiperazine, 1-[4-acetamidophenylsulfonyl]-4-[3-(4-fluorobenzyl)-1,2,4-thiadiazol-5-yl]-2-methylpiperazine, N-(3-cyanophenyl)-4-[3-(4-fluorobenzyl)-1,2,4-thiadiazol-5-yl]-2-methylpiperazine-1-carboxamide, or 1-(4-propionyloxy)benzene-sulfonyl-4-[3-(4-fluoro-benzyl)-1,2,4-thiadiazol-5-yl]piperazine.

According to another aspect, the present invention provides pharmaceutical compositions comprising an effective amount of one or more 1,2,4-thiadiazole derivatives represented by the structural formula (D), said compositions being useful for the prevention and/or treatment of an α-synucleopathy such as, but not limited to, Parkinson's disease, diffuse Lewy body disease, multiple system atrophy and Alzheimer's disease. Accordingly, the present invention also relates to a method of preventing or treating an α-synucleopathy, comprising the administration of a therapeutic effective amount of a 1,2,4-thiadiazole derivative represented by the structural formula (D) to a patient in need thereof, optionally in combination with one or more pharmaceutically acceptable carriers, and optionally in combination with a therapeutic amount of one or more drugs selected from the group consisting of neuro-protective agents and α-synuclein deposition inhibitors. In a third aspect, the present invention provides a method for preparing the novel 1,2,4-thiadiazole derivatives represented by the structural formula (D) in a limited number of steps and starting from commercially available materials or easily obtainable analogues thereof.

Definitions

As used herein with respect to a substituting group, and unless otherwise stated, the term "$C_{1-4}$ alkyl" means straight and branched chain saturated acyclic hydrocarbon monovalent groups having from 1 to 4 carbon atoms such as, for example, methyl, ethyl, propyl, n-butyl, 1-methylethyl (isopropyl), 2-methylpropyl (isobutyl) and 1,1-dimethylethyl (ter-butyl). By analogy, the term "$C_{1-6}$ alkyl" refers to such radicals having from 1 to 6 carbon atoms, including 2-methylbutyl, n-pentyl, dimethylpropyl, n-hexyl, 2-methylpentyl, 3-methylpentyl, and the like.

As used herein with respect to a substituting group, and unless otherwise stated, the term "$C_{3-6}$ cycloalkyl" means a mono- or polycyclic saturated hydrocarbon monovalent group having from 3 to 6 carbon atoms, such as for instance cyclopropyl, cyclobutyl, cyclopentyl, cyclohexyl, and the like. By analogy, the term "$C_{3-8}$ cycloalkyl" refers to such radicals having from 3 to 8 carbon atoms, including cycloheptyl, cyclooctyl, and the like.

As used herein with respect to a substituting group, and unless otherwise stated, the term "aryl" designate any mono- or polycyclic aromatic monovalent hydrocarbon group having from 6 up to 30 carbon atoms such as but not limited to phenyl, naphthyl, anthracenyl, phenantracyl, fluoranthenyl, chrysenyl, pyrenyl, biphenylyl, terphenyl, picenyl, indenyl, biphenyl, indacenyl, benzocyclobutenyl, benzocyclooctenyl and the like, including fused benzo-$C_{4-8}$ cycloalkyl groups such as, for instance, indanyl, tetrahydronaphtyl, fluorenyl and the like, all of the said radicals being optionally substituted with one or more substituents independently selected from the group consisting of halogen, amino, trifluoromethyl, hydroxyl, sulfhydryl and nitro, such as for instance 4-fluorophenyl, 4-chlorophenyl, 3,4-dichlorophenyl, 4-cyanophenyl, 2,6-dichlorophenyl, 2-fluorophenyl, 3-chlorophenyl, 3,5-dichlorophenyl and the like.

As used herein with respect to a (part of a) substituting group, and unless otherwise stated, the term "$C_{2-4}$ alkenyl" refers to straight and branched chain ethylenically unsaturated acyclic hydrocarbon monovalent groups having from 2 to 4 carbon atoms such as, for example, ethenyl, propenyl and butenyl; for instance, "aryl-$C_{2-4}$ alkenyl" refers in particular to styryl.

As used herein with respect to a substituting group, and unless otherwise stated, the term "$C_{2-6}$ alkynyl" refers to straight and branched acyclic hydrocarbon monovalent groups having from 2 to 6 carbon atoms comprising at least one triple carbon-carbon bond such as, but not limited to, propargyl.

As used herein with respect to a substituting group, and unless otherwise stated, the terms "heterocyclic" and "heterocyclyl" mean a mono- or polycyclic, saturated or mono-unsaturated or polyunsaturated monovalent hydrocarbon radical having from 2 up to 15 carbon atoms and including one or more heteroatoms in one or more heterocyclic rings, each of said rings having from 3 to 10 atoms (and optionally further including one or more heteroatoms attached to one or more carbon atoms of said ring, for instance in the form of a carbonyl or thiocarbonyl or selenocarbonyl group, and/or to one or more heteroatoms of said ring, for instance in the form of a sulfone, sulfoxide, N-oxide, phosphate, phosphonate or selenium oxide group), each of said heteroatoms being independently selected from the group consisting of nitrogen, oxygen, sulfur, selenium and phosphorus, also including radicals wherein a heterocyclic ring is fused to one or more aromatic hydrocarbon rings for instance in the form of benzo-fused, dibenzo-fused and naphtho-fused heterocyclic radicals; within this definition are included heterocyclic radicals such as, but not limited to, diazepinyl, oxadiazinyl, thiadiazinyl, dithiazinyl, triazolonyl, diazepinonyl, triazepinyl, triazepinonyl, tetrazepinonyl, benzoquinolinyl, benzothiazinyl, benzothiazinonyl, benzoxathiinyl, benzodioxinyl, benzodithiinyl, benzoxazepinyl, benzothiazepinyl, benzodiazepinyl, benzodioxepinyl, benzodithiepinyl, benzoxazocinyl, benzothiazocinyl, benzodiazocinyl, benzoxathiocinyl, benzodioxocinyl, benzotrioxepinyl, benzoxathiazepinyl, benzoxadiazepinyl, benzothiadiazepinyl, benzotriazepinyl, benzoxathiepinyl, benzotriazinonyl, benzoxazolinonyl, azetidinonyl, azaspiroundecyl, dithiaspirodecyl, selenazinyl, selenazolyl, selenophenyl, hypoxanthinyl, azahypo-xanthinyl, bipyrazinyl, bipyridinyl, oxazolidinyl, diselenopyrimidinyl, benzodioxocinyl, benzopyrenyl, benzopyranonyl, benzophenazinyl, benzoquinolizinyl, dibenzocarbazolyl, dibenzoacridinyl, dibenzophenazinyl, dibenzothiepinyl, dibenzoxepinyl, dibenzopyranonyl, dibenzoquinoxalinyl, dibenzothiazepinyl, dibenzisoquinolinyl, tetraazaadamantyl, thiatetraazaadamantyl, oxauracil, oxazinyl, dibenzothiophenyl, dibenzofuranyl, oxazolinyl, oxazolonyl, azaindolyl, azolonyl, thiazolinyl, thiazolonyl, thiazolidinyl, thiazanyl, pyrimidonyl, thiopyrimidonyl, thiamorpholinyl, aziactonyl, naphthindazolyl, naphthindolyl, naphthothiazolyl, naphthothioxolyl, naphthoxindolyl, naphthotriazolyl, naphthopyranyl, oxabicycloheptyl, azabenzimidazolyl, azacycloheptyl, azacyclooctyl, azacyclononyl, azabicyclononyl, tetrahydrofuryl, tetrahydropyranyl, tetrahydropyronyl, tetrahydroquinoleinyl, tetrahydro-thienyl and dioxide thereof, dihydrothienyl dioxide, dioxindolyl, dioxinyl, dioxenyl, dioxazinyl, thioxanyl, thioxolyl, thiourazolyl, thiotriazolyl, thiopyranyl, thiopyronyl, coumarinyl, quinoleinyl, oxyquinoleinyl, quinuclidinyl, xanthinyl, dihydropyranyl, benzodihydrofuryl, benzothiopyronyl, benzothiopyranyl, benzoxazinyl, benzoxazolyl, benzodioxolyl, benzodioxanyl, benzothiadiazolyl, benzotriazinyl, benzothiazolyl, benzoxazolyl, phenothioxinyl, phenothiazolyl, phenothienyl (benzothiofuranyl), phenopyronyl, phenoxazolyl, pyridinyl, dihydropyridinyl, tetrahydropyridinyl, piperidinyl, morpholinyl, thiomorpholinyl, pyrazinyl, pyrimidinyl, pyridazinyl, triazinyl, tetrazinyl, triazolyl, benzotriazolyl, tetrazolyl, imidazolyl, pyrazolyl, thiazolyl, thiadiazolyl, isothiazolyl, oxazolyl, oxadiazolyl, pyrrolyl, furyl, dihydrofuryl, furoyl, hydantoinyl, dioxolanyl, dioxolyl, dithianyl, dithienyl, dithiinyl, thienyl, indolyl, indazolyl, benzofuryl, quinolyl, quinazolinyl, quinoxalinyl, carbazolyl, phenoxazinyl, phenothiazinyl, xanthenyl, purinyl, benzothienyl, naphthothienyl, thianthrenyl, pyranyl, pyronyl, benzopyronyl, isobenzofuranyl, chromenyl, phenoxathiinyl, indolizinyl, quinolizinyl, isoquinolyl, phthalazinyl, naphthiridinyl, cinnolinyl, pteridinyl, carbolinyl, acridinyl, perimidinyl, phenanthrolinyl, phenazinyl, phenothiazinyl, imidazolinyl, imidazolidinyl, benzimidazolyl, pyrazolinyl, pyrazolidinyl, pyrrolinyl, pyrroli-dinyl, piperazinyl, uridinyl, thymidinyl, cytidinyl, azirinyl, aziridinyl, diazirinyl, diaziridinyl, oxiranyl, oxaziridinyl, dioxiranyl, thiiranyl, azetyl, dihydroazetyl, azetidinyl, oxetyl, oxetanyl, oxetanonyl, homopiperazinyl, homopiperidinyl, thietyl, thietanyl, diazabicyclooctyl, diazetyl, diaziridinonyl, diaziridinethionyl, chromanyl, chromanonyl, thiochromanyl, thiochromanonyl, thiochromenyl, benzofuranyl, benzisothiazolyl, benzocarbazolyl, benzochromonyl, benzisoalloxazinyl, benzocoumarinyl, thiocoumarinyl, phenometoxazinyl, phenoparoxazinyl, phentriazinyl, thiodiazinyl, thiodiazolyl, indoxyl, thioindoxyl, benzodiazinyl (e.g. phthalazinyl), phthalidyl, phthalimidinyl, phthalazonyl, alloxazinyl, dibenzopyronyl (i.e. xanthonyl), xanthionyl, isatyl, isopyrazolyl, isopyrazolonyl, urazolyl, urazinyl, uretinyl, uretidinyl, succinyl, succinimido, benzylsultimyl, benzylsultamyl and the like, including all possible isomeric forms thereof, wherein each carbon atom of said heterocyclic ring may furthermore be independently substituted with a substituent selected from the group consisting of halogen, nitro, $C_{1-7}$ alkyl and the like; depending upon the number of unsaturations in each ring, heterocyclyl may be sub-divided into heteroaromatic (or "heteroaryl") radicals and non-aromatic heterocyclic radicals; when a heteroatom of said non-aromatic heterocyclic radical is nitrogen, the latter may be substituted with a substituent selected from the group consisting of $C_{1-6}$ alkyl, $C_{3-6}$ cycloalkyl, aryl (in particular phenyl) and benzyl.

For the purpose of the present invention and unless otherwise defined, each alkyl, alkenyl, alkynyl, aryl, heterocyclyl and cycloalkyl—both as substituent as such, as well as when part of a larger substituent, e.g. alkyl in arylalkyl—optionally substituted with one or more substituent independently selected from the group consisting of halogen, OH, $NH_2$, CN, $C_{1-6}$ alkyl, $C_{1-6}$ alkoxy, $C_{1-6}$ alkylamino and di-$C_{1-6}$ alkylamino.

As used herein with respect to a substituting group, and unless otherwise stated, the terms "$C_{1-4}$ alkoxy", "$C_{1-6}$ alkoxy" and "aryloxy", refer to substituents wherein a carbon atom of a $C_{1-4}$ alkyl, respectively a $C_{1-6}$ alkyl or an aryl group (each of them such as defined herein), is attached to an oxygen atom through a single bond such as, but not limited to, methoxy, ethoxy, propoxy, butoxy, pentoxy, isopropoxy, sec-butoxy, tert-butoxy, isopentoxy, phenyloxy, and the like.

As used herein and unless otherwise stated, the term "stereoisomer" refers to all possible different isomeric as well as conformational forms which the compounds of structural formula (A) may possess, in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

As used herein and unless otherwise stated, the term "enantiomer" means each individual optically active form of a compound of the invention, having an optical purity or enantiomeric excess (as determined by methods standard in the art) of at least 80% (i.e. at least 90% of one enantiomer and at most 10% of the other enantiomer), preferably at least 90% and more preferably at least 98%.

As used herein and unless otherwise stated, the term "solvate" includes any combination which may be formed by a derivative of this invention with a suitable inorganic solvent (e.g. hydrates) or organic solvent, such as but not limited to alcohols (thus forming alcoholates), ketones, esters, ethers, nitriles (e.g. acetonitrile) and the like.

The term "α-synucleopathy" as used herein, unless otherwise stated, refers to a disease characterised by the presence of pathological deposition of insoluble α-synuclein polymers or aggregates intracellularly and/or extracellularly. Such diseases include, but are not limited to, Parkinson's disease, diffuse Lewy body disease, traumatic brain injury, amyotrophic lateral sclerosis, Niemann-Pick disease, Hallervorden-Spatz syndrome, Down syndrome, neuroaxonal dystrophy, multiple system atrophy and Alzheimer's disease.

As used herein, the term "Parkinson's disease" refers to a chronic progressive nervous disease characterised by neurodegeneration, especially degeneration of dopaminergic neurons. Symptoms include stooped posture, resting tremor, weakness of resting muscles, a shuffling gait, speech impediments, movement difficulties and an eventual slowing of mental processes and dementia.

The term "neuroprotective" agent, as used herein, refers to drugs or chemical agents intended to prevent neurodegeneration, including drugs that slow down or stop the progression of neuronal degeneration.

DETAILED DESCRIPTION OF THE INVENTION

The present invention relates to various groups of novel 1,2,4-thiadiazole derivatives which have desirable biological properties such as an inhibitory effect on α-synuclein mediated toxicity. Based on this inhibitory activity, and the fact that these compounds are not toxic to neural cells, these compounds are useful in the prevention and/or treatment of α-synucleopathies.

In the broadest expression, the class of novel biologically active 1,2,4-thiadiazole derivatives according to the first aspect of this invention may be represented by the structural formula (A), including stereoisomers, enantiomers, solvates, N-oxides and pharmaceutically acceptable salts thereof, with all possible meanings of substituents present therein. This broad class may be sub-divided into several sub-classes wherein each substituent $R_1$ to $R_{13}$, and/or the divalent group (A'), and/or the linking moiety X may independently be defined in a more restricted manner, at will and independently from each other. Exemplary but non-limiting embodiments of such sub-classes may be defined as follows:

the divalent group schematically represented by the structural formula (A') may include, in addition to the at least two nitrogen atoms, one or more further heteroatoms in the heterocyclic ring or attached to one or more carbon atoms of the heterocyclic ring;

the divalent group schematically represented by the structural formula (A') may include two non-adjacent nitrogen atoms and four or five carbon atoms in the heterocyclic ring;

the divalent group schematically represented by the structural formula (A') may be selected from the group consisting of piperazinyl, 2,3-dioxopiperazinyl, 2,5-dioxopiperazinyl, 2-methylpiperazinyl, trans-2,5-dimethylpiperazinyl, 3,6-dimethyl-2,5-dioxopiperazinyl, 3-isopropyl-2,5-dioxopiperazinyl, 3-tert-butyl-2,5-dioxopiperazinyl, 2,4-dioxoimidazolidinyl, 2,4,5-trioxoimidazolidinyl and homopiperazinyl;

the divalent group schematically represented by the structural formula (A') may be an optionally monosubstituted piperazinyl ring such that the 1,2,4-thiadiazole derivative is represented by the structural formula ($A_1$)

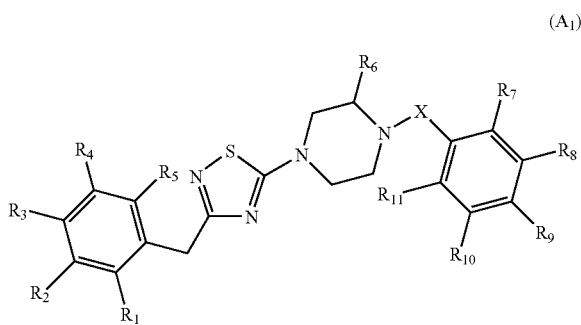

(A₁)

wherein X, $R_1$, $R_2$, $R_3$, $R_4$, $R_5$, $R_7$, $R_8$, $R_9$, $R_{10}$ and $R_{11}$ are as defined above, and $R_6$ is hydrogen or is as defined above, or a stereoisomer or a solvate thereof, or a pharmaceutically acceptable salt thereof;

X may be a divalent saturated or unsaturated non-cyclic hydrocarbon group comprising from 1 to 3 carbon atoms but no heteroatom in the main chain, wherein each carbon atom in the main chain is optionally substituted with one substituent (when said substituent is divalent such as oxo or thioxo) or two substituents (when said substituent is monovalent such as halogen or $C_{1-4}$ alkyl) independently selected from the group consisting of oxo, thioxo, $C_{1-4}$ alkyl and halogen;

X may be selected from the group consisting of CO, $C_{1-6}$ alkylene, —CO—CH₂—, —CO—(CH₂)₂—, —CO—CH=CH—, —CO—CHR₁₄—, —CH₂—CH=CH— and —CO—CHX'—, wherein $R_{14}$ is $C_{1-4}$ alkyl and X' is halogen;

X may be a divalent saturated or unsaturated non-cyclic hydrocarbon group comprising from 1 to 5 carbon atoms and one single nitrogen, oxygen or sulfur atom in the main chain, wherein each of said carbon atoms in the main chain is optionally substituted with one or more substituents independently selected from the group consisting of oxo, thioxo and $C_{1-4}$ alkyl, and wherein a sulfur atom in the main chain is optionally substituted with oxo;

X may be selected from the group consisting of —CO—NH—, —(CH₂)₂—NH—CO, —(CH₂)₂—NH—CO—CH₂—, —(CH₂)₂—NH—CO—(CH₂)₂—, —(CH₂)₂—NH—CO—CHR₁₄, —SO₂—CH=CH— and —SO₂—CH₂—, wherein $R_{14}$ is $C_{1-4}$ alkyl;

X may be a divalent saturated or unsaturated non-cyclic hydrocarbon group comprising from 1 to 5 carbon atoms and one single oxygen atom in the main chain, wherein said oxygen atom is not adjacent to the nitrogen atom of the divalent group (A'), e.g. X may be —C(=O)—O—CH₂—;

X may be a divalent saturated or unsaturated non-cyclic hydrocarbon group comprising from 1 to 4 carbon atoms and two non-adjacent nitrogen atoms in the main chain, wherein none of said nitrogen atoms is adjacent to the nitrogen atom of the divalent group (A'), e.g. X may be —(CH₂)₂—NH—CO—NH—CH₂—;

X may be a 1,2,4-thiadiazolyl;

each of $R_1$, $R_2$, $R_3$, $R_4$ and $R_5$ may be fluoro;

at least two of $R_1$, $R_2$, $R_3$, $R_4$ and $R_5$ may be hydrogen;

three of $R_1$, $R_2$, $R_3$, $R_4$ and $R_5$ may be methoxy;

three of $R_1$, $R_2$, $R_3$, $R_4$ and $R_5$ may be hydrogen, and two of $R_1$, $R_2$, $R_3$, $R_4$ and $R_5$ are identical and are selected from the group consisting of halogen, $C_{1-4}$ alkoxy and trifluoromethyl;

three of $R_1$, $R_2$, $R_3$, $R_4$ and $R_5$ are hydrogen, and wherein two of $R_1$, $R_2$, $R_3$, $R_4$ and $R_5$ are halogen and are independently selected from the group consisting of fluoro, chloro and bromo;

three of $R_1$, $R_2$, $R_3$, $R_4$ and $R_5$ are hydrogen, and two adjacent substituents selected from the group consisting of $R_1$, $R_2$, $R_3$, $R_4$ and $R_5$ form, together with the phenyl ring carbon atoms to which they are attached, a phenyl or methylenedioxy ring fused to said phenyl ring;

four of $R_1$, $R_2$, $R_3$, $R_4$ and $R_5$ are hydrogen, and one of $R_1$, $R_2$, $R_3$, $R_4$ and $R_5$ is selected from the group consisting of $C_{1-4}$ alkyl, $C_{1-4}$ alkoxy, aryl, aryloxy, aryl-$C_{1-4}$ alkyloxy, heteroaryloxy, benzenesulfonate, amino, hydroxy, nitro, trifluoromethyl, trifluoromethoxy and halogen;

$R_{12}$ and $R_{13}$ may together form a ring selected from the group consisting of cyclopropyl, cyclobutyl, cyclopentyl, cyclohexyl and piperidinyl;

$R_{12}$ is hydrogen and $R_{13}$ is selected from the group consisting of piperidinyl and morpholinyl;

two adjacent substituents selected from the group consisting of $R_7$, $R_8$, $R_9$, $R_{10}$ and $R_{11}$ may form, together with the phenyl ring carbon atoms to which they are attached, a methylenedioxy group fused to said phenyl ring;

at least three of $R_7$, $R_8$, $R_9$, $R_{10}$ and $R_{11}$ are hydrogen, and at most two of $R_7$, $R_8$, $R_9$, $R_{10}$ and $R_{11}$ are independently selected from the group consisting of $C_{1-6}$ alkyl, $C_{1-6}$ alkoxy, phenyl, hydroxy, acetyl, nitro, trifluoromethyl and halogen;

X is a single bond, at least three of $R_7$, $R_8$, $R_9$, $R_{10}$ and $R_{11}$ are hydrogen, and at most two of $R_7$, $R_8$, $R_9$, $R_{10}$ and $R_{11}$ are independently selected from the group consisting of $C_{1-6}$ alkyl, $C_{1-6}$ alkoxy, phenyl, hydroxy, acetyl, nitro, trifluoromethyl and halogen;

(A') is piperazinyl, X is a single bond, at least three of $R_7$, $R_8$, $R_9$, $R_{10}$ and $R_{11}$ are hydrogen, and at most two of $R_7$, $R_8$, $R_9$, $R_{10}$ and $R_{11}$ are independently selected from the group consisting of $C_{1-6}$ alkyl, $C_{1-6}$ alkoxy, phenyl, hydroxy, acetyl, nitro, trifluoromethyl and halogen.

In the broadest expression, the class of novel 1,2,4-thiadiazole derivatives of this invention represented by the above structural formula (B) including stereoisomers, enantiomers, solvates, N-oxides and pharmaceutically acceptable salts thereof, with all possible meanings of substituents present therein. This broad class may be sub-divided into several sub-classes wherein each substituent $R_1$ to $R_7$, $R_{12}$, $R_{13}$, and/or the divalent group (A') may be defined in a more restricted manner, at will and independently from each other. Exemplary but non-limiting embodiments of such sub-classes include the following:

the divalent group represented by the structural formula (A') includes one or more further heteroatoms in the heterocyclic ring or attached to one or more carbon atoms of the heterocyclic ring;

the divalent group schematically represented by the structural formula (A') may include two non-adjacent nitrogen atoms and four or five carbon atoms in the heterocyclic ring;

the divalent group (A') is selected from the group consisting of piperazinyl, 2,3-dioxopiperazinyl, 2,5-dioxopiperazinyl, 2-methylpiperazinyl, trans-2,5-dimethylpiperazinyl, 3,6-dimethyl-2,5-dioxopiperazinyl, 3-isopropyl-2,5-dioxopiperazinyl, 3-tert-butyl-2,5-dioxopiperazinyl, 2,4-dioxoimidazolidinyl, 2,4,5-trioxoimidazolidinyl and homopiperazinyl;

each of $R_1$, $R_2$, $R_3$, $R_4$ and $R_5$ is fluoro;

at least two of $R_1$, $R_2$, $R_3$, $R_4$ and $R_5$ are hydrogen;

three of $R_1$, $R_2$, $R_3$, $R_4$ and $R_5$ are methoxy;

three of $R_1$, $R_2$, $R_3$, $R_4$ and $R_5$ are hydrogen, and two of $R_1$, $R_2$, $R_3$, $R_4$ and $R_5$ are identical and are selected from the group consisting of halogen, $C_{1-4}$ alkoxy and trifluoromethyl;

three of $R_1$, $R_2$, $R_3$, $R_4$ and $R_5$ are hydrogen, and two of $R_1$, $R_2$, $R_3$, $R_4$ and $R_5$ are halogen and are independently selected from the group consisting of fluoro, chloro and bromo;

three of $R_1$, $R_2$, $R_3$, $R_4$ and $R_5$ are hydrogen, and two adjacent substituents selected from the group consisting of $R_1$, $R_2$, $R_3$, $R_4$ and $R_5$ form, together with the phenyl ring carbon atoms to which they are attached, a phenyl or methylenedioxy ring fused to said phenyl ring;

four of $R_1$, $R_2$, $R_3$, $R_4$ and $R_5$ are hydrogen, and one of $R_1$, $R_2$, $R_3$, $R_4$ and $R_5$ is selected from the group consisting of $C_{1-4}$ alkyl, $C_{1-14}$ alkoxy, aryl, aryloxy, aryl-$C_{1-4}$ alkyloxy, heteroaryloxy, benzenesulfonate, amino, hydroxy, nitro, trifluoromethyl, trifluoromethoxy and halogen;

$R_{12}$ and $R_{13}$ together form a ring selected from the group consisting of cyclopropyl, cyclobutyl, cyclopentyl, cyclohexyl and piperidinyl;

$R_{12}$ is hydrogen and $R_{13}$ is piperidinyl or morpholinyl;

$R_7$ is cyclopropyl, cyclopentyl, cyclohexyl or cyclohexylmethyl;

$R_7$ is perfluoro-$C_{1-8}$ alkyl, i.e. a $C_{1-8}$ alkyl group wherein all hydrogen atoms are replaced with fluor;

$R_7$ is styryl or substituted styryl;

$R_7$ is benzyl wherein the phenyl ring of said benzyl is optionally substituted with one or more substituents independently selected from the group consisting of nitro, bromo, chloro, fluoro, tert-butyl, trifluoromethyl, methyl, and cyano;

$R_7$ is methyl substituted with three substituents, e.g. two fluoro and one carboxylic acid or carboxylic acid methyl ester.

In the broadest expression, the class of novel 1,2,4-thiadiazole derivatives of this invention represented by the above structural formula (C), include stereoisomers, solvates, N-oxides and pharmaceutically acceptable salts thereof, with all possible meanings of substituents present therein. This broad class may be sub-divided into several sub-classes wherein each substituent $R_1$ to $R_9$, $R_{12}$ to $R_{15}$, and/or the divalent group (A'), and/or the linking moiety X may be defined in a more restricted manner, at will and independently from each other. Exemplary but non-limiting embodiments of such sub-classes include the following:

the divalent group represented by the structural formula (A') includes one or more further heteroatoms in the heterocyclic ring or attached to one or more carbon atoms of the heterocyclic ring;

the divalent group schematically represented by the structural formula (A') may include two non-adjacent nitrogen atoms and four or five carbon atoms in the heterocyclic ring;

the divalent group (A') is selected from the group consisting of piperazinyl, 2,3-dioxopiperazinyl, 2,5-dioxopiperazinyl, 2-methylpiperazinyl, trans-2,5-dimethylpiperazinyl, 3,6-dimethyl-2,5-dioxopiperazinyl, 3-isopropyl-2,5-dioxopiperazinyl, 3-tert-butyl-2,5-dioxopiperazinyl, 2,4-dioxoimidazolidinyl, 2,4,5-trioxoimidazolidinyl and homopiperazinyl;

X may be a divalent saturated or unsaturated non-cyclic hydrocarbon group comprising from 1 to 3 carbon atoms but no heteroatom in the main chain, wherein each carbon atom in the main chain is optionally substituted with one substituent (when said substituent is divalent such as oxo or thioxo) or two substituents (when said substituent is monovalent such as halogen or $C_{1-4}$ alkyl) independently selected from the group consisting of oxo, thioxo, $C_{1-4}$ alkyl and halogen;

X may be selected from the group consisting of CO, $C_{1-6}$ alkylene, —CO—$CH_2$—, —CO—$(CH_2)_2$—, —CO—CH=CH—, —CO—$CHR_{14}$—, —$CH_2$—CH=CH— and —CO—CHX'—, wherein $R_{14}$ is $C_{1-4}$ alkyl and X' is halogen;

X may be a divalent saturated or unsaturated non-cyclic hydrocarbon group comprising from 1 to 5 carbon atoms and one single nitrogen, oxygen or sulfur atom in the main chain, wherein each of said carbon atoms in the main chain is optionally substituted with one or more substituents independently selected from the group consisting of oxo, thioxo and $C_{1-4}$ alkyl, and wherein a sulfur atom in the main chain is optionally substituted with oxo;

X may be selected from the group consisting of —CO—NH—, —$(CH_2)_2$—NH—CO, —$(CH_2)_2$—NH—CO—$CH_2$—, —$(CH_2)_2$—NH—CO—$(CH_2)_2$—, —$(CH_2)_2$—NH—CO—$CHR_{14}$, —$SO_2$—CH=CH— and —$SO_2$—$CH_2$—, wherein $R_{14}$ is $C_{1-4}$ alkyl;

X may be a divalent saturated or unsaturated non-cyclic hydrocarbon group comprising from 1 to 5 carbon atoms and one single oxygen atom in the main chain, wherein said oxygen atom is not adjacent to the nitrogen atom of the divalent group (A'); e.g. X may be —C(=O)—O—$CH_2$—;

X may be a divalent saturated or unsaturated non-cyclic hydrocarbon group comprising from 1 to 4 carbon atoms and two non-adjacent nitrogen atoms in the main chain, wherein none of said nitrogen atoms is adjacent to the nitrogen atom of the divalent group (A'); e.g. X may be —$(CH_2)_2$—NH—CO—NH—$CH_2$—;

each of $R_1$, $R_2$, $R_3$, $R_4$ and $R_5$ is fluoro;

at least two of $R_1$, $R_2$, $R_3$, $R_4$ and $R_5$ are hydrogen;

three of $R_1$, $R_2$, $R_3$, $R_4$ and $R_5$ are methoxy;

three of $R_1$, $R_2$, $R_3$, $R_4$ and $R_5$ are hydrogen, and two of $R_1$, $R_2$, $R_3$, $R_4$ and $R_5$ are identical and are selected from the group consisting of halogen, $C_{1-4}$ alkoxy and trifluoromethyl;

three of $R_1$, $R_2$, $R_3$, $R_4$ and $R_5$ are hydrogen, and two of $R_1$, $R_2$, $R_3$, $R_4$ and $R_5$ are halogen and are independently selected from the group consisting of fluoro, chloro and bromo;

three of $R_1$, $R_2$, $R_3$, $R_4$ and $R_5$ are hydrogen, and two adjacent substituents selected from the group consisting of $R_1$, $R_2$, $R_3$, $R_4$ and $R_5$ form, together with the phenyl ring carbon atoms to which they are attached, a phenyl or methylenedioxy ring fused to said phenyl ring;

four of $R_1$, $R_2$, $R_3$, $R_4$ and $R_5$ are hydrogen, and one of $R_1$, $R_2$, $R_3$, $R_4$ and $R_5$ is selected from the group consisting of $C_{1-4}$ alkyl, $C_{1-4}$ alkoxy, aryl, aryloxy, aryl-$C_{1-4}$ alkyloxy, heteroaryloxy, benzenesulfonate, amino, hydroxy, nitro, trifluoromethyl, trifluoromethoxy and halogen;

$R_{12}$ and $R_{13}$ together form a ring selected from the group consisting of cyclopropyl, cyclobutyl, cyclopentyl, cyclohexyl and piperidinyl;

$R_{12}$ is hydrogen and $R_{13}$ is piperidinyl or morpholinyl;

$R_7$ is a non-substituted heteroaryl;

$R_7$ is heteroaryl substituted with one $R_8$;

$R_7$ is heteroaryl substituted with one $R_9$; or $R_7$ is heteroaryl substituted with one $R_8$ and one $R_9$.

In the broadest expression the class of novel 1,2,4-thiadiazole derivatives of this invention represented by the above structural formula (D) include stereoisomers, solvates and pharmaceutically acceptable salts thereof, with all possible meanings of substituents present therein. This broad class may be sub-divided into several sub-classes wherein each substituent $R_1$ to $R_{15}$, and/or the divalent group (A'), and/or the linking moiety X may be defined in a more restricted manner, at will and independently from each other. Exemplary but non-limiting embodiments of such sub-classes are as follows:

- the divalent group represented by the structural formula (A') includes one or more further heteroatoms in the heterocyclic ring or attached to one or more carbon atoms of the heterocyclic ring;
- the divalent group schematically represented by the structural formula (A') may include two non-adjacent nitrogen atoms and four or five carbon atoms in the heterocyclic ring;
- the divalent group (A') is selected from the group consisting of piperazinyl, 2,3-dioxopiperazinyl, 2,5-dioxopiperazinyl, 2-methylpiperazinyl, trans-2,5-dimethylpiperazinyl, 3,6-dimethyl-2,5-dioxopiperazinyl, 3-isopropyl-2,5-dioxopiperazinyl, 3-tert-butyl-2,5-dioxopiperazinyl, 2,4-dioxoimidazolidinyl, 2,4,5-trioxoimidazolidinyl and homopiperazinyl;
- X is a $C_{1-6}$ alkylene group;
- X is a divalent saturated or unsaturated hydrocarbon group comprising from 1 to 3 carbon atoms but no heteroatom in the main chain, wherein each of said carbon atoms in the main chain is optionally substituted with one or more substituents independently selected from the group consisting of oxo, $C_{1-4}$ alkyl, aryl and halogen;
- X is selected from the group consisting of —CO—CH$_2$—, —CO—(CH$_2$)$_2$— and —CO—CHR$_{16}$—, wherein $R_{16}$ is $C_{1-4}$ alkyl or phenyl;
- X is a divalent saturated or unsaturated hydrocarbon group comprising from 1 to 5 carbon atoms and one single nitrogen, oxygen or sulfur atom in the main chain, and wherein each of said carbon atoms in the main chain is optionally substituted with one or more substituents independently selected from the group consisting of oxo, and $C_{1-4}$ alkyl;
- each of $R_1$, $R_2$, $R_3$, $R_4$ and $R_5$ is fluoro;
- at least two of $R_1$, $R_2$, $R_3$, $R_4$ and $R_5$ are hydrogen;
- three of $R_1$, $R_2$, $R_3$, $R_4$ and $R_5$ are methoxy;
- three of $R_1$, $R_2$, $R_3$, $R_4$ and $R_5$ are hydrogen, and two of $R_1$, $R_2$, $R_3$, $R_4$ and $R_5$ are identical and are selected from the group consisting of halogen, $C_{1-4}$ alkoxy and trifluoromethyl;
- three of $R_1$, $R_2$, $R_3$, $R_4$ and $R_5$ are hydrogen, and two of $R_1$, $R_2$, $R_3$, $R_4$ and $R_5$ are halogen and are independently selected from the group consisting of fluoro, chloro and bromo;
- three of $R_1$, $R_2$, $R_3$, $R_4$ and $R_5$ are hydrogen, and two other adjacent substituents selected from the group consisting of $R_1$, $R_2$, $R_3$, $R_4$ and $R_5$ form, together with the phenyl ring carbon atoms to which they are attached, a phenyl or methylenedioxy ring fused to said phenyl ring;
- four of $R_1$, $R_2$, $R_3$, $R_4$ and $R_5$ are hydrogen, and one of $R_1$, $R_2$, $R_3$, $R_4$ and $R_5$ is selected from the group consisting of $C_{1-4}$ alkyl, $C_{1-4}$ alkoxy, aryl, aryloxy, aryl-$C_{1-4}$ alkyloxy, heteroaryloxy, benzenesulfonate, amino, hydroxy, nitro, trifluoromethyl, trifluoromethoxy and halogen;
- $R_{12}$ and $R_{13}$ together form a ring selected from the group consisting of cyclopropyl, cyclobutyl, cyclopentyl, cyclohexyl and piperidinyl;
- $R_{12}$ is hydrogen and $R_{13}$ is selected from the group consisting of piperidinyl and morpholinyl;
- two adjacent substituents selected from the group consisting of $R_7$, $R_8$, $R_9$, $R_{10}$ and $R_{11}$ form, together with the phenyl ring carbon atoms to which they are attached, a methylenedioxy group fused to said phenyl ring;
- only one of $R_7$, $R_8$, $R_9$, $R_{10}$ and $R_{11}$ is R', and the remaining of $R_7$, $R_8$, $R_9$, $R_{10}$ and $R_{11}$ is hydrogen.

The ability of the compounds of the invention, being represented by the structural formulae (A), (B), (C) and (D), to inhibit α-synuclein mediated toxicity is based on their activity in the α-synuclein cytotoxicity test described in the examples section herein. Treatment of mice with mitochondrial complex I inhibitors such as paraquat or MPTP (1-methyl-4-phenyl-1,2,3,6-tetrahydropyridine) is a well-accepted and commonly used experimental set-up to study neuronal degeneration. Paraquat triggers synuclein-aggregation, which allegedly triggers a specific loss of dopaminergic neurons and ultimately a decline in the locomotion function. Briefly, one or more compounds are administered to paraquat-receiving mice and the onset of motoric dysfunction is assessed using a rotary rod device. A delay or absence in the occurrence of motoric problems in compound treated mice (compared to control mice treated with only vehicle) indicates that the compound(s) inhibit(s) synuclein-dependent degeneration of dopaminergic cells.

In the assays used herein, compounds were considered to be active when inhibiting α-synuclein cytotoxicity by more than 25% relative to controls at a concentration of 20 µg/mL or lower. Dose responses were carried out on all compounds found to be active (10 point curves in duplicate). Although the pharmacological properties of the compounds disclosed in this invention vary with structural change, active compounds particularly possess EC50's in a cell-based assay of synuclein cytotoxicity in a range from about 0.0001 to 10 µM. Based on these findings, methods for treating and preventing disorders or diseases provoked by cytotoxic intracellular α-synuclein are provided herein. These methods comprise administering to a subject suffering from or susceptible to such a disease or disorder, an effective amount of one or more inhibitors of α-synuclein cytotoxicity as defined by the broad structural formula (A) of the invention, or sub-classes thereof. As used herein, the term "effective amount" designates an amount sufficient to effect beneficial or desired clinical or biochemical results. An effective amount can be administered one or more times. For purposes of this invention, an effective amount of an inhibitor of α-synuclein cytotoxicity is an amount that is sufficient to palliate, ameliorate, stabilize, reverse, slow down or delay the progression of a disease state or condition. In a particular embodiment of the invention, the "effective amount" is defined as an amount of compound capable of preventing deposition of insoluble α-synuclein polymers or aggregates and/or capable of preventing the cytotoxic effects triggered by aggregation or polymerization of α-synuclein, and is an amount that substantially reduces the symptoms of an α-synucleopathy, such as Parkinson's disease. Other forms of effective amount may be for the treatment or prevention of the learning or memory impairment related to Alzheimer's disease. As used herein, the terms "mammal", "subject" or "patient" for the purposes of a therapeutic or prophylactic treatment refers to any animal classified as a mammal, including humans, domestic and farm animals, such as but not limited to dogs, cats, pigs, horses, sheep, and the like. Most particularly, the mammal is a human being.

The various 1,2,4-thiadiazole compounds of the present invention can be synthesised in an effective manner according to the methods described in the following examples. These methods comprise a limited number of steps and start from commercially available, or readily accessible, materials. Generally, 1,2,4-thiadiazole compounds of this invention being represented by the structural formulae (A), (B), (C) and (D) can be synthesised by making use of the reaction scheme 1 described hereafter. Subsequently, 1,2,4-thiadiazole compounds of this invention being represented by the structural formulae (A) and (D) can be synthesised by making use of the reaction scheme 2 described hereinafter.

Scheme 1

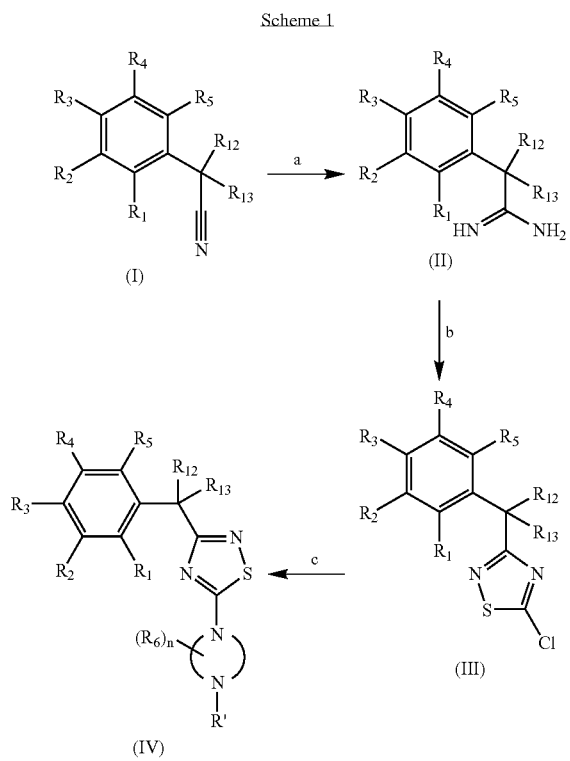

In step (a) of scheme 1, the benzonitrile derivative having the structural formula (I), optionally substituted on the aromatic ring and/or in alpha position to the cyano group, may be reacted with ammonia yielding the corresponding amidine (II).

The direct synthesis of amidines from nitriles and ammonia may be greatly facilitated by the presence of electron-withdrawing groups on the benzonitrile derivative (I). Optionally, this reaction may be carried out in the presence of an effective amount of one or more Lewis acids such as but not limited to $AlCl_3$ or $ZnCl_2$ at temperatures ranging from 20° C. up to a maximum of 150-200° C. Nitriles or cyanides that may be used in step (a) include, but are not limited to, 4-Aminobenzylcyanide, 4-bromo-2,2-diphenylbutyronitrile, 3-chlorobenzyl-cyanide, 4-chlorobenzyl-cyanide, cyclohexylphenyl-acetonitrile, 4-hydroxybenzyl-cyanide, α-methylbenzylcyanide, 2-methylbenzyl-cyanide, 3-methylbenzyl-cyanide, 4-methylbenzylcyanide, 4-cyano-4-phenylcyclohexanone, 1-(2,4-dichlorophenyl)-1-cyclopropylcyanide, 4-fluorophenylacetonitrile, diphenylacetonitrile, 3,4,5-trimethoxy-phenylacetonitrile, 2,2-diphenylpropionitrile, 4-bromophenylacetonitrile, 1-phenyl-cyclobutanecarbonitrile, 2,6-dichlorophenylacetonitrile, (3,4-dimethoxyphenyl)-acetonitrile, 4-nitrophenylacetonitrile, 1-phenyl-1-cyclopropanecarbonitrile, 1-(4-chlorophenyl)-1-cyclopropanecarbonitrile, 1-(4-methylphenyl)-1-cyclopropanecarbonitrile, 1-phenyl-1-cyclohexanecarbonitrile, 1-(4-chlorophenyl)-1-cyclohexanecarbonitrile, 1-(4-methylphenyl)-1-cyclohexanecarbonitrile, 1-(4-methoxyphenyl)-1-cyclohexanecarbonitrile, 2-nitrophenylacetonitrile, (4-methoxyphenyl)acetonitrile, 2,4-dichlorophenyl-acetonitrile, (2-methoxyphenyl)acetonitrile, benzyl cyanide, 2-chlorobenzylcyanide, 3-phenoxybenzaldehyde-cyanohydrin, 3-(trifluoromethyl)-phenylacetonitrile, (3-methoxyphenyl)-acetonitrile, 2-chloro-6-fluorophenylacetonitrile, 3,4-dichlorophenylacetonitrile, 4-amino-2-chlorodiphenylacetonitrile, 2-fluorophenylacetonitrile, 3-fluorophenylacetonitrile, 2,3,4,5,6-pentafluorophenylacetonitrile, 3,4-difluorophenylacetonitrile, 3-bromophenylacetonitrile, 2-chloro-4-fluorobenzyl cyanide, 1-(2-fluorophenyl)-cyclopentanecarbonitrile, 1-(2-fluorophenyl)-cyclohexanecarbonitrile, 1-(3-fluorophenyl)-cyclopentanecarbonitrile, 1-(3-fluorophenyl)-cyclohexanecarbonitrile, 1-(4-fluorophenyl)-cyclopentanecarbonitrile, 1-(4-fluorophenyl)-cyclohexanecarbonitrile, 1-(2-chloro-4-fluorophenyl)-cyclopentane-carbonitrile, 1-(2-chloro-4-fluorophenyl)-cyclohexanecarbonitrile, 1-(2-chloro-6-fluorophenyl)-cyclopentanecarbonitrile, 1-(2-chloro-6-fluorophenyl)-cyclohexane-carbonitrile, 2,4-difluorophenylacetonitrile, 2,5-difluorophenylacetonitrile, 2,6-difluorophenyl-acetonitrile, 4-(trifluoromethyl)phenylacetonitrile, 2-(trifluoromethyl)-phenylacetonitrile, 3,5-bis(trifluoromethyl)phenylacetonitrile, 2,5-dimethylphenyl-acetonitrile, 2-bromophenylacetonitrile, 2,4,6-trimethylbenzylcyanide, 2,3-dichloro-phenylacetonitrile, 3,4-(methylenedioxy)phenylacetonitrile, 1-(4-methoxyphenyl)-1-cyclopentanecarbonitrile, 1-(4-chlorophenyl)-1-cyclobutanecarbonitrile, 2-(4-chloro-2-fluorophenyl)-acetonitrile, 2-(3,5-difluorophenyl)-acetonitrile, 2-(4-isobutylphenyl)-propanenitrile, 2-[-4-[(4-methylbenzyl)-oxy]phenyl]acetonitrile, 1-(3-chlorophenyl)-1-cyclohexanecarbonitrile, 3-chloro-5-fluorophenylcetonitrile, 4-(trifluoromethoxy)-phenylacetonitrile, 2-phenyl-2-piperidinoacetonitrile, 4-bromo-2-fluorobenzylcyanide, 2-(4-chlorophenyl)-2-morpholinoacetonitrile, 1-(4-methoxyphenyl)-1-cyclopropane-carbonitrile, 2-(4-aminophenyl)-3-[4-(dimethylamino)phenyl]propanenitrile and 2-(4-hydroxyphenyl)-2-morpholinoacetonitrile.

According to a particular embodiment of the invention, the starting materials are selected from the group comprising 4-fluorobenzyl cyanide, 4-chlorobenzyl cyanide, 4-methylbenzyl cyanide, 3-methoxybenzyl cyanide and benzyl cyanide.

Alternatively an amidine having the structural formula (II) may be commercially available, for example 2-(2,6-dichlorophenyl)ethanimidamide in its hydrochloride salt form, and may then be used as the starting point of scheme 1.

Subsequently, the thiadiazole core of the compounds of this invention is synthesised in step (b) in a manner similar as described in WO 99/51584. For instance, the amidine compound having the structural formula (II) may be reacted with $CCl_3SCl$ to form the corresponding 3-substituted,5-chloro-thiadiazole (III) (step (b) of scheme 1) which may then be reacted with an (A')-containing N-substituted amine (wherein (A') is as defined above) such as a piperazine derivative, a diazepane derivative or an imidazolidine derivative to obtain a final compound of the invention having the structural formula (IV) wherein R' is according to formula

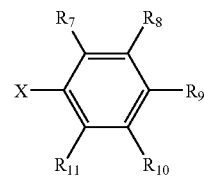

(wherein X, $R_7$, $R_8$, $R_9$, $R_{10}$, $R_{11}$ are as defined above), including intermediates having the structural formula (IV-A) (i.e. wherein R' is H) and intermediates having the structural formula (IV-B) (i.e. wherein R' is aminoethyl) shown below.

Piperazine compounds when used for the displacement reaction in step (c) directly yielding compounds of the present invention include, but are not limited to, 1-(4-nitrophenyl)piperazine, 1-(2-methoxyphenyl)piperazine, 1-(3-methoxyphenyl)-piperazine dihydrochloride, 1-phenylpiperazine, 1-(3-chlorophenyl)piperazine, 1-(4-chlorophenyl)piperazine, 1-(3,4-dichlorophenyl)piperazine, 1-(2,3-dimethylphenyl)-piperazine, 1-(2,4-dimethylphenyl)piperazine, 1-(2,5-dimethylphenyl)piperazine, 1-(3,4-dimethylphenyl)piperazine, 1-(5-chloro,2-methylphenyl)piperazine, 2-methyl-1-(3-methylphenyl)piperazine, 4-piperazinoacetophenone, 1-(4-fluorophenyl)piperazine, 1-(2-methoxyphenyl)piperazine hydrochloride, 1-(4-methoxyphenyl)piperazine, 1-(2-fluorophenyl)piperazine, 1-(3-methylphenyl)piperazine, 1-(4-methoxyphenyl)-2-methylpiperazine, 1-(2,4-di-fluorophenyl)piperazine, N-(alpha,alpha,alpha-trifluoro-p-tolyl)piperazine, 1-(4-Hydroxyphenyl)piperazine, 1-(4-methylphenyl)piperazine, 1-[2-nitro-4-(trifluoromethyl)phenyl]piperazine, 1-(2-hydroxyphenyl)piperazine, benzyl 3-oxopiperazine-1-carboxylate, 1-(2-chlorophenyl)piperazine, 1-(2-methylphenyl)-piperazine, 1-cinnamylpiperazine, trans-1-cinnamylpiperazine, 1-(4-fluorobenzyl)-piperazine and 2-methyl-4-piperazinoquinoline.

Alternatively, using the same synthetic pathway, another saturated or partly unsaturated heterocyclic ring having the structural formula (A') with at least two nitrogen atoms in the said heterocyclic ring and with a total of 5 to 7 atoms such as, but not limited to, homopiperazinyl or imidazolidinyl, may be introduced onto the thiadiazole core.

Commercially available reagents for such synthesis, yielding final compounds of the present invention with homopiperazinyl connected to the thiadiazole core, include, but are not limited to, 1-(4-bromo-2-fluorobenzyl)-1,4-diazepane, 1-(4-bromo-2-fluorobenzyl)-1,4-diazepane, 1-(mesitylmethyl)-1,4-diazepane, 1-(4-bromobenzyl)-1,4-diazepane, 6-chloro-2-(1,4-diazepan-1-yl)-1,3-benzothiazole, 1-(2-chloro-6-fluorobenzyl)-1,4-diazepane, 1-(4-fluorobenzyl)-1,4-diazepane, 5-(1,4-diazepan-1-yl)-3-phenyl-1,2,4-thiadiazole, 1-phenyl-1,4-diazepane, 1-(3-trifluoromethylphenyl)-1,4-diazepane, 1-(2-nitrophenyl)-1,4-diazepane, 1-(3-nitrophenyl)-1,4-diazepane and 1-(4-nitrophenyl)-1,4-diazepane. Imidazolidine compounds when used for the displacement reaction in step (c) directly yielding compounds of the present invention include, but are not limited to, 3-phenylimidazolidine-2,4-dione and 1-phenylimidazolidine-2,4,5-trione.

Scheme 2

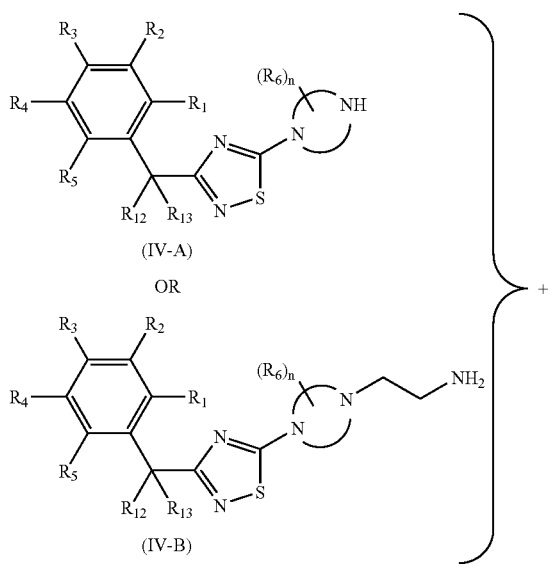

-continued

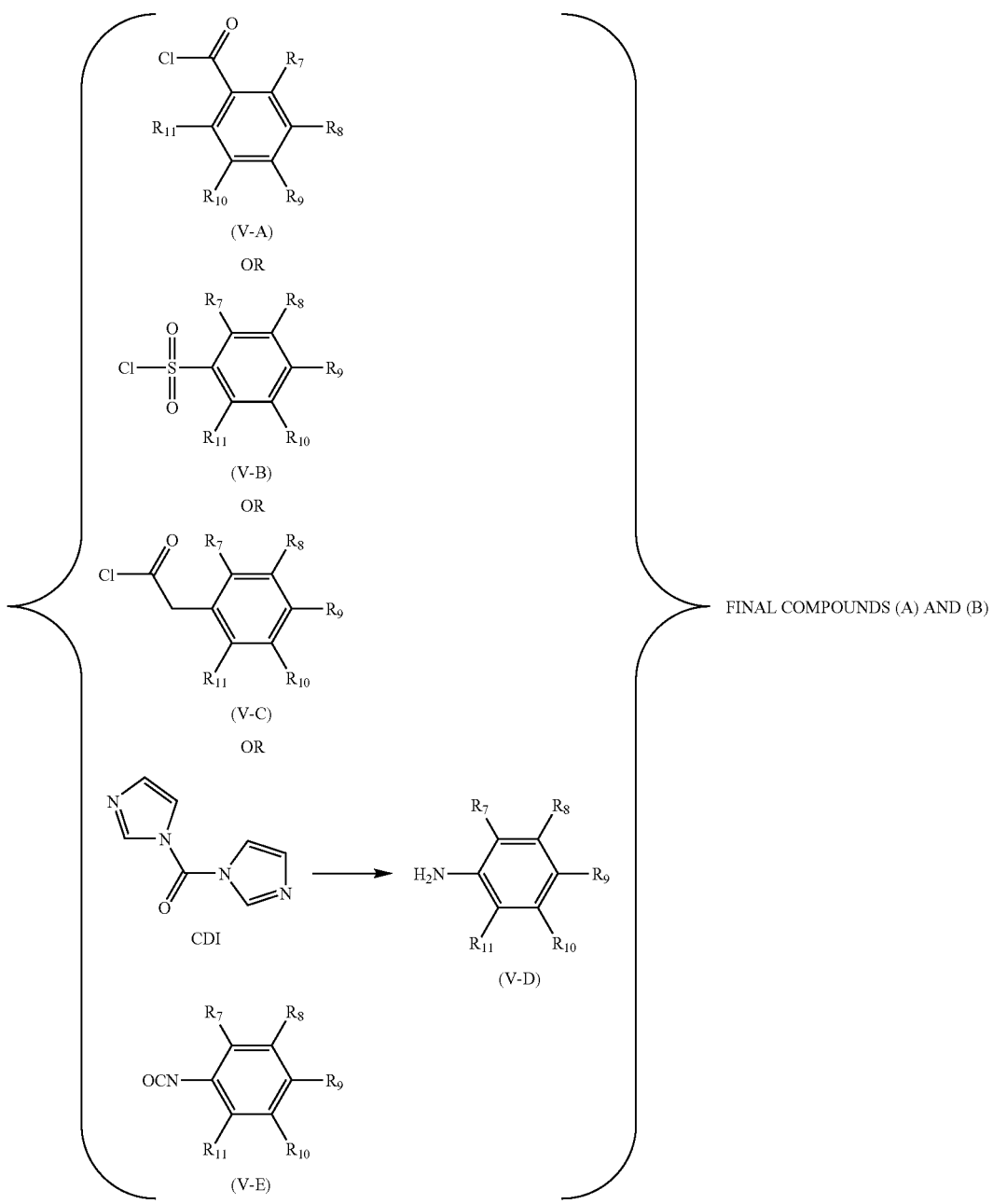

Scheme 2 schematically illustrates methods to prepare compounds according to structural formulae (A) and (D) wherein step (c) comprises two subsequent reaction sub-steps. In a first sub-step, a thiadiazole compound having the structural formula (III) may first be derivatised by reaction with a diamino compound including the optionally $R_6$-substituted heterocyclic ring (A') with at least two nitrogen atoms in the said heterocyclic ring and with a total of 5 to 7 atoms.

Such optionally substituted heterocyclic diamino compounds may be represented by the structural formula (A'')

wherein n and $R_6$ are as defined above, and R' is hydrogen or an amino protecting group; or a substituted heterocyclic compound represented by the structural formula (A''')

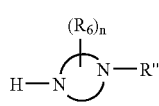

(A''')

wherein n and $R_6$ are as defined above, and R" is aminoalkyl or (protected amino)alkyl.

Examples of such heterocyclic diamino compounds for use in the first sub-step of step (c) comprise, but are not limited to, piperazine, 2-methylpiperazine (either (R)-(−)-2-methylpiperazine or (S)-(+)-2-methylpiperazine), trans-2,5-dimethylpiperazine, homopiperazine, 1-(2-aminoethyl)piperazine, 1,3-diazepane-2-thione, 1,3-diazepane-2,4,6-trione, hydantoin, 2-imidazolidinethione, imidazolidinetrione and glycine anhydride. In this way, intermediate compounds as illustrated by the non-limiting structural formulae (IV-A) and (IV-B) in scheme 2 may be obtained.

In a second reaction sub-step comprised within step (c) (scheme 2), these intermediate compounds represented by the non-limiting structural formulae (IV-A) and (IV-B) may be reacted with a reagent susceptible to nucleophilic attack by a non-tertiary amino group, e.g. the NH group present in intermediate compounds according to structural formula (IVA), or the terminal amino group present in intermediate compounds according to structural formula (IVB). Suitable such reagents include, but are not limited to, acid chlorides such as carbonyl chlorides or sulfonyl chlorides, or other activated acids such as carboxylic acid anhydrides. Particular carbonyl chlorides for use in this reaction sub-step include benzoyl chlorides (as shown in formula V-A) and phenyl acetyl chlorides (as shown in formula V-C). Particular sulfonyl chlorides for use in this reaction sub-step include, but are not limited to, phenylsulfonyl chlorides (as shown in formula V-B) and styrylsulfonyl chlorides.

Benzoyl chlorides (as shown in formula V-A) suitable for use in the synthesis of the compounds of the present invention include, but are not limited to, benzoyl chloride, p-anisoyl chloride, 2-bromobenzoyl chloride, 4-bromobenzoyl chloride, 3-chlorobenzoyl chloride, pentafluorobenzoyl chloride, 2-chlorobenzoyl chloride, p-toluoyl chloride, 4-chlorobenzoyl chloride, 2,4-dichlorobenzoyl chloride, 3,4-dichlorobenzoyl chloride, 4-nitrobenzoyl chloride, 4-fluorobenzoyl chloride, 2-fluorobenzoyl chloride, o-toluoyl chloride, m-toluoyl chloride, 4-cyanobenzoyl chloride, 3-nitrobenzoyl chloride, 4-tert-butyl-benzoyl chloride, 4-biphenylcarbonyl chloride, 3,5-dimethoxybenzoyl chloride, 3-fluorobenzoyl chloride, 2,6-dichlorobenzoyl chloride, 4-butylbenzoyl chloride, 4-heptyloxybenzoyl chloride, 4-hexylbenzoyl chloride, 4-hexyloxybenzoyl chloride, 4-pentylbenzoyl chloride, m-anisoyl chloride, 2,6-difluorobenzoyl chloride, 2-nitrobenzoyl chloride, 4-chloro3nitrobenzoylchloride, 3,4-difluorobenzoyl chloride, 2-iodobenzoyl chloride, 1-naphthoyl chloride, o-anisoyl chloride, 2,4-difluorobenzoyl chloride, 4-(trifluoromethyl)benzoyl chloride, m-anisoyl chloride, 2,6-Difluorobenzoyl chloride, 2-nitrobenzoyl chloride, 4-chloro-3-nitrobenzoylchloride, 3,4-difluorobenzoyl chloride, 2-iodobenzoyl chloride, 1-naphthoyl chloride, o-anisoyl chloride, 2,4-difluorobenzoyl chloride, 4-(trifluoromethyl) benzoyl chloride, 3-(chloromethyl)-benzoyl chloride, 4-(chloromethyl)-benzoyl chloride, 3-(dichloromethyl)-benzoyl chloride, 2,3,4,5-tetrafluorobenzoyl chloride, 2,4,6-trichlorobenzoyl chloride, 2,3,4-trifluorobenzoyl chloride, 2,4,6-trifluorobenzoyl chloride, 4-bromo-2-fluorobenzoyl chloride, 2,3,5,6-tetrafluorobenzoyl chloride, 3,5-dinitrobenzoyl chloride, 4-heptylbenzoyl chloride, 4-iodobenzoyl chloride, 4-octylbenzoyl chloride, 4-pentyloxybenzoyl chloride, 4-phenylazobenzoyl chloride, 4-propylbenzoyl chloride, methyl 4-chlorocarbonylbenzoate, 3,5-dichlorobenzoyl chloride, 3-fluoro-4-(trifluoromethyl)benzoyl chloride, 2,6-dimethoxybenzoyl chloride, piperonyloyl chloride, 2,4-dimethoxybenzoyl chloride, 3,4-dihydro-2H-1,5-benzodioxepine-6-carbonyl chloride, 2,3-dihydro-1,4-benzodioxine-6-carbonyl chloride, 2,3-dihydro-1,4-benzodioxine-5-carbonyl chloride, 1-benzofuran-5-carbonyl chloride, 2,1,3-benzothiadiazole-4-carbonyl chloride, 2,1,3-Benzothiadiazole-5-carbonyl chloride, 1,2,3-benzothiadiazole-5-carbonyl chloride, 2,1,3-benzoxadiazole-5-carbonyl chloride, 6-quinoxalinecarbonyl chloride, 4-(2-thienyl)-benzoyl chloride, 4-methyl-3,4-dihydro-2H-1,4-benzoxazine-7-carbonyl chloride, 4-(1,2,3-thiadiazol-4-yl)benzoyl chloride, 4-(1H-pyrazol-1-yl)benzoyl chloride, 1-methyl-1H-1,2,3-benzotriazole-5-carbonyl chloride, 1-benzothiophene-5-carbonyl chloride, 2,2-dimethyl-2,3-dihydro-1-benzofuran-7-carbonyl chloride, 4-[(dipropylamino)sulfonyl] benzene-1-carbonyl chloride, 4-[3-(trifluoromethyl)-1H-pyrazol-1-yl]-benzoyl chloride, 2-bromo-5-methoxybenzene-1-carbonyl chloride, 5-bromo-2,3,4-trimethylbenzoyl chloride, 2-chloro-6-fluorobenzene-1-carbonyl chloride, 2,3-dimethylbenzene-1-carbonyl chloride, 3,4-dimethylbenzene-1-carbonyl chloride, 2-chloro-4-fluorobenzoyl chloride, 5,5,8,8-tetramethyl-5,6,7,8-tetrahydro-2-naphthalenecarbonyl chloride, 2-(4-methoxyphenoxy)-5-nitrobenzene-1-carbonyl chloride, 2,3-difluorobenzoyl chloride, 2-Fluoro-5-(trifluoromethyl)benzoyl chloride, 2,3,6-trifluorobenzoyl chloride, 1-isopropyl-1h-1,2,3-benzotriazole-5-carbonyl chloride, 1-isopropyl-1H-1,2,3-benzotriazole-5-carbonyl chloride, 3-fluoro-4-methylbenzoyl chloride, 3-(cyclopentyloxy)-4-methoxybenzoyl chloride, 4-fluoro-3-(trifluoromethyl)benzoyl chloride, 2,3-dihydro-1-benzofuran-7-carbonyl chloride, 3-(2-methyl-thiazol-4-yl)-benzoyl chloride, 1-isopropyl-2-(trifluoromethyl)-1H-benzimidazole-5-carbonyl chloride, 5-bromo-2,3-dihydrobenzo[b]furan-7-carbonyl chloride, 2,4,6-trimethylbenzoyl chloride, 2-(2-thienyl)-benzoyl chloride, 3-cyanobenzoyl chloride, acetylsalicyloyl chloride, 3-(5-methyl-1,2,4-oxadiazol-3-yl)-benzoyl chloride and 4-(5-methyl-1,2,4-oxadiazol-3-yl)-benzoyl chloride.

According to a particular embodiment the benzoyl chloride reagent may be selected from the group consisting of 2-fluorobenzoyl chloride, 4-ethylbenzoyl chloride, 4-butylbenzoyl chloride, 4-methoxybenzoyl chloride, piperonyloyl chloride, 4-hexylbenzoyl chloride, 3-chlorobenzoyl chloride, 4-fluorobenzoyl chloride, p-toluoyl chloride, 3-fluorobenzoyl chloride, 4-chlorobenzoyl chloride, benzoyl chloride, 4-tert-butylbenzoyl chloride, 4-biphenylcarbonyl chloride, o-anisoyl chloride, 1-naphthoyl chloride, 2-naphthoyl chloride, 4-pentylbenzoyl chloride, 4-bromobenzoyl chloride, 2,4-dimethoxybenzoyl chloride, 3,5-dichlorobenzoyl chloride, 3-bromobenzoyl chloride, 2-bromobenzoyl chloride 3-trifluoromethylbenzoyl chloride, 4-trifluoromethylbenzoyl chloride and 2-ethylbenzoyl chloride.

Numerous other carbonyl chlorides are known to the person skilled in the art and commercially available for use as acylating reagent for use in the reaction step illustrated in scheme 2. Particular carbonyl chlorides for use in the method of the invention include, but are not limited to, cinnamoyl chloride, hydrocinnamoyl chloride, 2-phenylbutyryl chloride, phenylacetyl chloride and 4-fluorophenylacetyl chloride.

Phenylsulfonyl chlorides (structural formula V-B) suitable for use in the synthesis of compounds represented by the structural formulae (A) and (D) of the present invention include, but are not limited to, 4-fluorobenzenesulfonyl chloride, 2-mesitylenesulfonyl chloride, 4-methoxybenzene-sulfonyl chloride, p-toluenesulfonyl chloride, pentafluorobenzenesulfonyl chloride, benzenesulfonyl chloride, 4-bromobenzenesulfonyl chloride, N-acetylsulfanilyl chloride, 2,4,6-triisopropylbenzenesulfonyl chloride 2-naphtalenesulfonylchloride, 4-chloro-benzenesulfonyl chloride 3,5-dichloro-2-hydroxy-benzenesulfonylchloride, 2,5-dichlorobenzenesulfonyl chloride, pipsyl chloride, 1-naphthalenesulfonylchloride, methyl 2-(chlorosulfonyl)-benzoate, 4-tert-butylbenzenesulfonyl chloride, 3-(trifluoromethyl)benzenesulfonyl chloride, 2-bromobenzenesulfonyl chloride, 4-acetylbenzenesulfonylchloride, 2-(trifluoromethyl)-benzenesulfonyl chloride, 3,4-dichlorobenzenesulfonyl chloride, 3,4-dimethoxybenzenesulfonyl chloride, 3-chlorobenzenesulfonyl chloride, 2-chloro-4-fluorobenzenesulfonyl chloride, 3,5-dichlorobenzenesulfonyl chloride, 3-chloro-4-fluorobenzenesulfonyl chloride, 2,4-dichlorobenzenesulfonyl chloride, 2,5-dimethoxybenzenesulfonyl chloride, 3-bromobenzenesulfonyl chloride, 2,3-dichlorobenzenesulfonyl chloride, 5-fluoro-2-methylbenzenesulfonyl chloride, 3-fluorobenzenesulfonyl chloride, 2,3,5,6-tetramethylbenzenesulfonyl chloride, 3-chloro-2-methylbenzenesulfonyl chloride, 2,5-dibromo-3,6-difluorobenzenesulfonyl chloride, 2,6-difluorobenzenesulfonyl chloride, 2-chlorobenzenesulfonyl chloride, 5-bromo-2-methoxybenzenesulfonyl chloride, 5-chloro-2-methoxybenzenesulfonyl chloride, 2,4-difluorobenzenesulfonyl chloride, 2-cyanobenzenesulfonyl chloride, 2-chloro-5-(trifluoromethyl)-benzenesulfonyl chloride, 4-bromomethylbenzenesulfonyl chloride, 2,4-dimethoxybenzenesulfonyl chloride, 4-chloro-3-nitrobenzenesulfonyl chloride, 4-(chlorosulfonyl)-benzoic acid, 3-nitrobenzenesulfonyl chloride, 4-nitrobenzenesulfonyl chloride, 2-(methylsulfonyl)-benzenesulfonyl chloride, 4-(methylsulfonyl)-benzenesulfonyl chloride, 3-(chlorosulfonyl)-benzoic acid, 2,4-dichloro-5-methylbenzenesulfonyl chloride, 4-(trifluoromethoxy)-benzenesulfonyl chloride, 2-methoxy-4-nitrobenzenesulfonyl chloride, 4-bromo-2-chlorobenzenesulfonyl chloride, 2,3-dihydro-1-benzofuran-5-sulfonyl chloride, 2,3-dihydro-1,4-benzodioxine-6-sulfonyl chloride, 1,3-benzothiazole-6-sulfonyl chloride, 2,1,3-benzothiadiazole 4 sulfonyl chloride, 2,1,3-benzothiadiazole-5-sulfonyl chloride, 2,1,3-benzoxadiazole-4-sulfonyl chloride, 3,4-dihydro-2H-1,5-benzodioxepine-7-sulfonyl chloride, 4-methyl-3,4-dihydro-2H-1,4-benzoxazine-7-sulfonyl chloride, 4-(1,3-oxazol-5-yl)benzenesulfonyl chloride, 4-(1,2,3-thiadiazol-4-yl)benzenesulfonyl chloride, 4-(1H-pyrazol-1-yl)benzenesulfonyl chloride, 4-(3-chloro-2-cyanophenoxy)-benzene-1-sulfonyl chloride, 5-chlorosulfonyl-2-hydroxybenzoic acid, 4-bromo-2,5-difluorobenzene-1-sulfonyl chloride, 4-(Acetylamino)-3-chlorobenzene-1-sulfonyl chloride, 3,5-di-(trifluoromethyl)-benzene-1-sulfonyl chloride, 2-fluorobenzenesulfonyl chloride, 4-methyl-3-nitrobenzene-1-sulfonyl chloride, 5-chloro-2,1,3-benzoxadiazole-4-sulfonyl chloride, 3-(5-methyl-1,3,4-oxadiazol-2-yl)benzenesulfonyl chloride, methyl 3-(chlorosulfonyl)-4-methoxy-benzoate, 4-bromo-2-(trifluoromethyl)-benzenesulfonyl chloride, 2,2-dimethyl-6-chromanesulfonyl chloride, 4-(morpholine-4-sulfonyl) benzenesulfonyl chloride, 4-(pyrrolidine-1-sulfonyl)-benzenesulfonyl chloride, 3-(2-methyl-4-pyrimidinyl) benzene-sulfonyl chloride, 2-cyano-5-methylbenzenesulfonyl chloride, 2,5-dimethylbenzenesulfonyl chloride, 4-chloro-3-(trifluoromethyl)-benzenesulfonyl chloride, 4-bromo-2-methylbenzene-1-sulfonyl chloride, 2-chloro-4-(trifluoromethyl)-benzene-1-sulfonyl chloride, 2-chloro-4-cyanobenzene-1-sulfonyl chloride, 2,6-dichloro-4-(trifluoro-methyl)benzene-1-sulfonyl chloride, 3,4-difluorobenzene-1-sulfonyl chloride, 2-Iodobenzene-1-sulfonyl chloride, 4-methyl-1-naphthalenesulfonyl chloride, 4-(trifluoromethyl)benzene-1-sulfonyl chloride, 2,6-dichlorobenzene-1-sulfonyl chloride, 2-(trifluoromethoxy)benzene-1-sulfonyl chloride, 4-cyanobenzene-1-sulfonyl chloride, 4-butoxybenzene-1-sulfonyl chloride, 2,3,4-trifluorobenzene-1-sulfonyl chloride, 4-bromo-2-(trifluoromethoxy)benzene-1-sulfonyl chloride, 3-cyanobenzene-1-sulfonyl chloride, 3-chloro-4-methylbenzene-1-sulfonyl chloride, 4-bromo-2-ethylbenzene-1-sulfonyl chloride, 5,5,8,8-tetramethyl-5,6,7,8-tetrahydro-2-naphthalenesulfonyl chloride, 4-(2-chloro-6-nitrophenoxy) benzene-1-sulfonyl chloride, 3,5-dichloro-4-(2-chloro-4-nitrophenoxy)benzene-1-sulfonyl chloride, 4-pentylbenzene-1-sulfonyl chloride, 4-ethylbenzene-1-sulfonyl chloride, 4-propylbenzene-1-sulfonyl chloride, 4-butylbenzene-1-sulfonyl chloride, 3-toluenesulfonyl chloride, 4-isopropylbenzene-sulfonyl chloride, 4-(2-oxo-1-pyrrolidinyl)benzene sulfonyl chloride, 4-(2-methoxyphenoxy)benzenesulfonyl chloride, 4-(2-chlorophenoxy)benzenesulfonyl chloride, 4-(2-methylphenoxy)-benzenesulfonyl chloride, 4'-chloro(1,1'-biphenyl)-4-sulfonyl chloride, 4'-Fluoro(1,1'-biphenyl)-4-sulfonyl chloride, 4'-Methoxy-(1,1'-biphenyl)-4-sulfonyl chloride, 3',4'-Dichloro-(1,1'-biphenyl)-4-sulfonyl chloride, 4-phenoxybenzenesulfonyl chloride, 4'-Methyl-(1,1'-biphenyl)-4-sulfonyl chloride, 5-bromo-2,3-dihydrobenzo[b]furan-7-sulfonyl chloride, 3,4,5-trifluorobenzenesulfonyl chloride, 3-(5-methyl-1,2,4-oxadiazol-3-yl)benzenesulfonyl chloride, 4-(2-methyl-1,3-thiazol-4-yl)benzenesulfonyl chloride, 1-acetyl-5-indolinesulfonyl chloride, 3-(2-methyl-1,3-thiazol-4-yl) benzenesulfonyl chloride and 1,3-benzodioxole-5-sulfonyl chloride.

Optionally substituted styrylsulfonyl chlorides suitable for use in the synthesis of compounds represented by the structural formula (A) of the present invention include, but are not limited to, α-bromostyrylsulfonyl chloride and analogues thereof, the synthesis of which is described in U.S. Pat. No. 3,855,218.

Phenylacetyl chlorides (structural formula V-C) suitable for use in the synthesis of the compounds of the present invention include, but are not limited to, phenylacetyl chloride, 4-methoxyphenylacetyl chloride, 2-(2-naphthyl)acetyl chloride, 2-(3,5-difluorophenyl)ethanoyl chloride, 2-(1-naphthyl)ethanoyl chloride, 4-chlorophenylacetyl chloride, 3-methoxyphenylacetyl chloride, and 4-fluorophenylacetyl chloride.

The intermediate compounds having the structural formulae (IV-A) and (IV-B) may also be reacted with an isocyanate (structural formula V-E shown above) to yield final compounds wherein X comprises a urea linkage.

Isocyanates suitable for use in the synthesis of the compounds of the present invention include, but are not limited to, 4-fluorophenyl isocyanate, phenyl isocyanate, m-tolyl isocyanate, p-tolyl isocyanate, 4-chlorophenyl isocyanate, ethyl 4-isocyanatobenzoate, 2-fluorophenyl isocyanate, 3-fluorophenyl isocyanate, α,α,α-trifluoro-o-tolyl isocyanate, tolylene-2,4-diisocyanate, tolylene 2,6-diisocyanate, 4-methoxyphenyl isocyanate, 4-bromophenyl isocyanate, 2-methoxyphenyl isocyanate, 3-methoxyphenyl isocyanate, 2,4-dichlorophenyl isocyanate, o-tolyl isocyanate, 3,4-dichlorophenyl isocyanate, 2-nitrophenyl isocyanate, 4-nitrophenyl isocyanate, 2,4-Difluorophenyl isocyanate, 2-bromophenyl isocyanate, 2,6-Difluorophenyl isocyanate, 2-(Trifluoromethoxy)phenyl isocyanate, 2-chloro-5-(trifluoromethyl)phenyl isocyanate, 4-chloro-2-(trifluoromethyl) phenyl isocyanate, 4-Chloro-3-(trifluoromethyl)phenyl isocyanate, 2,5-Difluorophenyl isocyanate, 4-(Trifluoromethoxy)phenyl isocyanate, 2-Ethoxyphenyl isocyanate, 4-Ethoxyphenyl isocyanate, 4-Isopropylphenyl isocyanate, 3-acetylphenyl isocyanate, 2,6-diisopropylphenyl isocyanate, 3-bromophenyl isocyanate, 3,5-Dichlorophenyl isocyanate, 4-Fluoro-3-nitrophenyl isocyanate, 3,5-dimethylphenyl isocyanate, 3,5-bis(trifluoromethyl)phenyl isocyanate, 3-cyanophenyl isocyanate, 4-(methylthio)-phenyl isocyanate, 2-Ethylphenyl isocyanate, 2,6-dimethylphenyl isocyanate, α,α,α-trifluoro-p-tolyl isocyanate, 2,3-dichlorophenyl isocyanate, 4-methyl-3-nitrophenyl isocyanate, 2,4-dimethoxyphenyl isocyanate, 4-(chloromethyl)-phenyl isocyanate, 4-Bromo-2-chlorophenyl isocyanate, 2-bromo-4,6-difluorophenyl isocyanate, 4-Bromo-2-fluorophenyl isocyanate, 4-(dimethylamino)phenyl isocyanate, 2-Fluoro-5-methylphenyl isocyanate, 4-fluoro-2-nitrophenyl isocyanate, 2-Fluoro-3-(trifluoromethyl)phenyl isocyanate, 2-fluoro-5-(trifluoromethyl)phenyl isocyanate, 2-fluoro-6-(trifluoromethyl)phenyl isocyanate, 4-fluoro-2-(trifluoromethyl)-phenyl isocyanate, 4-fluoro-3-(trifluoromethyl)phenyl isocyanate, 4-(heptyloxy)phenyl isocyanate, 2-iodophenyl isocyanate, 2-naphthyl isocyanate, 2-n-propylphenyl isocyanate, 4-(trifluoromethylthio)phenyl isocyanate, 2,3,4-trifluorophenyl isocyanate, 2,6-dichlorophenyl isocyanate, 3-Nitrophenyl isocyanate, 3-chlorophenyl isocyanate, 2-chlorophenyl isocyanate, 1-naphthyl isocyanate, 2,3-dimethylphenyl isocyanate, 3-chloro-4-fluorophenyl isocyanate, 2,5-dimethylphenyl isocyanate, 3,4-difluorophenyl isocyanate, 2,3-dihydro-1-benzofuran-5-yl isocyanate, 2,3-dihydro-1,4-benzodioxin-6-yl isocyanate, 6-fluoro-4H-1,3-benzodioxin-8-yl isocyanate, 2,1,3-benzothiadiazol-4-yl isocyanate, 3,4-dihydro-2H-1,5-benzodioxepin-7-yl isocyanate, 3-(cyclopentyloxy)-4-methoxyphenyl isocyanate, 2-(methylthio)phenyl isocyanate, 2-(tert-butyl)phenyl isocyanate, 4-(tert-butyl)phenyl isocyanate, 3-chloro-2-methylphenyl isocyanate, 4-butyl-2-methylphenyl isocyanate, 2-ethyl-6-methylphenyl isocyanate, 4-chloro-3-nitrophenyl isocyanate, 4-bromo-2-methylphenyl isocyanate, 3-(methylthio)phenyl isocyanate, 5,5,8,8-tetramethyl-5,6,7,8-tetrahydro-2-naphthalenyl isocyanate, 5-fluoro-2-methylphenyl isocyanate, 4-phenoxyphenyl isocyanate, 4-methoxy-2-methylphenyl isocyanate, α,α,α-trifluoro-m-tolyl isocyanate, 2,6-dibromo-4-isopropylphenyl isocyanate, 2,6-dimethoxyphenyl isocyanate, 2-(4-Isocyanato-phenyl) thiophene, 4-(3-Isocyanatophenyl)-2-methyl-1,3-thiazole, 3-(3-isocyanatophenyl)-5-methyl-1,2,4-oxadiazole, 1-benzothiophen-5-yl isocyanate, 1-(3-isocyanatophenyl)-1h-pyrrole, 1-(4-isocyanatophenyl)-1H-pyrrole, 3,5-dimethoxyphenyl isocyanate and 2,4,6-trichlorophenyl isocyanate.

Alternatively, intermediates having the structural formula (IV-A) or (IV-B) may be derivatised with a carbonylation agent such as, but not limited to, trisphosgene, carbonyl diimidazole (hereinafter abbreviated as CDI) or carbonyl ditriazole. The resulting imidazo-carbonyl or triazo-carbonyl intermediate compound may then be further reacted with a phenyl-containing amino compound, particularly an aniline derivative (represented by the structural formula (V-D) in scheme 2) wherein $R_7$, $R_8$, $R_9$, $R_{10}$, $R_{11}$ are as defined above, thereby providing further compounds of the invention. The carbonylation and further urea formation with an amine may be most particularly carried out in a one-pot procedure. Phenyl-containing amino compounds suitable for the latter reaction include arylamines (e.g. aniline, aniline derivatives and naphthylamines), arylalkylamines (e.g. benzylamines), arylalkenylamines, arylalkynylamines wherein said one or more of the carbon atoms in the alkyl, alkenyl or alkynyl moiety is optionally replaced by a heteroatom selected from the group comprising O, N and S, and wherein each of said phenyl-containing amino compounds is optionally substituted as specified above.

Suitable aniline derivatives (represented by the structural formula (V-D) in scheme 2) for the above reaction step include, but are not limited, to:

$C_{1-6}$ alkoxy-substituted and $C_{1-4}$ alkylthio-substituted anilines including, but not limited to, 2-methoxyaniline, 3-methoxyaniline, 4-methoxyaniline, 2-ethoxyaniline, 3-ethoxyaniline, 4-ethoxyaniline, 4-bromo-3-ethoxyaniline hydrochloride, 2-propoxyaniline, 3-propoxyaniline, 4-propoxyaniline, 3-isopropoxyaniline, 4-isopropoxyaniline, 2,5-diethoxyaniline, 3,4-diethoxyaniline, 4-n-butoxyaniline, 3-n-butoxyaniline, 2-n-butoxyaniline, 4-iso-butoxyaniline, 3-isobutoxyaniline, 2-isobutoxyaniline, 2-methyl-4-methoxyaniline, 2-(methylthio)aniline, 3-(methylthio)aniline, 4-(methylthio)aniline, 2-(trifluoromethoxy)aniline, 3-(trifluoromethoxy)aniline, 4-(trifluoromethoxy)aniline, 5-chloro-2-(methylthio)aniline, 2-bromo-4-methoxyaniline, 2-bromo-5-methoxyaniline, 3-bromo-4-methoxyaniline, 4-bromo-3-methoxyaniline, 5-bromo-2-methoxyaniline, 2-iodo-5-methoxyaniline, 3-iodo-4-methoxyaniline, 5-iodo-2-methoxyaniline, 2-chloro-5-methoxyaniline, 3-chloro-2-methoxyaniline, 3-chloro-4-methoxyaniline, 4-chloro-3-methoxyaniline, 5-chloro-2-methoxyaniline, 2-fluoro-4-methoxyaniline, 2-fluoro-6-methoxyaniline, 3-fluoro-2-methoxyaniline, 3-fluoro-4-methoxyaniline, 3-fluoro-5-methoxyaniline, 4-fluoro-3-methoxyaniline, 5-fluoro-2-methoxyaniline, 2-(difluoromethoxy)aniline, 3-(difluoromethoxy)aniline, 4-(difluoromethoxy) aniline and 2,4-dichloro-5-methoxyaniline;

halo-substituted anilines including, but not limited to, 2-fluoroaniline, 3-fluoroaniline, 4-fluoroaniline, 2,3-difluoroaniline, 2,4-difluoroaniline, 2,5-difluoroaniline, 2,6-difluoroaniline, 3,4-difluoroaniline, 2,3,4-trifluoroaniline, 2,3,5-trifluoroaniline, 2,3,6-trifluoroaniline, 2,4,6-trifluoroaniline, 2,4,5-trifluoroaniline, 3,4,5-trifluoroaniline, 3-chloro-2-fluoroaniline, 4-chloro-2-fluoroaniline, 5-chloro-2-fluoroaniline, 2-chloro-3-fluoroaniline, 2-chloro-4-fluoroaniline, 2-chloro-6-fluoroaniline, 3-chloro-5-fluoroaniline, 2-bromo-3-fluoroaniline, 2-bromo-4-fluoroaniline, 2-bromo-5-fluoroaniline, 2-bromo-6-fluoroaniline, 4-bromo-2-fluoroaniline, 4-bromo-3-fluoroaniline, and 5-bromo-2-fluoroaniline;

$C_{1-10}$ alkyl-substituted anilines including, but not limited to, 4-methylaniline, 3-methylaniline, 2-methylaniline, 2,3-dimethylaniline, 2,4-dimethylaniline, 2,5-dimethylaniline, 2,6-dimethylaniline, 3,4-dimethylaniline, 3,5-dimethylaniline, 2,4,6-trimethylaniline, 3,4,5-trimethylaniline, 2,4,5-trimethylaniline, 2,4,6-triethylaniline, 4-ethylaniline, 3-ethylaniline, 2-ethylaniline, 2-n-propylaniline, 4-n-propylaniline, 2-isopropylaniline, 3-isopropylaniline, 4-isopropylaniline, 2,6-diisopropylaniline, 2-n-butylaniline, 4-n-butylaniline, 2-sec-butylaniline, 4-sec-butylaniline, 2-tert-butylaniline, 3-tert-butylaniline, 4-tert-butylaniline, 3,5-di-tert-butylaniline, 4-n-pentylaniline, 4-n-hexylaniline, 4-n-heptylaniline, 4-n-octylaniline, 4-nonylaniline, 4-n-decylaniline and 4-n-dodecylaniline;

$C_{3-8}$ cycloalkyl-substituted anilines including, but not limited to, 4-cyclohexylaniline;

$C_{2-4}$ alkenyl-substituted anilines including, but not limited to, 4-vinylaniline and 2-isopropenylaniline;

2-nitroaniline, 3-nitroaniline, 4-nitroaniline, 2-trifluoromethylaniline, 3-trifluoromethylaniline, 4-trifluoromethylaniline, and the like.

Suitable benzylamine derivatives (not shown in scheme 2) for the above reaction step include, but are not limited to: 2-chlorobenzylamine, 4-chlorobenzylamine, 2,4-dichlorobenzylamine, 3,4-dichlorobenzylamine, 4-methoxybenzylamine, 4-methylbenzylamine, piperonylamine, 3,4-dimethoxybenzylamine, 3-methylbenzylamine, 3-fluorobenzylamine, 2-methylbenzylamine, 2-methoxybenzylamine, 3-methoxybenzylamine, 2-fluorobenzylamine, 4-fluorobenzylamine, 3,4-dihydroxybenzylamine, 3-chlorobenzylamine, 4-(trifluoromethoxy)benzylamine, 2,6-difluorobenzylamine, 3,5-bis(trifluoromethyl)benzylamine, 2,4-difluorobenzylamine, 2,5-difluoro benzylamine, 3,4-difluorobenzylamine, 2-(trifluoromethyl)benzylamine, 3-(trifluoromethyl)benzylamine, 2-bromobenzylamine, 4-bromobenzylamine, 2-chloro-6-fluorobenzylamine, 2,5-dimethylbenzylamine, 3,4,5-trimethoxybenzylamine, 2,4,6-trimethylbenzylamine, 2,4-dimethylbenzylamine, 2,3-dichlorobenzylamine, 1-naphthalenemethylamine, 3-Iodobenzylamine, 2-hydroxybenzylamine, 3-bromo benzylamine, 2,6-dichlorobenzylamine, 3,4-dihydro-2H-1,5-benzodioxepin-6-ylmethylamine, 2,3-dihydro-1,4-benzodioxin-6-ylmethylamine, 2,3-dihydro-1,4-benzodioxin-5-ylmethylamine, 1-benzofuran-5-ylmethylamine, 4-(2-thienyl)benzylamine, 3,4-dihydro-2H-1,5-benzodioxepin-7-ylmethylamine, 4-morpholino benzylamine, 4-(1H-pyrazol-1-yl)benzylamine, 4-(4-methylpiperazino)benzylamine, 2-piperidinobenzylamine, 3-(1H-Pyrrol-1-yl)benzylamine, 2-Morpholinobenzylamine, 4-(1H-pyrrol-1-yl)benzylamine, 2-chloro-6-phenoxy benzylamine, 2-(methylthio)benzylamine, 2-(trifluoromethoxy)benzylamine, 2,3-dimethylbenzylamine, 4-(trifluoromethyl)benzylamine, 3,5-dichlorobenzylamine, 2-(Aminomethyl)-3-fluoroaniline, 3-chloro-4-fluorobenzylamine, 2,5-dimethoxybenzylamine, 2,5-dichloro benzylamine, 2,6-dimethoxybenzylamine, 2,4-dichloro-6-methylbenzylamine, 3-chloro-4-methylbenzylamine, 4-fluoro-3-(trifluoromethyl)benzylamine, 4-fluoro-2-(trifluoromethyl)benzylamine, 3-piperidin-1-ylmethyl benzylamine, 1-benzothiophen-5-ylmethylamine, 4-(Morpholinomethyl)benzylamine, (3-((4-methylpiperidino)methyl)phenyl)methanamine, (4-Piperidinophenyl)methylamine, (3-piperidinophenyl)methylamine, 1-[2-(4-methylpiperazin-1-yl)phenyl]methanamine, (1,4-dimethyl-1,2,3,4-tetrahydroquinoxalin-6-yl)methylamine, 3-(Trifluoromethoxy)benzylamine, 4-bromo-2-fluorobenzylamine, 2-(1 h-pyrazol-1-yl)benzylamine, tert-butyl 4-(2-(aminomethyl)phenyl)piperazine-1-carboxylate, (3-Morpholinophenyl)methylamine, tert-Butyl N-[4-(aminomethyl)phenyl]carbamate, [2-(1H-Pyrrol-1-yl)phenyl]methylamine, 1-[3-(4-Methylpiperazin-1-yl)phenyl]methanamine, [4-(1-pyrrolidinyl)phenyl]methanamine, (3-pyrrolidin-1-ylphenyl)methylamine, [4-(2-morpholinoethoxy)phenyl]methylamine, [2-(2-morpholinoethoxy)phenyl]methylamine, [3-(2-morpholinoethoxy)phenyl]methylamine, [3-(morpholinomethyl)phenyl]methylamine, [4-(piperidinomethyl)phenyl]methylamine, {4-[(4-Methylpiperazin-1-yl)methyl]phenyl}methylamine, [4-(2-furyl)phenyl]methylamine, tert-Butyl 4-[4-(aminomethyl)phenyl]tetrahydro-1(2H)-pyrazinecarboxylate, (2,2-dimethyl-2,3-dihydro-1-benzofuran-7-yl)methylamine, [3-(1 h-1,2,4-triazol-1-yl)phenyl]methylamine, (4-thien-3-ylphenyl)methylamine, 1-[2-(morpholin-4-ylmethyl)phenyl]methanamine, {2-[(4-methylpiperazin-1-yl)methyl]phenyl}methylamine, [3-(2-furyl)phenyl]methylamine, (3-thien-2-ylphenyl)methylamine, [2-(2-furyl)phenyl]methylamine, 4-(Pyrrolidin-1-ylmethyl)benzylamine, 4-[(4-methylperhydro-1,4-diazepin-1-yl)methyl]benzylamine, 4-[2-(dimethylamino) ethoxy]benzylamine, (2-Pyrrolidin-1-ylphenyl)methylamine, [3-(1-Pyrrolidinylmethyl)phenyl]methanamine, (3-thien-3-ylphenyl)methylamine, 2-[2-(dimethylamino)ethoxy]benzylamine, 2-(phenoxymethyl) benzylamine, (1-methyl-1h-indol-4-yl)methylamine, 4-(4-methylperhydro-1,4-diazepin-1-yl)benzylamine, (1-methyl-1H-indol-6-yl)methylamine, [3-(1,3-thiazol-2-yl)phenyl]methylamine, 3-(1H-pyrazol-1-ylmethyl)benzylamine, (1-methyl-1H-indol-5-yl)methylamine, 3-(phenoxymethyl)benzylamine, 2-morpholino-5-(trifluoromethyl)benzylamine, [4-(1,3-Thiazol-2-yl)phenyl]methylamine, 3-(1-Methyl-1H-pyrazol-3-yl)benzylamine, 2-(4-Methylperhydro-1,4-diazepin-1-yl)benzylamine, 4-[3-(dimethylamino)propoxy]benzylamine, 3-(2-Methyl-1H-imidazol-1-yl)benzylamine, 4-(2-Methyl-1H-imidazol-1-yl)benzylamine, 2-(2-methyl-1H-imidazol-1-yl)benzylamine, [4-(tetrahydropyran-4-yloxy)phenyl]methylamine, 3-[3-(dimethylamino)propoxy] benzylamine, 2-[3-(dimethylamino) propoxy]benzylamine, 3-pyrimidin-2-ylbenzylamine, 4-(1-methyl-1H-pyrazol-3-yl)benzylamine, 3-(1-methyl-1h-pyrazol-5-yl)benzylamine and 1-(1-benzothien-7-yl)methanamine.

Suitable phenylalkenylamines (not shown in scheme 2) for the above reaction step include, but are not limited to, cinnamylamine.

When step (c) comprises two sub-steps as described herein-above, the order of performing the different reactions is usually not critical for the present invention and therefore can be changed. For example, the diamine including the optionally $R_6$-substituted heterocyclic ring (A') with at least two nitrogen atoms in the said heterocyclic ring and with a total of 5 to 7 atoms may first be reacted with either one of the reagents having the structural formula (V-A), (V-B), or (V-C), or with a carbonylation agent (e.g. CDI) followed by reaction with a phenyl-containing amino compound, e.g. an aniline derivative represented by the structural formula (V-D) or a benzylamine derivative. The resulting intermediate compound may then be used for reaction with the 3-substituted-5-chloro-thiadiazole having the structural formula (III) to yield a final compound according to the present invention.

Clearly, when scheme 2 is used for making 1,2,4-thiadiazole compounds of this invention being represented by the structural formula (D), it is required that the reactant used for introducing the group

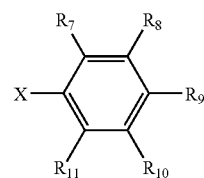

be such that at least one of $R_7$, $R_8$, $R_9$, $R_{10}$ and $R_{11}$ is R' as defined with respect to the structural formula (D), i.e. is selected from the group consisting of cyano, trifluoromethoxy, NO, —C(O)—NR$_{14}$R$_{15}$, —NH—C(O)—R$_{14}$, —O—C(O)—R$_{14}$, —C(O)—O—R$_{14}$, —S(O)—R$_{14}$, —S(O)$_2$—R$_{14}$, —S(O)$_2$—NR$_{14}$R$_{15}$, $C_{1-6}$ alkylthio, $C_{3-10}$ cycloalkyloxy, aryl (in particular phenyl), benzyloxy, aryloxy and heterocyclyl (in particular heteroaryl), R$_{14}$ and R$_{15}$ being as defined with respect to the structural formula (D); wherein said heterocyclyl is optionally substituted with one or more substituents independently selected from the group consisting of oxo, halogen, $C_{1-6}$ alkyl and halo $C_{1-6}$ alkyl; and wherein said aryloxy is optionally substituted with $C_{1-6}$ alkoxy.

Scheme 3

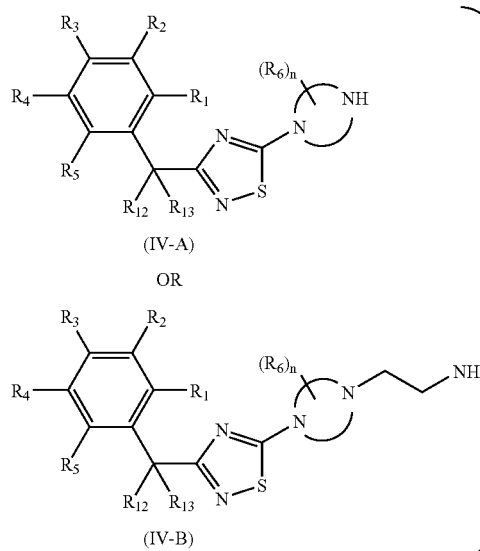

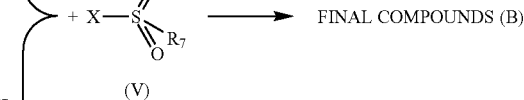

Scheme 3 schematically illustrates methods to prepare compounds according to structural formula (B) wherein step (c) comprises two subsequent reaction sub-steps. In a first sub-step, a thiadiazole compound having the structural formula (III) may first be derivatised as explained with respect to scheme 2. In the second reaction sub-step (shown in scheme 3), intermediate compounds having the structural formulae (IV-A) or (IV-B) may be reacted with a sulphonating reagent represented by the structural formula X—SO$_2$—R$_7$ and being susceptible to nucleophilic attack by a non-tertiary amino group, e.g. the NH group present in compounds according to structural formula (IV-A), or the terminal amino group present in compounds according to structural formula (IV-B). In the structural formula X—SO$_2$—R$_7$, X represents a leaving group for nucleophilic substitution at the sulphur atom and R$_7$ is as defined hereinabove. Such leaving groups X are well known to the skilled person and include, but are not limited to, halogen, more particularly chloro. Suitable reagents include, but are not limited to, sulfonic acid halides such as sulfonyl chlorides, or otherwise activated sulfonic acids such as anhydrides. Exemplary sulfonyl halides suitable for use in the synthesis of compounds represented by the structural formula (B) of the present invention include, but are not limited to, 1-hexadecane sulfonyl chloride, 3-chloropropanesulfonyl chloride, D(+)-10-camphorsulfonyl chloride, L(−)-10-camphorsulfonyl chloride, ethanesulfonyl chloride, 2,2,2-trifluoroethanesulfonyl chloride, 1-butanesulfonyl chloride, 2-chloroethanesulfonyl chloride, 1-decanesulfonyl chloride, ethylsulfonyl chloride, 3,3,3-trifluoropropane-1-sulfonyl chloride, cyclopropanesulfonyl chloride, 2-propanesulfonyl chloride, nonafluoro-1-butanesulfonyl chloride, nonafluoro-1-butanesulfonyl fluoride, isobutanesulfonyl chloride, cyclopentanesulfonyl chloride, cyclohexanesulfonyl chloride, heptadecafluoro-1-octanesulfonyl chloride, 1-octanesulfonyl chloride, 1-octanesulfonyl fluoride, trichloromethanesulfonyl chloride, 1-hexanesulfonyl chloride, cyclohexylmethylsulfonyl chloride and 5,7,7-trimethyl-2-(1,3,3-trimethylbutyl)-1-octanesulfonyl chloride. Optionally substituted styrylsulfonyl chlorides suitable for use in the synthesis of compounds represented by the structural formula (B) of the present invention include, but are not limited to, α-bromostyrylsulfonyl chloride and analogues thereof, the synthesis of which is described in U.S. Pat. No. 3,855,218.

Scheme 4

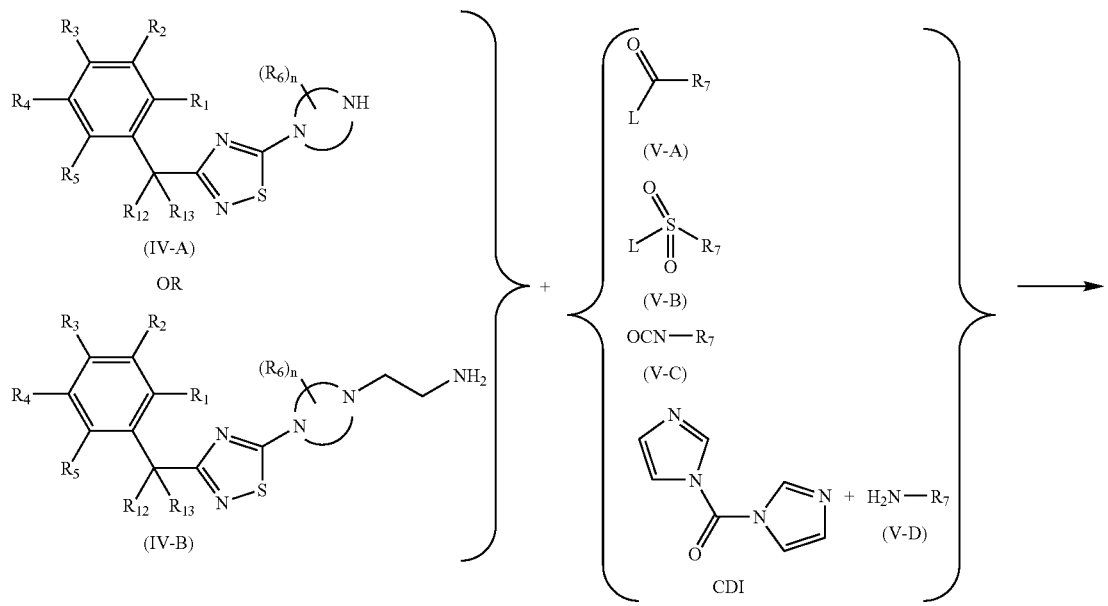

Scheme 4 schematically illustrates methods to prepare compounds according to structural formula (C) wherein step (c) comprises two subsequent reaction sub-steps. In a first sub-step, a thiadiazole compound having the structural formula (III) may first be derivatised by reaction with a diamino compound including the optionally $R_6$-substituted heterocyclic ring with at least two nitrogen atoms in the said heterocyclic ring (A') and with a total of 5 to 7 atoms, e.g. a substituted heterocyclic compound represented by the structural formula (A")

(A")

wherein n and $R_6$ are as defined above, and R' is hydrogen or an amino protecting group; or a substituted heterocyclic compound represented by the structural formula (A''')

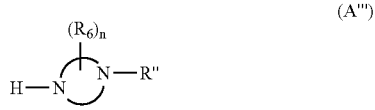

(A''')

wherein n and $R_6$ are as defined in claim 1, and R" is aminoalkyl or (protected amino)alkyl.

Examples of such heterocyclic diamino compounds for use in the first sub-step of step (c) for the synthesis of appropriate intermediates comprise, but are not limited to, piperazine, 2-methylpiperazine (either (R)-(−)-2-methylpiperazine or (S)-(+)-2-methylpiperazine), trans-2,5-dimethylpiperazine, homopiperazine, 1-(2-aminoethyl)piperazine, 1,3-diazepane-2-thione, 1,3-diazepane-2,4,6-trione, hydantoin, 2-imidazolidinethione, imidazolidinetrione and glycine anhydride. In this way, intermediate compounds as illustrated by structural formulae (IV-A) and (IV-B) in scheme 4 may be obtained.

In a second reaction sub-step comprised within step (c) (scheme 4), these intermediate compounds represented by the non-limiting structural formulae (IV-A) and (IV-B) may be reacted with a heterocyclic reagent susceptible to nucleophilic attack by a non-tertiary amino group, e.g. the NH group present in intermediate compounds according to structural formula (IV-A), or the terminal amino group present in intermediate compounds according to structural formula (IV-B). Suitable such heterocyclic reagents include, but are not limited to those represented in scheme 4 by structural formulae V-A, V-B, V-C and V-D (the latter in combination with carbonyl diimidazole (CDI) or carbonyl ditriazole), wherein for V-A and V-B, "L" represents a leaving group for nucleophilic substitution at the carbon, respectively the sulfur atom, to which L is attached, and wherein alternatively to the isocyanate compounds represented by structural formula V-C also heterocyclic isothiocyanate reagents represented by the structural formula SCN—$R_7$ can be used. Such leaving groups L are well known to the skilled person and include, but are not limited to, halogen, more particularly chloro.

FINAL COMPOUNDS (C)

Reaction with heterocyclic carbonyl chlorides (particular example of V-A) yields final compounds (C) wherein X comprises a carbamide, carbamate or urea linkage. Exemplary heterocyclic carbonyl chlorides suitable for use in the synthesis of the compounds of the present invention include, but are not limited to, the following: 4-isocyanato-3-furancarbonyl chloride, 5-[(2-chlorophenoxy)methyl]-2-furancarbonyl chloride, 5-[(4-methyl-2-nitrophenoxy)methyl]-2-furancarbonyl chloride, 5-[(2-bromophenoxy)methyl]-2-furancarbonyl chloride, 2-bromo-3-furancarbonyl chloride, 5-[(3,5-dimethyl-4-isoxazolyl)methyl]-2-furancarbonyl chloride, 5-(1-piperidinylmethyl)-2-furancarbonyl chloride, 5-(1-pyrrolidinylmethyl)-2-furancarbonyl chloride, 5-(3-bromophenyl)-2-furancarbonyl chloride, 5-(2-naphthyl)-2-furancarbonyl chloride, 2-[5-(chlorocarbonyl)-2-furanyl]-benzoic acid methyl ester, 5-(3-methoxy-5-nitrophenyl)-2-furancarbonyl chloride, 5-(4-ethoxy-3-nitrophenyl)-2-furancarbonyl chloride, 3-[5-(chlorocarbonyl)-2-furanyl]-benzoic acid methyl ester, 3-[5-(chlorocarbonyl)-2-furanyl]-benzoic acid ethyl ester, 3-[5-(chlorocarbonyl)-2-furanyl]-benzoic acid butyl ester, 3-[5-(chlorocarbonyl)-2-furanyl]-benzoic acid 1-methylethyl ester, 2-methyl-5-(2-thienyl)-3-furancarbonyl chloride, 5-(2,4-dibromophenyl)-2-furancarbonyl chloride, 5-(4-methoxy-2-nitrophenyl)-2-furancarbonyl chloride, 5-(3-pyridinyloxy)-2-furancarbonyl chloride, 5-phenoxy-2-furancarbonyl chloride, 5-(3-chloro-4-fluorophenyl)-2-furancarbonyl chloride, 5-[2-chloro-5-(trifluoromethyl)phenyl]-2-furancarbonyl chloride, 5-(methoxymethyl)-2-furancarbonyl chloride, 3,4-dimethoxy-2-furancarbonyl chloride, 4-[5-(chlorocarbonyl)-2-furanyl]-benzoic acid propyl ester, 5-(2-chloro-4-iodophenyl)-2-furancarbonyl chloride, 5-(2-pyridinyl)-2-furancarbonyl chloride, 5-(2-chloro-4-nitrophenyl)-2-furancarbonyl chloride, 4-[5-(chlorocarbonyl)-2-furanyl]-benzoic acid ethyl ester, 4-(chloromethyl)-2,5-dimethyl-3-furancarbonyl chloride, 5-(chloromethyl)-3-furancarbonyl chloride, 2-(chloromethyl)-3-furancarbonyl chloride, 5-(4-bromophenyl)-2-(trifluoromethyl)-3-furancarbonyl chloride, 4,5-dimethyl-2-furancarbonyl chloride, 5-methyl-2-phenyl-3-furancarbonyl chloride, 5-(chlorocarbonyl)-2-furancarboxylic acid ethyl ester, 5-(3,5-dichlorophenoxy)-2-furancarbonyl chloride, 5-methyl-2-(trifluoromethyl)-3-furancarbonyl chloride, 5-(4-chlorophenyl)-2-methyl-3-furancarbonyl chloride, 5-(4-chlorophenyl)-2-(trifluoromethyl)-3-furancarbonyl chloride, 2-methyl-5-phenyl-3-furancarbonyl chloride, 5-bromo-3-furancarbonyl chloride, 5-chloro-2-methyl-3-furancarbonyl chloride, (E)-3-[5-(chlorocarbonyl)-2-furanyl]-2-propenoic acid methyl ester, 5-acetyl-2-furancarbonyl chloride, 5-[(ethylthio)methyl]-2-furoyl chloride, 5-[(methylthio)methyl]-2-furoyl chloride, 3,5-dichloro-2-furoyl chloride, 5-(chloromethyl)-2-furancarbonyl chloride, 5-(1,1-dimethylethyl)-2-methyl-3-furancarbonyl chloride, 5-butyl-2-furoyl chloride, 5-(1-ethoxyethyl)-2-furoyl chloride, 5-(3-chlorophenyl)-2-furancarbonyl chloride, 5-[2-(trifluoromethyl)phenyl]-2-furancarbonyl chloride, 5-propyl-2-furancarbonyl chloride, 4-chloro-2,5-dimethyl-3-furancarbonyl chloride, 5-(hydroxymethyl)-2-methyl-3-furancarbonyl chloride, 5-(chloromethyl)-2-methyl-3-furancarbonyl chloride, 3-chloro-2-furancarbonyl chloride, 5-(trifluoromethyl)-2-furancarbonyl chloride, 4-bromo-1-methyl-1H-pyrazole-3-carbonyl chloride, 1-ethyl-1H-pyrazole-4-carbonyl chloride, 5-(2-furanyl)-1-methyl-1H-pyrazole-3-carbonyl chloride, 1-methyl-5-(2-thienyl)-1H-pyrazole-3-carbonyl chloride, 1-methyl-3-(2-thienyl)-1H-pyrazole-5-carbonyl chloride, 1-methyl-5-phenyl-1H-pyrazole-3-carbonyl chloride, 1,5-dimethyl-1H-pyrazole-4-carbonyl chloride, 1-methyl-3-propyl-1H-pyrazole-5-carbonyl chloride, 4-chloro-1H-pyrazole-3-carbonyl chloride, 1-methyl-5-propyl-1H-pyrazole-4-carbonyl chloride, 1-(4-fluorophenyl)-5-(trifluoromethyl)-1H-pyrazole-4-carbonyl chloride, 1-methyl-3-nitro-1H-pyrazole-5-carbonyl chloride, 4-nitro-1H-pyrazole-3-carbonyl chloride, 3-methoxy-1-methyl-1H-pyrazole-4-carbonyl chloride, 1,3,4-trimethyl-1H-pyrazole-5-carbonyl chloride, 1-(1,1-dimethylethyl)-5-methyl-1H-pyrazole-3-carbonyl chloride, 3-chloro-1-cyclopropyl-1H-pyrazole-4-carbonyl chloride, 3-(chlorocarbonyl)-1-methyl-1H-pyrazole-5-carboxylic acid methyl ester, 5-fluoro-1,3-dimethyl-1H-pyrazole-4-carbonyl chloride, 4-chloro-1,5-dimethyl-1H-pyrazole-3-carbonyl chloride, 1-(1,1-dimethylethyl)-3-methyl-1H-pyrazole-5-carbonyl chloride, 4-bromo-1-ethyl-3-methyl-1H-pyrazole-5-carbonyl chloride, 1-(4-nitrophenyl)-5-(trifluoromethyl)-1H-pyrazole-4-carbonyl chloride, 1-phenyl-5-propyl-1H-pyrazole-4-carbonyl chloride, 1-phenyl-5-(trifluoromethyl)-1H-Pyrazole-4-carbonyl chloride, 3-chloro-1-methyl-1H-Pyrazole-5-carbonyl chloride, 4-chloro-3-methoxy-1-methyl-1H-pyrazole-5-carbonyl chloride, 3-(1,1-dimethylethyl)-1-(phenylmethyl)-1H-pyrazole-5-carbonyl chloride, 1-(cyclopropylmethyl)-3-methyl-1H-pyrazole-5-carbonyl chloride, 1-cyclopentyl-3-methyl-1H-pyrazole-5-carbonyl chloride, 3-cyclobutyl-1-methyl-1H-pyrazole-4-carbonyl chloride, 3-cyclopropyl-1-methyl-1H-pyrazole-5-carbonyl chloride, 1-(phenylmethyl)-1H-pyrazole-3,5-dicarbonyl dichloride, 5-(trifluoromethyl)-1H-pyrazole-3-carbonyl chloride, 1-methyl-3-(trifluoromethyl)-1H-pyrazole-5-carbonyl chloride, 5-chloro-1-methyl-3-(trifluoromethyl)-1H-pyrazole-4-carbonyl chloride, 1-ethyl-3-methyl-1H-pyrazole-5-carbonyl chloride, 3-methyl-1-[(methylamino)carbonyl]-1H-pyrazole-4-carbonyl chloride, 3-methoxy-1-methyl-1H-pyrazole-5-carbonyl chloride, 1-methyl-3-(trifluoromethyl)-1H-Pyrazole-4-carbonyl chloride, 1,3-diethyl-1H-pyrazole-5-carbonyl chloride, 1-methyl-5-nitro-1H-Pyrazole-4-carbonyl chloride, 3-methyl-1-(2-propenyl)-1H-pyrazole-4-carbonyl chloride, 1H-pyrazole-4-carbonyl chloride, pyrazolo[1,5-a]pyrimidine-3-carbonyl chloride, 3-bromo-5-phenyl-7-(trifluoromethyl)-pyrazolo[1,5-a]pyrimidine-2-carbonyl chloride, 6-chloro-Pyrazolo[1,5-a]pyrimidine-2-carbonyl chloride, 5-methyl-7-(pentafluoroethyl)-pyrazolo[1,5-a]pyrimidine-3-carbonyl chloride, 5-cyclopropyl-7-(trifluoromethyl)-pyrazolo[1,5-a]pyrimidine-2-carbonyl chloride, 4-cyano-2-thiophenecarbonyl chloride, 5-(2-furanyl)-2-thiophenecarbonyl chloride, 5-(1,1-dimethylethyl)-2-thiophenecarbonyl chloride, 3-chloro-4-methyl-2-thiophenecarbonyl chloride, 5-(2-methyl-4-thiazolyl)-2-thiophenecarbonyl chloride, 4-phenyl-2-thiophenecarbonyl chloride, 4-(4-bromophenyl)-2-thiophenecarbonyl chloride, 5-(trifluoromethyl)-2-thiophenecarbonyl chloride, 3,5-dimethyl-2-thiophenecarbonyl chloride, 3-cyano-2-thiophenecarbonyl chloride, 2-chloro-3-thiophenecarbonyl chloride, 4-bromo-3-methyl-2-thiophenecarbonyl chloride, 3-chloro-5-methyl-2-thiophenecarbonyl chloride, 4-methoxy-3-thiophenecarbonyl chloride, 4-phenyl-5-(trifluoromethyl)-2-thiophenecarbonyl chloride, 5-fluoro-2-thiophenecarbonyl chloride, 3-(difluoromethoxy)-2-thiophenecarbonyl chloride, 2-bromo-3-thiophenecarbonyl chloride, 3-chloro-4-[(1-methylethyl)sulfonyl]-2-thiophenecarbonyl chloride, 3-chloro-4-(methylsulfonyl)-2-thiophenecarbonyl chloride, 4-[(4-chlorophenyl)sulfonyl]-3-methyl-2-thiophenecarbonyl chloride, 5-chloro-4-methoxy-3-thiophenecarbonyl chloride, 5-bromo-4-methoxy-3-thiophenecarbonyl chloride, 3-ethoxy-2-thiophenecarbonyl chloride, 3-methoxy-5-methyl-2-thiophenecarbonyl chloride, [2,2'-bisthiophene]-5-carbonyl chloride, 5-(methoxymethyl)-2-thiophenecarbonyl chloride, 4-(methoxymethyl)-2-thiophenecarbonyl chloride, 5-ethoxy-2-thiophenecarbonyl chloride, 5-(methylthio)-2-thiophenecarbonyl chloride, 3-methoxy-4,5-dimethyl-2-thiophenecarbonyl chloride, 5-(chlorocarbonyl)-2-thiophenecarboxylic acid methyl ester, 4-methoxy-2-thiophenecarbonyl chloride, 5-(2-pyridinyl)-2-thiophenecarbonyl chloride, 4-(chlorocarbonyl)-3-thiophenecarboxylic acid methyl ester, 5-(ethoxymethyl)-3-thiophenecarbonyl chloride, 4-methyl-5-nitro-3-thiophenecarbonyl chloride, 5-ethyl-3-thiophenecarbonyl chloride, 5-nitro-3-thiophenecarbonyl chloride, 5-chloro-3-methyl-2-thiophenecarbonyl chloride, 5-chloro-4-methyl-2-thiophenecarbonyl chloride, 5-(chloroformyl)-2-thiophenecarboxylic acid, 3-chloro-2-thiophenecarbonyl chloride, 2-chloro-4-methyl-3-thiophenecarbonyl chloride, 4-(methylthio)-2-thiophenecarbonyl chloride, 3-fluoro-2-thiophenecarbonyl chloride, 2-methoxy-3-thiophenecarbonyl chloride, 4-bromo-2-thiophenecarbonyl chloride, 2-methyl-4-Thiazolecarbonyl chloride, 3-(4-methoxyphenyl)-5-Isoxazolecarbonyl chloride, 2-(3-chlorophenyl)-4-thiazolecarbonyl chloride, 2-[4-(trifluoromethyl)phenyl]-4-thiazolecarbonyl chloride, 2,4-diphenyl-5-thiazolecarbonyl chloride, 5-(2-methylpropyl)-3-isoxazolecarbonyl chloride, 5-(difluoromethyl)-2-methyl-4-thiazolecarbonyl chloride, 4-methyl-2-[4-(trifluoromethyl)phenyl]-5-thiazolecarbonyl chloride, 3-(4-fluorophenyl)-5-methyl-4-isoxazolecarbonyl chloride, 3-methyl-5-(4-methyl-1,2,3-thiadiazol-5-yl)-4-isoxazolecarbonyl chloride, 5-(2-methyl-4-thiazolyl)-3-isoxazolecarbonyl chloride, 3',5-dimethyl-[3,5'-bisisoxazole]-4'-carbonyl chloride, 2-(2,3-dihydro-5-benzofuranyl)-4-thiazolecarbonyl chloride, 2-(2-thienyl)-4-thiazolecarbonyl chloride, 2-[(2,6-dichlorophenyl)methyl]-4-thiazolecarbonyl chloride, 4-methyl-2-pyrazinyl-5-thiazolecarbonyl chloride, 5-amino-3-methyl-4-isoxazolecarbonyl chloride, 4-(difluoromethyl)-2-methyl-5-thiazolecarbonyl chloride, 4-(chloromethyl)-2-thiazolecarbonyl chloride, 5-cyano-3-(1-methylethyl)-4-Isoxazolecarbonyl chloride, 2-(dimethylamino)-4-methyl-5-thiazolecarbonyl chloride, 2-chloro-5-thiazolecarbonyl chloride, 5-(chloromethyl)-4-isoxazolecarbonyl chloride, 5-phenyl-4-isoxazolecarbonyl chloride, 5-(1,1-dimethylethyl)-4-isoxazolecarbonyl chloride, 4-cyclopropyl-2-methyl-5-thiazolecarbonyl chloride, 5-(dichloromethyl)-3-isoxazolecarbonyl chloride, 4-(chloromethyl)-2-methyl-5-thiazolecarbonyl chloride, 3-phenyl-5-isoxazolecarbonyl chloride, 5-cyclopropyl-4-isoxazolecarbonyl chloride, 5-methyl-4-thiazolecarbonyl chloride, 2-methyl-4-(trifluoromethyl)-5-thiazolecarbonyl chloride, 3-chloro-5-isoxazolecarbonyl chloride, 5-ethyl-4-isoxazolecarbonyl chloride, 3-ethyl-4-isoxazolecarbonyl chloride, 3-methyl-5-phenyl-4-isoxazolecarbonyl chloride, 5-isobutyl-3-methyl-4-isoxazole-carbonyl chloride, 5-butyl-3-methyl-4-isoxazolecarbonyl chloride, 5-(2-furyl)-3-methyl-4-isoxazolecarbonyl chloride, 5-(2-thienyl)-3-isoxazolecarbonyl chloride, 5-(chloromethyl)-3-isoxazolecarbonyl chloride, 5-(trifluoromethyl)-4-isoxazolecarbonyl chloride, 3-(2-chloro-6-fluorophenyl)-5-methyl-4-isoxazolecarbonyl chloride, 5-isoxazole-carbonyl chloride, 5-methyl-2-thiazolecarbonyl chloride, 2-methyl-5-thiazolecarbonyl chloride, 2-nitro-5-thiazolecarbonyl chloride, 3-methoxy-5-isoxazolecarbonyl chloride, 4-methyl-2-phenyl-5-thiazolecarbonyl chloride, 5-cyclopropyl-3-isoxazolecarbonyl chloride, 5-ethyl-3-isoxazolecarbonyl chloride, 2-cyclopropyl-4-(trifluoromethyl)-5-pyrimidinecarbonyl chloride, 1-acetyl-3-piperidinecarbonyl chloride, 1-(aminoiminomethyl)-3-piperidinecarbonyl chloride, 2-amino-4-methoxy-5-pyrimidinecarbonyl chloride, 1-(phenylmethyl)-3-piperidinecarbonyl chloride, (S)-2-piperidinecarbonyl chloride, 2-(2-propenyl)-1-piperidinecarbonyl chloride, (2S)-1-(phenylmethyl)-2-pyrrolidinecarbonyl chloride, 1,2-dihydro-4-methyl-2-oxo-5-pyrimidinecarbonyl chloride, 4,6-dimethoxy-2-pyrimidinecarbonyl chloride, 4-(acetyloxy)-1-piperidinecarbonyl chloride, 1-(1-methylethyl)-4-piperidinecarbonyl chloride, (2S)-1-(chlorocarbonyl)-2-piperidine-carboxylic acid methyl ester, 2-(hydroxymethyl)-1-piperidinecarbonyl chloride, 3-(hydroxymethyl)-1-piperidinecarbonyl chloride, 1-(methylsulfonyl)-2-pyrrolidinecarbonyl chloride, 2-chloro-6-methyl-4-pyrimidinecarbonyl chloride, 2-methyl-4-(trifluoromethyl)-5-pyrimidinecarbonyl chloride, 2-chloro-4-ethyl-5-pyrimidinecarbonyl chloride, 1-[4-(trifluoromethyl)-2-pyrimidinyl]-4-piperidinecarbonyl chloride, 6-chloro-4-pyrimidinecarbonyl chloride, 4-(chlorocarbonyl)-2-methyl-5-pyrimidinecarboxylic acid methyl ester, 2-phenyl-1-pyrrolidinecarbonyl chloride, 2-pyrimidinecarbonyl chloride, 3-(chlorocarbonyl)-1-piperidinecarboxylic acid phenylmethyl ester, 1-(4-bromophenyl)-5-oxo-3-pyrrolidinecarbonyl chloride, 4-oxo-1-piperidinecarbonyl chloride, (2S)-2-(methoxymethyl)-1-pyrrolidinecarbonyl chloride, 4-(dimethylamino)-1-piperidinecarbonyl chloride, 4-(chlorocarbonyl)-1-piperidinecarboxylic acid methyl ester, 1-methyl-3-Piperidinecarbonyl chloride, 4-piperidinecarbonyl chloride, 2-chloro-4-methyl-5-Pyrimidinecarbonyl chloride, 4-pyrimidinecarbonyl chloride, (S)-2-(chlorocarbonyl)-5-oxo-1-pyrrolidinecarboxylic acid methyl ester, (R)-2-methyl-1-piperidinecarbonyl chloride, (2R,5R)-2,5-dimethyl-1-pyrrolidinecarbonyl chloride, 2-chloro-4-(trifluoromethyl)-5-pyrimidinecarbonyl chloride, 2-chloro-4-pyrimidinecarbonyl chloride, hydrochloride [1,4'-bispiperidine]-1'-carbonyl chloride, (S)-1-(aminocarbonyl)-2-pyrrolidinecarbonyl chloride, 2-piperidinecarbonyl chloride, 4-acetyl-1-piperidinecarbonyl chloride, 3-(chlorocarbonyl)-1-pyrrolidinecarboxylic acid ethyl ester, 2-(chlorocarbonyl)-1-pyrrolidinecarboxylic acid ethyl ester, (S)-1-acetyl-5-oxo-2-pyrrolidinecarbonyl chloride, 2-ethyl-1-pyrrolidinecarbonyl chloride, 3-chloro-5-(1-methylethyl)-benzo[b]thiophene-2-carbonyl chloride, 3-chloro-6-ethyl-benzo[b]-thiophene-2-carbonyl chloride, 5-(1,1-dimethylethyl)-benzo[b]thiophene-2-carbonyl chloride, 5-propyl-benzo[b]thiophene-2-carbonyl chloride, 3-chloro-5,6-difluorobenzo[b]thiophene-2-carbonyl chloride, 1-(phenylsulfonyl)-1H-indole-2-carbonyl chloride, 5-chloro-2,3,5-trideoxy-2-(1-methylethyl)-5-oxo-D-glycero-pentonic acid, tetrahydro-3,3-dimethyl-5-oxo-2-furancarbonyl chloride, 5-(acetyloxy)-3-chloro-Benzo[b]thiophene-2-carbonyl chloride, 5-fluoro-1-methyl-1H-indole-2-carbonyl chloride, 5,6-dimethyl-1H-indole-3-carbonyl chloride, 5,6-dimethyl-1H-indole-3-carbonyl chloride, 1-ethyl-1H-indole-3-carbonyl chloride, 6-fluoro-benzo[b]thiophene-2-carbonyl chloride, tetrahydro-2-oxo-3-Furancarbonyl chloride, 1-methoxy-1H-indole-3-carbonyl chloride, (2S)-5-chloro-2,3,5-trideoxy-2-methyl-5-oxo-2-(2-propenyl)-D-glycero-pentonic acid gamma-lactone and (3R-cis)-tetrahydro-4-methoxy-3-furancarbonyl chloride.

Reaction with heterocyclic sulfonyl chlorides (particular example of V-B) yields final compounds (A) wherein X comprises a sulfonamide linkage. Exemplary heterocyclic sulfonyl chlorides suitable for use in the synthesis of the compounds of the present invention include, but are not limited to, the following: 4-methyl-2-[3-(pentyloxy)phenyl]-5-thiazolesulfonyl chloride, 2-(5-chloro-2-propoxyphenyl)-4-methyl-5-thiazolesulfonyl chloride, 2-(3-chloro-4-ethoxy-5-methoxyphenyl)-4-methyl-5-thiazolesulfonyl chloride, 2-(3-chloro-4,5-dimethoxyphenyl)-4-methyl-5-thiazolesulfonyl chloride, 2-(2-methoxy-1-naphthyl)-4-methyl-5-thiazolesulfonyl chloride, 2-[3-[2-(dimethylamino)ethoxy]-4-methoxyphenyl]-4-methyl-5-thiazolesulfonyl chloride, 2-[4-[3-(dimethylamino)propoxy]phenyl]-4-methyl-5-thiazolesulfonyl chloride, 2-[3-(hexyloxy)phenyl]-4-methyl-5-thiazolesulfonyl chloride, 2-(5-bromo-2-ethoxyphenyl)-4-methyl-5-thiazolesulfonyl chloride, 2-(2-butoxy-3-methoxyphenyl)-4-methyl-5-Thiazolesulfonyl chloride, 2-[2-[2-(dimethylamino)ethoxy]-3-methoxyphenyl]-4-methyl-5-thiazolesulfonyl chloride, 2-[2-[2-(dimethylamino)ethoxy]-4-methoxyphenyl]-4-methyl-5-Thiazolesulfonyl chloride, 2-(3-ethoxy-4-methoxyphenyl)-4-methyl-5-thiazolesulfonyl chloride, 2-(3,4-diethoxyphenyl)-4-methyl-5-thiazolesulfonyl chloride, 2-(2-butoxy-4-methoxyphenyl)-4-methyl-5-thiazolesulfonyl chloride, 2-[4-(hexyloxy)phenyl]-4-methyl-5-thiazolesulfonyl chloride, 2-(3-ethoxy-4-propoxyphenyl)-4-methyl-5-thiazolesulfonyl chloride, 2-[3-[2-(diethylamino)ethoxy]phenyl]-4-methyl-5-thiazolesulfonyl chloride, 2-(3-chloro-5-ethoxy-4-methoxyphenyl)-4-methyl-5-thiazolesulfonyl chloride, 2-(3-methoxy-2-propoxyphenyl)-4-methyl-5-thiazolesulfonyl chloride, 4-methyl-2-[2-(2-phenylethoxy)phenyl]-5-thiazolesulfonyl chloride, 2-[4-methoxy-2-(pentyloxy)phenyl]-4-methyl-5-thiazolesulfonyl chloride, 2-[3-methoxy-4-(pentyloxy)-phenyl]-4-methyl-5-thiazolesulfonyl chloride, 2-(3-methoxy-4-propoxyphenyl)-4-methyl-5-thiazolesulfonyl chloride, 2-(3-bromo-4-hydroxy-5-methoxyphenyl)-4-methyl-5-thiazolesulfonyl chloride, 5-(chlorosulfonyl)-2-thiopheneacetic acid methyl ester, 5-[[(2,2,2-trifluoroacetyl)amino]methyl]-2-thiophenesulfonyl chloride, 5-[2-[(2,2,2-trifluoroacetyl)amino]ethyl]-2-thiophenesulfonyl chloride, 5-formyl-2-thiophenesulfonyl chloride, 5-(3-amino-3-oxo-1-propen-1-yl)-2-thiophenesulfonyl chloride, 5-(2H-tetrazol-5-yl)-2-thiophenesulfonyl chloride, 5-(5-isoxazolyl)-2-methyl-3-furansulfonyl chloride, 3-(1,3-dioxolan-2-yl)-2-furansulfonyl chloride, 5-(chlorosulfonyl)-3-Thiophenecarboxylic acid, 4-[2-(methylthio)-4-pyrimidinyl]-2-Thiophenesulfonyl chloride, 5-(1,3-dioxolan-2-yl)-2-Thiophenesulfonyl chloride, 5-(chlorosulfonyl)-2-Thiopheneacetic acid, 5-(acetamidomethyl)-2-Thiophenesulfonyl chloride, 5-(chlorosulfonyl)-3-methyl-2,4-Thiophenedicarboxylic acid dimethyl ester, 4-phenyl-5-(trifluoromethyl)-3-Thiophenesulfonyl chloride, 5-(5-isoxazolyl)-2-Furansulfonyl chloride, 5-(5-Isoxazolyl) thiophene-2-sulfonyl chloride, 3-(chlorosulfonyl)-4-[(1-methylethyl)sulfonyl]-2-Thiophenecarboxylic acid methyl ester, 5-Chlorosulfonyl-4-methylthiophene-2-carboxylic acid methyl ester, 5-[5-(chloromethyl)-1,2,4-oxadiazol-3-yl]-2-Thiophenesulfonyl chloride, 5-[(3-Chloro-5-trifluoromethylpyridin-2-yl)methyl]thiophene-2-sulfonyl chloride, 5-(1,2,3-thiadiazol-4-yl)-2-Thiophenesulfonyl chloride, 5-(5-chloro-1,2,4-thiadiazol-3-yl)-2-Thiophenesulfonyl chloride, 5-(chlorosulfonyl)-2-methyl-3-Furancarboxylic acid methyl ester, 4-(chlorosulfonyl)-2,5-dimethyl-3-Furancarboxylic acid methyl ester, 4-(chlorosulfonyl)-2,5-dimethyl-3-Furancarboxylic acid ethyl ester, 5-(4-chlorophenyl)-4-(chlorosulfonyl)-2-methyl-3-Furancarboxylic acid ethyl ester, 3-(chlorosulfonyl)-4-phenyl-5-(trifluoromethyl)-2-Thiophenecarboxylic acid methyl ester, 5-Methyl-2-trifluoromethylfuran-3-sulfonyl chloride, 5-(2-Methyl-5-trifluoromethyl-2H-pyrazol-3-yl)thiophene-2-sulfonyl chloride, 5-(2-Methyl-1,3-thiazol-4-yl)thiophene-2-sulfonyl chloride, 3-Bromo-5-chloro-2-thiophenesulfonyl chloride, 5-(chlorosulfonyl)-4-methoxy-3-Thiophenecarboxylic acid methyl ester, 5-(2-Methylsulfanylpyrimidin-4-yl)thiophene-2-sulfonyl chloride, 3-Bromothiophene-2-sulfonyl chloride, 5-(Benzenesulfonyl)thiophene-2-sulfonyl chloride, 5-[[3-chloro-5-(trifluoromethyl)-2-pyridinyl]sulfonyl]-2-Thiophenesulfonyl chloride, 3-Bromo-2,5-dichlorothiophene-4-sulfonyl chloride, 4-Bromo-5-chlorothiophene-2-sulfonyl chloride, 5-(((4-Chlorobenzoyl)amino)methyl)-2-thiophenesulfonyl chloride, 2-[1-Methyl-5-(trifluoromethyl)-3-pyrazolyl]thiophene-5-sulfonyl chloride, 2,5-Dimethylfuran-3-sulfonyl chloride, 2-Phenylthiophene-3-sulfonyl chloride, 4-(phenylsulfonyl)-2-Thiophenesulfonyl chloride, 2-(Isoxazol-3-yl)thiophene-5-sulfonyl chloride, 3-Quinolinesulfonyl chloride, Dimethyl 3-chlorosulfonyl-2,5-thiophenedicarboxylate, 4-Chloro-3-quinolinesulfonyl chloride, 2-(2-Pyridyl)thiophene-5-sulfonyl chloride, 2-(Benzoylaminomethyl)thiophene-5-sulfonyl chloride, 5-chloro-3-(chlorosulfonyl)-2-Thiophenecarboxylic acid methyl ester, 2,3-Dichlorothiophene-5-sulfonyl chloride, 4-Bromo-3-thiophenesulfonyl chloride, 3-(1,3-dioxolan-2-yl)-2-Thiophenesulfonyl chloride, 2,5-Dimethylthiophene-3-sulfonyl chloride, 2-Chlorosulfonyl-5-phenylthiophene, 2,3-Dibromothiophene-5-sulfonyl chloride, 2,5-dibromo-3-Thiophenesulfonyl chloride, 2,5-Dichloro-4-nitro-3-thiophenesulfonyl chloride, 4-(chlorosulfonyl)-3-Thiophenecarboxylic acid methyl ester, 5-Chloro-4-nitro-2-thiophenesulfonyl chloride, 2,4,5-Trichloro-3-thiophenesulfonyl chloride, 5-Ethyl-2-thiophenesulfonyl chloride, 5-(dichloromethyl)-2-Furansulfonyl chloride, 5-Iodo-2-thiophenesulfonyl chloride, 5-bromo-2-Thiophenesulfonyl chloride, 1,4-dimethyl-1H-Imidazole-2-sulfonyl chloride, 2-(chlorosulfonyl)-1-methyl-1H-Imidazole-5-carboxylic acid methyl ester, 1,5-dimethyl-1H-Imidazole-2-sulfonyl chloride, 3-chloro-5-(2,2,2-trichloroacetyl)-1H-pyrrole-2-sulfonyl chloride, 2,3-dihydro-2-methyl-1-(methylsulfonyl)-1H-Indole-5-sulfonyl chloride, 2-methyl-1-piperidinesulfonyl chloride, 5-(2H-tetrazol-5-yl)-1H-Pyrrole-2-sulfonyl chloride, 1-(chlorosulfonyl)-4-piperidine-carboxylic acid methyl ester, 3,5-dimethyl-1-piperidinesulfonyl chloride, 5-bromo-3-pyridinesulfonyl chloride, 5-chloro-3-cyano-4,6-dimethyl-2-pyridinesulfonyl chloride, 6-chloro-4-methyl-3-pyridinesulfonyl chloride, 6-chloro-2-methylpyridine-3-sulfonyl chloride, 3-bromo-4-pyridinesulfonyl chloride, 6-bromo-3-pyridinesulfonyl chloride, 3,5-dichloro-2-pyridinesulfonyl chloride, 3-(phenylmethoxy)-2-pyridinesulfonyl chloride, 5-chloro-2-pyridinesulfonyl chloride, 6-phenyl-3-pyridinesulfonyl chloride, 1-methyl-5-(trichloroacetyl)-1H-Pyrrole-3-sulfonyl chloride, 5-(trichloroacetyl)-1H-pyrrole-3-sulfonyl chloride, 1,2-dimethyl-1H-Imidazole-5-sulfonyl chloride, 1-(chlorosulfonyl)-3-piperidinecarboxylic acid ethyl ester, 1-(chlorosulfonyl)-4-piperidinecarboxylic acid ethyl ester, 3-chloro-1,5-dimethyl-1H-pyrazole-4-sulfonyl chloride, 3-methyl-1-piperidinesulfonyl chloride, 1-methyl-3-(trifluoromethyl)-1H-pyrazole-4-sulfonyl chloride, 1-methylimidazol-5-ylsulfonyl chloride, 2-(4-morpholinyl)-3-pyridinesulfonyl chloride, 5-fluoro-2-chlorosulfonyl-3-methylbenzo[b]thiophene, 6-Phenoxypyridine-3-sulfonyl chloride, 4-(chlorosulfonyl)-3,5-dimethyl-1H-pyrrole-2-carboxylic acid ethyl ester, 5-methyl-1-phenyl-1H-pyrazole-4-sulfonyl chloride, 4-methyl-2-pyridinesulfonyl chloride, 5-bromo-3-methyl-benzo[b]thiophene-2-sulfonyl chloride, 1-[3-chloro-5-(trifluoromethyl)-2-pyridinyl]-1H-pyrrole-2-sulfonyl chloride, 6-(morpholin-4-yl)pyridine-3-sulfonyl chloride, 6-methoxypyridine-3-sulfonyl chloride, 5-(chlorosulfonyl)-1-methyl-1H-pyrrole-2-carboxylic acid methyl ester, 3-(chlorosulfonyl)-4-pyridinecarboxylic acid ethyl ester, 1-methyl-1H-pyrazole-4-sulfonyl chloride, benzyl 4-(chlorosulfonyl)-1-piperidinecarboxylate, 6-methyl-2-pyridinesulfonyl chloride, 2,6-dichloro-3-pyridinesulfonyl chloride, 3-bromo-2-chloropyridine-5-sulfonyl chloride, 5-methyl-2-pyridinesulfonyl chloride, 5-nitro-2-pyridinesulfonyl chloride, 5-(trifluoromethyl)pyridine-2-sulfonyl chloride, 5-chloro-2-(chlorosulfonyl)-3-methylbenzo[b]thiophene, 1,2-dimethyl-1H-imidazole-4-sulfonyl chloride, 5-chloro-1-methyl-1H-Imidazole-4-sulfonyl chloride, 6-chlorobenzo[b]thiophene-2-sulfonyl chloride, 4-chloro-benzo[b]thiophene-2-sulfonyl chloride, 2-pyridinesulfonyl chloride, 5,6-dichloro-3-pyridinesulfonyl chloride, ethyl 3-(chlorosulfonyl)-1-methylpyrazole-4-carboxylate, 5-methyl-benzo[b]thiophene-2-sulfonyl chloride, 1-benzothiophene-2-sulfonyl chloride, 1,3-dimethyl-1H-Pyrazole-4-sulfonyl chloride, 1-methyl-1H-pyrazole-3-sulfonyl chloride, 5-chloro-1,3-dimethyl-1H-pyrazole-4-sulfonyl chloride, 3,5-dimethyl-pyrazole-4-sulfonyl chloride, 5-bromo-3-pyridinesulfonyl chloride, 3,5-dimethyl-1-phenyl-1H-pyrazole-4-sulfonyl chloride, 3-methylbenzo[b]thiophene-2-sulfonyl chloride, 1-methyl-1H-imidazole-2-sulfonyl chloride, 3-pyridinesulfonyl chloride, 4-methyl-1-piperidinesulfonyl chloride, 1-piperidinesulfonyl chloride, 4-chloro-3-pyridinesulfonyl chloride, benzo[b]thiophene-3-sulfonyl chloride, 5-(chlorosulfonyl)-1,3,4-thiadiazole-2-acetic acid methyl ester, 3,4-dihydro-4-oxo-2H-1-benzopyran-3-sulfonyl chloride, 4-isoxazolesulfonyl chloride, 5-formyl-1,3,4-thiadiazole-2-sulfonyl chloride, 5-methyl-1H-Imidazole-2-sulfonyl chloride, 5-(chlorosulfonyl)-1,3,4-thiadiazole-2-carboxylic acid methyl ester, 2,3-dihydro-2-oxo-5-thiazolesulfonyl chloride, 2,3-dihydro-4-methyl-2-oxo-5-thiazolesulfonyl chloride, 6-amino-1,2,3,4-tetrahydro-1,3-dimethyl-2,4-dioxo-5-pyrimidinesulfonyl chloride, 1,2,3,4-tetrahydro-1,3,6-trimethyl-2,4-dioxo-5-pyrimidinesulfonyl chloride, 2,6-dimethyl-4-morpholinesulfonyl chloride, 2,4-dimethyl-5-pyrimidinesulfonyl chloride, 1H-indole-3-sulfonyl chloride, 5-methyl-3-phenyl-4-isoxazolesulfonyl chloride, 1,3,4-thiadiazole-2-sulfonyl chloride, 5-methyl-4-isoxazole-sulfonyl chloride, 1H-imidazole-2-sulfonyl chloride, 2-methyl-1H-imidazole-5-sulfonyl chloride, 3,4-dihydro-1H-isoquinoline-2-sulfonyl chloride, 3-(chlorosulfonyl)-4-methyl-3-thiolene 1,1-dioxide, 1,2,3,4-tetrahydro-1,3-dimethyl-2,4-dioxo-5-pyrimidinesulfonyl chloride, 4-chlorotetrahydro-3-Thiophenesulfonyl chloride 1,1-dioxide, 3-(chlorosulfonyl)-3-thiolene-1,1-dioxide, tetrahydro-4-hydroxy-3-thiophenesulfonyl chloride-1,1-dioxide, 3,5-dimethyl-4-isoxazolesulfonyl chloride, 4,5,6,7-tetrahydro-5-methyl-thiazolo[5,4-c]pyridine-2-sulfonyl chloride, 4,5,6,7-tetrahydro-5-(2,2,2-trifluoroacetyl)-thiazolo[5,4-c]pyridine-2-sulfonyl chloride, and 2-(chlorosulfonyl)-4,7-dihydro-thieno[2,3-c]pyridine-6(5H)-carboxylic acid 1,1-dimethylethyl ester.

Reaction with heterocyclic isocyanate compounds (V-C) yields final compounds (A) wherein X comprises a urea linkage. Exemplary heterocyclic isocyanate compounds suitable for use in the synthesis of the compounds of the present invention include, but are not limited to, the following: 4-isocyanato-2-(trifluoromethyl)-pyridine, 3-isocyanato-2-methyl-furan, 5-isocyanato-2-[(tetrahydro-2H-pyran-4-yl)oxy]-pyridine, 2-bromo-3-isocyanato-thiophene, 3-isocyanato-5-methyl-2-phenyl-furan, 4-(6-isocyanato-2-pyridinyl)-morpholine, 4-(4-isocyanato-2-pyridinyl)-morpholine, 2-(3-chlorophenyl)-4-isocyanato-thiazole, 4-isocyanato-2-[4-(trifluoromethyl)phenyl]-thiazole, 5-isocyanato-4-methyl-2-phenyl-thiazole, 2-isocyanato-4-methyl-thiophene, 3-isocyanato-1-(trifluoroacetyl)-piperidine, 4-isocyanato-5-methyl-1-phenyl-1H-pyrazole, (5-isocyanato-4-methyl-2-thiazolyl)-Pyrazine, 3-isocyanato-1-propyl-1H-pyrrole, 3-isocyanato-1-(1-methylethyl)-1H-pyrrole, 1-ethyl-3-isocyanato-1H-pyrrole, 3-isocyanato-1-methyl-1H-pyrrole, 5-isocyanato-1,3-dimethyl-1H-pyrazole, 3-isocyanato-1-propyl-1H-pyrazole, 3-isocyanato-1-(1-methylethyl)-1H-pyrazole, 2-ethyl-5-isocyanato-1,3,4-thiadiazole, 5-isocyanato-2-methyl-pyridine, 4-isocyanato-pyridine 1-oxide, 3-isocyanato-2(1H)-pyridinone, 4-isocyanato-3,5-dimethyl-1-phenyl-1H-pyrazole, 3-isocyanato-2-methyl-5-phenyl-furan, 1-ethynyl-4-isocyanato-2(1H)-azetone, 1-ethynyl-3-isocyanato-2(1H)-azetone, tetrahydro-3-isocyanato-3-methyl-thiophene 1,1-dioxide, 5-isocyanato-1-methyl-1H-imidazole, 2,2,2-trifluoro-1-(4-isocyanato-1-piperidinyl)-ethanone, 3-isocyanato-6-methoxy-2H-1-benzopyran-2-one, 4-isocyanato-3-methyl-5-phenyl-isoxazole, 3-isocyanato-benzo-[b]thiophene, 2-isocyanato-5-phenyl-thiophene, 4-isocyanato-1-piperidinecarboxylic acid 1,1-dimethylethyl ester, 3-isocyanato-5-methyl-2-(trifluoromethyl)-furan, 4-isocyanato-5-methyl-3-phenyl-Isoxazole, 4-isocyanato-1,3,5-trimethyl-1H-pyrazole, 4-isocyanato-1-piperidinecarboxylic acid phenylmethyl ester, 2-isocyanato-1,3,4-thiadiazole, 3-isocyanato-1-piperidinecarboxylic acid 1,1-dimethylethyl ester, 4-isocyanato-1-piperidinecarboxaldehyde, 3-bromo-5-isocyanato-pyridine, 2-isocyanato-1-methyl-1H-pyrrole, 2-isocyanato-2-(trifluoromethyl)-1,3-benzoxathiole, 2,6-dichloro-4-isocyanato-pyridine, 4-isocyanato-1-piperazineethanol, 2-isocyanato-4,6-dimethyl-pyrimidine, 4-isocyanato-3,5-dimethyl-isoxazole, 5,6-dichloro-2-isocyanato-2-(trifluoromethyl)-1,3-benzodioxole, 5-chloro-2-isocyanato-2-(trifluoromethyl)-1,3-benzodioxole, 2-isocyanato-2-(trifluoromethyl)-1,3-benzodioxole, 5-isocyanato-2-pyridinecarbonitrile, 2-chloro-5-isocyanato-pyridine, 2-phenyl-4-oxazolyl isocyanic acid ester, 1-isocyanato-3-oxabicyclo[3.1.1]heptan-2-one, 5-bromo-2-isocyanato-pyridine, 3-phenyl-1,2,4-oxadiazol-5-yl isocyanic acid ester, 4-isocyanato-2,2,6,6-tetramethyl-1-piperidinyloxy, 2-isocyanato-furan, 3-isocyanato-thiophene, 2-isocyanato-pyrimidine, 4-isocyanato-2,6-dimethyl-pyrimidine, 3,4-diethyl-5-isocyanato-isoxazole, 2-isocyanato-thiazole, 4-isocyanato-pyridine, 5-fluoro-2-isocyanato-benzothiazole, 2-isocyanato-4-methoxy-benzothiazole, 6-chloro-2-isocyanato-benzothiazole, 2-isocyanato-5-methyl-benzothiazole, 2-isocyanato-benzothiazole, 2,3-dihydro-3-isocyanato-thiophene 1,1-dioxide, 3-cyclopropyl-5-isocyanato-isoxazole, 5-isocyanato-3-(1-methylethyl)-isoxazole, and 5-isocyanato-3-propyl-isoxazole, and 3-(1,1-dimethylethyl)-5-isocyanato-isoxazole.

Intermediates having the structural formula (IV-A) or (IV-B) may be derivatised with a carbonylation agent such as, but not limited to, trisphosgene, carbonyl diimidazole (as illustrated in scheme 4, and hereinafter abbreviated as CDI) or carbonyl ditriazole. The resulting imidazo-carbonyl or triazo-carbonyl compound may then be further reacted with an amino compound represented by structural formula V-D), thereby providing further compounds of the invention wherein X comprises a urea linkage. The carbonylation and further urea formation with an amine may be most particularly carried out in a one-pot procedure. Amino compounds suitable for the latter reaction include heterocyclyl amines, heterocyclylalkylamines, heterocyclylalkenylamines and heterocyclylalkynylamines wherein said one or more of the carbon atoms in the alkyl, alkenyl or alkynyl moiety is optionally replaced by a heteroatom selected from the group comprising O, N and S, and wherein each of said amino compounds is optionally substituted.

Exemplary heterocyclyl amines suitable for this embodiment of the invention comprise, but are not limited to, the following: 1-(2-thiazolyl)-3-Piperidinamine, N2-(2-methoxyethyl)-2,5-pyridinediamine, 2-amino-5-cyano-N-(3-methoxyphenyl)-6-(pentylthio)-3-pyridinecarboxamide, N-(5-amino-2-pyridinyl)-cyclohexane-carboxamide, (2S,5R)-5-amino-1,2-Piperidinedicarboxylic acid 1-(1,1-dimethylethyl) 2-methyl ester, (3R,4S)-4-amino-3-fluoro-1-Piperidinecarboxylic acid 1,1-dimethylethyl ester, 4-amino-3-fluoro-1-Piperidinecarboxylic acid 1,1-dimethylethyl ester, 2-chloro-6-ethoxy-4-pyridinamine, 4-methyl-6-(methylsulfonyl)-pyridinamine, 2-methyl-6-(methyl-sulfonyl)-3-Pyridinamine, 1-(4-chlorophenyl)-4-Piperidinamine, N2-cyclopropyl-2,5-pyridinediamine, 5-amino-N,N-dimethyl-3-pyridinesulfonamide, 3-bromo-2,5-pyridinediamine, 6-amino-2-ethoxy-4-methyl-3-pyridinecarbonitrile, 5-[4-(trifluoromethyl)phenyl]-2-pyridinamine, 3-(4-amino-1-piperidinyl)-benzonitrile, 1-(5-amino-3-pyridinyl)-ethanone, 1,4-dimethyl-4-piperidinamine, 4-(5-amino-2-pyridinyl)-1-piperidinecarboxylic acid 1,1-dimethylethyl ester, 2-amino-6-methyl-3-pyridinecarboxaldehyde, 6-fluoro-5-iodo-2-pyridinamine, N-(6-amino-5-iodo-2-pyridinyl)-acetamide, 2-amino-5-bromo-4-pyridinecarboxylic acid methyl ester, N-[(5-amino-2-pyridinyl)methyl]-methanesulfonamide, 1-(2-methyl-1-oxopropyl)-4-piperidinamine, 5-(1H-benzimidazol-2-yl)-2-pyridinamine, 2-(4-methyl-1-piperazinyl)-4-pyridinamine, 5-[2-(trifluoromethyl)phenyl]-2-pyridinamine, 5-(2-chlorophenyl)-2-pyridinamine, 3-amino-5-phenyl-1-piperidinecarboxylic acid 1,1-dimethylethyl ester, 4-(chloromethyl)-2-pyridinamine, 1-[4-(methylsulfonyl)benzoyl]-4-piperidinamine, 4-amino-4-(aminomethyl)-1-piperidinecarboxylic acid 1,1-dimethylethyl ester, 3-amino-6-methoxy-2-Pyridinecarboxylic acid, 2-chloro-N4,6-dimethyl-3,4-Pyridinediamine, 4-amino-2-(trifluoromethyl)-3-Pyridinecarboxylic acid ethyl ester, 2-amino-α-methyl-3-pyridinemethanol, (2-amino-3-pyridinyl)cyclohexyl-methanone, 3-(2-furanylimino-methyl)-6-methyl-2-pyridinamine, 3-bromo-5-fluoro-2-pyridinamine, 5-(1,4,5,6-tetrahydro-2-pyrimidinyl)-2-pyridinamine, 6-methoxy-5-methyl-3-pyridinamine, 3-amino-6-chloro-2-pyridinecarboxylic acid, 5-(2-thienyl)-2-pyridinamine, 5-(3-fluorophenyl)-2-pyridinamine, 5-(2-methoxyphenyl)-2-pyridinamine, 4-(4-amino-3-fluorophenoxy)-2-pyridinamine, 3-amino-1,3-piperidinedicarboxylic acid 1-(1,1-dimethylethyl) ester, (3R)-amino-1,3-piperidinedicarboxylic acid 1-(1,1-dimethylethyl) ester, 5-bromo-2-chloro-4-pyridinamine, 3-iodo-2,6-pyridinediamine, N2-[2-(dimethylamino)ethyl]-2,5-pyridinediamine, 5-bromo-4-methyl-3-Pyridinamine, 6-amino-5-bromo-3-Pyridinecarboxylic acid ethyl ester, 6-(hexahydro-1H-azepin-1-yl)-3-Pyridinamine, 5-methoxy-2-phenyl-4-Pyridinamine, 5-bromo-N-3-(phenylmethylene)-2,3-Pyridinediamine, [N3(E)]-N-3-[(4-methoxyphenyl)methylene]-2,3-Pyridinediamine, N3-[(4-methylphenyl)methylene]-2,3-Pyridinediamine, 2-[(6-amino-2-pyridinyl)amino]-N-phenyl-2-thioxo-Acetamide, 2-amino-5-[(2,5-dimethoxyphenyl)methyl]-4-methyl-3-Pyridinecarbonitrile, 6-amino-1,2-dihydro-4-[4-(1-methylethyl)phenyl]-2-thioxo-3,5-Pyridinedicarbonitrile, 2-amino-6-methyl-3-Pyridinecarboxylic acid, 5-fluoro-3-iodo-2-Pyridinamine, 6-[(1-methyl-4-piperidinyl)thio]-2-Pyridinamine, 2-amino-5-bromo-N-cyclopropyl-3-pyridinecarboxamide, 4-amino-3-pyridineethanol, 5-amino-4,6-dichloro-N-cyclopropyl-2-Pyridinecarboxamide, 4-amino-2-Pyridinecarboxylic acid ethyl ester, 1-(ethylsulfonyl)-4-piperidinamine, 2-ethynyl-6-methyl-3-pyridinamine, 5-(1-ethylpropoxy)-3-pyridinamine, 6-(1-ethylpropoxy)-2-pyridinamine, 6-(1-ethylpropoxy)-2-pyridinamine, (3R,4R)-

4-amino-3-hydroxy-4-methyl-1-piperidinecarboxylic acid methyl ester, 4-amino-4-ethyl-1-piperidinecarboxylic acid 1,1-dimethylethyl ester, (3R,4R)-(+)-4-amino-3-hydroxy-4-methyl-1-Piperidinecarboxylic acid methyl ester, 4-amino-4-piperidinemethanol, 7-bromo-pyrrolo[2,1-f][1,2,4]triazin-4-amine, 1-cyclopentyl-4-methyl-1H-pyrazol-5-amine, 6-amino-2,3-dihydro-1-(2-methyl-2-propen-1-yl)-2-thioxo-4(1H)-pyrimidinone, 6-(phenylthio)-4,5-pyrimidinediamine, 4-amino-2-(propylamino)-5-pyrimidinecarboxylic acid, 4-(2-thiazolyl)-2-pyrimidinamine, 6-amino-2,3-dihydro-1-(2-propen-1-yl)-2-thioxo-4(1H)-pyrimidinone, 5-ethynyl-2-pyrimidinamine, 4,6-dibromo-2-Pyrimidinamine, 4-(5-bromo-2-thienyl)-2-Pyrimidinamine, 6-chloro-N4-(3-chlorophenyl)-4,5-Pyrimidinediamine, N4-(4-bromo-2-fluorophenyl)-6-chloro-4,5-pyrimidinediamine, 6-ethyl-N2, N2,N4, N4-tetramethyl-2,4,5-pyrimidinetriamine, 4-methyl-2,6-bis(methylthio)-5-Pyrimidinamine, 2-chloro-N4,N4-dimethyl-4,5-pyrimidinediamine, 1-[(2-amino-6-methyl-5-nitro-4-pyrimidinyl)amino]-2-propanone, 4,6-diethyl-2-Pyrimidinamine, 5-(chloromethyl)-2-Pyrimidinamine, N4-methyl-6-phenyl-4,5-Pyrimidinediamine, 2-amino-1,6-dihydro-5-hydroxy-1-methyl-6-oxo-4-Pyrimidinecarboxylic acid ethyl ester, 4-amino-5-Pyrimidinecarboxylic acid methyl ester, 4-amino-1-pentofuranosyl-2(1H)-Pyrimidinone, 2-amino-4,6-dimethyl-5-Pyrimidinol, 4-(3,4-dimethoxyphenyl)-2-Pyrimidinamine, 6-amino-1-(2-furanylmethyl)-2,3-dihydro-2-thioxo-4(1H)-Pyrimidinone, 2-chloro-5-iodo-4-Pyrimidinamine, 4-amino-1-ethenyl-5-fluoro-2(1H)-Pyrimidinone, 5,6-diamino-3-methyl-1-(1-methylpropyl)-2,4(1H,3H)-Pyrimidinedione, 5,6-diamino-1-(1,1-dimethylethyl)-3-methyl-2,4(1H,3H)-Pyrimidinedione, 4-(dimethoxymethyl)-6-ethoxy-2-Pyrimidinamine, 4-(cyclobutyloxy)-6-methoxy-2-Pyrimidinamine, 1-cyclopentyl-4-methyl-1H-pyrazol-5-amine, 3-(4-fluorophenyl)-1H-pyrazol-5-amine, 4-amino-1-ethyl-1H-pyrazole-3-carboxylic acid methyl ester, 4-amino-1-methyl-1H-Pyrazole-5-carboxylic acid methyl ester, 1-(2,2,2-trifluoroethyl)-1H-pyrazol-4-amine, 5-amino-3-(1,1-dimethylethyl)-1H-pyrazole-1-ethanol, 4-amino-N-methyl-1H-pyrazole-3-carboxamide, 4-amino-1,2-dihydro-1-methyl-5-(1-methylethyl)-2-phenyl-3H-Pyrazol-3-one, 1-(2-methoxyethyl)-1H-Pyrazol-3-amine, 3-amino-1H-Pyrazole-1-acetic acid ethyl ester, 1-ethyl-1H-Pyrazol-4-amine, 5-(4-morpholinyl)-2-Thiazolamine, 2-(1-methylethyl)-5-Thiazolamine, 2-amino-5-chloro-4-Thiazolecarboxylic acid methyl ester, 2-amino-5-(2-methylpropyl)-4-Thiazolecarboxylic acid methyl ester, 2-amino-4-phenyl-5-Thiazolecarboxylic acid hydrazide, 2-amino-5-iodo-4-Thiazolecarboxylic acid ethyl ester, 2-amino-5-methyl-4-Thiazoleacetic acid ethyl ester, 2-amino-5-bromo-4-Thiazolecarboxylic acid methyl ester, N5,N5-dimethyl-2,5-Thiazolediamine, 5-(2,6-dimethyl-4-pyrimidinyl)-4-methyl-2-Thiazolamine, 5-(2,6-dimethyl-4-pyridinyl)-4-methyl-2-Thiazolamine, 2,5-dimethyl-4-Thiazolamine, 2-amino-4-(methoxymethyl)-5-Thiazolecarboxylic acid methyl ester, 4-(2-amino-4-thiazolyl)-1-Piperidinecarboxylic acid 1,1-dimethylethyl ester, 2-amino-5-methyl-4-Thiazolecarboxylic acid, 2-amino-4-cyano-5-Thiazolecarboxylic acid ethyl ester, 2-amino-4-cyano-5-Thiazolecarboxylic acid ethyl ester, 5-(2-furanyl)-2-Pyridinamine, 2,5-dihydro-4-Thiazolamine, 5-cyclopropyl-2-Thiazolamine, 4-(3-fluoro-2-thienyl)-2-Thiazolamine, 2-amino-5-methyl-4-Thiazolecarboxaldehyde, 4-ethyl-5-(1-methylethyl)-2-Thiazolamine, 5-acetyl-2-amino-4-methyl-3-Thiophenecarboxylic acid, 1-(2-amino-3-thienyl)-Ethanone, 2-amino-5-propyl-3-Thiophenecarbonitrile, 3-amino-5-methyl-2-Thiophenecarboxaldehyde, 5-amino-3-methyl-2,4-Thiophenedicarboxylic acid 2-(1,1-dimethylethyl) 4-methyl ester, 2-amino-5-methyl-3,4-thiophenedicarboxylic acid dimethyl ester, 3-amino-5-(hydroxymethyl)-2-Thiophenecarboxylic acid methyl ester, 5-amino-3-cyano-4-methyl-2-Thiophenecarboxylic acid methyl ester, 3-amino-5-(1,1-dimethylethyl)-2-thiophenecarboxylic acid, 4-chlorotetrahydro-3-thiophenamine 1,1-dioxide, 4-amino-2,5-dihydro-5-methyl-3-Thiophenecarboxylic acid ethyl ester, (3S,4S)-4-aminotetrahydro-thiophene-3-ol 1,1-dioxide, 2-amino-1H-Pyrrole-3-carboxylic acid methyl ester, 3-methoxy-1-Pyrrolidinamine, 4-amino-1,2-Pyrrolidinedicarboxylic acid 1-(1,1-dimethylethyl) 2-ethyl ester, 2-amino-5-(1,1-dimethylethyl)-1H-Pyrrole-3-carboxylic acid ethyl ester, 3-amino-5-methyl-1H-Pyrrole-2-carboxylic acid, 1-amino-4-(1,1-dimethylethyl)-1H-Pyrrole-2-carboxylic acid ethyl ester, (3R)-1-(2-furanylmethyl)-3-Pyrrolidinamine, 3-amino-4-cyano-1-(phenylmethyl)-1H-Pyrrole-2-carboxylic acid ethyl ester, (1-amino-5-ethyl-1H-pyrrol-2-yl)-3-pyridinyl-Methanone, (1-amino-5-ethyl-1H-pyrrol-2-yl)pyrazinyl-Methanone, (1-amino-5-ethyl-1H-pyrrol-2-yl)-4-pyridinyl-methanone, 1-amino-3,4-dimethyl-1H-pyrrole-2-carboxamide, (2S,4R)-4-amino-2-methyl-1-Pyrrolidinecarboxylic acid 1,1-dimethylethyl ester, (2S,4S)-1-acetyl-4-amino-2-Pyrrolidinecarboxamide, (3S)-3-amino-2,5-dioxo-1-pyrrolidine-acetonitrile, 3-amino-1-(phenylmethyl)-3-pyrrolidine-carboxylic acid ethyl ester 4-aminotetrahydro-3-furancarboxylic acid methyl ester 4-amino-5-ethoxydihydro-2(3H)-furanone, 4-amino-5-ethoxydihydro-2(3H)-furanone, 3-amino-4-(4-bromophenyl)-2-furancarboxylic acid ethyl ester and 5-amino-2-furancarbonitrile.

The above description provides various synthetic schemes for making the 1,2,4-thiadiazole compounds of the present invention. A list of exemplary, but non-limiting, compounds being synthesised according to the described methods is provided in Table 1 and the Examples herein.

According to another aspect, the present invention provides, as useful intermediates, a class of amidines represented by the structural formula (II)

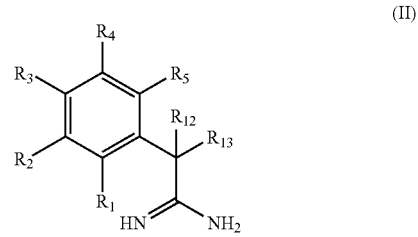

(II)

wherein $R_1$, $R_2$, $R_3$, $R_4$, $R_5$, $R_{12}$ and $R_{13}$ are as defined above with respect to formula (A), provided that $R_{12}$ and $R_{13}$ are not both hydrogen.

According to yet another aspect, the present invention provides, as useful intermediates, a class of 3-substituted-5-chloro-1,2,4-thiadiazole derivatives represented by the structural formula (III):

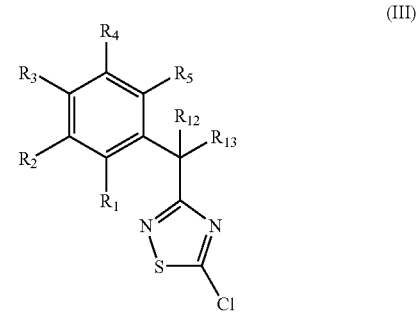

(III)

wherein $R_1$, $R_2$, $R_3$, $R_4$, $R_5$, $R_{12}$ and $R_{13}$ are as defined above with respect to formula (A), provided that $R_{12}$ and $R_{13}$ are not both hydrogen.

The 1,2,4-thiadiazole derivatives having the above structural formulae (A), (B), (C) and (D) may be in the form of a pharmaceutically acceptable salt. The latter include any therapeutically active non-toxic addition salt which 1,2,4-thiadiazole compounds having the general formulae (A), (B), (C) and (D) are able to form with a salt-forming agent. Such addition salts may conveniently be obtained by treating the said derivative of the invention with an appropriate salt-forming acid or base. For instance, derivatives having basic properties may be converted into the corresponding therapeutically active, non-toxic acid addition salt form by treating the free base form with a suitable amount of an appropriate acid following conventional procedures. Examples of such appropriate salt-forming acids include, for instance, inorganic acids resulting in forming salts such as but not limited to hydrohalides (e.g. hydrochloride and hydrobromide), sulfate, nitrate, phosphate, diphosphate, carbonate, bicarbonate, and the like; and organic monocarboxylic or dicarboxylic acids resulting in forming salts such as, for example, acetate, propanoate, hydroxyacetate, 2-hydroxypropanoate, 2-oxopropanoate, lactate, pyruvate, oxalate, malonate, succinate, maleate, fumarate, malate, tartrate, citrate, methanesulfonate, ethanesulfonate, benzoate, 2-hydroxy-benzoate, 4-amino-2-hydroxybenzoate, benzenesulfonate, p-toluenesulfonate, salicylate, p-aminosalicylate, pamoate, bitartrate, camphorsulfonate, edetate, 1,2-ethanedisulfonate, fumarate, glucoheptonate, gluconate, glutamate, hexylresorcinate, hydroxynaphthoate, hydroxyethanesulfonate, mandelate, methylsulfate, pantothenate, stearate, as well as salts derived from ethanedioic, propanedioic, butanedioic, (Z)-2-butenedioic, (E)2-butenedioic, 2-hydroxybutanedioic, 2,3-dihydroxybutane-dioic, 2-hydroxy-1,2,3-propanetricarboxylic and cyclohexanesulfamic acids and the like.

The 1,2,4-thiadiazole derivatives of the structural formulae (A), (B), (C) and (D) having acidic properties may be converted in a similar manner into the corresponding therapeutically active, non-toxic base addition salt form. Examples of appropriate salt-forming bases include, for instance, inorganic bases like metallic hydroxides such as but not limited to those of alkali and alkaline-earth metals like calcium, lithium, magnesium, potassium and sodium, or zinc, resulting in the corresponding metal salt; organic bases such as but not limited to ammonia, alkylamines, benzathine, hydrabamine, arginine, lysine, N,N'-dibenzylethylenediamine, chloroprocaine, choline, diethanolamine, ethylene-diamine, N-methylglucamine, procaine and the like.

Reaction conditions for treating the 1,2,4-thiadiazole derivatives having the structural formulae (A), (B), (C) and (D) of this invention with an appropriate salt-forming acid or base are similar to standard conditions involving the same acid or base but different organic compounds with basic or acidic properties, respectively. Preferably, in view of its use in a pharmaceutical composition or in the manufacture of a medicament for treating specific diseases, the pharmaceutically acceptable salt will be designed, i.e. the salt-forming acid or base will be selected so as to impart greater water-solubility, lower toxicity, greater stability and/or slower dissolution rate to the derivative of this invention.

In order to suitably use a 1,2,4-thiadiazole compound disclosed in this invention or a pharmaceutically acceptable salt, pro-drug or solvate thereof, for the therapeutic treatment (including prophylactic treatment) of mammals including humans, it is usually formulated in accordance with standard pharmaceutical practice as a pharmaceutical composition including one or more appropriate pharmaceutically acceptable excipients.

In another embodiment, this invention provides combinations, preferably synergistic combinations, of one or more derivatives represented by the structural formulae (A), (B), (C) and (D) with one or more biologically-active drugs being preferably selected from the group consisting of neuro-protective agents and α-synuclein deposition inhibitors. As is conventional in the art, the evaluation of a synergistic effect in a drug combination may be made by analysing the quantification of the interactions between individual drugs, using the median effect principle described by Chou et al. in *Adv. Enzyme Reg.* (1984) 22:27. Briefly, this principle states that interactions (synergism, additivity, antagonism) between two drugs can be quantified using the combination index (hereinafter referred as CI) defined by the following equation:

$$CI_x = \frac{ED_x^{1c}}{ED_x^{1a}} + \frac{ED_x^{2c}}{ED_x^{2a}}$$

wherein $ED_x$ is the dose of the first or respectively second drug used alone (1a, 2a), or in combination with the second or respectively first drug (1c, 2c), which is needed to produce a given effect. The said first and second drug have synergistic or additive or antagonistic effects depending upon CI<1, CI=1, or CI>1, respectively. As will be explained in more detail herein below, this principle may be applied to a number of desirable effects such as, but not limited to, an activity against neurodegenerative disorders.

The term "pharmaceutically acceptable carrier or excipient" as used herein in relation to pharmaceutical compositions and combined preparations means any material or substance with which the active principle, i.e. the 1,2,4-thiadiazole derivative of the structural formulae (A), (B), (C) and (D), and optionally the neuro-protective agent or α-synuclein deposition inhibitor, may be formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, pellets or powders.

Suitable pharmaceutical carriers for use in the said pharmaceutical compositions and their formulation are well known to those skilled in the art. There is no particular restriction to their selection within the present invention although, due to the usually low or very low water-solubility of the derivatives of this invention, special attention will be paid to the selection of suitable carrier combinations that can assist in properly formulating them in view of the expected time release profile. Suitable pharmaceutical carriers include additives such as wetting agents, dispersing agents, stickers, adhesives, emulsifying or surface-active agents, thickening agents, complexing agents, gelling agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals.

The pharmaceutical compositions of the present invention may be prepared in any known manner, for instance by homogeneously mixing, dissolving, spray-drying, coating and/or grinding the active ingredients, in a one-step or a multi-steps procedure, with the selected carrier material and, where appropriate, the other additives such as surface-active agents, may also be prepared by micronisation, for instance in view to obtain them in the form of microspheres usually having a diameter of about 1 to 10 μm, namely for the manufacture of microcapsules for controlled or sustained release of the biologically active ingredient(s).

Suitable surface-active agents to be used in the pharmaceutical compositions of the present invention are non-ionic, cationic and/or anionic surfactants having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcanolamine salts of dodecylbenzene sulphonic acid or dibutyl-naphtalenesulphonic acid or a naphtalenesulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanylphosphatidylcholine, dipalmitoylphoshatidylcholine and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with polypropylene glycol, ethylenediamino-polypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, preferably halides, having four hydrocarbon radicals optionally substituted with halo, phenyl, substituted phenyl or hydroxy; for instance quaternary ammonium salts containing as N-substituent at least one $C_8$-$C_{22}$ alkyl radical (e.g. cetyl, lauryl, palmityl, myristyl, oleyl and the like) and, as further substituents, unsubstituted or halogenated lower alkyl, benzyl and/or hydroxy-$C_{1-4}$ alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbuch", $2^{nd}$ ed. (Hanser Verlag, Vienna, 1981) and "Encyclopaedia of Surfactants (Chemical Publishing Co., New York, 1981).

Structure-forming, thickening or gel-forming agents may be included into the pharmaceutical compositions and combined preparations of the invention. Suitable such agents are in particular highly dispersed silicic acid, such as the product commercially available under the trade name Aerosil; bentonites; tetraalkyl ammonium salts of montmorillonites (e.g., products commercially available under the trade name Bentone), wherein each of the alkyl groups may contain from 1 to 20 carbon atoms; cetostearyl alcohol and modified castor oil products (e.g. the product commercially available under the trade name Antisettle).

Gelling agents which may be included into the pharmaceutical compositions and combined preparations of the present invention include, but are not limited to, cellulose derivatives such as carboxymethylcellulose, cellulose acetate and the like; natural gums such as arabic gum, xanthum gum, tragacanth gum, guar gum and the like; gelatin; silicon dioxide; synthetic polymers such as carbomers, and mixtures thereof. Gelatin and modified celluloses represent a preferred class of gelling agents.

Other optional excipients which may be included in the pharmaceutical compositions and combined preparations of the present invention include additives such as magnesium oxide; azo dyes; organic and inorganic pigments such as titanium dioxide; UV-absorbers; stabilisers; odor masking agents; viscosity enhancers; antioxidants such as, for example, ascorbyl palmitate, sodium bisulfite, sodium metabisulfite and the like, and mixtures thereof; preservatives such as, for example, potassium sorbate, sodium benzoate, sorbic acid, propyl gallate, benzylalcohol, methyl paraben, propyl paraben and the like; sequestering agents such as ethylene-diamine tetraacetic acid; flavoring agents such as natural vanillin; buffers such as citric acid and acetic acid; extenders or bulking agents such as silicates, diatomaceous earth, magnesium oxide or aluminum oxide; densification agents such as magnesium salts; and mixtures thereof.

Additional ingredients may be included in order to control the duration of action of the biologically-active ingredient in the compositions and combined preparations of the invention. Control release compositions may thus be achieved by selecting appropriate polymer carriers such as for example polyesters, polyamino-acids, polyvinyl-pyrrolidone, ethylene-vinyl acetate copolymers, methylcellulose, carboxy-methylcellulose, protamine sulfate and the like. The rate of drug release and duration of action may also be controlled by incorporating the active ingredient into particles, e.g. microcapsules, of a polymeric substance such as hydrogels, polylactic acid, hydroxymethyl-cellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition or combined preparation of the invention may also require protective coatings.

Pharmaceutical forms suitable for injectable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol, complexing agents such as cyclodextrins and the like, and mixtures thereof.

In another aspect the present invention relates to a method of preventing or treating an α-synucleopathy, comprising the administration of a therapeutic effective amount of a 1,2,4-thiadiazole derivative as defined in any specific embodiment above, in particular being represented by any of the structural formulae (A), (B), (C) and (D), to a patient in need thereof, optionally in combination with one or more pharmaceutically acceptable carriers, and optionally in combination with a therapeutic amount of one or more drugs selected from the group consisting of neuro-protective agents and α-synuclein deposition inhibitors. An α-synucleopathy relevant to said method may be selected from the group consisting of Parkinson's disease, diffuse Lewy body disease, traumatic brain injury, amyotrophic lateral sclerosis, Niemann-Pick disease, Hallervorden-Spatz syndrome, Down syndrome, neuroaxonal dystrophy, multiple system atrophy and Alzheimer's disease.

In order to suitably use compounds disclosed in this invention for therapeutic or prophylactic purpose, such compounds are preferably administered so that a daily dose in the range of, for example, 0.1 mg to 75 mg per kg body weight is received, said daily dose being given if required in divided sub-doses. In general, lower doses will be administered when a parenteral route is employed. Thus, for example, for intravenous administration, a dose in the range of, for example, 0.5 mg to 30 mg per kg body weight will preferably be used. Similarly, for administration by inhalation, a dose in the range of, for example, 0.5 mg to 25 mg per kg body weight will preferably be used. According to a particular embodiment, the envisaged administration route for the compounds of the invention is oral administration, particularly in tablet form. Typically, unit dosage forms will contain about 1 mg to 500 mg of a compound of this invention.

Another embodiment of this invention includes the various precursor or "pro-drug" forms of the compounds of the present invention. It may be desirable to formulate the compounds of the present invention in the form of a chemical species which itself is not significantly biologically-active, but which when delivered to the body of a human being or higher mammal will undergo a chemical reaction catalysed by the normal function of the body, inter alia, enzymes present in the stomach or in blood serum, said chemical reaction having the effect of releasing a compound as defined herein. The term "pro-drug" thus relates to these species which are converted in vivo into the active pharmaceutical ingredient. The pro-drugs of the present invention can have any form suitable to the formulator, e.g. esters. In the present case, however, the pro-drug may necessarily exist in a form wherein a covalent bond is cleaved by the action of an enzyme present at the target locus. For example, a C—C covalent bond may be selectively cleaved by one or more enzymes at said target locus and, therefore, a pro-drug in a form other than an easily hydrolysable precursor, inter alia an ester, an amide, and the like, may be used.

For the purposes of the present invention the term "therapeutically suitable pro-drug" is defined herein as a compound modified in such a way as to be transformed in vivo to the therapeutically active form, whether by way of a single or by multiple biological transformations, when in contact with the tissues of humans or mammals to which the pro-drug has been administered, and without undue toxicity, irritation, or allergic response, and achieving the intended therapeutic outcome.

EXAMPLE 1

Amidine Formation

Figure 1:
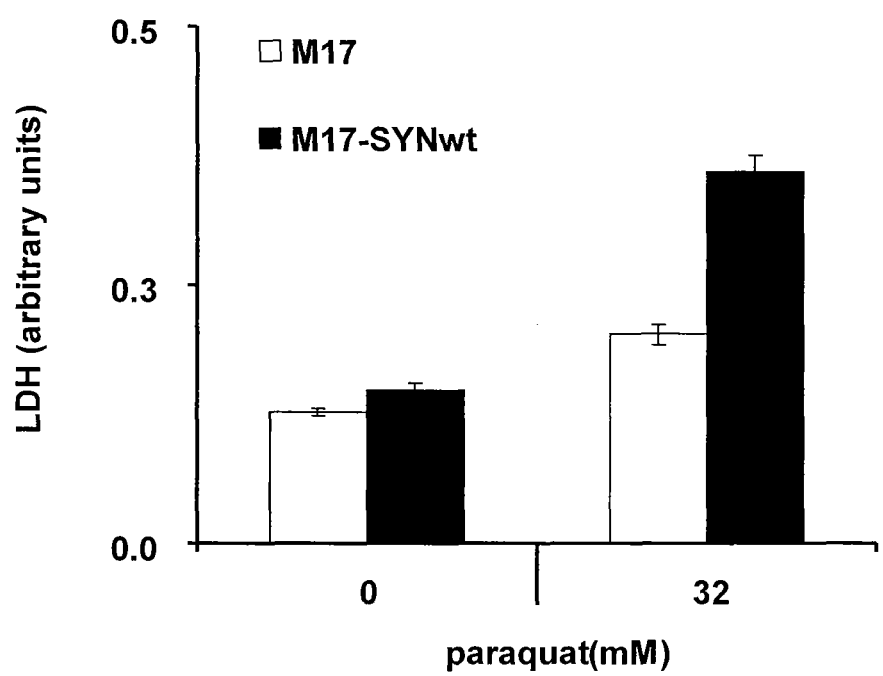
FIG. 1 shows the sensitivity of an α-synuclein expressing neuroblastoma cell line to paraquat according to one embodiment of the invention.

Illustrative compounds of the present invention have been prepared according to the synthetic pathway illustrated in schemes 1 and 2 herein-description.

Amidine formation according to step (a) of scheme 1, is schematically shown below:

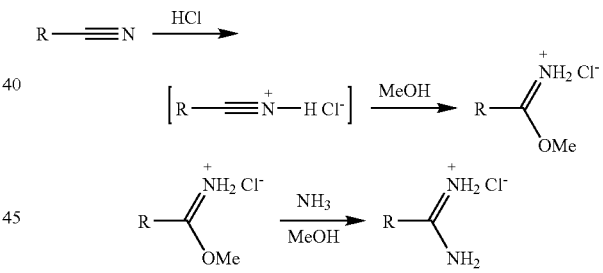

The nitrile compound is treated with gaseous HCl in a mixture of anhydrous chloroform and methanol to yield the imino ether hydrochloride. Subsequently, the mixture is treated with dry ammonia to yield the amidine compound.

EXAMPLE 2

Synthesis of Intermediate
3-benzyl-5-chloro-1,2,4-thiadiazole Derivatives

The intermediate 3-benzyl-5-chloro-1,2,4-thiadiazole derivatives in step (b) of scheme 1 have been obtained according to the following procedure. In a three-necked 500 mL flask equipped with a mechanical stirrer, a dropping funnel and a thermometer, dichloromethane (DCM) (130 ml) was charged and the appropriate amidine hydrochloride (0.1 mol) was suspended in it upon efficient stirring. Then perchloromethyl mercaptane (16.73 g) was added to the suspension. The stirred solution was cooled to −14° C. by using ammonium chloride-ice cooling bath. Then aqueous NaOH solution (0.5 mole dissolved in 30 ml distilled water) was added dropwise to the solution upon efficient stirring while keeping the inner temperature accurately below −8° C. When the addition was finished the reaction mixture was stirred for another hour while the temperature was let to rise to room temperature. The precipitated NaCl was filtered off and washed with DCM. The organic phase of the filtrate was separated and saved. The aqueous phase was washed with 3×20 ml DCM. The collected organic phases including the previously saved solution were washed with water (4×20 ml). The organic phase was dried over anhydrous sodium sulphate and evaporated to dryness. The residue was distilled in high motor vacuum using a vacuum-jacketed Vigreaux-column.

For different intermediate species, the following data were obtained:

5-Chloro-3-(4-methylbenzyl)-[1,2,4]thiadiazole: starting from 31.8 g of 4-methylbenzyl amidine hydrochloride, 16.7 g of the title compound was obtained (yield: 48%); boiling point (b.p.): 130-135° C./1 Hg mm.

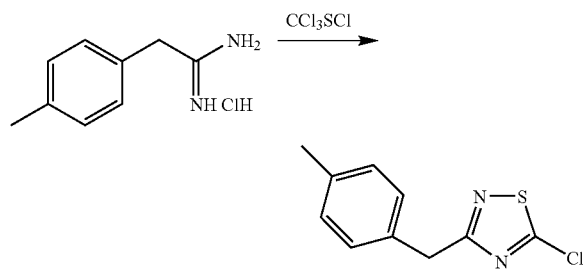

5-Chloro-3-(4-fluorobenzyl)-[1,2,4]thiadiazole: starting from 18.4 g (97.5 mmole) 4-fluorobenzyl amidine hydrochloride, 13.45 g of the title compound was obtained (yield: 67%); b.p.: 120-125° C./1 Hg mm.

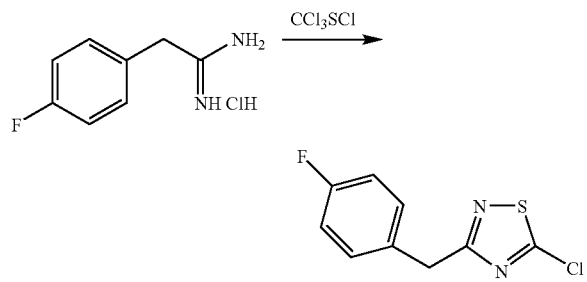

5-Chloro-3-(3-methoxybenzyl)-[1,2,4]thiadiazole: starting from 84.8 g of 3-methoxybenzyl amidine hydrochloride, 68.7 g of the title compound was obtained (yield: 75%); b.p.: 132-135° C./1 Hg mm.

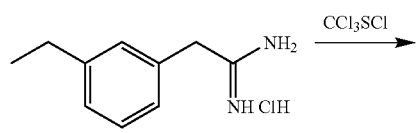

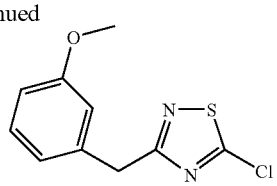

5-chloro-3-(4-chlorobenzyl)-[1,2,4] thiadiazole and 5-chloro-3-benzyl-[1,2,4] thiadiazole were also synthesised using these experimental conditions.

EXAMPLE 3

Nucleophilic Replacement of 5-chloro-3-(substituted benzyl)-thiadiazole Derivatives with Cyclic Diamines

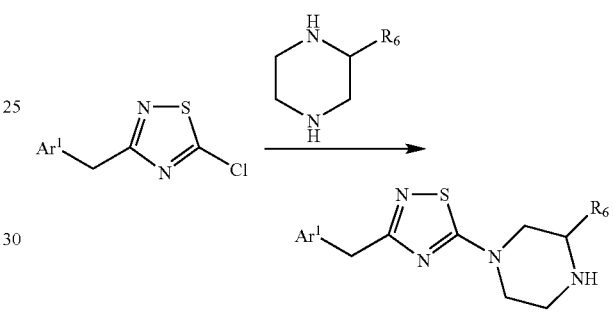

A cyclic diamine represented by the structural formula (A″) (such as, but not limited to, the optionally $R_6$-substituted piperazine derivative shown in the above scheme) (50 mmole) was dissolved in ethanol (EtOH) (10-20 ml) and a 3-(substituted benzyl)-5-chloro-1,2,4-thiadiazole derivative (10 mmole) from example 2 (in the above scheme, $Ar^1$ designates an optionally monosubstituted or polysubstituted phenyl group, thus the derivative corresponds to structural formula (III) wherein $R_{12}$ and $R_{13}$ are both hydrogen) was added in portions. The reaction mixture was refluxed until the reaction was complete. The course of the reaction was monitored by thin layered chromatography (TLC) in an eluent mixture of DCM-EtOH 5:1. When reaction was complete (usually after 3 to 6 hours), the reaction mixture was evaporated to dryness. The residue was dissolved in water and the product was extracted with DCM. The organic phase was washed with water in order to remove the traces of the diamine then it was dried over $MgSO_4$ and evaporated to dryness. The purity of the product was checked by TLC in an eluent mixture DCM:EtOH 5:1 containing some drop of 25% aq. ammonium hydroxide solution. If the TLC showed apolar impurities the product was dissolved in 5% aqueous HCl solution and the impurities were washed away with ethyl-acetate. The aqueous phase was made alkaline (pH: 10-11) with 10% aqueous NaOH solution and the product was extracted with DCM. The following data were obtained for certain species:

3-methyl-1-[3-(4-methyl-benzyl)-[1,2,4]thiadiazol-5-yl]-piperazine: starting from 3.37 g of 5-chloro-3-(4-methylbenzyl)-[1,2,4]thiadiazole (15 mmol) and a 5-fold excess of 2-methyl-piperazine, 4.05 g of the title compound was obtained after 3 hours reaction time (94% yield).

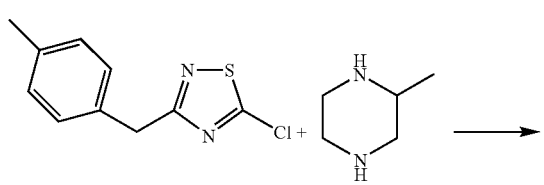

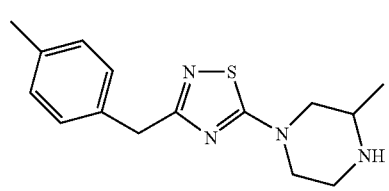

1-[3-(4-fluoro-benzyl)-[1,2,4]thiadiazol-5-yl]-piperazine: starting with 3.43 g of 5-chloro-3-(4-fluorobenzyl)-[1,2,4]thiadiazole (15 mmol), 3.73 g of the title compound was obtained after 6 hours reaction in the presence of a 5-fold excess of piperazine (89% yield).

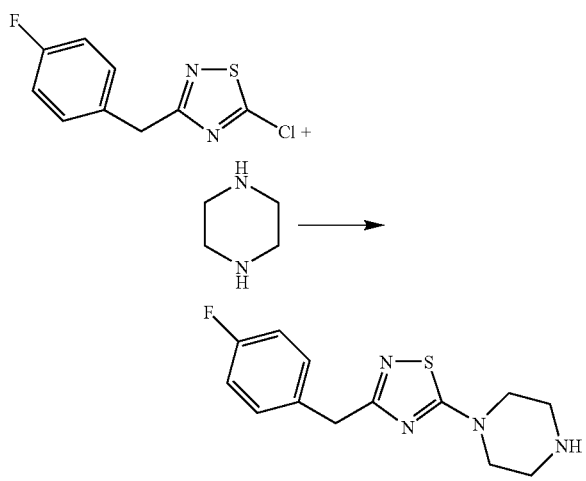

1-[3-(3-methoxy-benzyl)-[1,2,4]thiadiazol-5-yl]-piperazine: starting from 2.41 g 5-chloro-3-(4-fluorobenzyl)-[1,2,4]thiadiazole (10 mmol) and a 5-fold excess of piperazine (4.31 g), 2.65 g of the title compound was obtained after 5 hours reaction time (91% yield).

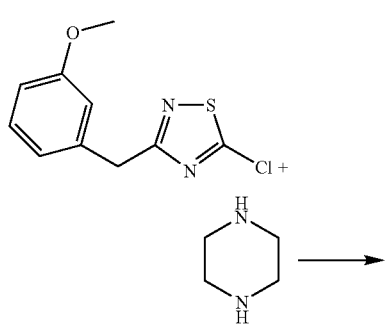

-continued

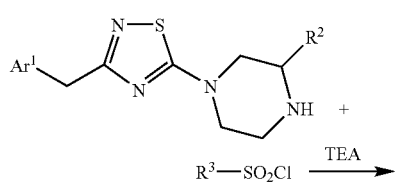

The following intermediate compounds have also been synthesised using these experimental conditions:
1-[3-(4-Fluoro-benzyl)-[1,2,4]thiadiazol-5-yl]-1,4-diazepine,
3-Methyl-1-[3-(4-methyl-benzyl)-[1,2,4]thiadiazol-5-yl]-piperazine
1-[3-(3-Methoxy-benzyl)-[1,2,4]thiadiazol-5-yl]-piperazine,
1-[3-(4-Fluoro-benzyl)-[1,2,4]thiadiazol-5-yl]-piperazine,
3-Methyl-1-[3-(4-Fluoro-benzyl)-[1,2,4]thiadiazol-5-yl]-piperazine
3-Methyl-1-[3-(4-Chloro-benzyl)-[1,2,4]thiadiazol-5-yl]-piperazine
1-[3-(4-Chloro-benzyl)-[1,2,4]thiadiazol-5-yl]piperazine,
1-[3-(4-methyl-benzyl)-[1,2,4]thiadiazol-5-yl]-piperazine,
3-Methyl-1-[3-benzyl-[1,2,4]thiadiazol-5-yl]-piperazine,
1-[3-benzyl-[1,2,4]thiadiazol-5-yl]-piperazine,
2-{4-[3-(4-fluorobenzyl)-1,2,4-thiadiazol-5-yl]piperazin-1-yl}ethanamine
2-{4-[3-benzyl-1,2,4-thiadiazol-5-yl]piperazin-1-yl}ethanamine,
2-{4-[3-(4-chlorobenzyl)-1,2,4-thiadiazol-5-yl]piperazin-1-yl}ethanamine, and
2-{4-[3-(4-methylbenzyl)-1,2,4-thiadiazol-5-yl]piperazin-1-yl}ethanamine.

In addition, compounds 113, 114 and 185 to 188 were synthesised according to these experimental conditions using N-substituted piperazine reagents (N-benzylpiperazine, N-(1,3-benzodioxol-5-ylmethyl)-piperazine, N-(2-methylphenyl)-piperazine, N-(2-ethoxyphenyl)-piperazine, N-(2-fluorophenyl)-piperazine and N-(3-trifluoromethylphenyl)-piperazine, respectively). However, for the isolation of the final product, the organic phase (DCM) was first washed with a 5% aqueous citric acid solution, water, a 5% aqueous Na2CO3 solution, and water, respectively. The organic phase was separated, dried over MgSO4, filtered and, evaporated to dryness. The residue was crystallised by diethyl ether to yield the desired compound.

EXAMPLE 4

N-arylsulfonylation, N-arylalkylsulfonylation, N-arylalkenyl-sulfonylation and N-alkylsulfonylation of 3-(substituted benzyl)-1,2,4-thiadiazol-5-ylpiperazine Derivatives and Analogues thereof

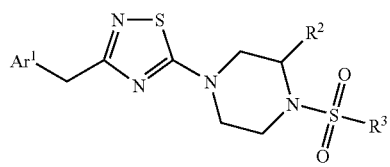

To a 3-(substituted benzyl)-1,2,4-thiadiazol-5-ylpiperazine derivative, or analogue thereof, obtained according to the procedure of example 3 (250 μmole) and dissolved in DCM (2-3 ml), triethylamine (TEA) (500 μmole) was added. The reaction mixture was stirred at room temperature and then the appropriate sulfonyl chloride derivative (wherein $R^3$ may be aryl, arylalkyl, arylalkenyl or alkyl) (250 μmole) was added. The reaction mixture was further stirred at room temperature until total consumption of the starting products. The course of the reaction was monitored by TLC using dichloroethane (DCE)-EtOH 10:1 as an eluent mixture. The reaction time varied between 3 and 5 hours. When the reaction was complete DCM (2-3 ml) was added and the resulting solution was washed with a 5% aqueous citric acid solution (5 ml), water (5 ml), a 5% aqueous $Na_2CO_3$ solution, and water (5 ml), respectively. The organic phase was separated, dried over $MgSO_4$, filtered and, evaporated to dryness. The residue was crystallised by diethyl ether to yield the desired compound.

The following data were obtained for the synthesized species:

compound 60: 1-[4-methoxyphenylsulfonyl]-4-[3-(4-methylbenzyl)-1,2,4-thiadiazol-5-yl]-2-methylpiperazine: starting from 3-methyl-1-[3-(4-methylbenzyl)-[1,2,4]thiadiazol-5-yl]-piperazine (1.25 mmole) and 1 molar equivalent of 4-methoxy-phenylsulphonyl chloride, after 4 hours reaction time the title compound was obtained in 99% yield:

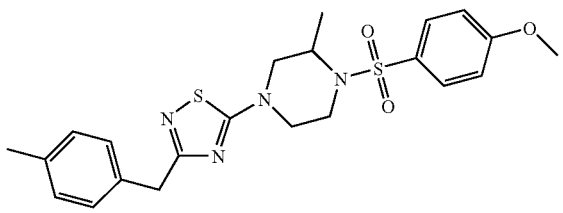

compound 32: 1-[4-methoxyphenylsulfonyl]-4-[3-(4-fluorobenzyl)-1,2,4-thiadiazol-5-yl]piperazine: starting from 400 mg 1-[3-(4-fluoro-benzyl)-[1,2,4]thiadiazol5-yl]-piperazine (1.237 mmole) and 1 molar equivalent of 4-methoxy-phenylsulphonyl chloride, 453 mg of the title compound was obtained after 3 hours of reaction (70% yield). -

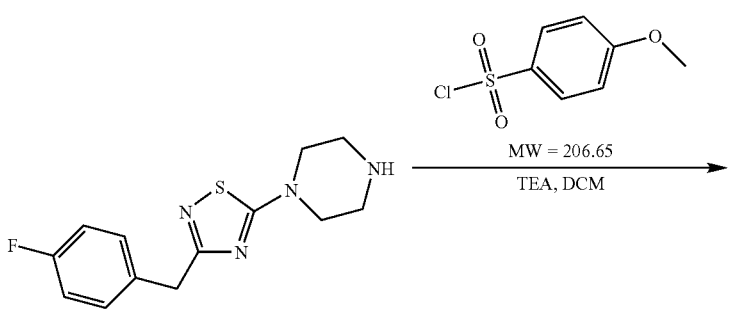

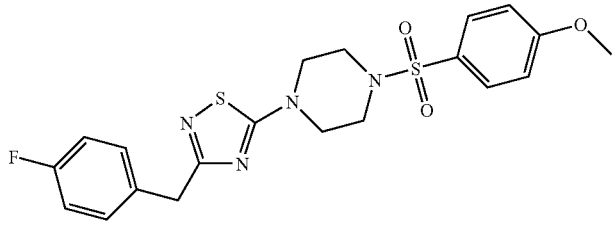

60 compound 44: 1-[3-methoxyphenylsulfonyl]-4-[3-(4-fluorobenzyl)-1,2,4-thiadiazol-5-yl]piperazine: starting from 80 mg 1-[3-(4-Fluoro-benzyl)-[1,2,4]thiadiazol-5-yl]-piperazine (0.287 mmol) and 1 molar equivalent of 3-methoxyphenylsulfonyl chloride, 102 mg of the title compound was obtained after 4 hours of reaction in 79% yield.

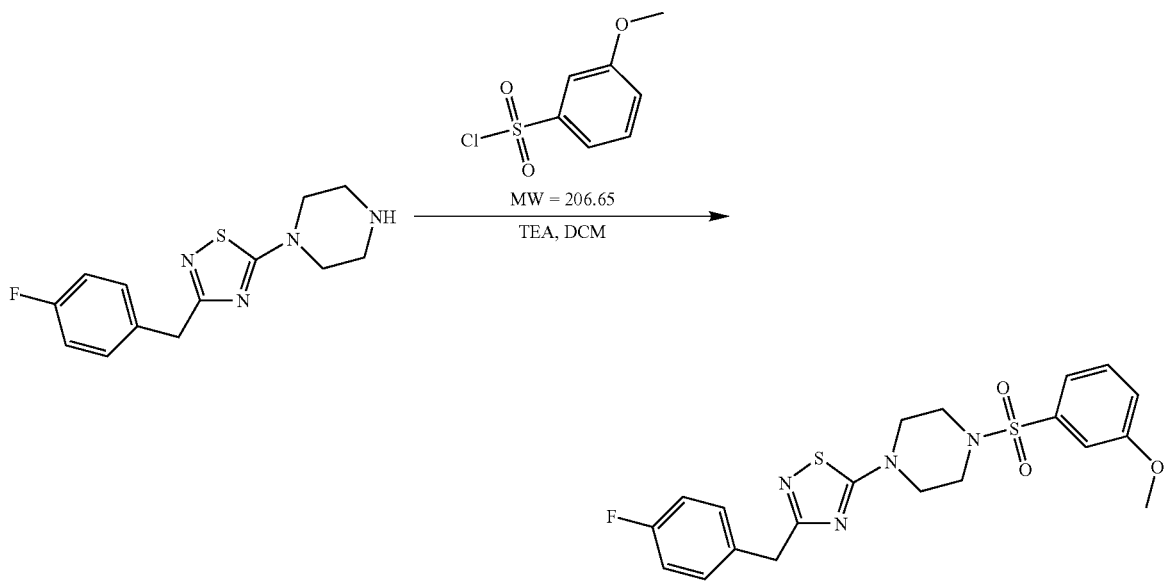

compound 53: 1-[4-methoxyphenylsulfonyl]-4-[3-(3-methoxybenzyl)-1,2,4-thiadiazol-5-yl]piperazine: starting from 150 mg 1-[3-(3-methoxybenzyl)-[1,2,4]thiadiazol-5-yl]-piperazine (0.517 mmol) and 1 molar equivalent of 4-methoxyphenylsulfonyl chloride, 156 mg of the title compound was obtained after 5 hours of reaction in 66% yield.

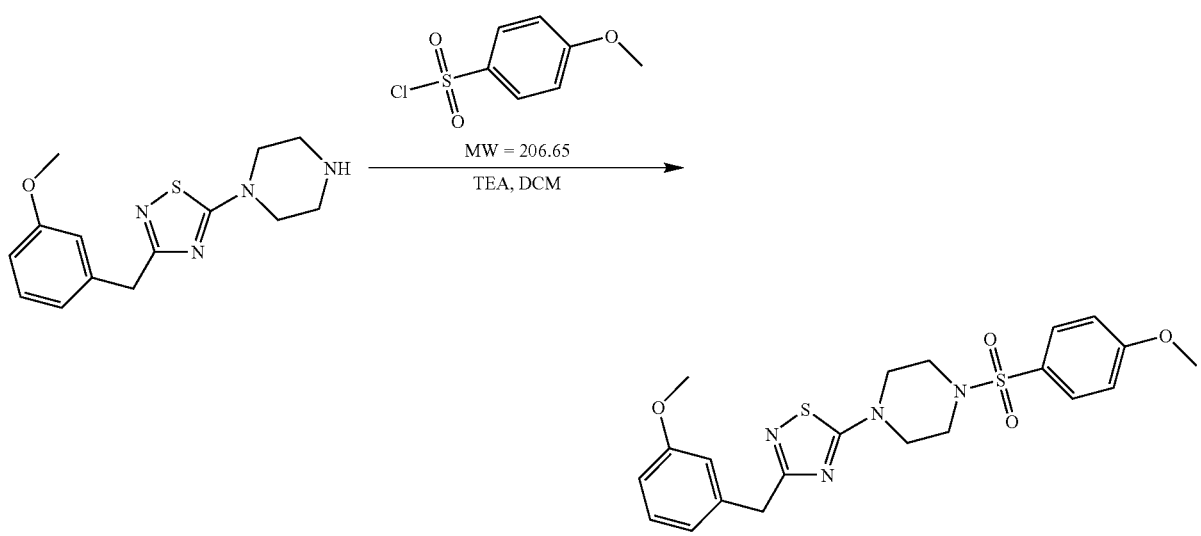

Compounds 30 to 75 and 193 to 217 were also synthesised, using these experimental conditions, starting from various arylsulfonyl chlorides (thus corresponding to formula (A) wherein X is $SO_2$), as well as compounds 76 to 80 starting from benzylsulfonyl chloride or styrylsulfonyl chloride (thus corresponding to formula (A) wherein X is $SO_2$—$CH_2$ or $SO_2$—CH=CH) and compounds 81 to 85 starting from various alkylsulfonyl chlorides (all of them included in table 1 below).

EXAMPLE 5

N-acylation of 3-(substituted benzyl)-1,2,4-thiadiazol-5-ylpiperazine Derivatives and Analogues thereof To a 3-(substituted benzyl)-1,2,4-thiadiazol-5-ylpiperazine derivative, or analogue thereof, obtained according to the procedure of example 3 (approximately 250 mmole) and dissolved in DCM (2-3 ml), triethylamine (TEA) (2.0 molar equivalents) was added. The reaction mixture was stirred at room temperature and then the appropriate acyl chloride derivative (1.0 molar equivalent) was added. The reaction mixture was further stirred at room temperature until total consumption of the starting products. The course of the reaction was monitored by TLC using dichloroethane (DCE)-EtOH 10:1 as an eluent mixture. The reaction time varied between 3-5 h in our practice. When the reaction was complete, DCM (2-3 ml) was added to it and the resulting solution was washed with a 5% aqueous citric acid solution (5 ml), water (5 ml), a 5% aqueous $Na_2CO_3$ solution, and water (5 ml), respectively. The organic phase was separated, dried over $MgSO_4$, filtered and, evaporated to dryness. The residue was crystallised by diethyl ether to yield the desired compound.

For instance 4-phenylacetyl-1-[3-(4-fluorobenzyl)-1,2,4-thiadiazol-5-yl]-piperazine (compound I) was obtained from 1-[3-(4-fluorobenzyl)-1,2,4-thiadiazol-5-yl]piperazine and phenylacetyl chloride, and characterised by mass spectrometry: MS (m/z): 397.18 ([M+H]$^+$, 100).

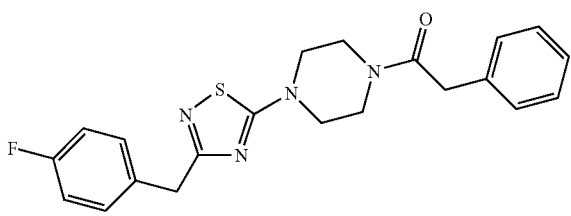 [SMILES: O=C(Cc1ccccc1)N1CCN(c2nc(Cc3ccc(F)cc3)ns2)CC1]

Compounds 1-8, 86-90, 94-112, 115-184 and 189-191 were synthesised using these experimental conditions (table 1 below).

EXAMPLE 6

N-alkylation of 3-(substituted benzyl)-1,24-thiadiazol-5-ylpiperazine Derivatives and Analogues thereof To 3-(substituted benzyl)-1,2,4-thiadiazol-5-ylpiperazine derivative, or analogue thereof, obtained according to the procedure of example 3 (approximately 250 µmole) and dissolved in DCM (2-3 ml), triethylamine (TEA) (2.0 molar equivalent) was added. The reaction mixture was stirred at room temperature and then the appropriate alkyl chloride derivative (1.0 molar equivalent) was added. The reaction mixture was further stirred at room temperature until total consumption of the starting products. The course of the reaction was monitored by TLC using dichloroethane (DCE)-EtOH 10:1 as an eluent mixture. The reaction time varied between 3 and 5 hours. When the reaction was complete, DCM (2-3 ml) was added to it and the resulting solution was washed with 5% aq. citric acid solution (5 ml), water (5 ml), 5% aq. $Na_2CO_3$ solution, and water (5 ml), respectively. The organic phase was separated, dried over $MgSO_4$, filtered and, evaporated to dryness. The residue was crystallized by diethyl ether to yield the desired compound. The final compounds 91-93 were synthesised using these experimental conditions (table 1 below) and starting from cinnamyl chloride.

EXAMPLE 7

Urea-Linkage Formation

To a solution of an optionally substituted aryl isocyanate derivative (approximately 250 µmole) in tetrahydrofuran with a trace of DMF (2-3 ml) diisopropylethyl amine (2.2 equivalent) was added. Subsequently, 1 equivalent of a substituted piperazine derivative was added. The reaction mixture was stirred at room temperature until total consumption of the starting products. The course of the reaction was monitored by TLC using dichloroethane (DCE)-EtOH 10:1 as an eluent mixture. Suitable reaction times were between 3 and 5 hours. When reaction was complete, the reaction mixture was evaporated until almost dry. DCM (2-3 ml) was added to it and the resulting mixture was washed with a 5% aqueous citric acid solution (5 ml), water (5 ml), a 5% aqueous $Na_2CO_3$ solution, and water (5 ml), respectively. The organic phase was separated, dried over $MgSO_4$, filtered and, evaporated to dryness. The residue was crystallised by diethyl ether to yield the desired compound. Compounds 9 to 29 were synthesised using these experimental conditions (table 1 below).

EXAMPLE 8

Control of the Structure of the Synthesised Compounds

A set of compounds falling within the scope of structural formulae (A), (B), (C) and (D) has been synthesised. An overview of these exemplary compounds and their chemical structure is provided in Table 1. The structure of the compounds was checked using both mass spectra (hereinafter referred as MS) and high performance liquid chromatography (hereinafter referred as HPLC).

HPLC analysis was performed on a LaChrom™ HPLC system (Merck-Hitachi, using a LiChroCART™ 30-4 Purospher STAR RP-18, endcapped, 3 µm column (Merck) and a gradient elution of eluant A (Acetonitrile-$H_2O$=5:95 with 20 mM, ammonium formate buffer, pH 7.4) and eluant B (Acetonitrile-$H_2O$=80:20 with 20 mM, ammonium formate buffer, pH 7.4, programmed as follows:

| Min. | A % | B % |
|---|---|---|
| 0.0 | 100 | 0 |
| 3.0 | 5 | 95 |
| 3.4 | 5 | 95 |
| 3.5 | 100 | 0 |
| 4.0 | 100 | 0 |

Elution was performed at room temperature with a flow rate of 2.0 mL/min. Samples were applied as 2.5 µl of a solution of about 2 mg/mL. Detection was performed at 220 nm. Parameters of the gradient programs were occasionally adjusted to the properties of the analysed compound in order to reach the optimal separation power.

Mass spectrometry was performed on either a Mariner™ (Perspective Biosystems) ES/APCI (Atmospheric Pressure Chemical Ionization) interface or a Micromass® ZQ2000 MS instrument (Waters Corp.) with electrospray (ESI) interface integrated with MUX™ technology (Waters Corp.). The ionization mode used Electrospray in a positive mode, with centroid data analysis and mass in the range of 120-700 µ.

EXAMPLE 9

Construction of an α-Synuclein Over-Expressing Cell Line

An α-synuclein expression plasmid was constructed by sub-cloning the NcoI/XhoI fragment from 212T-SYN(WT) (Griffioen et al., Biochem Biophys Acta (2006) 1762(3):312-318) containing the cDNA of human wild type α-synuclein correspondingly into a standard mammalian expression vector pcDNA3.1 resulting in plasmid pcDNA3.1-SYNwt. Plasmid pcDNA3.1 and pcDNA3.1-SYNwt were transfected to human neuroblastoma cells (ATCC No. CRL-2267) and independent clonal lines with the plasmids stably integrated into the genome were selected. These resulted in cell lines named M17 (transfected with pcDNA3.1) and M17-SYNwt (transfected with pcDNA3.1-SYNwt). Over-expression of α-synuclein in M17-SYNwt cell lines was confirmed by Western analysis.

EXAMPLE 10

Use of α-Synuclein Expressing Cells as a Model for Neuronal Degradation

Due to the high levels of α-synuclein M17-SYNwt cells are exquisitely sensitivity to paraquat, a well-known risk factor of synuclein-dependent neuronal degeneration. In degenerated or dead cells lactate dehydrogenase (LDH) is leaked out of the cells into the extracellular environment due to a loss of plasma-membrane integrity. This principle was used to determine cytotoxicity by quantifying the level of leaked LDH into the growth medium.

The detailed method for determining α-synuclein cytotoxicity was as follows: From appropriate precultures of M17 and M17-SYN cells were seeded at 50000 cells/cm$^2$ in Optimem Reduced Serum without phenol red (InVitrogen, Cat. 31985-047) supplemented with 5% fetal calf serum, 1 mM sodium pyruvate, 1× non-essential amino acids, 500 µg/ml G418 0.5× antibiotic/antimycotic. After 3 hours of incubation at 37° C./5% CO$_2$ paraquat was added to the cells (final concentration of 32 mM), together with the test compound and the cells were further incubated for 40 hours. Subsequently, LDH activity was determined using Promega Cytotox 96 Non-Radioactive cytotoxicity assay, (Cat. G1780) according to the supplier's instructions.

FIG. 1 shows that treatment of M17-SYNwt cells, but not of M17 cells with paraquat led to a relatively high level of LDH leaked into the medium demonstrating that α-synuclein mediates cellular degeneration or cell death in response to paraquat.

EXAMPLE 11

Use of the α-Synuclein Expressing Cells in the Screening of Exemplary Compounds

This α-synuclein expressing neuroblastoma cells made it possible to assess the ability of novel compounds to counteract α-synuclein cytotoxicity. Active inhibitors of α-synuclein cytotoxicity were found to provoke a decrease of LDH leakage in paraquat-treated M17-SYNwt cells. Since this method monitors leaked LDH from degenerated or dead cells only non-toxic compounds will be identified as active inhibitors of α-synuclein-mediated cytotoxicity. Lack of toxicity is an important characteristic for compounds to be used as a medicament to patients in need. A compound was considered to be active in this test when it inhibits α-synuclein cytotoxicity by more than 25% relative to untreated M17-SYNwt cells at a concentration of 20 µg/mL or lower. In the experiments, the control group consisted of M17-SYNwt cells treated with DMSO, the untreated paraquat group consisted of M17-SYNwt cells treated with paraquat and DMSO, and the treated paraquat group consisted of M17-SYNwt cells treated with paraquat and the test compound dissolved in DMSO.

In order to determine EC$_{50}$ compounds were tested at different concentrations ranging from non-effective (thus at a relatively low concentration) to an effective (relatively high) concentration of test compound. These data were also used for calculation of percent inhibition (% I). Percent inhibition was calculated as the synuclein toxicity inhibition by the compound in treated paraquat cells, relative to the synuclein cytotoxicity in untreated paraquat cells. This corresponds to the following equation:

$$\frac{(\text{LDH release of treated paraquat cells at non-effective concentration of test cmpd}) - (\text{LDH release of treated paraquat cells at most effective concentration of test cmpd})}{(\text{LDH release of untreated paraquat cells}) - (\text{LDH release control cells})} * 100\%$$

Figure 2:
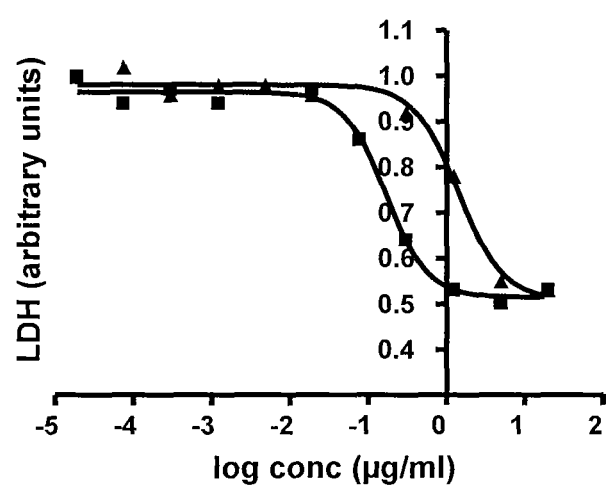
FIG. 2 shows the inhibition of α-synuclein mediated toxicity by two exemplary compounds of this invention, being N-(2,6-dimethylphenyl)-4-[3-(4-fluorobenzyl)-1,2,4-thiadiazol-5-yl]-2-methylpiperazine-1-carboxamide (compound 19, squares) and 2-phenyl-N-{2-[4-[3-(4-fluorobenzyl)-1,2,4-thiadiazol-5-yl]piperazin-1-yl]ethyl}butanamide (compound III, triangles).

Compounds 19 (N-(2,6-dimethylphenyl)-4-[3-(4-fluorobenzyl)-1,2,4-thiadiazol-5-yl]-2-methylpiperazine-1-carboxamide) and 111 (2-phenyl-N-{2-[4-[3-(4-fluorobenzyl)-1,2,4-thiadiazol-5-yl]piperazin-1-yl]ethyl}butanamide) were tested using the α-synuclein cytotoxicity assay as described above. FIG. 2 shows that these compounds (compound 19=squares; compound 111=triangles) were able, in a dose-dependent manner, to reduce LDH activity in the medium demonstrating that the respective compounds alleviate α-synuclein-mediated cytotoxicity.

EXAMPLE 12

Inhibition of Synuclein-Mediated Toxicity 1,2,4-thiadazole compounds made according to the methods described herein were screened for activity using the α-synuclein cytotoxicity assay as described above. Dose responses were carried out on all compounds found to be active (10 point curves in duplicate). Although the pharmacological properties of the compounds disclosed in this invention vary with structural change as expected, active compounds most particularly possess EC$_{50}$ in a cell-based assay of synuclein cytotoxicity in a range from about 0.0001 to 10 µM. Data obtained for the compounds of Table 1 are presented in Table 2. Based on these results the novel class of inhibitors of α-synuclein cytotoxicity as claimed herein was identified.

EXAMPLE 13

In Vivo Inhibition of Synuclein-Mediated Instigated Loss of Substantia Nigra Neurons In order to model neuronal loss in the substantia nigra region of the brain, mice were treated with paraquat (intraperitoneal) at a dose not higher than 8 mg/kg/day for a continuous period of 15-100 days. These mice were also chronically co-treated during that period with:
compound 60 (1-[4-methoxyphenylsulfonyl]-4-[3-(4-methylbenzyl)-1,2,4-thiadiazol-5-yl]-2-methylpiperazine), or
compound 32 (1-[4-methoxyphenylsulfonyl]-4-[3-(4-fluorobenzyl)-1,2,4-thiadiazol-5-yl]piperazine), or compound 53 (1-[4-methoxyphenylsulfonyl]-4-[3-(3-methoxy-benzyl)-1,2,4-thiadiazol-5-yl]piperazine), each being administered at a dose not higher than 20 mg/kg body weight/day), or by vehicle only (no active compound). Mice treatment by means of vehicle or a compound of the invention started 2 days before administration of paraquat.

At the end of the treatment period, mice were sacrificed and the corresponding brains were used for immunohistochemical analysis. The substantia nigra brain region has a relatively high percentage of cells with high levels of tyrosine hydroxylase. Using antibodies raised against tyrosin hydroxylase (anti-tyrosin hydroxylase), tyrosine hydroxylase containing neurons in the brains were detected. Quantitative and comparative analysis of the tyrosin hydroxylase-positive stained substantia nigra areas revealed a significantly larger TH-positive area in mice treated with compound (group 3) versus vehicle treated mice (group 2). The TH-positive area of group 3 is similar of that observed in mouse group 1 (not treated with paraquat), suggesting a strong and possibly complete inhibition of degeneration. These results indicate that the corresponding compound is able to inhibit paraquat-triggered degeneration of substantia nigra cells in vivo.

Figure 3:
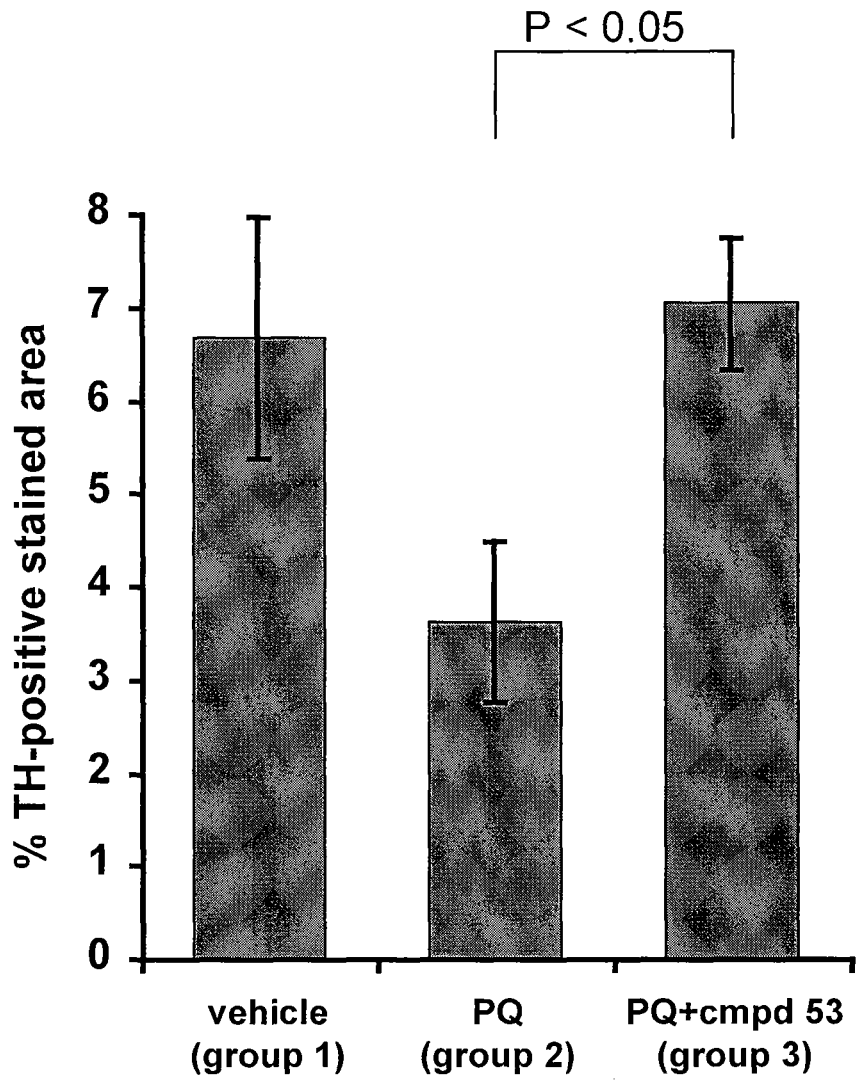
FIG. 3 shows inhibition of paraquat-triggered degeneration of substantia nigra cells, using 1-[4-methoxyphenylsulfonyl]-4-[3-(3-methoxybenzyl)-1,2,4-thiadiazol-5-yl]piperazine (compound 53), in vivo.

FIG. 3 shows that compound 53 protects dopaminergic substantia nigra neurons against paraquat-triggered degeneration. Three groups of mice were treated with either paraquat and compound 53 (group 3; n=6), or paraquat and vehicle of compound 53 (group 2; n=4), or vehicle paraquat and vehicle of compound 53 (group 1; n=3). After 8 weeks treatment, brains were collected and used for immunohistochemistry (6 sections per brain per staining). Mouse brain were fixed overnight in 4% paraformaldehyde, and stored in PBS with 0.1% sodium azide. Free-floating vibratome-sections of 40 μm were prepared and stored in PBS containing 0.1% sodium azide. 6 midbrain sections of each brain were selected for tyrosine hydroxylase (TH) immunohistochemistry. After quenching the endogenous peroxidase by using 1.5% $H_2O_2$ in 1/1 PBS/methanol, sections were blocked in 10% fetal calf serum (30 minutes) and subsequently incubated overnight at 4° C. with mouse anti-TH (1:10.000; MAB318; Chemicon International). After washing and incubation with a HRP-conjugated goat-anti-mouse secondary antibody (1:500; P 0447; DakoCytomation) for 60 minutes, immunostaining was visualized with 3,3'-diaminobenzidine. Sections were counterstained with Mayers hematoxylin. Per mouse, the median % TH-positive areas (of the substantia nigra regions) was determined. Results shown (FIG. 3) are the mean±SEM of the median % TH-positive areas of the different mouse brains of each group.

EXAMPLE 14

In Vivo Inhibition of 6-hydroxydopamine (6-OHDA) Instigated Loss of Substantia Nigra Neurons Unilateral substantia nigra lesions are obtained by stereotactic striatal injections of 6-hydroxydopamine in brains of living rats as described by Vercammen et al. in *Molecular Therapy*, 14(5) 716-723 (2006). These rats are also chronically co-treated with the same exemplary compounds and at the same dose as mentioned in example 13, or by vehicle only (no active compound). Daily treatment of compound or vehicle is started preferably 1 or 2 days before administration of 6-OHDA and lasts between 7 to 30 days after the 6-OHDA injection.

At the end of the treatment period, rats are sacrificed and the corresponding brains are used for immunohistochemical analysis. The substantia nigra brain region has a relatively high percentage of cells with high levels of tyrosine hydroxylase. Using antibodies raised against tyrosin hydroxylase (anti-tyrosine hydroxylase) tyrosine hydroxylase containing neurons in the brains are detected. The nigral lesion volumes and/or the tyrosine hydroxylase positive cell numbers are quantified as described in Vercammen et al. (cited supra). This analysis reveals that:

- the nigral lesion volumes are significantly reduced in rats treated with a compound according to this invention, as compared to vehicle treated rats, thus indicating that the compound is able to inhibit 6-OHDA triggered degeneration of substantia nigra cells in vivo; and
- tyrosine hydroxylase positive cell numbers are higher in rats treated with a compound according to this invention as compared to vehicle treated rats, thus providing confirmation that the compound is able to inhibit 6-OHDA triggered degeneration of substantia nigra cells in vivo.

EXAMPLE 15

In Vitro Inhibition of α-Synuclein Aggregation

α-synucleinopathies are characterised by aggregation of α-synuclein in neurons. Aggregation of purified α-synuclein is performed essentially as described by Gerard et al. *FASEB*. 20(3):524-6 (2006). 20-100 μg purified α-synuclein (Sigma; S7820) at a concentration of about 2.5 μg/mL is incubated in the presence of spermin (250 μM) or paraquat (32 mM) or 6-hydroxydopamine (400 μM) or vehicle in a 384 well plate. Spermin, paraquat and 6-hydroxydopamine promote the α-synuclein aggregation process. Aggregation kinetics is determined by measuring turbidity at 340 nm, every 1-15 minutes for at least one hour. The same exemplary compounds as mentioned in example 13, or vehicle only, is added to the different α-synuclein mixtures described above. This analysis reveals that, when a compound is present, the measured turbidity is lower compared to reactions containing vehicle only. This finding shows that the compound is able to inhibit aggregation of α-synuclein.

TABLE 1

| No. | Compound name | Compound structure |
| --- | --- | --- |
| 1 | 4-phenylacetyl-1-[3-(4-fluorobenzyl)-1,2,4-thiadiazol-5-yl]piperazine | 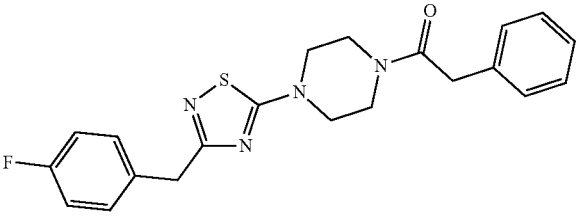 [SMILES: O=C(Cc1ccccc1)N1CCN(c2nc(Cc3ccc(F)cc3)ns2)CC1] |

TABLE 1-continued

| No. | Compound name | Compound structure |
|---|---|---|
| 2 | 4-(4-fluorophenylacetyl),1-[3-(4-fluorobenzyl)-1,2,4-thiadiazol-5-yl]piperazine | 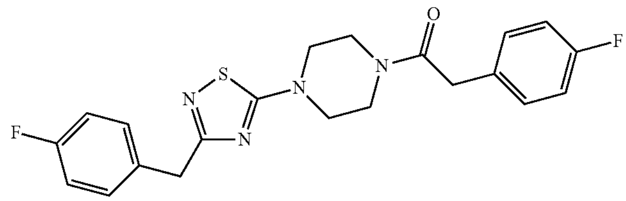 [SMILES: O=C(Cc1ccc(F)cc1)N1CCN(c2nc(Cc3ccc(F)cc3)ns2)CC1] |
| 3 | 1-(4-fluorophenylacetyl)-4-[3-(4-methylbenzyl)-1,2,4-thiadiazol-5-yl]-2-methylpiperazine | 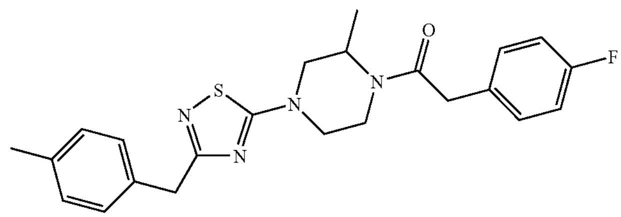 [SMILES: Cc1ccc(Cc2nsc(N3CCN(C(=O)Cc4ccc(F)cc4)C(C)C3)n2)cc1] |
| 4 | 1-(4-methoxyphenylacetyl)-4-[3-(4-fluorobenzyl)-1,2,4-thiadiazol-5-yl]-2-methylpiperazine | 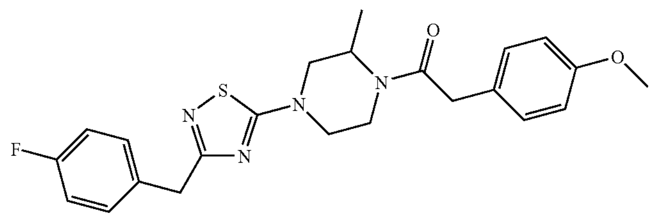 [SMILES: COc1ccc(CC(=O)N2CCN(c3nc(Cc4ccc(F)cc4)ns3)CC2C)cc1] |
| 5 | 1-phenylacetyl-4-[3-(4-fluorobenzyl)-1,2,4-thiadiazol-5-yl]-2-methylpiperazine | 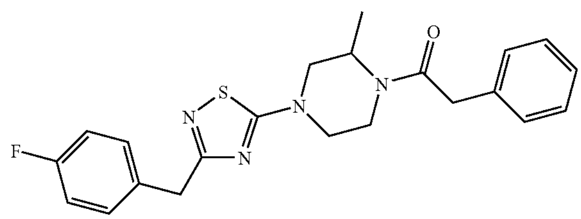 [SMILES: CC1CN(c2nc(Cc3ccc(F)cc3)ns2)CCN1C(=O)Cc1ccccc1] |
| 6 | 1-(4-fluorophenylacetyl)-4-[3-(4-fluorobenzyl)-1,2,4-thiadiazol-5-yl]-2-methylpiperazine | 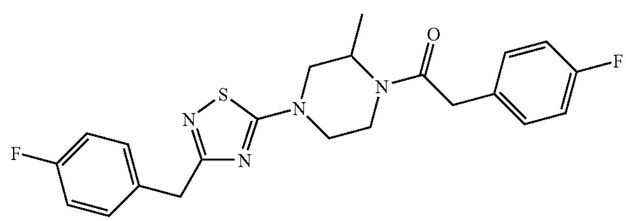 [SMILES: CC1CN(c2nc(Cc3ccc(F)cc3)ns2)CCN1C(=O)Cc1ccc(F)cc1] |
| 7 | 1-[chloro(phenyl)acetyl]-4-[3-(4-fluorobenzyl)-1,2,4-thiadiazol-5-yl]-2-methylpiperazine | 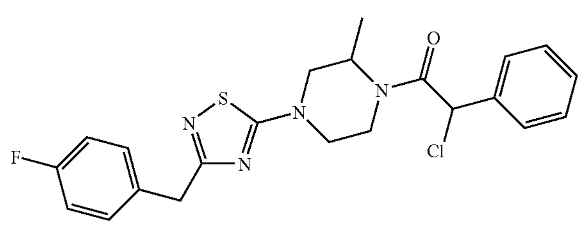 [SMILES: CC1CN(c2nc(Cc3ccc(F)cc3)ns2)CCN1C(=O)C(Cl)c1ccccc1] |
| 8 | 1-(2-phenylbutanoyl)-4-[3-(4-fluorobenzyl)-1,2,4-thiadiazol-5-yl]-2-methylpiperazine | 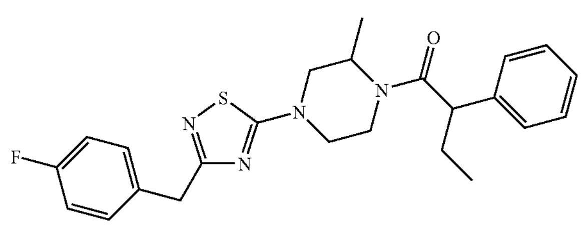 [SMILES: CCC(C(=O)N1CCN(c2nc(Cc3ccc(F)cc3)ns2)CC1C)c1ccccc1] |

TABLE 1-continued

| No. | Compound name | Compound structure |
|---|---|---|
| 9 | N-(3-fluorophenyl)-4-[3-(4-fluorobenzyl)-1,2,4-thiadiazol-5-yl]piperazine-1-carboxamide | 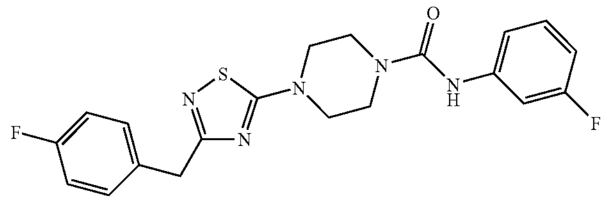 [SMILES: O=C(Nc1cccc(F)c1)N1CCN(c2nc(Cc3ccc(F)cc3)ns2)CC1] |
| 10 | N-(2-methylphenyl)-4-[3-(4-fluorobenzyl)-1,2,4-thiadiazol-5-yl]-2-methylpiperazine-1-carboxamide | 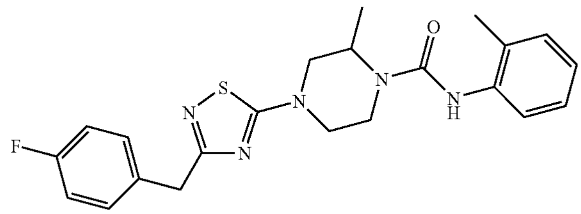 [SMILES: Cc1ccccc1NC(=O)N1CCN(c2nc(Cc3ccc(F)cc3)ns2)CC1C] |
| 11 | N-(4-ethylphenyl)-4-[3-(4-fluorobenzyl)-1,2,4-thiadiazol-5-yl]-2-methylpiperazine-1-carboxamide | 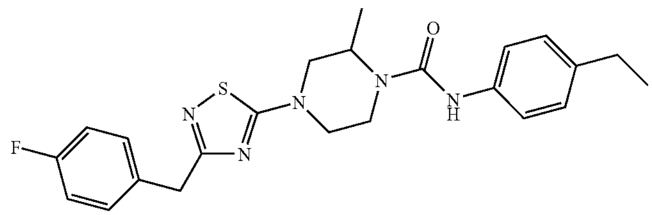 [SMILES: CCc1ccc(NC(=O)N2CCN(c3nc(Cc4ccc(F)cc4)ns3)CC2C)cc1] |
| 12 | N-(2-ethylphenyl)-4-[3-(4-fluorobenzyl)-1,2,4-thiadiazol-5-yl]-2-methylpiperazine-1-carboxamide | 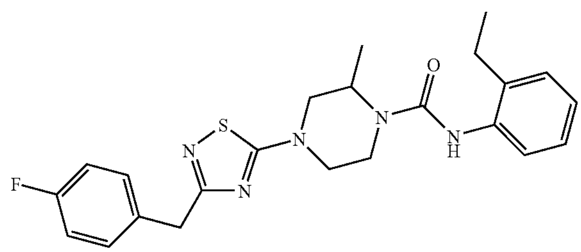 [SMILES: CCc1ccccc1NC(=O)N1CCN(c2nc(Cc3ccc(F)cc3)ns2)CC1C] |
| 13 | N-phenyl-4-[3-(4-fluorobenzyl)-1,2,4-thiadiazol-5-yl]-yl]piperazine-1-carboxamide | 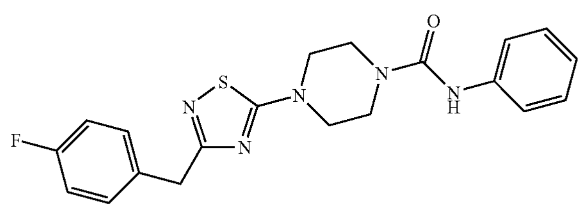 [SMILES: O=C(Nc1ccccc1)N1CCN(c2nc(Cc3ccc(F)cc3)ns2)CC1] |
| 14 | N-(4-ethoxyphenyl)-4-[3-(4-fluorobenzyl)-1,2,4-thiadiazol-5-yl]-2-methylpiperazine-1-carboxamide | 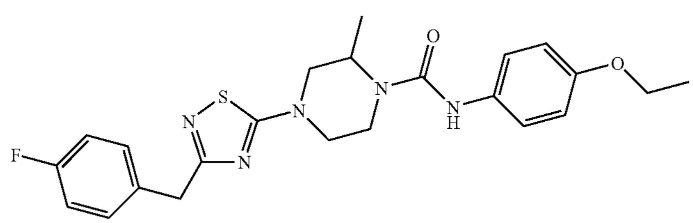 [SMILES: CCOc1ccc(NC(=O)N2CCN(c3nc(Cc4ccc(F)cc4)ns3)CC2C)cc1] |
| 15 | N-(2-methylphenyl)-4-[3-(4-fluorobenzyl)-1,2,4-thiadiazol-5-yl]piperazine-1-carboxamide | 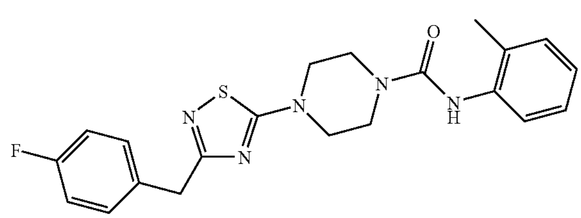 [SMILES: Cc1ccccc1NC(=O)N1CCN(c2nc(Cc3ccc(F)cc3)ns2)CC1] |

TABLE 1-continued

| No. | Compound name |
|---|---|
| 16 | N-(2-fluorophenyl)-4-[3-(4-fluorobenzyl)-1,2,4-thiadiazol-5-yl]piperazine-1-carboxamide |
| 17 | N-(2-trifluoromethylphenyl)-4-[3-(4-fluorobenzyl)-1,2,4-thiadiazol-5-yl]piperazine-1-carboxamide |
| 18 | N-(2-trifluoromethylphenyl)-4-[3-(4-fluorobenzyl)-1,2,4-thiadiazol-5-yl]-2-methylpiperazine-1-carboxamide |
| 19 | N-(2,6-dimethylphenyl)-4-[3-(4-fluorobenzyl)-1,2,4-thiadiazol-5-yl]-2-methylpiperazine-1-carboxamide |
| 20 | N-(2,4-dimethylphenyl)-4-[3-(4-fluorobenzyl)-1,2,4-thiadiazol-5-yl]-2-methylpiperazine-1-carboxamide |
| 21 | N-(2,6-dichlorophenyl)-4-[3-(4-fluorobenzyl)-1,2,4-thiadiazol-5-yl]-2-methylpiperazine-1-carboxamide |
| 22 | N-(3-cyanophenyl)-4-[3-(4-fluorobenzyl)-1,2,4-thiadiazol-5-yl]-2-methylpiperazine-1-carboxamide |

TABLE 1-continued

| No. | Compound name | Compound structure |
|---|---|---|
| 23 | N-(2,4-difluorophenyl)-4-[3-(4-fluorobenzyl)-1,2,4-thiadiazol-5-yl]-2-methylpiperazine-1-carboxamide | 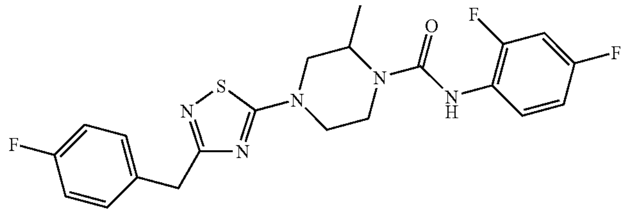 [SMILES: CC1CN(c2nc(Cc3ccc(F)cc3)ns2)CCN1C(=O)Nc1ccc(F)cc1F] |
| 24 | N-(2,6-dimethylphenyl)-4-[3-(4-fluorobenzyl)-1,2,4-thiadiazol-5-yl]piperazine-1-carboxamide | 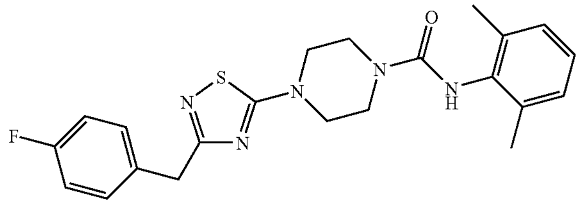 [SMILES: Cc1cccc(C)c1NC(=O)N1CCN(c2nc(Cc3ccc(F)cc3)ns2)CC1] |
| 25 | N-1-naphthyl-4-[3-(4-fluorobenzyl)-1,2,4-thiadiazol-5-yl]-2-methylpiperazine-1-carboxamide | 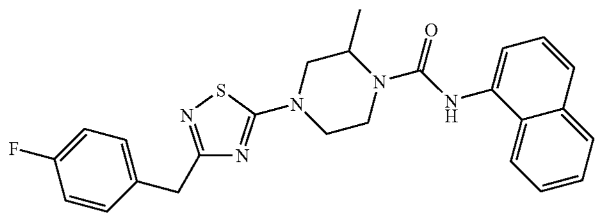 [SMILES: CC1CN(c2nc(Cc3ccc(F)cc3)ns2)CCN1C(=O)Nc1cccc2ccccc12] |
| 26 | N-(3,4-difluorophenyl)-4-[3-(4-fluorobenzyl)-1,2,4-thiadiazol-5-yl]-2-methylpiperazine-1-carboxamide | 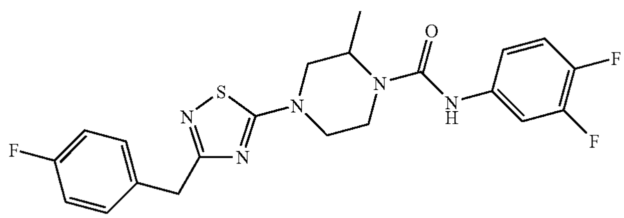 [SMILES: CC1CN(c2nc(Cc3ccc(F)cc3)ns2)CCN1C(=O)Nc1ccc(F)c(F)c1] |
| 27 | N-(2,4-dimethoxyphenyl)-4-[3-(4-fluorobenzyl)-1,2,4-thiadiazol-5-yl]piperazine-1-carboxamide | 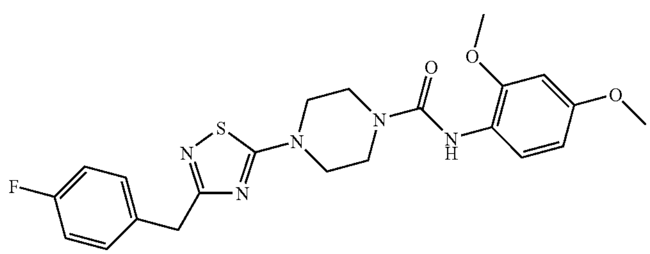 [SMILES: COc1ccc(NC(=O)N2CCN(c3nc(Cc4ccc(F)cc4)ns3)CC2)c(OC)c1] |
| 28 | N-(3,4-difluorophenyl)-4-[3-(4-fluorobenzyl)-1,2,4-thiadiazol-5-yl]piperazine-1-carboxamide | 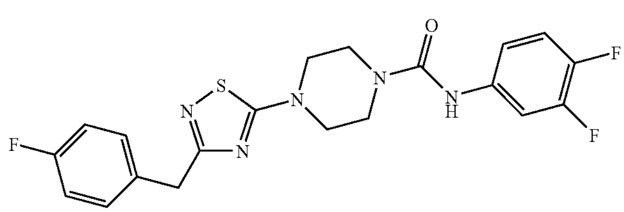 [SMILES: O=C(Nc1ccc(F)c(F)c1)N1CCN(c2nc(Cc3ccc(F)cc3)ns2)CC1] |
| 29 | N-(3,5-dimethoxyphenyl)-4-[3-(4-fluorobenzyl)-1,2,4-thiadiazol-5-yl]-2-methylpiperazine-1-carboxamide | 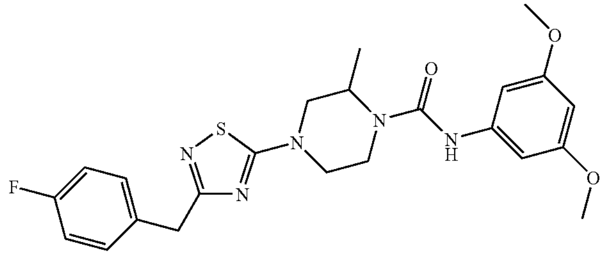 [SMILES: COc1cc(NC(=O)N2CCN(c3nc(Cc4ccc(F)cc4)ns3)CC2C)cc(OC)c1] |

TABLE 1-continued

| No. | Compound name |
|---|---|
| 30 | 1-[4-tert-butylphenylsulfonyl]-4-[3-(4-fluorobenzyl)-1,2,4-thiadiazol-5-yl]piperazine |
| 31 | 1-[4-methoxyphenylsulfonyl]-4-[3-(4-chlorobenzyl)-1,2,4-thiadiazol-5-yl]piperazine |
| 32 | 1-[4-methoxyphenylsulfonyl]-4-[3-(4-fluorobenzyl)-1,2,4-thiadiazol-5-yl]piperazine |
| 33 | 1-[4-fluorophenylsulfonyl]-4-[3-(4-chlorobenzyl)-1,2,4-thiadiazol-5-yl]piperazine |
| 34 | 1-[4-chlorophenylsulfonyl]-4-[3-(4-methylbenzyl)-1,2,4-thiadiazol-5-yl]-2-methylpiperazine |
| 35 | 1-[1-naphthylsulfonyl]-4-[3-(4-methylbenzyl)-1,2,4-thiadiazol-5-yl]piperazine |

TABLE 1-continued

| No. | Compound name |
|---|---|
| 36 | 1-[2,5-dichlorophenylsulfonyl]-4-[3-(4-methylbenzyl)-1,2,4-thiadiazol-5-yl]-2-methylpiperazine |
| 37 | 1-[2,4,6-trimethylphenylsulfonyl]-4-[3-(4-methylbenzyl)-1,2,4-thiadiazol-5-yl]piperazine |
| 38 | 1-[2-naphthylsulfonyl]-4-[3-(4-methylbenzyl)-1,2,4-thiadiazol-5-yl]-2-methylpiperazine |
| 39 | 1-[2,5-dichlorophenylsulfonyl]-4-[3-(4-chlorobenzyl)-1,2,4-thiadiazol-5-yl]piperazine |
| 40 | 1-[4-bromophenylsulfonyl]-4-[3-(4-methylbenzyl)-1,2,4-thiadiazol-5-yl]-3-methylpiperazine |
| 41 | 1-[1-naphthylsulfonyl]-4-[3-(4-methylbenzyl)-1,2,4-thiadiazol-5-yl]-3-methylpiperazine |

TABLE 1-continued

| No. | Compound name | Compound structure |
| --- | --- | --- |
| 42 | 1-[4-tert-butylphenylsulfonyl]-4-[3-(4-methylbenzyl)-1,2,4-thiadiazol-5-yl]-2-methylpiperazine | 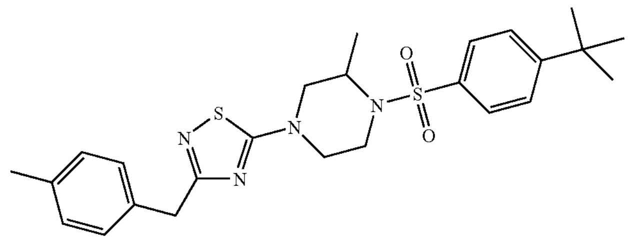 [SMILES: Cc1ccc(Cc2nsc(N3CCN(S(=O)(=O)c4ccc(C(C)(C)C)cc4)C(C)C3)n2)cc1] |
| 43 | 1-[1-naphthylsulfonyl]-4-[3-(4-chlorobenzyl)-1,2,4-thiadiazol-5-yl]-2-methylpiperazine | 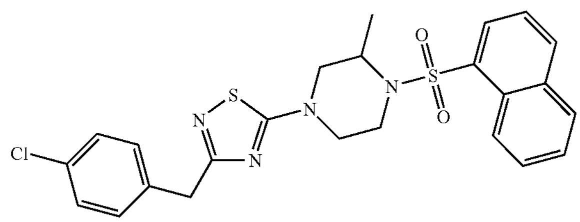 [SMILES: CC1CN(c2nc(Cc3ccc(Cl)cc3)ns2)CCN1S(=O)(=O)c1cccc2ccccc12] |
| 44 | 1-[3-methoxyphenylsulfonyl]-4-[3-(4-fluorobenzyl)-1,2,4-thiadiazol-5-yl]piperazine | 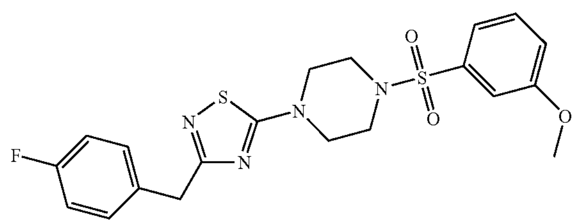 [SMILES: COc1cccc(S(=O)(=O)N2CCN(c3nc(Cc4ccc(F)cc4)ns3)CC2)c1] |
| 45 | 1-[2,4,6-trimethylphenylsulfonyl]-4-[3-(4-methylbenzyl)-1,2,4-thiadiazol-5-yl]-2-methylpiperazine | 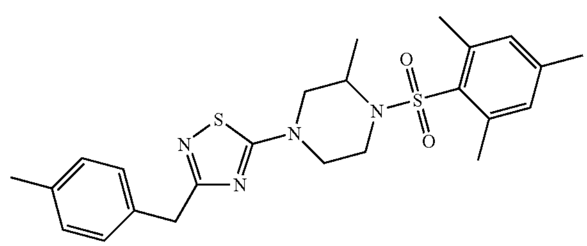 |
| 46 | 1-[3-trifluorophenylsulfonyl]-4-[3-(4-fluorobenzyl)-1,2,4-thiadiazol-5-yl]-2-methylpiperazine | 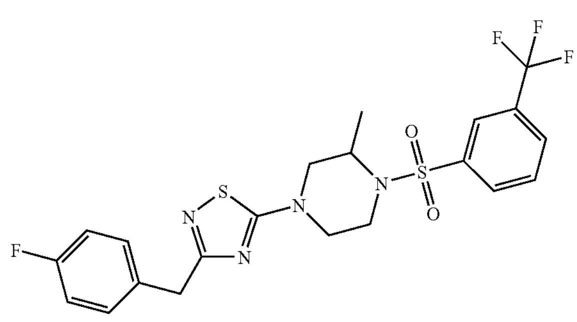 [SMILES: CC1CN(c2nc(Cc3ccc(F)cc3)ns2)CCN1S(=O)(=O)c1cccc(C(F)(F)F)c1] |
| 47 | 1-phenylsulfonyl-4-[3-(4-fluorobenzyl)-1,2,4-thiadiazol-5-yl]-2-methylpiperazine | 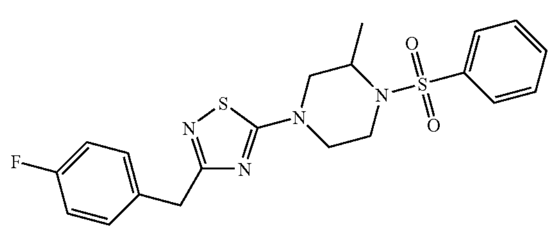 [SMILES: CC1CN(c2nc(Cc3ccc(F)cc3)ns2)CCN1S(=O)(=O)c1ccccc1] |

TABLE 1-continued

| No. | Compound name |
|---|---|
| 48 | 1-[4-acetamidophenylsulfonyl]-4-[3-(4-methylbenzyl)-1,2,4-thiadiazol-5-yl]-2-methylpiperazine |
| 49 | 1-[4-acetamidophenylsulfonyl]-4-[3-(4-methylbenzyl)-1,2,4-thiadiazol-5-yl]piperazine |
| 50 | 1-[4-methylphenylsulfonyl]-4-[3-(4-methylbenzyl)-1,2,4-thiadiazol-5-yl]-2-methylpiperazine |
| 51 | 1-[4-methoxyphenylsulfonyl]-4-[3-(4-chlorobenzyl)-1,2,4-thiadiazol-5-yl]-2-methylpiperazine |
| 52 | 1-[2-naphthylsulfonyl]-4-[3-(4-chlorobenzyl)-1,2,4-thiadiazol-5-yl]piperazine |
| 53 | 1-[4-methoxyphenylsulfonyl]-4-[3-(3-methoxyphenyl)-1,2,4-thiadiazol-5-yl]piperazine |
| 54 | 1-[4-tert-butylphenylsulfonyl]-4-[3-(4-fluorobenzyl)-1,2,4-thiadiazol-5-yl]-2-methylpiperazine |

TABLE 1-continued

| No. | Compound name | Compound structure |
|-----|---------------|--------------------|
| 55 | 1-[4-acetamidophenylsulfonyl]-4-[3-(4-fluorobenzyl)-1,2,4-thiadiazol-5-yl]-2-methylpiperazine | 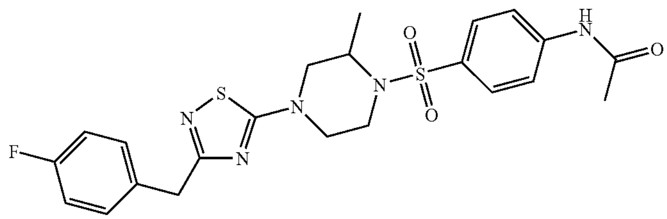 [SMILES: CC(=O)Nc1ccc(S(=O)(=O)N2CCN(c3nc(Cc4ccc(F)cc4)ns3)CC2C)cc1] |
| 56 | 1-[3-trifluoromethylphenylsulfonyl]-4-[3-(4-methylbenzyl)-1,2,4-thiadiazol-5-yl]-2-methylpiperazine | 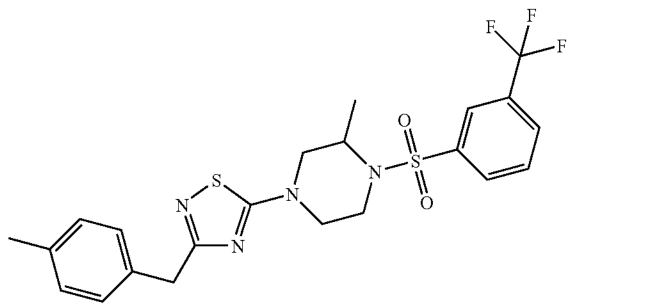 [SMILES: Cc1ccc(Cc2nsc(N3CCN(S(=O)(=O)c4cccc(C(F)(F)F)c4)C(C)C3)n2)cc1] |
| 57 | 1-[4-fluorophenylsulfonyl]-4-[3-(4-methylbenzyl)-1,2,4-thiadiazol-5-yl]piperazine | 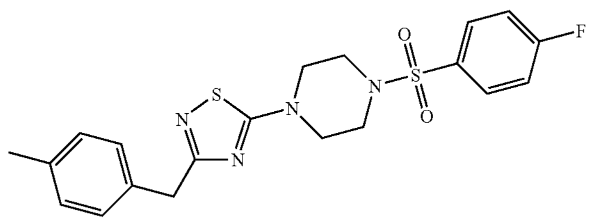 [SMILES: Cc1ccc(Cc2nsc(N3CCN(S(=O)(=O)c4ccc(F)cc4)CC3)n2)cc1] |
| 58 | 1-[4-fluorophenylsulfonyl]-4-[3-(4-methylbenzyl)-1,2,4-thiadiazol-5-yl]-2-methylpiperazine | 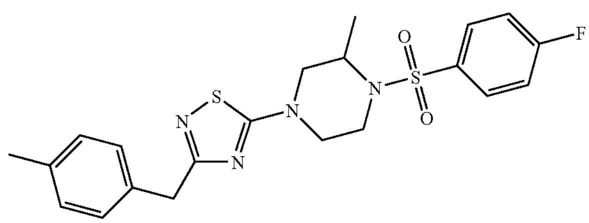 [SMILES: Cc1ccc(Cc2nsc(N3CCN(S(=O)(=O)c4ccc(F)cc4)C(C)C3)n2)cc1] |
| 59 | 1-[4-fluorophenylsulfonyl]-4-[3-(4-fluorobenzyl)-1,2,4-thiadiazol-5-yl]-2-methylpiperazine | 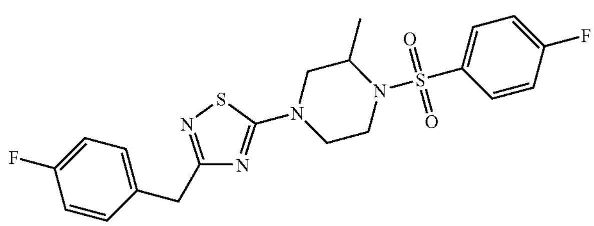 [SMILES: CC1CN(c2nc(Cc3ccc(F)cc3)ns2)CCN1S(=O)(=O)c1ccc(F)cc1] |
| 60 | 1-[4-methoxyphenylsulfonyl]-4-[3-(4-methylbenzyl)-1,2,4-thiadiazol-5-yl]-2-methylpiperazine | 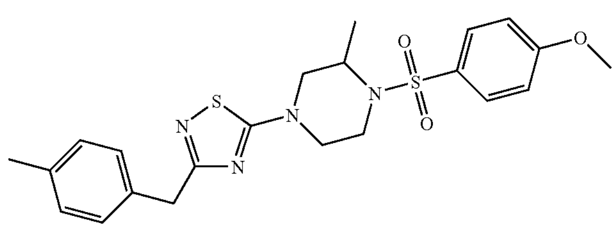 |

TABLE 1-continued

| No. | Compound name |
|---|---|
| 61 | 1-[4-ter-butylphenylsulfonyl]-4-[3-(4-fluorobenzyl)-1,2,4-thiadiazol-5-yl]piperazine |
| 62 | 1-[3-trifluoromethylphenylsulfonyl]-4-[3-(4-methylbenzyl)-1,2,4-thiadiazol-5-yl]piperazine |
| 63 | 1-[4-methylphenylsulfonyl]-4-[3-(4-chlorobenzyl)-1,2,4-thiadiazol-5-yl]piperazine |
| 64 | 1-[4-bromophenylsulfonyl]-4-[3-(4-methylbenzyl)-1,2,4-thiadiazol-5-yl]piperazine |
| 65 | 1-[2-naphthylsulfonyl]-4-[3-(4-methylbenzyl)-1,2,4-thiadiazol-5-yl]piperazine |
| 66 | 1-[4-chlorophenylsulfonyl]-4-[3-(4-methylbenzyl)-1,2,4-thiadiazol-5-yl]piperazine |

TABLE 1-continued

| No. | Compound name |
|---|---|
| 67 | 1-[4-tert-butylphenylsulfonyl]-4-[3-(4-methylphenyl)-1,2,4-thiadiazol-5-yl]piperazine |
| 68 | 1-[4-methoxyphenylsulfonyl]-4-[3-(4-methylbenzyl)-1,2,4-thiadiazol-5-yl]piperazine |
| 69 | 1-[4-tert-butylphenylsulfonyl]-4-[3-(4-chlorobenzyl)-1,2,4-thiadiazol-5-yl]piperazine |
| 70 | 1-[quinoline-8-sulfonyl]-4-[3-(4-methylbenzyl)-1,2,4-thiadiazol-5-yl]piperazine |
| 71 | 1-[4-nitrophenylsulfonyl]-4-[3-(4-methylbenzyl)-1,2,4-thiadiazol-5-yl]-2-methylpiperazine |
| 72 | 1-[3-nitro-4-chlorophenylsulfonyl]-4-[3-(4-methylbenzyl)-1,2,4-thiadiazol-5-yl]-2-methylpiperazine |

TABLE 1-continued

| No. | Compound name |
|---|---|
| 73 | 1-[4-nitrophenylsulfonyl]-4-[3-(4-fluorobenzyl)-1,2,4-thiadiazol-5-yl]-2-methylpiperazine |
| 75 | 1-[3-nitro-4-chlorophenylsulfonyl]-4-[3-(4-methylbenzyl)-1,2,4-thiadiazol-5-yl]piperazine |
| 76 | 1-(benzylsulfonyl)-4-[3-(4-chlorobenzyl)-1,2,4-thiadiazol-5-yl]piperazine |
| 77 | 1-(benzylsulfonyl)-4-[3-(4-methylbenzyl)-1,2,4-thiadiazol-5-yl]piperazine |
| 78 | 1-(phenylprop-2-ensulfonyl)-4-[3-(4-fluorobenzyl)-1,2,4-thiadiazol-5-yl]piperazine |
| 79 | 1-(phenylprop-2-ensulfonyl)-4-[3-(4-methylbenzyl)-1,2,4-thiadiazol-5-yl]-2-methylpiperazine |
| 80 | 1-(phenylprop-2-ensulfonyl)-4-[3-(4-methylbenzyl)-1,2,4-thiadiazol-5-yl]piperazine |

TABLE 1-continued

| No. | Compound name |
|---|---|
| 81 | 1-(butylsulfonyl)-4-[3-(4-chlorobenzyl)-1,2,4-thiadiazol-5-yl]piperazine |
| 82 | 1-(octylsulfonyl)-4-[3-(4-methylbenzyl)-1,2,4-thiadiazol-5-yl]piperazine |
| 83 | 1-(butylsulfonyl)-4-[3-(4-methylbenzyl)-1,2,4-thiadiazol-5-yl]piperazine |
| 84 | 1-(ethylsulfonyl)-4-[3-(4-chlorobenzyl)-1,2,4-thiadiazol-5-yl]piperazine |
| 85 | 1-(isopropylsulfonyl)-4-[3-(4-methylbenzyl)-1,2,4-thiadiazol-5-yl]piperazine |
| 86 | 1-[(2E)-3-phenylprop-2-enoyl]-4-[3-(4-chlorobenzyl)-1,2,4-thiadiazol-5-yl]-2-methylpiperazine |

TABLE 1-continued

| No. | Compound name | Compound structure |
|---|---|---|
| 87 | 1-[(2E)-3-phenylprop-2-enoyl]-4-[3-(4-fluorobenzyl)-1,2,4-thiadiazol-5-yl]-2-methylpiperazine | 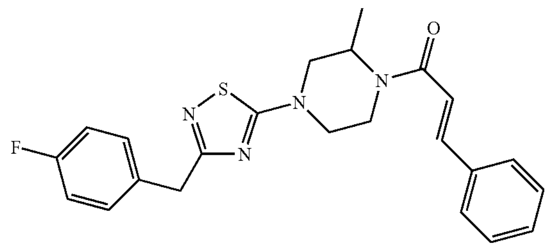 [SMILES: CC1CN(c2nc(Cc3ccc(F)cc3)ns2)CCN1C(=O)/C=C/c1ccccc1] |
| 88 | 1-[(2E)-3-phenylprop-2-enoyl]-4-[3-(4-chlorobenzyl)-1,2,4-thiadiazol-5-yl]piperazine | 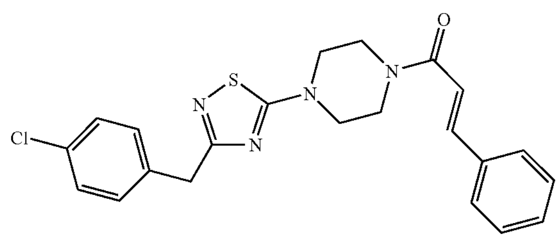 [SMILES: O=C(/C=C/c1ccccc1)N1CCN(c2nc(Cc3ccc(Cl)cc3)ns2)CC1] |
| 89 | 1-(3-phenylpropanoyl)-4-[3-(4-fluorobenzyl)-1,2,4-thiadiazol-5-yl]-2-methylpiperazine | 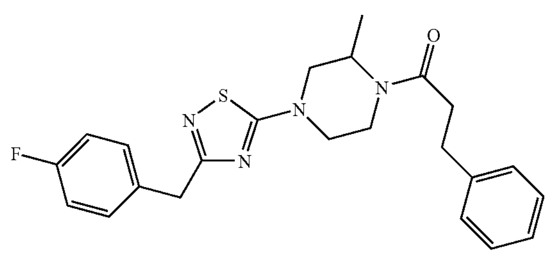 [SMILES: CC1CN(c2nc(Cc3ccc(F)cc3)ns2)CCN1C(=O)CCc1ccccc1] |
| 90 | 1-(3-phenylpropanoyl)-4-[3-(4-fluorobenzyl)-1,2,4-thiadiazol-5-yl]piperazine | 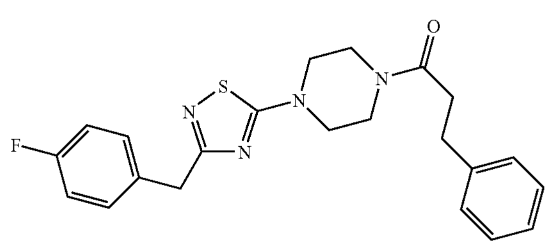 [SMILES: O=C(CCc1ccccc1)N1CCN(c2nc(Cc3ccc(F)cc3)ns2)CC1] |
| 91 | 1-[3-phenylprop-2-enyl]-4-[3-(4-methylbenzyl)-1,2,4-thiadiazol-5-yl]piperazine | 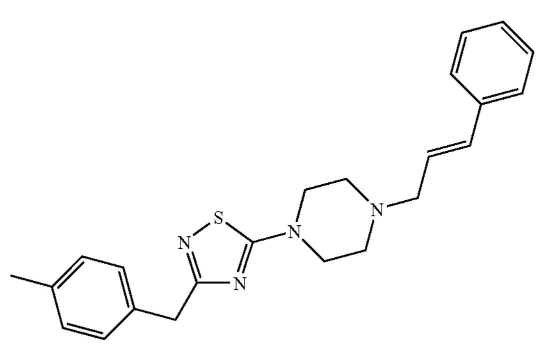 [SMILES: Cc1ccc(Cc2nsc(N3CCN(C/C=C/c4ccccc4)CC3)n2)cc1] |

TABLE 1-continued

| No. | Compound name | Compound structure |
|---|---|---|
| 92 | 1-[3-phenylprop-2-enyl]-4-[3-(4-chlorobenzyl)-1,2,4-thiadiazol-5-yl]piperazine | 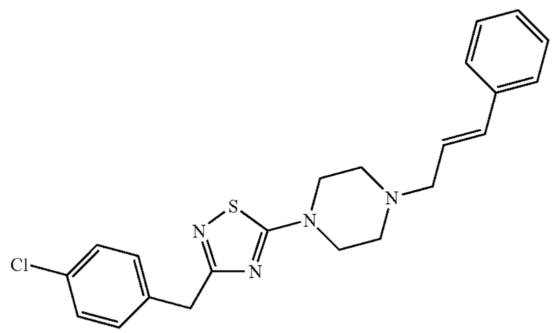 [SMILES: Clc1ccc(Cc2nsc(N3CCN(C/C=C/c4ccccc4)CC3)n2)cc1] |
| 93 | 1-[3-phenylprop-2-enyl]-4-[3-(4-fluorobenzyl)-1,2,4-thiadiazol-5-yl]piperazine | 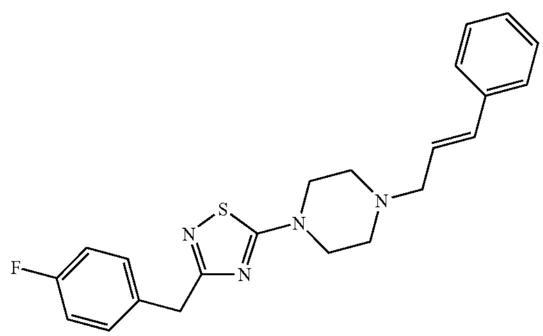 [SMILES: Fc1ccc(Cc2nsc(N3CCN(C/C=C/c4ccccc4)CC3)n2)cc1] |
| 94 | 4-pentyl-N-{2-[4-[3-(4-fluorobenzyl)-1,2,4-thiadiazol-5-yl]piperazin-1-yl]ethyl}benzamide | 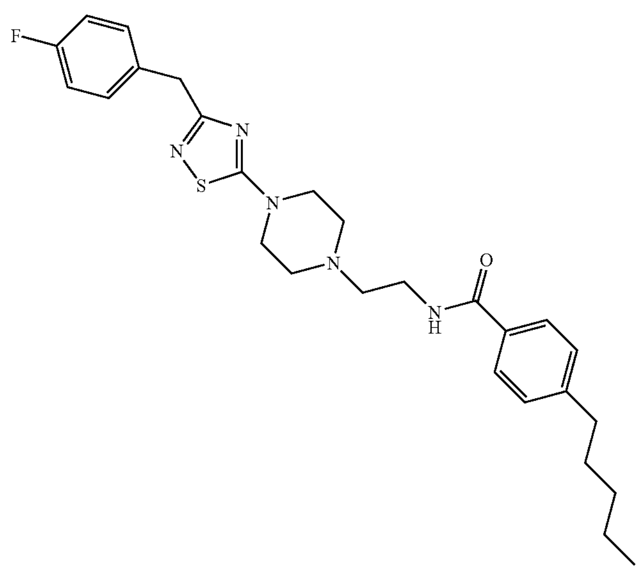 [SMILES: CCCCCc1ccc(C(=O)NCCN2CCN(c3nc(Cc4ccc(F)cc4)ns3)CC2)cc1] |

TABLE 1-continued

| No. | Compound name | Compound structure |
|---|---|---|
| 95 | 4-butyl-N-{2-[4-[3-(4-fluorobenzyl)-1,2,4-thiadiazol-5-yl]piperazin-1-yl]ethyl}benzamide | 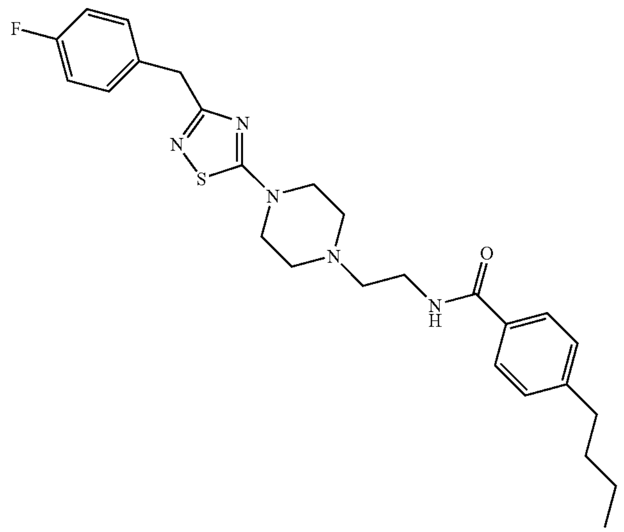 [SMILES: CCCCc1ccc(C(=O)NCCN2CCN(c3nc(Cc4ccc(F)cc4)ns3)CC2)cc1] |
| 96 | 4-hexyl-N-{2-[4-[3-(4-fluorobenzyl)-1,2,4-thiadiazol-5-yl]piperazin-1-yl]ethyl}benzamide | 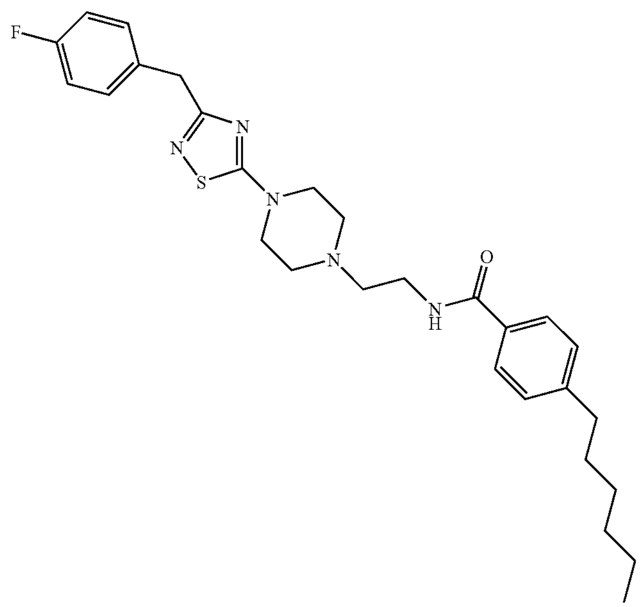 [SMILES: CCCCCCc1ccc(C(=O)NCCN2CCN(c3nc(Cc4ccc(F)cc4)ns3)CC2)cc1] |
| 97 | 4-chloro-N-{2-[4-[3-(4-fluorobenzyl)-1,2,4-thiadiazol-5-yl]piperazin-1-yl]ethyl}benzamide | 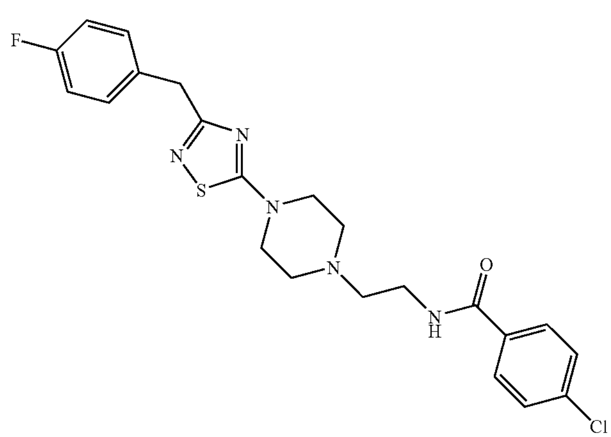 [SMILES: O=C(NCCN1CCN(c2nc(Cc3ccc(F)cc3)ns2)CC1)c1ccc(Cl)cc1] |

TABLE 1-continued

| No. | Compound name | Compound structure |
|---|---|---|
| 98 | 3,5-dichloro-N-{2-[4-[3-(4-fluorobenzyl)-1,2,4-thiadiazol-5-yl]piperazin-1-yl]ethyl}benzamide | 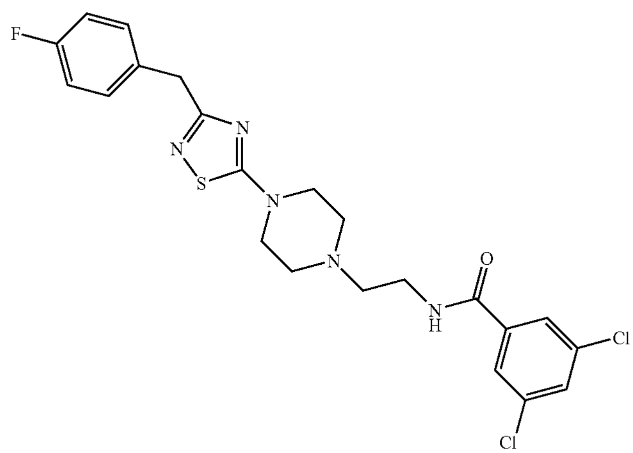 [SMILES: O=C(NCCN1CCN(c2nc(Cc3ccc(F)cc3)ns2)CC1)c1cc(Cl)cc(Cl)c1] |
| 99 | 2-methyl-N-{2-[4-[3-(4-fluorobenzyl)-1,2,4-thiadiazol-5-yl]piperazin-1-yl]ethyl}benzamide | 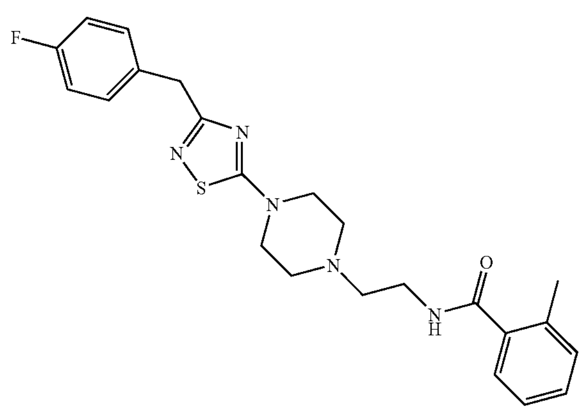 [SMILES: Cc1ccccc1C(=O)NCCN1CCN(c2nc(Cc3ccc(F)cc3)ns2)CC1] |
| 100 | 3-fluoro-N-{2-[4-[3-(4-chlorobenzyl)-1,2,4-thiadiazol-5-yl]piperazin-1-yl]ethyl}benzamide | 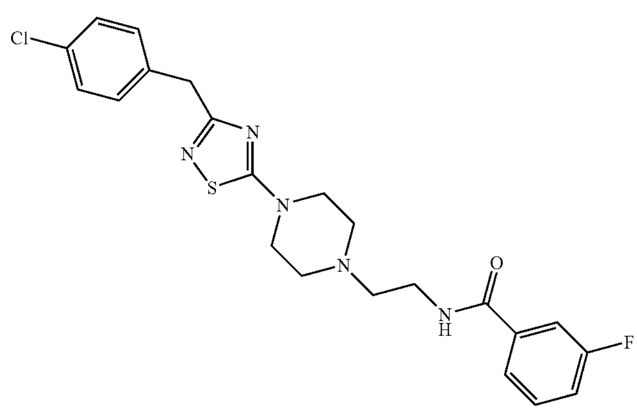 [SMILES: O=C(NCCN1CCN(c2nc(Cc3ccc(Cl)cc3)ns2)CC1)c1cccc(F)c1] |

TABLE 1-continued

| No. | Compound name | Compound structure |
|---|---|---|
| 101 | 4-methyl-N-{2-[4-[3-(4-fluorobenzyl)-1,2,4-thiadiazol-5-yl]piperazin-1-yl]ethyl}benzamide | 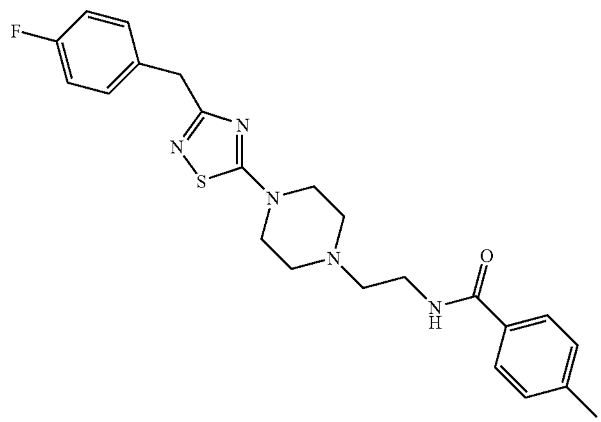 [SMILES: Cc1ccc(C(=O)NCCN2CCN(c3nc(Cc4ccc(F)cc4)ns3)CC2)cc1] |
| 102 | 4-fluoro-N-{2-[4-[3-(4-fluorobenzyl)-1,2,4-thiadiazol-5-yl]piperazin-1-yl]ethyl}benzamide | 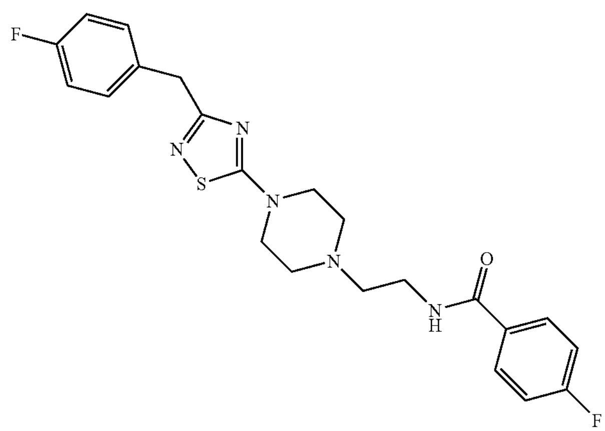 [SMILES: O=C(NCCN1CCN(c2nc(Cc3ccc(F)cc3)ns2)CC1)c1ccc(F)cc1] |
| 103 | 4-ethyl-N-{2-[4-[3-(4-fluorobenzyl)-1,2,4-thiadiazol-5-yl]piperazin-1-yl]ethyl}benzamide | 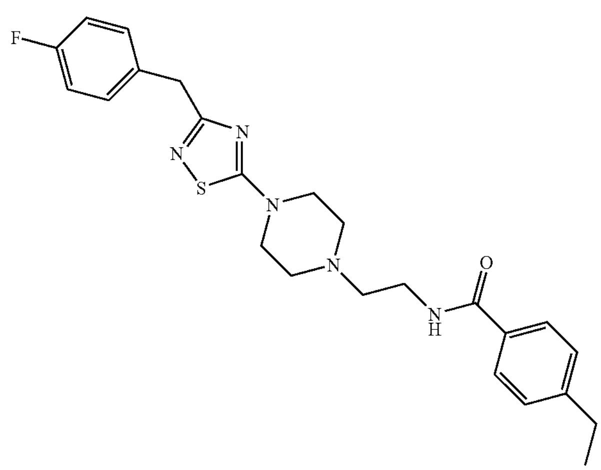 [SMILES: CCc1ccc(C(=O)NCCN2CCN(c3nc(Cc4ccc(F)cc4)ns3)CC2)cc1] |

TABLE 1-continued

| No. | Compound name | Compound structure |
| --- | --- | --- |
| 104 | N-{2-[4-[3-(4-fluorobenzyl)-1,2,4-thiadiazol-5-yl]piperazin-1-yl]ethyl}benzamide | 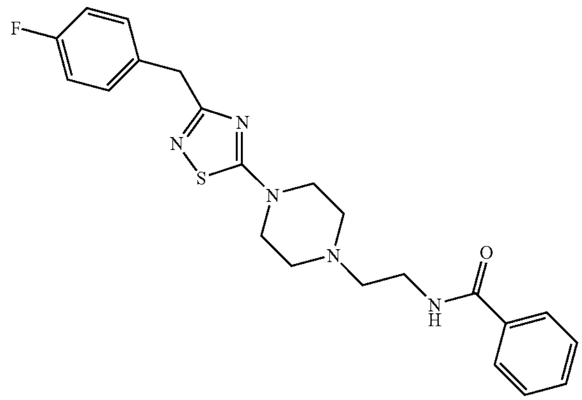 [SMILES: O=C(NCCN1CCN(c2nc(Cc3ccc(F)cc3)ns2)CC1)c1ccccc1] |
| 105 | 3-fluoro-N-{2-[4-[3-(4-fluorobenzyl)-1,2,4-thiadiazol-5-yl]piperazin-1-yl]ethyl}benzamide | 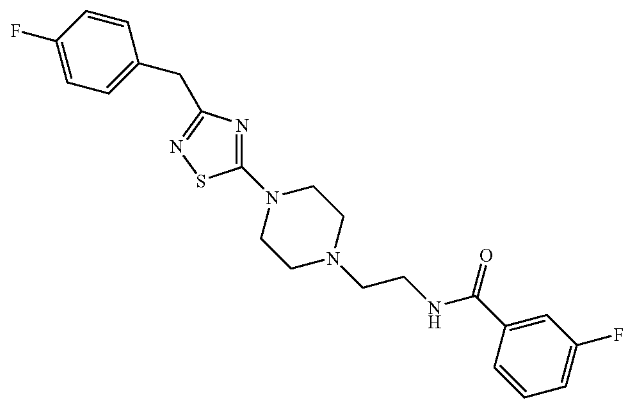 [SMILES: O=C(NCCN1CCN(c2nc(Cc3ccc(F)cc3)ns2)CC1)c1cccc(F)c1] |
| 106 | 3-fluoro-N-{2-[4-[3-benzyl-1,2,4-thiadiazol-5-yl]piperazin-1-yl]ethyl}benzamide | 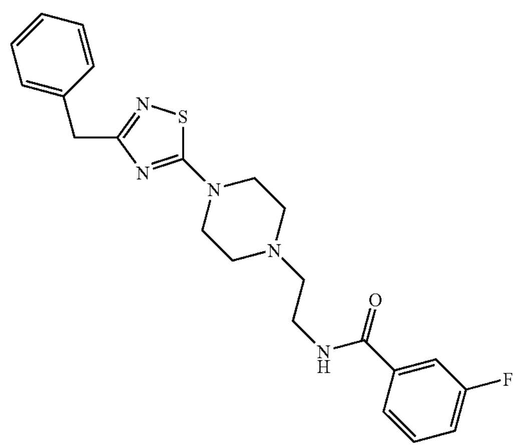 [SMILES: O=C(NCCN1CCN(c2nc(Cc3ccccc3)ns2)CC1)c1cccc(F)c1] |
| 107 | 2-(4-fluorophenyl)-N-{2-[4-[3-(4-fluorobenzyl)-1,2,4-thiadiazol-5-yl]piperazin-1-yl]ethyl}acetamide | 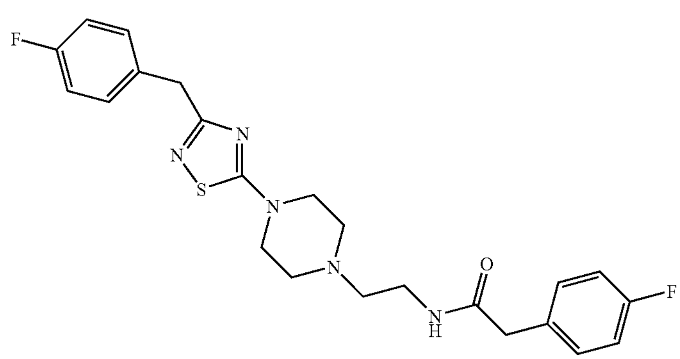 [SMILES: O=C(Cc1ccc(F)cc1)NCCN1CCN(c2nc(Cc3ccc(F)cc3)ns2)CC1] |

TABLE 1-continued

| No. | Compound name |
|-----|---------------|
| 108 | 2-phenyl-N-{2-[4-[3-(4-fluorobenzyl)-1,2,4-thiadiazol-5-yl]piperazin-1-yl]ethyl}acetamide |
| 109 | 2-(4-fluorophenyl)-N-{2-[4-[3-(4-methylbenzyl)-1,2,4-thiadiazol-5-yl]piperazin-1-yl]ethyl}acetamide |
| 110 | N-benzyl-N'-{2-[4-[3-(4-fluorobenzyl)-1,2,4-thiadiazol-5-yl]piperazin-1-yl]ethyl}urea |

TABLE 1-continued

| No. | Compound name | Compound structure |
|---|---|---|
| 111 | 2-phenyl-N-{2-[4-[3-(4-fluorobenzyl)-1,2,4-thiadiazol-5-yl]piperazin-1-yl]ethyl}butanamide | 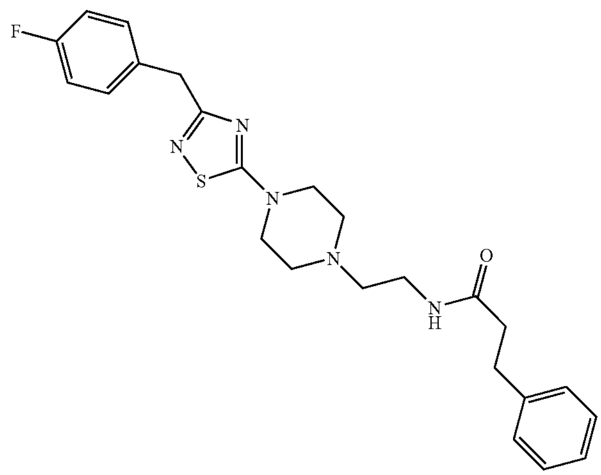 [SMILES: O=C(CCc1ccccc1)NCCN1CCN(c2nc(Cc3ccc(F)cc3)ns2)CC1] |
| 112 | 3-phenyl-N-{2-[4-[3-(4-fluorobenzyl)-1,2,4-thiadiazol-5-yl]piperazin-1-yl]ethyl}propanamide | 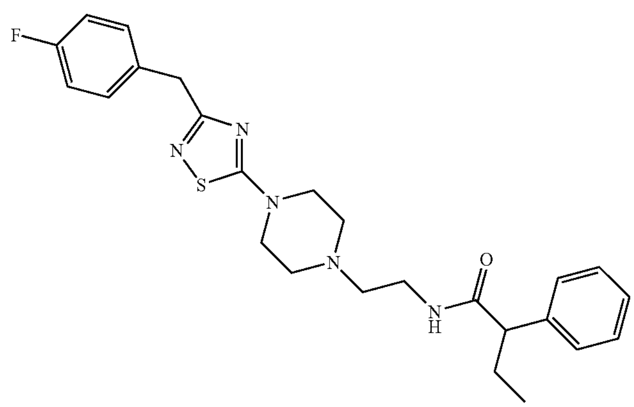 [SMILES: CCC(C(=O)NCCN1CCN(c2nc(Cc3ccc(F)cc3)ns2)CC1)c1ccccc1] |
| 113 | 1-benzyl-4-[3-(4-fluorobenzyl)-1,2,4-thiadiazol-5-yl]piperazine | 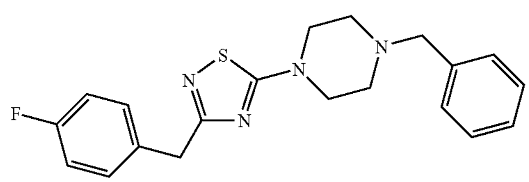 [SMILES: Fc1ccc(Cc2nsc(N3CCN(Cc4ccccc4)CC3)n2)cc1] |
| 114 | 1-(1,3-benzodioxol-5-ylmethyl)-4-[3-(4-fluorobenzyl)-1,2,4-thiadiazol-5-yl]piperazine | 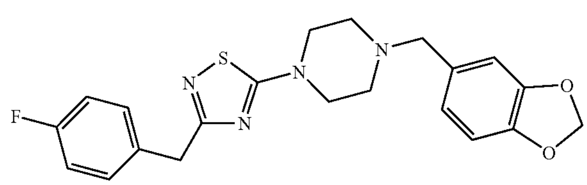 [SMILES: Fc1ccc(Cc2nsc(N3CCN(Cc4ccc5c(c4)OCO5)CC3)n2)cc1] |
| 115 | 1-(2-fluorobenzyl)-4-[3-(3-methoxyphenyl)-1,2,4-thiadiazol-5-yl]-2-methylpiperazine | 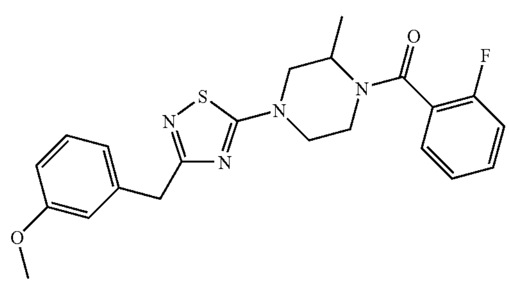 [SMILES: COc1cccc(Cc2nsc(N3CCN(C(=O)c4ccccc4F)C(C)C3)n2)c1] |

TABLE 1-continued

| No. | Compound name | Compound structure |
|---|---|---|
| 116 | 1-(4-ethylbenzoyl)-4-[3-(4-fluorobenzyl)-1,2,4-thiadiazol-5-yl]-2-methylpiperazine | 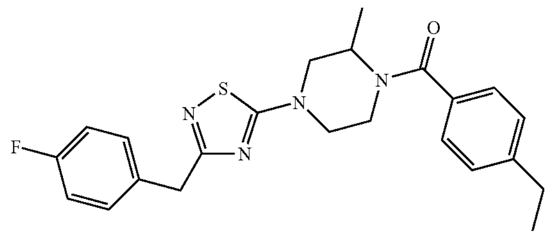 [SMILES: CCc1ccc(C(=O)N2CCN(c3nc(Cc4ccc(F)cc4)ns3)CC2C)cc1] |
| 117 | 1-(4-butylbenzoyl)-4-[3-(4-methylbenzyl)-1,2,4-thiadiazol-5-yl]-2-methylpiperazine | 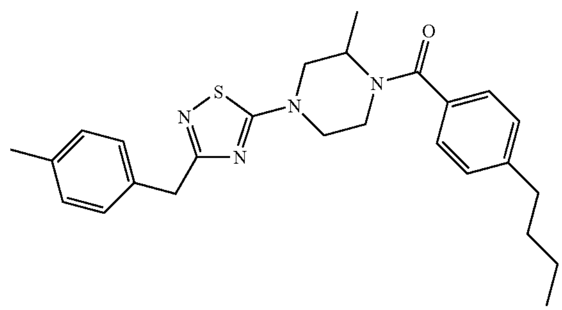 [SMILES: CCCCc1ccc(C(=O)N2CCN(c3nc(Cc4ccc(C)cc4)ns3)CC2C)cc1] |
| 118 | 1-(4-methoxybenzoyl)-4-[3-(4-fluorobenzyl)-1,2,4-thiadiazol-5-yl]-2-methylpiperazine | 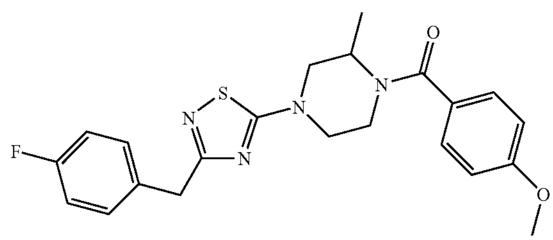 [SMILES: COc1ccc(C(=O)N2CCN(c3nc(Cc4ccc(F)cc4)ns3)CC2C)cc1] |
| 119 | 1-(1,3-benzodioxol-5-ylcarbonyl)-4-[3-(3-methoxybenzyl)-1,2,4-thiadiazol-5-yl]-2-methylpiperazine | 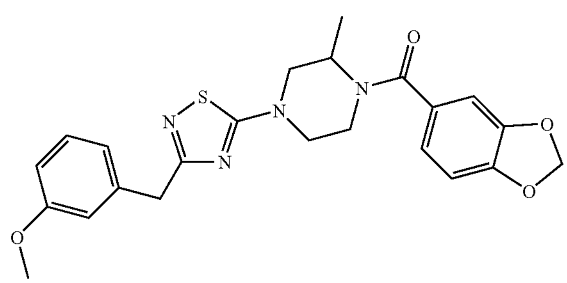 [SMILES: COc1cccc(Cc2nsc(N3CCN(C(=O)c4ccc5c(c4)OCO5)C(C)C3)n2)c1] |
| 120 | 1-(4-butylbenzoyl)-4-[3-(4-fluorobenzyl)-1,2,4-thiadiazol-5-yl]-2-methylpiperazine | 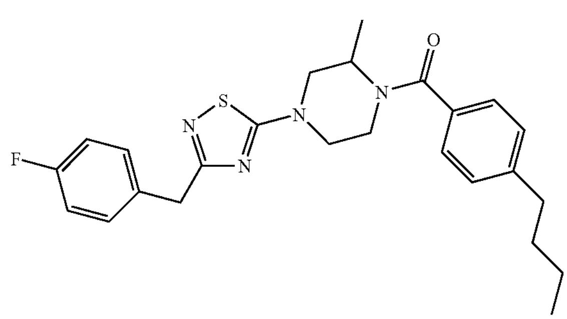 [SMILES: CCCCc1ccc(C(=O)N2CCN(c3nc(Cc4ccc(F)cc4)ns3)CC2C)cc1] |

TABLE 1-continued

| No. | Compound name | Compound structure |
|---|---|---|
| 121 | 1-(4-hexylbenzoyl)-4-[3-(4-fluorobenzyl)-1,2,4-thiadiazol-5-yl]piperazine | 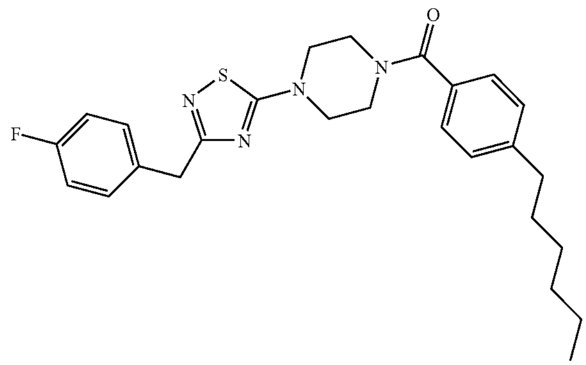 [SMILES: CCCCCCc1ccc(C(=O)N2CCN(c3nc(Cc4ccc(F)cc4)ns3)CC2)cc1] |
| 122 | 1-(3-chlorobenzoyl)-4-[3-(4-fluorobenzyl)-1,2,4-thiadiazol-5-yl]-2-methylpiperazine | 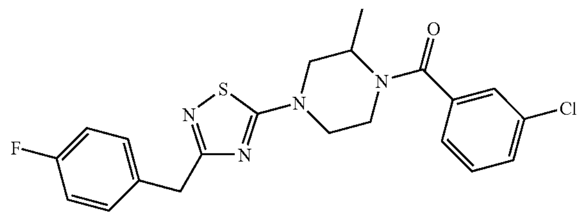 [SMILES: CC1CN(c2nc(Cc3ccc(F)cc3)ns2)CCN1C(=O)c1cccc(Cl)c1] |
| 123 | 1-(4-fluorobenzoyl)-4-[3-(3-methoxybenyl)-1,2,4-thiadiazol-5-yl]-2-methylpiperazine | 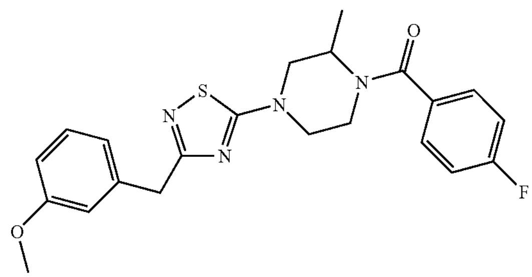 [SMILES: COc1cccc(Cc2nsc(N3CCN(C(=O)c4ccc(F)cc4)C(C)C3)n2)c1] |
| 124 | 1-(4-methylbenzoyl)-4-[3-(3-methoxybenzyl)-1,2,4-thiadiazol-5-yl]-2-methylpiperazine | 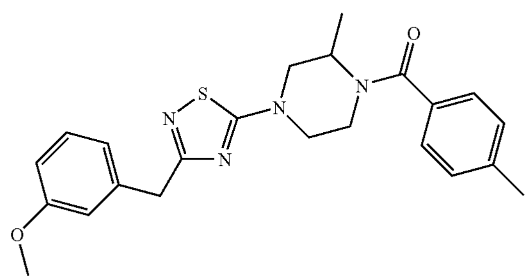 [SMILES: COc1cccc(Cc2nsc(N3CCN(C(=O)c4ccc(C)cc4)C(C)C3)n2)c1] |
| 125 | 1-(3-fluorobenzoyl)-4-[3-(4-chlorobenzyl)-1,2,4-thiadiazol-5-yl]-2-methylpiperazine | 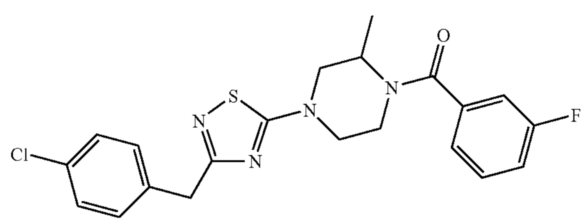 [SMILES: CC1CN(c2nc(Cc3ccc(Cl)cc3)ns2)CCN1C(=O)c1cccc(F)c1] |
| 126 | 1-benzoyl-4-[3-(4-fluorobenzyl)-1,2,4-thiadiazol-5-yl]-2-methylpiperazine | 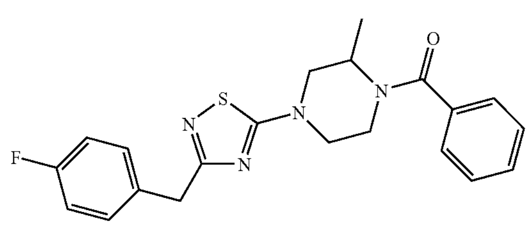 [SMILES: CC1CN(c2nc(Cc3ccc(F)cc3)ns2)CCN1C(=O)c1ccccc1] |

TABLE 1-continued

| No. | Compound name |
|---|---|
| 127 | 1-(4-fluorobenzoyl)-4-[3-(4-fluorobenzyl)-1,2,4-thiadiazol-5-yl]-2-methylpiperazine |
| 128 | 1-(4-tert-butylbenzoyl)-4-[3-(4-fluorobenzyl)-1,2,4-thiadiazol-5-yl]-2-methylpiperazine |
| 129 | 1-(1,1'-biphenyl-4-ylcarbonyl)-4-[3-(4-fluorobenzyl)-1,2,4-thiadiazol-5-yl]-2-methylpiperazine |
| 130 | 1-(4-methoxybenzoyl)-4-[3-(4-methylbenzyl)-1,2,4-thiadiazol-5-yl]-2-methylpiperazine |
| 131 | 1-(4-ethylbenzoyl)-4-[3-(4-methylbenzyl)-1,2,4-thiadiazol-5-yl]piperazine |
| 132 | 1-(2-naphthoyl)-4-[3-(4-fluorobenzyl)-1,2,4-thiadiazol-5-yl]-2-methylpiperazine |

TABLE 1-continued

| No. | Compound name | Compound structure |
|---|---|---|
| 133 | 1-(2-methoxybenzoyl)-4-[3-(4-fluorobenzyl)-1,2,4-thiadiazol-5-yl]-2-methylpiperazine | 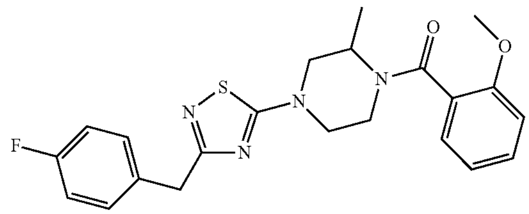 [SMILES: COc1ccccc1C(=O)N1CCN(c2nc(Cc3ccc(F)cc3)ns2)CC1C] |
| 134 | 1-(4-pentylbenzoyl)-4-[3-(4-methylbenzyl)-1,2,4-thiadiazol-5-yl]-2-methylpiperazine | 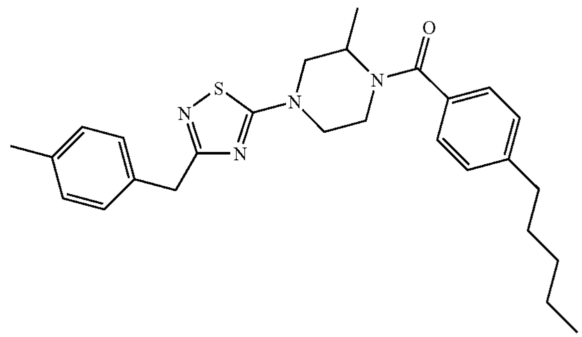 [SMILES: CCCCCc1ccc(C(=O)N2CCN(c3nc(Cc4ccc(C)cc4)ns3)CC2C)cc1] |
| 135 | 1-(4-bromophenyl)-4-[3-(4-fluorobenzyl)-1,2,4-thiadiazol-5-yl]-2-methylpiperazine | 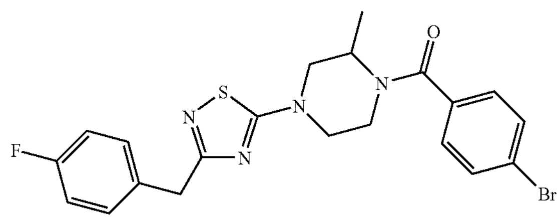 [SMILES: CC1CN(c2nc(Cc3ccc(F)cc3)ns2)CCN1C(=O)c1ccc(Br)cc1] |
| 136 | 1-(2,4-dimethoxybenzoyl)-4-[3-(4-fluorobenzyl)-1,2,4-thiadiazol-5-yl]-2-methylpiperazine | 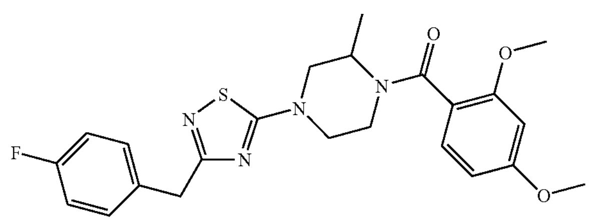 [SMILES: COc1ccc(C(=O)N2CCN(c3nc(Cc4ccc(F)cc4)ns3)CC2C)c(OC)c1] |
| 137 | 1-(3,5-dichlorobenzoyl)-4-[3-(4-fluorobenzyl)-1,2,4-thiadiazol-5-yl]piperazine | 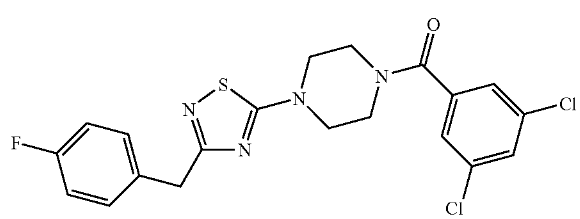 [SMILES: O=C(c1cc(Cl)cc(Cl)c1)N1CCN(c2nc(Cc3ccc(F)cc3)ns2)CC1] |
| 138 | 1-(3-chlorobenzoyl)-4-[3-(4-fluorobenzyl)-1,2,4-thiadiazol-5-yl]piperazine | 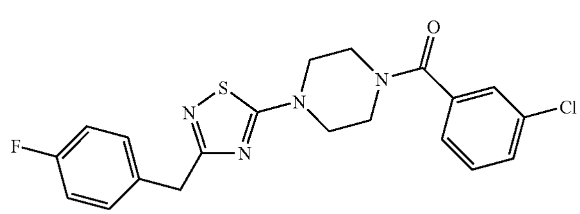 [SMILES: O=C(c1cccc(Cl)c1)N1CCN(c2nc(Cc3ccc(F)cc3)ns2)CC1] |

TABLE 1-continued

| No. | Compound name |
|---|---|
| 139 | 1-(4-methylbenzoyl)-4-[3-(4-fluorobenzyl)-1,2,4-thiadiazol-5-yl]-2-methylpiperazine |
| 140 | 1-(2-methylbenzoyl)-4-[3-(4-fluorobenzyl)-1,2,4-thiadiazol-5-yl]-2-methylpiperazine |
| 141 | 1-(4-methylbenzoyl)-4-[3-(4-fluorobenzyl)-1,2,4-thiadiazol-5-yl]piperazine |
| 142 | 1-(3-bromobenzoyl)-4-[3-(4-fluorobenzyl)-1,2,4-thiadiazol-5-yl]-2-methylpiperazine |
| 143 | 1-(4-ethylbenzoyl)-4-[3-(3-methoxybenzyl)-1,2,4-thiadiazol-5-yl]-2-methylpiperazine |
| 144 | 1-(3-methylbenzoyl)-4-[3-(4-methylbenzyl)-1,2,4-thiadiazol-5-yl]-2-methylpiperazine |
| 145 | 1-(3-trifluoromethylbenzoyl)-4-[3-(4-fluorobenzyl)-1,2,4-thiadiazol-5-yl]-2-methylpiperazine |

TABLE 1-continued

| No. | Compound name | Compound structure |
|-----|---------------|--------------------|
| 146 | 1-(4-tert-butylbenzoyl)-4-[3-(3-methoxybenzyl)-1,2,4-thiadiazol-5-yl]-2-methylpiperazine | 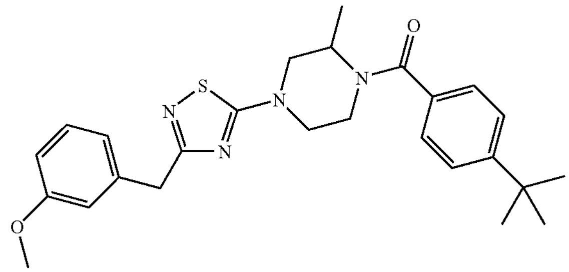 [SMILES: COc1cccc(Cc2nsc(N3CCN(C(=O)c4ccc(C(C)(C)C)cc4)C(C)C3)n2)c1] |
| 147 | 1-(4-ethylbenzoyl)-4-[3-(4-mthylbenzyl)-1,2,4-thiadiazol-5-yl]-2-methylpiperazine | 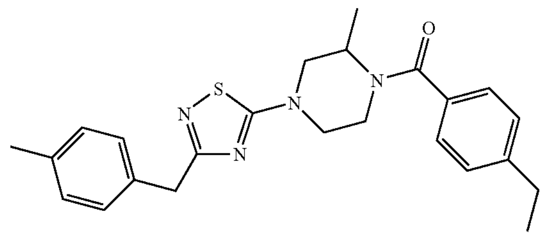 [SMILES: CCc1ccc(C(=O)N2CCN(c3nc(Cc4ccc(C)cc4)ns3)CC2C)cc1] |
| 148 | 1-(2-bromobenzoyl)-4-[3-(4-fluorobenzyl)-1,2,4-thiadiazol-5-yl]-2-methylpiperazine | 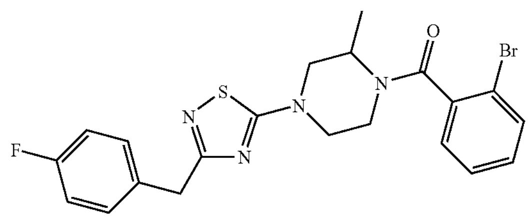 |
| 149 | 1-(2-fluorobenzoyl)-4-[3-(4-methylbenzyl)-1,2,4-thiadiazol-5-yl]-2-methylpiperazine | 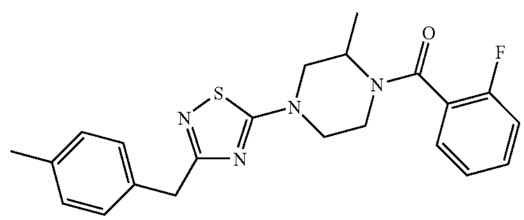 [SMILES: Cc1ccc(Cc2nsc(N3CCN(C(=O)c4ccccc4F)C(C)C3)n2)cc1] |
| 150 | 1-(3-fluorobenzoyl)-4-[3-benzyl-1,2,4-thiadiazol-5-yl]-2-methylpiperazine | 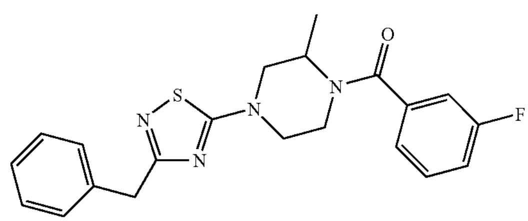 [SMILES: CC1CN(c2nc(Cc3ccccc3)ns2)CCN1C(=O)c1cccc(F)c1] |
| 151 | 1-(4-fluorobenzoyl)-4-[3-(4-methylbenzyl)-1,2,4-thiadiazol-5-yl]-2-methylpiperazine | 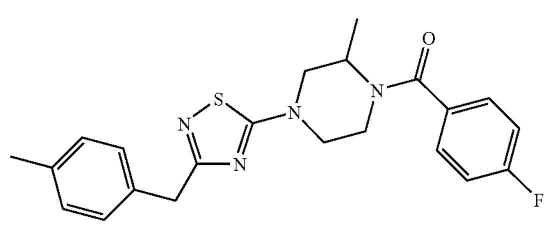 [SMILES: Cc1ccc(Cc2nsc(N3CCN(C(=O)c4ccc(F)cc4)C(C)C3)n2)cc1] |
| 152 | 1-(2-methylbenzoyl)-4-[3-(4-fluorobenzyl)-1,2,4-thiadiazol-5-yl]piperazine | 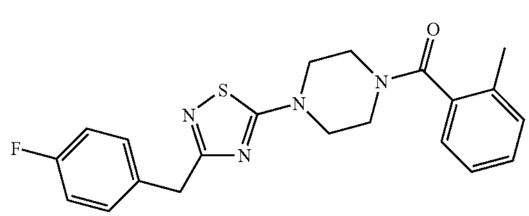 [SMILES: Cc1ccccc1C(=O)N1CCN(c2nc(Cc3ccc(F)cc3)ns2)CC1] |

TABLE 1-continued

| No. | Compound name | Compound structure |
|-----|---------------|---------------------|
| 153 | 1-(4-fluorobenzoyl)-4-[3-(4-chlorobenzyl)-1,2,4-thiadiazol-5-yl]piperazine | 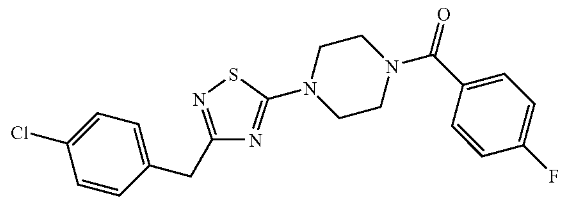 [SMILES: O=C(c1ccc(F)cc1)N1CCN(c2nc(Cc3ccc(Cl)cc3)ns2)CC1] |
| 154 | 1-(4-fluorobenzoyl)-4-[3-benzyl-1,2,4-thiadiazol-5-yl]-2-methylpiperazine | 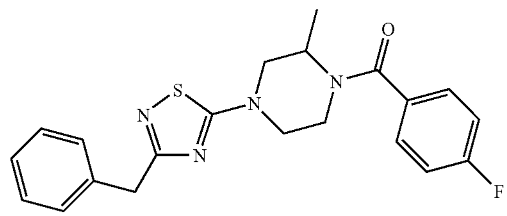 [SMILES: CC1CN(c2nc(Cc3ccccc3)ns2)CCN1C(=O)c1ccc(F)cc1] |
| 155 | 1-(4-chlorobenzoyl)-4-[3-(4-methylbenzyl)-1,2,4-thiadiazol-5-yl]piperazine | 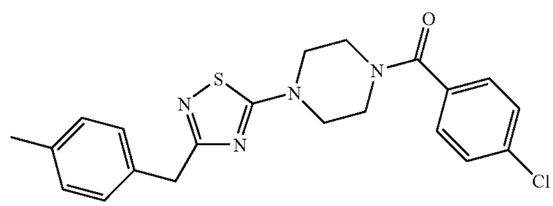 [SMILES: Cc1ccc(Cc2nsc(N3CCN(C(=O)c4ccc(Cl)cc4)CC3)n2)cc1] |
| 156 | 1-(3-fluorobenzoyl)-4-[3-(4-methylbenzyl)-1,2,4-thiadiazol-5-yl]-2-methylpiperazine | 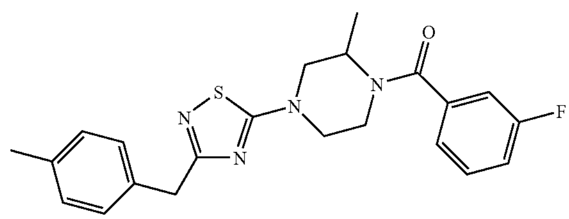 [SMILES: Cc1ccc(Cc2nsc(N3CCN(C(=O)c4cccc(F)c4)C(C)C3)n2)cc1] |
| 157 | 1-(3-fluorobenzoyl)-4-[3-(4-chlorobenzyl)-1,2,4-thiadiazol-5-yl]piperazine | 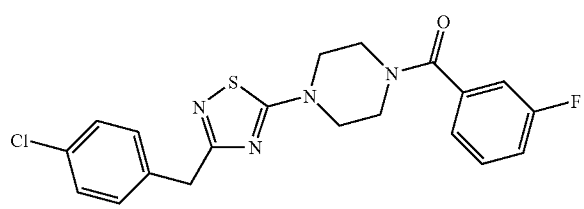 [SMILES: O=C(c1cccc(F)c1)N1CCN(c2nc(Cc3ccc(Cl)cc3)ns2)CC1] |
| 158 | 1-benzoyl-4-[3-(4-methylbenzyl)-1,2,4-thiadiazol-5-yl]piperazine | 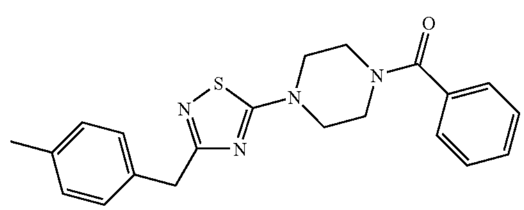 [SMILES: Cc1ccc(Cc2nsc(N3CCN(C(=O)c4ccccc4)CC3)n2)cc1] |
| 159 | 1-(2-fluorobenzoyl)-4-[3-(4-chlorobenzyl)-1,2,4-thiadiazol-5-yl]piperazine | 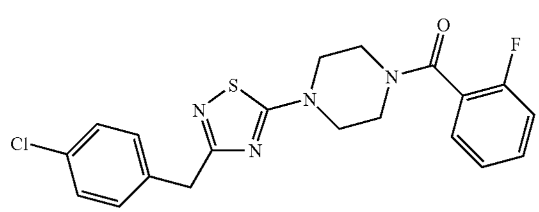 [SMILES: O=C(c1ccccc1F)N1CCN(c2nc(Cc3ccc(Cl)cc3)ns2)CC1] |

TABLE 1-continued

| No. | Compound name |
|---|---|
| 160 | 1-(4-fluorobenzoyl)-4-[3-(4-methylbenzyl)-1,2,4-thiadiazol-5-yl]piperazine |
| 161 | 1-(1,3-benzodioxol-5-ylcarbonyl)-4-[3-(4-methylbenzyl)-1,2,4-thiadiazol-5-yl]-2-methylpiperazine |
| 162 | 1-(3-fluorobenzoyl)-4-[3-(4-methylbenzyl)-1,2,4-thiadiazol-5-yl]piperazine |
| 163 | 1-(4-fluorobenzoyl)-4-[3-benzyl-1,2,4-thiadiazol-5-yl]piperazine |
| 164 | 1-(4-bromobenzoyl)-4-[3-(4-methylbenzyl)-1,2,4-thiadiazol-5-yl]piperazine |
| 165 | 1-(4-ethylbenzoyl)-4-[3-(4-chlorobenzyl)-1,2,4-thiadiazol-5-yl]piperazine |
| 166 | 1-(2-chlorobenzoyl)-4-[3-(4-fluorobenzoyl)-1,2,4-thiadiazol-5-yl]-2-methylpiperazine |

TABLE 1-continued

| No. | Compound name | Compound structure |
|-----|---------------|--------------------|
| 167 | 1-(2-fluorobenzoyl)-4-[3-(4-chlorobenzyl)-1,2,4-thiadiazol-5-yl]-2-methylpiperazine | 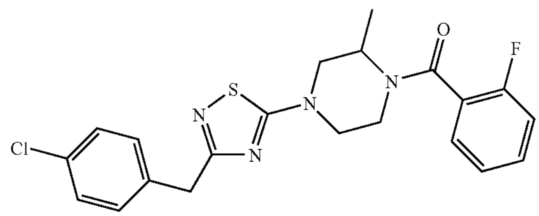 [SMILES: CC1CN(c2nc(Cc3ccc(Cl)cc3)ns2)CCN1C(=O)c1ccccc1F] |
| 168 | 1-(4-trifluoromethylbenzoyl)-4-[3-(3-methoxybenzyl)-1,2,4-thiadiazol-5-yl]-2-methylpiperazine | 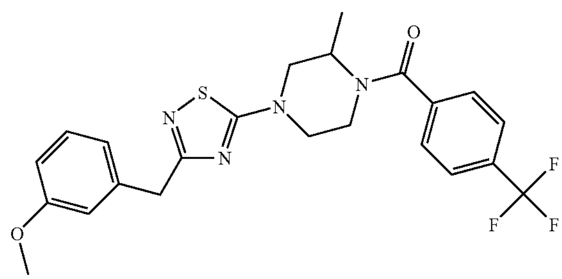 [SMILES: COc1cccc(Cc2nsc(N3CCN(C(=O)c4ccc(C(F)(F)F)cc4)C(C)C3)n2)c1] |
| 169 | 1-benzoyl-4-[3-(4-methylbenzyl)-1,2,4-thiadiazol-5-yl]-2-methylpiperazine | 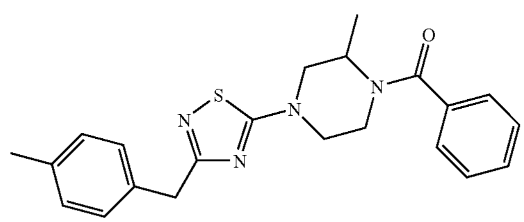 [SMILES: Cc1ccc(Cc2nsc(N3CCN(C(=O)c4ccccc4)C(C)C3)n2)cc1] |
| 170 | 1-(4-bromobenzoyl)-4-[3-(3-methoxybenzyl)-1,2,4-thiadiazol-5-yl]-2-methylpiperazine | 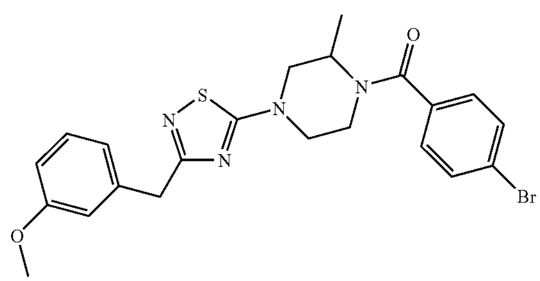 [SMILES: COc1cccc(Cc2nsc(N3CCN(C(=O)c4ccc(Br)cc4)C(C)C3)n2)c1] |
| 171 | 1-(4-trifluoromethylbenzoyl)-4-[3-(4-methylbenzyl)-1,2,4-thiadiazol-5-yl]piperazine | 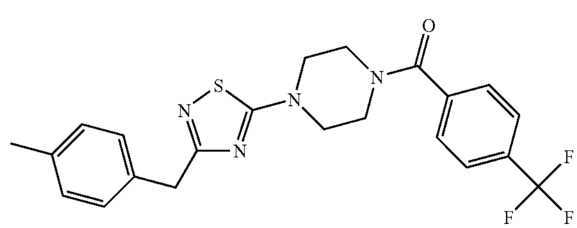 [SMILES: Cc1ccc(Cc2nsc(N3CCN(C(=O)c4ccc(C(F)(F)F)cc4)CC3)n2)cc1] |
| 172 | 1-(3-nitro-4-methylbenzoyl)-4-[3-(4-fluorobenzyl)-1,2,4-thiadiazol-5-yl]-2-methylpiperazine | 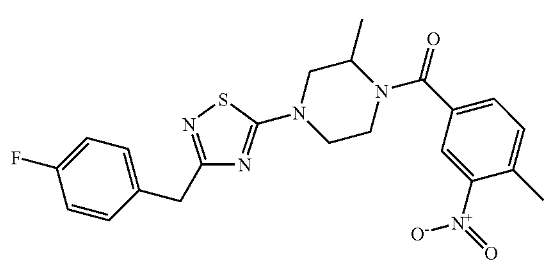 [SMILES: Cc1ccc(C(=O)N2CCN(c3nc(Cc4ccc(F)cc4)ns3)CC2C)cc1[N+](=O)[O-]] |

TABLE 1-continued

| No. | Compound name | Compound structure |
|---|---|---|
| 173 | 1-benzoyl-4-[3-(3-methoxybenzyl)-1,2,4-thiadiazol-5-yl]-2-methylpiperazine | 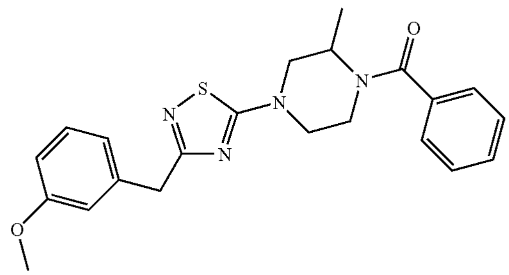 [SMILES: COc1cccc(Cc2nsc(N3CCN(C(=O)c4ccccc4)C(C)C3)n2)c1] |
| 174 | 1-(4-chlorobenzoyl)-4-[3-(3-methoxybenzyl)-1,2,4-thiadiazol-5-yl]-2-methylpiperazine | 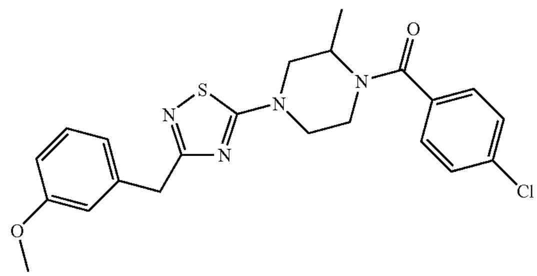 [SMILES: COc1cccc(Cc2nsc(N3CCN(C(=O)c4ccc(Cl)cc4)C(C)C3)n2)c1] |
| 175 | 1-(2-fluorobenzoyl)-4-[3-(4-methylbenzyl)-1,2,4-thiadiazol-5-yl]piperazine | 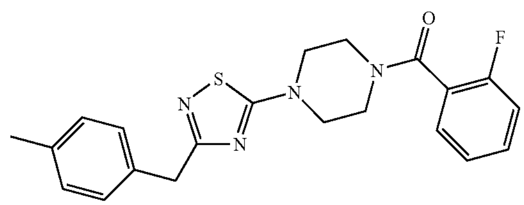 [SMILES: Cc1ccc(Cc2nsc(N3CCN(C(=O)c4ccccc4F)CC3)n2)cc1] |
| 176 | 1-(4-hexylbenzoyl)-4-[3-(4-methylbenzyl)-1,2,4-thiadiazol-5-yl]piperazine | 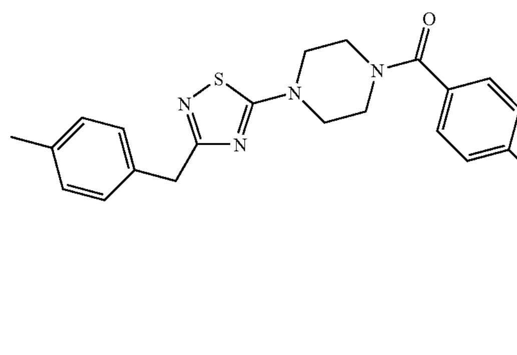 |
| 177 | 1-(2-chloro-4-nitrobenzoyl)-4-[3-(4-fluorobenzyl)-1,2,4-thiadiazol-5-yl]-2-methylpiperazine | 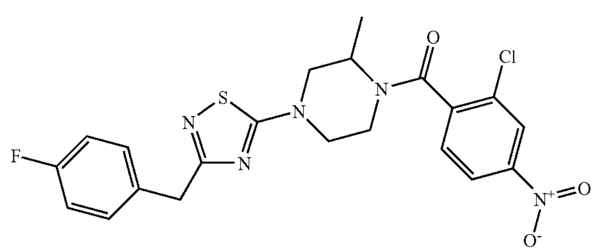 [SMILES: CC1CN(c2nc(Cc3ccc(F)cc3)ns2)CCN1C(=O)c1ccc([N+](=O)[O-])cc1Cl] |
| 178 | 1-(1,3-benzodioxol-5-ylcarbonyl)-4-[3-(4-fluorobenzyl)-1,2,4-thiadiazol-5-yl]-2-methylpiperazine | 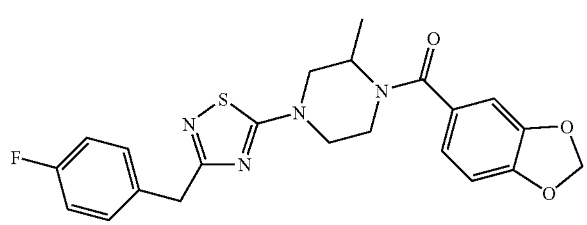 [SMILES: CC1CN(c2nc(Cc3ccc(F)cc3)ns2)CCN1C(=O)c1ccc2c(c1)OCO2] |

TABLE 1-continued

| No. | Compound name | Compound structure |
|---|---|---|
| 179 | 1-(3-fluorobenzoyl)-4-[3-(4-fluorobenzyl)-1,2,4-thiadiazol-5-yl]-2-methylpiperazine | 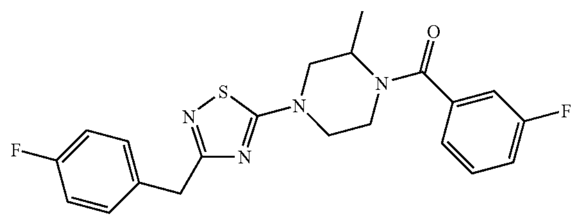 [SMILES: CC1CN(c2nc(Cc3ccc(F)cc3)ns2)CCN1C(=O)c1cccc(F)c1] |
| 180 | 1-(4-tert-butylbenzoyl)-4-[3-(4-fluorobenzyl)-1,2,4-thiadiazol-5-yl]piperazine | 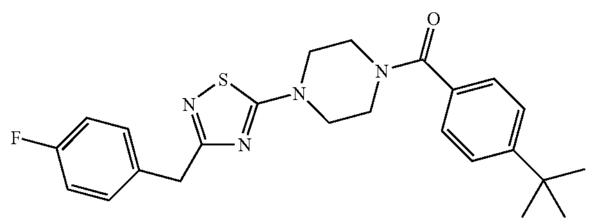 [SMILES: CC(C)(C)c1ccc(C(=O)N2CCN(c3nc(Cc4ccc(F)cc4)ns3)CC2)cc1] |
| 181 | 1-benzoyl-4-[3-(4-fluorobenzyl)-1,2,4-thiadiazol-5-yl]piperazine | 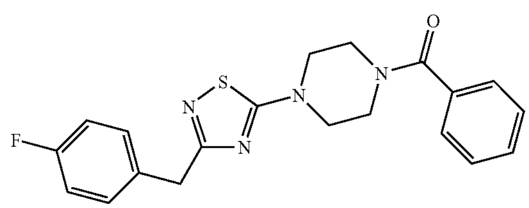 [SMILES: O=C(c1ccccc1)N1CCN(c2nc(Cc3ccc(F)cc3)ns2)CC1] |
| 182 | 1-(4-butylbenzoyl)-4-[3-(4-methylbenzyl)-1,2,4-thiadiazol-5-yl]piperazine | 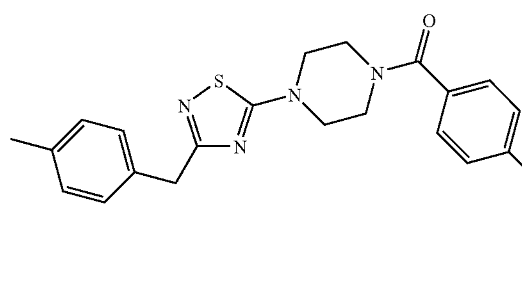 |
| 183 | 1-(4-tert-butylbenzoyl)-4-[3-(4-methylbenzyl)-1,2,4-thiadiazol-5-yl]piperazine | 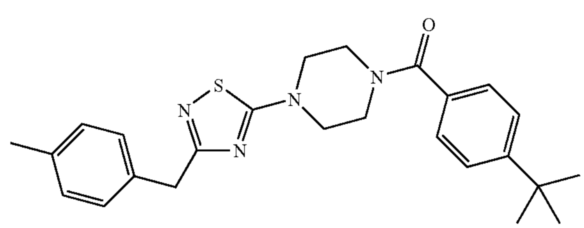 [SMILES: Cc1ccc(Cc2nsc(N3CCN(C(=O)c4ccc(C(C)(C)C)cc4)CC3)n2)cc1] |
| 184 | 1-(4-nitrobenzoyl)-4-[3-(4-fluorobenzyl)-1,2,4-thiadiazol-5-yl]-2-methylpiperazine | 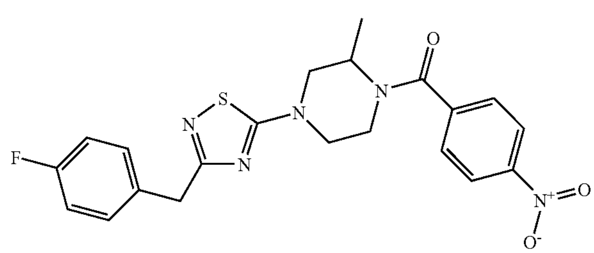 [SMILES: CC1CN(c2nc(Cc3ccc(F)cc3)ns2)CCN1C(=O)c1ccc([N+](=O)[O-])cc1] |
| 185 | 1-(2-methylphenyl)-4-[3-(4-fluorobenzyl)-1,2,4-thiadiazol-5-yl]piperazine | 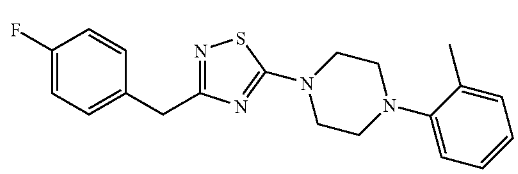 [SMILES: Cc1ccccc1N1CCN(c2nc(Cc3ccc(F)cc3)ns2)CC1] |

TABLE 1-continued

| No. | Compound name |
|---|---|
| 186 | 1-(2-ethoxyphenyl)-4-[3-(4-fluorobenzyl)-1,2,4-thiadiazol-5-yl]piperazine |
| 187 | 1-(2-fluorophenyl)-4-[3-(4-fluorobenzyl)-1,2,4-thiadiazol-5-yl]piperazine |
| 188 | 1-(3-trifluoromethylphenyl)-4-[3-(4-fluorobenzyl)-1,2,4-thiadiazol-5-yl]piperazine |
| 189 | 1-(4-chlorobenzoyl)-4-[3-(4-fluorobenzyl)-1,2,4-thiadiazol-5-yl]-1,4-diazepane |
| 190 | 1-(4-methylbenzoyl)-4-[3-(4-fluorobenzyl)-1,2,4-thiadiazol-5-yl]-1,4-diazepane |
| 191 | 1-(1,3-benzodioxol-5-ylcarbonyl)-4-[3-(4-fluorobenzyl)-1,2,4-thiadiazol-5-yl]-1,4-diazepane |

TABLE 1-continued

| No. | Compound name | Compound structure |
|---|---|---|
| 193 | 1-[4-methoxyphenylsulfonyl]-4-[3-(3-fluoro-benzyl)-1,2,4-thiadiazol-5-yl]piperazine | 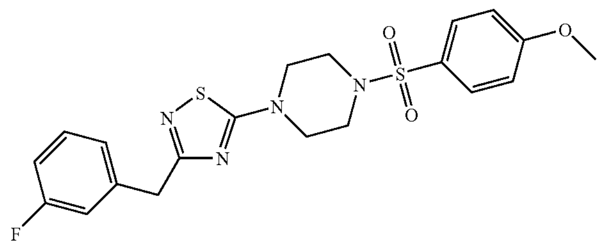 [SMILES: COc1ccc(S(=O)(=O)N2CCN(c3nc(Cc4cccc(F)c4)ns3)CC2)cc1] |
| 194 | 1-[4-methoxyphenylsulfonyl]-4-[3-(2-fluoro-benzyl)-1,2,4-thiadiazol-5-yl]piperazine | 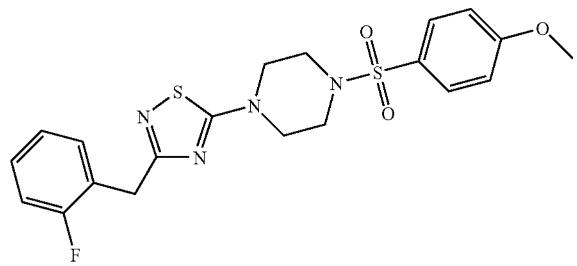 [SMILES: COc1ccc(S(=O)(=O)N2CCN(c3nc(Cc4ccccc4F)ns3)CC2)cc1] |
| 195 | 1-[2-methoxyphenylsulfonyl]-4-[3-(4-fluoro-benzyl)-1,2,4-thiadiazol-5-yl]piperazine | 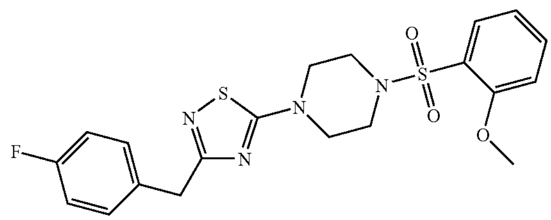 [SMILES: COc1ccccc1S(=O)(=O)N1CCN(c2nc(Cc3ccc(F)cc3)ns2)CC1] |
| 196 | 1-[4-ethoxyphenylsulfonyl]-4-[3-(4-fluoro-benzyl)-1,2,4-thiadiazol-5-yl]piperazine | 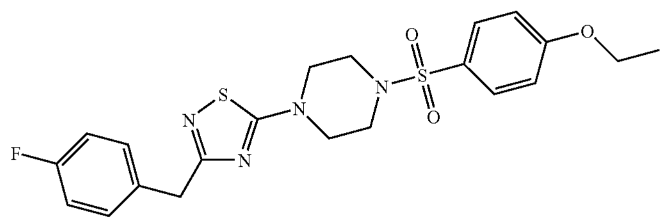 [SMILES: CCOc1ccc(S(=O)(=O)N2CCN(c3nc(Cc4ccc(F)cc4)ns3)CC2)cc1] |
| 197 | 1-[4-ethylphenylsulfonyl]-4-[3-(4-fluoro-benzyl)-1,2,4-thiadiazol-5-yl]piperazine | 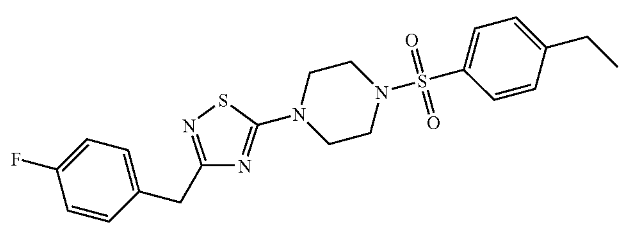 [SMILES: CCc1ccc(S(=O)(=O)N2CCN(c3nc(Cc4ccc(F)cc4)ns3)CC2)cc1] |
| 198 | 1-phenylsulfonyl-4-[3-(4-fluoro-benzyl)-1,2,4-thiadiazol-5-yl]piperazine | 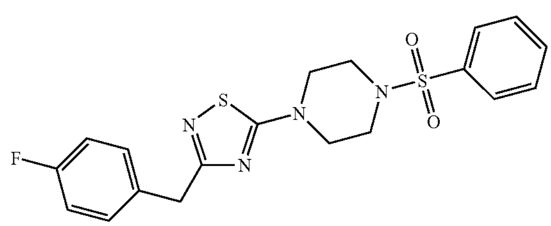 [SMILES: O=S(=O)(c1ccccc1)N1CCN(c2nc(Cc3ccc(F)cc3)ns2)CC1] |

TABLE 1-continued

| No. | Compound name | Compound structure |
| --- | --- | --- |
| 199 | 1-[4-methoxyphenylsulfonyl]-4-[3-benzyl-1,2,4-thiadiazol-5-yl]piperazine | 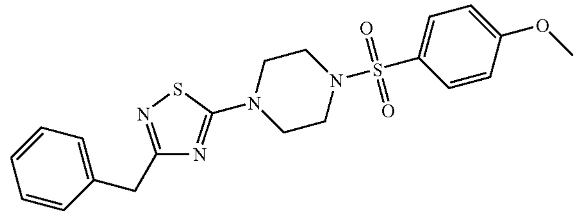 [SMILES: COc1ccc(S(=O)(=O)N2CCN(c3nc(Cc4ccccc4)ns3)CC2)cc1] |
| 200 | 1-(4-propionyloxy)benzene-sulfonyl-4-[3-(4-fluoro-benzyl)-1,2,4-thiadiazol-5-yl]piperazine | 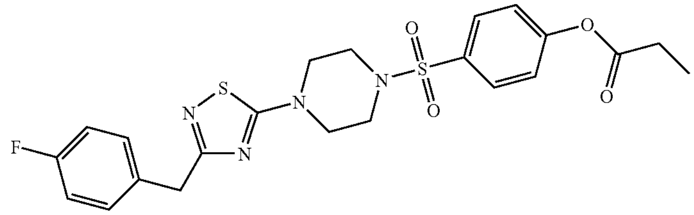 [SMILES: CCC(=O)Oc1ccc(S(=O)(=O)N2CCN(c3nc(Cc4ccc(F)cc4)ns3)CC2)cc1] |
| 201 | 1-[4-methoxyphenylsulfonyl]-4-[3-(3-methyl-benzyl-1,2,4-thiadiazol-5-yl]piperazine | 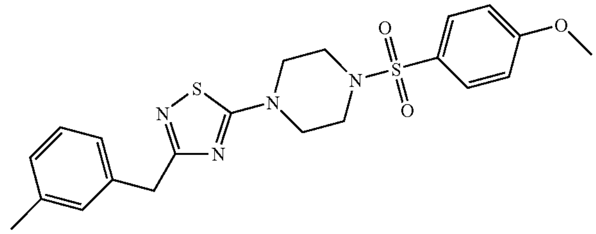 |
| 202 | 1-[4-methoxyphenylsulfonyl]-4-[3-(2-methyl-benzyl-1,2,4-thiadiazol-5-yl]piperazine | 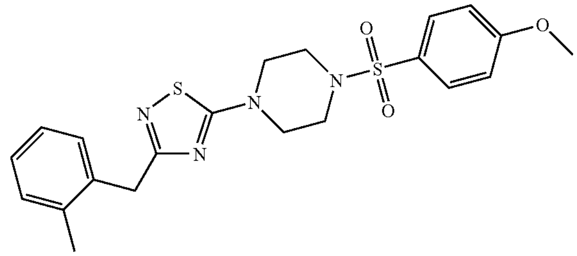 [SMILES: COc1ccc(S(=O)(=O)N2CCN(c3nc(Cc4ccccc4C)ns3)CC2)cc1] |
| 203 | 1-[4-methoxyphenylsulfonyl]-4-[3-(2-methoxy-benzyl-1,2,4-thiadiazol-5-yl]piperazine | 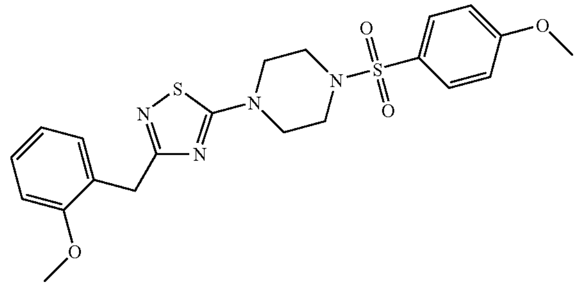 [SMILES: COc1ccc(S(=O)(=O)N2CCN(c3nc(Cc4ccccc4OC)ns3)CC2)cc1] |
| 204 | 1-[4-methoxyphenylsulfonyl]-4-[3-(3-methyl-4-fluoro-benzyl-1,2,4-thiadiazol-5-yl]piperazine | 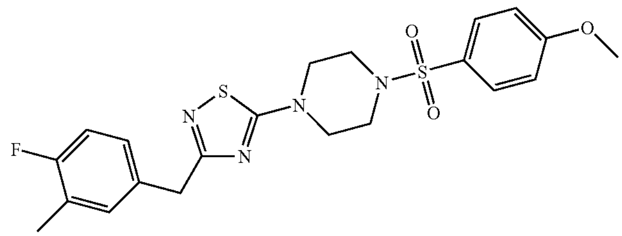 [SMILES: COc1ccc(S(=O)(=O)N2CCN(c3nc(Cc4ccc(F)c(C)c4)ns3)CC2)cc1] |

TABLE 1-continued

| No. | Compound name | Compound structure |
|-----|---------------|--------------------|
| 205 | 1-[4-methoxyphenylsulfonyl]-4-[3-(4-methoxy-benzyl-1,2,4-thiadiazol-5-yl]piperazine | 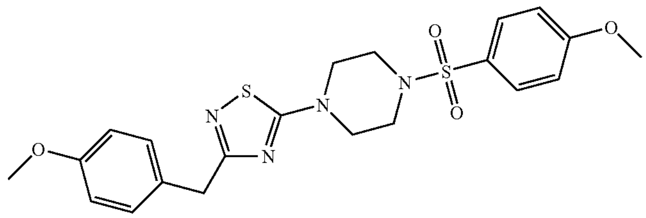 |
| 207 | 1-[4-bromophenylsulfonyl]-4-[3-(3-methoxy-benzyl-1,2,4-thiadiazol-5-yl]piperazine | 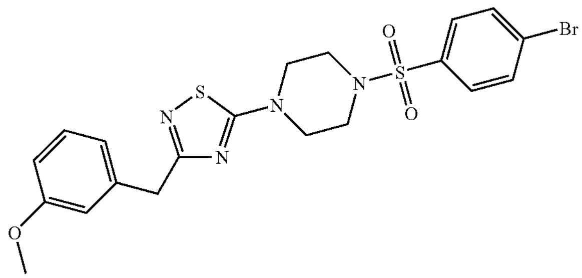 [SMILES: COc1cccc(Cc2nsc(N3CCN(S(=O)(=O)c4ccc(Br)cc4)CC3)n2)c1] |
| 208 | 1-[4-methoxyphenylsulfonyl]-4-[3-(3-methoxybenzyl)-1,2,4-thiadiazol-5-yl]-2-methyl-piperazine | 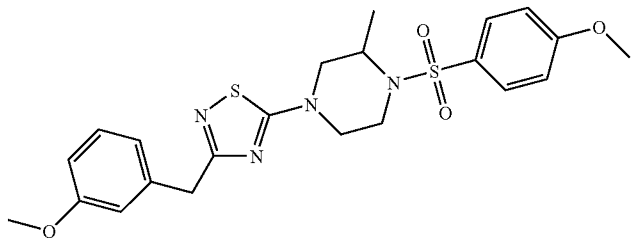 |
| 217 | 1-(4-hydroxybenzenesulfonyl)-4-[3-(4-fluoro-benzyl)-1,2,4-thiadiazol-5-yl]piperazine | 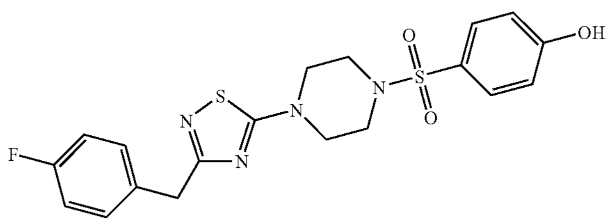 [SMILES: O=S(=O)(c1ccc(O)cc1)N1CCN(c2nc(Cc3ccc(F)cc3)ns2)CC1] |

(end of Table 1)

TABLE 2

| No. | Name | % I | EC50 (μg/mL) |
|-----|------|-----|--------------|
| 60 | 1-[4-methoxyphenylsulfonyl]-4-[3-(4-methylbenzyl)-1,2,4-thiadiazol-5-yl]-2-methylpiperazine | 93 | 0.0013 |
| 49 | 1-[4-acetamidophenylsulfonyl]-4-[3-(4-methylbenzyl)-1,2,4-thiadiazol-5-yl]piperazine | 77 | 0.000106 |
| 31 | 1-[4-methoxyphenylsulfonyl]-4-[3-(4-chlorobenzyl)-1,2,4-thiadiazol-5-yl]piperazine | 59 | 0.000169 |
| 68 | 1-[4-methoxyphenylsulfonyl]-4-[3-(4-methylbenzyl)-1,2,4-thiadiazol-5-yl]piperazine | 53 | 0.000255 |
| 51 | 1-[4-methoxyphenylsulfonyl]-4-[3-(4-chlorobenzyl)-1,2,4-thiadiazol-5-yl]-2-methylpiperazine | 94 | 0.001346 |
| 33 | 1-[4-fluorophenylsulfonyl]-4-[3-(4-chloro-benzyl)-1,2,4-thiadiazol-5-yl]piperazine | 53 | 0.002818 |
| 48 | 1-[4-acetamidophenylsulfonyl]-4-[3-(4-methylbenzyl)-1,2,4-thiadiazol-5-yl]-2-methylpiperazine | 91 | 0.008439 |
| 57 | 1-[4-fluorophenylsulfonyl]-4-[3-(4-methyl-benzyl)-1,2,4-thiadiazol-5-yl]piperazine | 88 | 0.010360 |
| 115 | 1-(2-fluorobenzoyl)-4-[3-(3-methoxybenzyl)-1,2,4-thiadiazol-5-yl]-2-methylpiperazine | 75 | 0.036080 |
| 65 | 1-[2-naphthylsulfonyl]-4-[3-(4-methylbenzyl)-1,2,4-thiadiazol-5-yl]piperazine | 78 | 0.039270 |
| 35 | 1-[1-naphthylsulfonyl]-4-[3-(4-methylbenzyl)-1,2,4-thiadiazol-5-yl]piperazine | 47 | 0.047235 |
| 116 | 1-(4-ethylbenzoyl)-4-[3-(4-fluorobenzyl)-1,2,4-thiadiazol-5-yl]-2-methylpiperazine | 71 | 0.052160 |
| 80 | 1-(phenylprop-2-ensulfonyl)-4-[3-(4-methylbenzyl)-1,2,4-thiadiazol-5-yl]piperazine | 70 | 0.056880 |
| 58 | 1-[4-fluorophenylsulfonyl]-4-[3-(4-methyl-benzyl)-1,2,4-thiadiazol-5-yl]-2-methyl-piperazine | 58 | 0.061030 |
| 34 | 1-[4-chlorophenylsulfonyl]-4-[3-(4-methylbenzyl)-1,2,4-thiadiazol-5-yl]-2-methyl-piperazine | 66 | 0.065695 |
| 37 | 1-[2,4,6-trimethylphenylsulfonyl]-4-[3-(4-methylbenzyl)-1,2,4-thiadiazol-5-yl]piperazine | 48 | 0.073110 |
| 55 | 1-[4-acetamidophenylsulfonyl]-4-[3-(4-fluorobenzyl)-1,2,4-thiadiazol-5-yl]-2-methylpiperazine | 114 | 0.078150 |
| 63 | 1-[4-methylphenylsulfonyl]-4-[3-(4-chloro-benzyl)-1,2,4-thiadiazol-5-yl]piperazine | 83 | 0.080740 |

TABLE 2-continued

| No. | Name | % I | EC50 (μg/mL) |
|---|---|---|---|
| 117 | 1-(4-butylbenzoyl)-4-[3-(4-methylbenzyl)-1,2,4-thiadiazol-5-yl]-2-methylpiperazine | 82 | 0.084110 |
| 118 | 1-(4-methoxybenzoyl)-4-[3-(4-fluorobenzyl)-1,2,4-thiadiazol-5-yl]-2-methylpiperazine | 64 | 0.091145 |
| 119 | 1-(1,3-benzodioxol-5-ylcarbonyl)-4-[3-(3-methoxybenzyl)-1,2,4-thiadiazol-5-yl]-2-methylpiperazine | 72 | 0.095050 |
| 120 | 1-(4-butylphenyl)-4-[3-(4-fluorobenzyl)-1,2,4-thiadiazol-5-yl]-2-methylpiperazine | 120 | 0.098730 |
| 40 | 1-[4-bromophenylsulfonyl]-4-[3-(4-methylbenzyl)-1,2,4-thiadiazol-5-yl]-3-methyl-piperazine | 77 | 0.099855 |
| 36 | 1-[2,5-dichlorophenylsulfonyl]-4-[3-(4-methylbenzyl)-1,2,4-thiadiazol-5-yl]-2-methylpiperazine | 52 | 0.10 |
| 52 | 1-[2-naphthylsulfonyl]-4-[3-(4-chlorobenzyl)-1,2,4-thiadiazol-5-yl]piperazine | 104 | 0.10 |
| 121 | 1-(4-hexylbenzoyl)-4-[3-(4-fluorobenzyl)-1,2,4-thiadiazol-5-yl]piperazine | 64 | 0.12 |
| 78 | 1-(phenylprop-2-ensulfonyl)-4-[3-(4-fluorobenzyl)-1,2,4-thiadiazol-5-yl]piperazine | 75 | 0.13 |
| 38 | 1-[2-naphthylsulfonyl]-4-[3-(4-fluorobenzyl)-1,2,4-thiadiazol-5-yl]-2-methylpiperazine | 78 | 0.13 |
| 122 | 1-(3-chlorobenzoyl)-4-[3-(4-fluorobenzyl)-1,2,4-thiadiazol-5-yl]-2-methylpiperazine | 92 | 0.14 |
| 123 | 1-(4-fluorobenzoyl)-4-[3-(3-methoxybenzyl)-1,2,4-thiadiazol-5-yl]-2-methylpiperazine | 95 | 0.14 |
| 124 | 1-(4-methylbenzoyl)-4-[3-(3-methoxybenzyl)-1,2,4-thiadiazol-5-yl]-2-methylpiperazine | 57 | 0.14 |
| 1 | 4-phenylacetyl-1-[3-(4-fluorobenzyl)-1,2,4-thiadiazol-5-yl]piperazine | 75 | 0.15 |
| 39 | 1-[2,5-dichlorophenylsulfonyl]-4-[3-(4-chlorobenzyl)-1,2,4-thiadiazol-5-yl]piperazine | 25 | 0.16 |
| 125 | 1-(3-fluorobenzoyl)-4-[3-(4-chlorobenzyl)-1,2,4-thiadiazol-5-yl]-2-methylpiperazine | 68 | 0.16 |
| 189 | 1-(4-chlorobenzoyl)-4-[3-(4-fluorobenzyl)-1,2,4-thiadiazol-5-yl]-1,4-diazepane | 85 | 0.17 |
| 79 | 1-(phenylprop-2-ensulfonyl)-4-[3-(4-methylbenzyl)-1,2,4-thiadiazol-5-yl]-2-methylpiperazine | 53 | 0.17 |
| 19 | N-(2,6-dimethylphenyl)-4-[3-(4-fluorobenzyl)-1,2,4-thiadiazol-5-yl]-2-methylpiperazine-1-carboxamide | 95 | 0.20 |
| 126 | 1-benzoyl-4-[3-(4-fluorobenzyl)-1,2,4-thiadiazol-5-yl]-2-methylpiperazine | 63 | 0.21 |
| 127 | 1-(4-fluorobenzoyl)-4-[3-(4-fluorobenzyl)-1,2,4-thiadiazol-5-yl]-2-methylpiperazine | 108 | 0.23 |
| 128 | 1-(4-tert-butylbenzoyl)-4-[3-(4-fluorobenzyl)-1,2,4-thiadiazol-5-yl]-2-methylpiperazine | 95 | 0.24 |
| 129 | 1-(1,1'-biphenyl-4-ylcarbonyl)-4-[3-(4-fluorobenzyl)-1,2,4-thiadiazol-5-yl]-2-methylpiperazine | 61 | 0.24 |
| 2 | 4-(4-fluorophenylacetyl),1-[3-(4-fluorobenzyl)-1,2,4-thiadiazol-5-yl]piperazine | 54 | 0.25 |
| 130 | 1-(4-methoxybenzoyl)-4-[3-(4-methylbenzyl)-1,2,4-thiadiazol-5-yl]-2-methylpiperazine | 118 | 0.25 |
| 131 | 1-(4-ethylbenzoyl)-4-[3-(4-methylbenzyl)-1,2,4-thiadiazol-5-yl]piperazine | 91 | 0.25 |
| 107 | 2-(4-fluorophenyl)-N-{2-[4-[3-(4-fluorobenzyl)-1,2,4-thiadiazol-5-yl]piperazin-1-yl]ethyl}acetamide | 80 | 0.26 |
| 132 | 1-(2-naphthoyl)-4-[3-(4-fluorobenzyl)-1,2,4-thiadiazol-5-yl]-2-methylpiperazine | 74 | 0.26 |
| 133 | 1-(2-methoxybenzoyl)-4-[3-(4-fluorobenzyl)-1,2,4-thiadiazol-5-yl]-2-methylpiperazine | 118 | 0.29 |
| 134 | 1-(4-pentylbenzoyl)-4-[3-(4-methylbenzyl)-1,2,4-thiadiazol-5-yl]-2-methylpiperazine | 75 | 0.30 |
| 135 | 1-(4-bromobenzoyl)-4-[3-(4-fluorobenzyl)-1,2,4-thiadiazol-5-yl]-2-methylpiperazine | 73 | 0.31 |
| 136 | 1-(2,4-dimethoxybenzoyl)-4-[3-(4-fluorobenzyl)-1,2,4-thiadiazol-5-yl]-2-methyl-piperazine | 83 | 0.34 |
| 137 | 1-(3,5-dichlorobenzoyl)-4-[3-(4-fluorobenzyl)-1,2,4-thiadiazol-5-yl]piperazine | 68 | 0.35 |
| 94 | 4-pentyl-N-{2-[4-[3-(4-fluorobenzyl)-1,2,4-thiadiazol-5-yl]piperazin-1-yl]ethyl}benzamide | 90 | 0.35 |
| 81 | 1-(butylsulfonyl)-4-[3-(4-chlorobenzyl)-1,2,4-thiadiazol-5-yl]piperazine | 80 | 0.35 |
| 138 | 1-(3-chlorobenzoyl)-4-[3-(4-fluorobenzyl)-1,2,4-thiadiazol-5-yl]piperazine | 81 | 0.36 |
| 185 | 1-(2-methylphenyl)-4-[3-(4-fluorobenzyl)-1,2,4-thiadiazol-5-yl]piperazine | 114 | 0.38 |
| 95 | 4-butyl-N-{2-[4-[3-(4-fluorobenzyl)-1,2,4-thiadiazol-5-yl]piperazin-1-yl]ethyl}benzamide | 78 | 0.38 |
| 139 | 1-(4-methylbenzoyl)-4-[3-(4-fluorobenzyl)-1,2,4-thiadiazol-5-yl]-2-methylpiperazine | 87 | 0.40 |
| 140 | 1-(2-methylbenzoyl)-4-[3-(4-fluorobenzyl)-1,2,4-thiadiazol-5-yl]-2-methylpiperazine | 56 | 0.45 |
| 141 | 1-(4-methylbenzoyl)-4-[3-(4-fluorobenzyl)-1,2,4-thiadiazol-5-yl]piperazine | 75 | 0.49 |
| 142 | 1-(3-bromobenzoyl)-4-[3-(4-fluorobenzyl)-1,2,4-thiadiazol-5-yl]-2-methylpiperazine | 72 | 0.50 |
| 9 | N-(3-fluorophenyl)-4-[3-(4-fluorobenzyl)-1,2,4-thiadiazol-5-yl]piperazine-1-carboxamide | 53 | 0.52 |
| 41 | 1-[1-naphthylsulfonyl]-4-[3-(4-methylbenzyl)-1,2,4-thiadiazol-5-yl]-3-methylpiperazine | 54 | 0.53 |
| 112 | 3-phenyl-N-{2-[4-[3-(4-fluorobenzyl)-1,2,4-thiadiazol-5-yl]piperazin-1-yl]ethyl}propanamide | 91 | 0.55 |
| 143 | 1-(4-ethylbenzoyl)-4-[3-(3-methoxybenzyl)-1,2,4-thiadiazol-5-yl]-2-methylpiperazine | 89 | 0.56 |
| 144 | 1-(3-methylbenzoyl)-4-[3-(4-methylbenzyl)-1,2,4-thiadiazol-5-yl]-2-methylpiperazine | 64 | 0.56 |
| 89 | 1-(3-phenylpropanoyl)-4-[3-(4-fluorobenzyl)-1,2,4-thiadiazol-5-yl]-2-methylpiperazine | 86 | 0.60 |
| 10 | N-(2-methylphenyl)-4-[3-(4-fluorobenzyl)-1,2,4-thiadiazol-5-yl]-2-methylpiperazine-1-carboxamide | 72 | 0.60 |
| 145 | 1-(3-trifluoromethylbenzoyl)-4-[3-(4-fluorobenzyl)-1,2,4-thiadiazol-5-yl]-2-methylpiperazine | 60 | 0.62 |
| 11 | N-(4-ethylphenyl)-4-[3-(4-fluorobenzyl)-1,2,4-thiadiazol-5-yl]-2-methylpiperazine-1-carboxamide | 73 | 0.69 |
| 91 | 1-[3-phenylprop-2-enyl]-4-[3-(4-methylbenzyl)-1,2,4-thiadiazol-5-yl]piperazine | 90 | 0.71 |
| 146 | 1-(4-tert-butylbenzoyl)-4-[3-(3-methoxy-benzyl)-1,2,4-thiadiazol-5-yl]-2-methyl-piperazine | 94 | 0.72 |
| 92 | 1-[3-phenylprop-2-enyl]-4-[3-(4-chlorobenzyl)-1,2,4-thiadiazol-5-yl]piperazine | 69 | 0.75 |
| 20 | N-(2,4-dimethylphenyl)-4-[3-(4-fluorobenzyl)-1,2,4-thiadiazol-5-yl]-2-methylpiperazine-1-carboxamide | 106 | 0.76 |
| 21 | N-(2,6-dichlorophenyl)-4-[3-(4-fluorobenzyl)-1,2,4-thiadiazol-5-yl]-2-methylpiperazin-1-carboxamide | 70 | 0.79 |
| 96 | 4-hexyl-N-{2-[4-[3-(4-fluorobenzyl)-1,2,4-thiadiazol-5-yl]piperazin-1-yl]ethyl}benzamide | 72 | 0.80 |
| 4 | 1-(4-methoxyphenylacetyl)-4-[3-(4-fluoro-benzyl)-1,2,4-thiadiazol-5-yl]-2-methyl-piperazine | 56 | 0.82 |
| 147 | 1-(4-ethylbenzoyl)-4-[3-(4-methylbenzyl)-1,2,4-thiadiazol-5-yl]-2-methylpiperazine | 88 | 0.84 |
| 148 | 1-(2-bromobenzoyl)-4-[3-(4-fluorobenzyl)-1,2,4-thiadiazol-5-yl]-2-methylpiperazine | 56 | 0.86 |
| 42 | 1-[4-tert-butylphenylsulfonyl]-4-[3-(4-methylbenzyl)-1,2,4-thiadiazol-5-yl]-2-methylpiperazine | 33 | 0.87 |
| 22 | N-(3-cyanophenyl)-4-[3-(4-fluorobenzyl)-1,2,4-thiadiazol-5-yl]-2-methylpiperazine-1-carboxamide | 59 | 0.88 |
| 43 | 1-[1-naphthylsulfonyl]-4-[3-(4-chloro-benzyl)-1,2,4-thiadiazol-5-yl]-2-methyl-piperazine | 35 | 0.89 |
| 12 | N-(2-ethylphenyl)-4-[3-(4-fluorobenzyl)-1,2,4-thiadiazol-5-yl]-2-methylpiperazine-1-carboxamide | 92 | 0.89 |
| 23 | N-(2,4-difluorophenyl)-4-[3-(4-fluorobenzyl)-1,2,4-thiadiazol-5-yl]-2-methylpiperazine-1-carboxamide | 66 | 0.94 |
| 149 | 1-(2-fluorobenzoyl)-4-[3-(4-methylbenzyl)-1,2,4-thiadiazol-5-yl]-2-methylpiperazine | 105 | 0.98 |

TABLE 2-continued

| No. | Name | % I | EC50 (µg/mL) |
|---|---|---|---|
| 86 | 1-[(2E)-3-phenylprop-2-enoyl]-4-[3-(4-chlorobenzyl)-1,2,4-thiadiazol-5-yl]-2-methylpiperazine | 81 | 1.13 |
| 150 | 1-(3-fluorobenzoyl)-4-[3-benzyl-1,2,4-thiadiazol-5-yl]-2-methylpiperazine | 99 | 1.14 |
| 151 | 1-(4-fluorobenzoyl)-4-[3-(4-methylbenzyl)-1,2,4-thiadiazol-5-yl]-2-methylpiperazine | 73 | 1.14 |
| 152 | 1-(2-methylbenzoyl)-4-[3-(4-fluorobenzyl)-1,2,4-thiadiazol-5-yl]piperazine | 66 | 1.15 |
| 45 | 1-[2,4,6-trimethylphenylsulfonyl]-4-[3-(4-methylbenzyl)-1,2,4-thiadiazol-5-yl]-2-methylpiperazine | 56 | 1.20 |
| 24 | N-(2,6-dimethylphenyl)-4-[3-(4-fluorobenzyl)-1,2,4-thiadiazol-5-yl]piperazine-1-carboxamide | 124 | 1.20 |
| 13 | N-phenyl-4-[3-(4-fluorobenzyl)-1,2,4-thiadiazol-yl]5-piperazine-1-carboxamide | 71 | 1.23 |
| 97 | 4-chloro-N-{2-[4-[3-(4-fluorobenzyl)-1,2,4-thiadiazol-5-yl]piperazine-1-yl]ethyl}benzamide | 68 | 1.29 |
| 46 | 1-[3-trifluorophenylsulfonyl]-4-[3-(4-fluorobenzyl)-1,2,4-thiadiazol-5-yl]-2-methylpiperazine | 64 | 1.34 |
| 90 | 1-(3-phenylpropanoyl)-4-[3-(4-fluorobenzyl)-1,2,4-thiadiazol-5-yl]piperazine | 73 | 1.41 |
| 98 | 3,5-dichloro-N-{2-[4-[3-(4-fluorobenzyl)-1,2,4-thiadiazol-5-yl]piperazin-1-yl]ethyl}benzamide | 102 | 1.42 |
| 153 | 1-(4-fluorobenzoyl)-4-[3-(4-chlorobenzyl)-1,2,4-thiadiazol-5-yl]piperazine | 53 | 1.44 |
| 8 | 1-(2-phenylbutanoyl)-4-[3-(4-fluorobenzyl)-1,2,4-thiadiazol-5-yl]-2-methylpiperazine | 71 | 1.49 |
| 113 | 1-benzyl-4-[3-(4-fluorobenzyl)-1,2,4-thiadiazol-5-yl]piperazine | 65 | 1.54 |
| 99 | 2-methyl-N-{2-[4-[3-(4-fluorobenzyl)-1,2,4-thiadiazol-5-yl]piperazin-1-yl]ethyl}benzamide | 97 | 1.58 |
| 154 | 1-(4-fluorobenzoyl)-4-[3-benzyl-1,2,4-thiadiazol-5-yl]-2-methylpiperazine | 75 | 1.58 |
| 82 | 1-(octylsulfonyl)-4-[3-(4-methylbenzyl)-1,2,4-thiadiazol-5-yl]piperazine | 50 | 1.58 |
| 155 | 1-(4-chlorobenzoyl)-4-[3-(4-methylbenzyl)-1,2,4-thiadiazol-5-yl]piperazine | 76 | 1.64 |
| 156 | 1-(3-fluorobenzoyl)-4-[3-(4-methylbenzyl)-1,2,4-thiadiazol-5-yl]-2-methylpiperazine | 86 | 1.67 |
| 25 | N-1-naphthyl-4-[3-(4-fluorobenzyl)-1,2,4-thiadiazol-5-yl]-2-methylpiperazine-1-carboxamide | 97 | 1.69 |
| 157 | 1-(3-fluorobenzoyl)-4-[3-(4-chlorobenzyl)-1,2,4-thiadiazol-5-yl]piperazine | 70 | 1.70 |
| 14 | N-(4-ethoxyphenyl)-4-[3-(4-fluorobenzyl)-1,2,4-thiadiazol-5-yl]-2-methylpiperazine-1-carboxamide | 70 | 1.73 |
| 111 | 2-phenyl-N-{2-[4-[3-(4-fluorobenzyl)-1,2,4-thiadiazol-5-yl]piperazin-1-yl]ethyl}butanamide | 79 | 1.79 |
| 100 | 3-fluoro-N-{2-[4-[3-(4-chlorobenzyl)-1,2,4-thiadiazol-5-yl]piperazin-1-yl]ethyl}benzmaide | 75 | 1.79 |
| 101 | 4-methyl-N-{2-[4-[3-(4-fluorobenzyl)-1,2,4-thiadiazol-5-yl]piperazin-1-yl]ethyl}benzamide | 68 | 1.94 |
| 102 | 4-fluoro-N-{2-[4-[3-(4-fluorobenzyl)-1,2,4-thiadiazol-5-yl]piperazin-1-yl]ethyl}benzamide | 80 | 1.99 |
| 93 | 1-[3-phenylprop-2-enyl]-4-[3-(4-fluorobenzyl)-1,2,4-thiadiazol-5-yl]piperazine | 91 | 1.99 |
| 186 | 1-(2-ethoxyphenyl)-4-[3-(4-fluorobenzyl)-1,2,4-thiadiazol-5-yl]piperazine | 94 | 2.05 |
| 108 | 2-phenyl-N-{2-[4-[3-(4-fluorobenzyl)-1,2,4-thiadiazol-5-yl]piperain-1-yl]ethyl}acetamide | 63 | 2.06 |
| 158 | 1-benzoyl-4-[3-(4-methylbenzyl)-1,2,4-thiadiazol-5-yl]piperazine | 57 | 2.10 |
| 3 | 1-(4-fluorophenylacetyl)-4-[3-(4-methylbenzyl)-1,2,4-thiadiazol-5-yl]-2-methylpiperazine | 76 | 2.20 |
| 103 | 4-ethyl-N-{2-[4-[3-(4-fluorobenzyl)-1,2,4-thiadiazol-5-yl]piperazin-1-yl]ethyl}benzamide | 139 | 2.32 |
| 87 | 1-[(2E)-3-phenylprop-2-enoyl]-4-[3-(4-fluorobenzyl)-1,2,4-thiadiazol-5-yl]-2-methylpiperazine | 94 | 2.49 |
| 83 | 1-(butylsulfonyl)-4-[3-(4-methylbenzyl)-1,2,4-thiadiazol-5-yl]piperazine | 36 | 2.64 |
| 190 | 1-(4-methylbenzoyl)-4-[3-(4-fluorobenzyl)-1,2,4-thiadiazol-5-yl]-1,4-diazepane | 87 | 2.77 |
| 187 | 1-(2-fluorophenyl)-4-[3-(4-fluorobenzyl)-1,2,4-thiadiazol-5-yl]piperazine | 83 | 2.81 |
| 159 | 1-(2-fluorobenzoyl)-4-[3-(4-fluorobenzyl)-1,2,4-thiadiazol-5-yl]piperazine | 48 | 2.85 |
| 160 | 1-(4-fluorobenzoyl)-4-[3-(4-methylbenzyl)-1,2,4-thiadiazol-5-yl]piperazine | 88 | 2.87 |
| 161 | 1-(1,3-benzodioxol-5-ylcarbonyl)-4-[3-(4-methylbenzyl)-1,2,4-thiadiazol-5-yl]-2-methylpiperazine | 101 | 3.36 |
| 162 | 1-(3-fluorobenzoyl)-4-[3-(4-methylbenzyl)-1,2,4-thiadiazol-5-yl]piperazine | 101 | 3.40 |
| 84 | 1-(ethylsulfonyl)-4-[3-(4-chlorobenzyl)-1,2,4-thiadiazol-5-yl]piperazine | 53 | 3.48 |
| 109 | 2-(4-fluorophenyl)-N-{2-[4-[3-(4-methylbenzyl)-1,2,4-thiadiazol-5-yl]piperazin-1-yl]ethyl}acetamide | 93 | 3.52 |
| 163 | 1-(4-fluorobenzoyl)-4-[3-benzyl-1,2,4-thiadiazol-5-yl]piperazine | 67 | 3.61 |
| 85 | 1-(isopropylsulfonyl)-4-[3-(4-methylbenzyl)-1,2,4-thiadiazol-5-yl]piperazine | 69 | 3.65 |
| 104 | N-{2-[4-[3-(4-fluorobenzyl)-1,2,4-thiadiazol-5-yl]piperazin-1-yl]ethyl}benzamide | 65 | 3.82 |
| 164 | 1-(4-bromobenzoyl)-4-[3-(4-methylbenzyl)-1,2,4-thiadiazol-5-yl]piperazine | 60 | 3.86 |
| 15 | N-(2-methylphenyl)-4-[3-(4-fluorobenzyl)-1,2,4-thiadiazol-5-yl]piperazine-1-carboxamide | 65 | 5.01 |
| 16 | N-(2-fluorophenyl)-4-[3-(4-fluorobenzyl)-1,2,4-thiadiazol-5-yl]piperazine-1-carboxamide | 72 | 5.68 |
| 30 | 1-[4-tert-butylphenylsulfonyl]-4-[3-(4-fluorobenzyl)-1,2,4-thiadiazol-5-yl]piperazine | 51 | |
| 77 | 1-(benzylsulfonyl)-4-[3-(4-methylbenzyl)-1,2,4-thiadiazol-5-yl]piperazine | 81 | |
| 5 | 1-phenylacetyl-4-[3-(4-fluorobenzyl)-1,2,4-thiadiazol-5-yl]-2-methylpiperazine | 83 | |
| 6 | 1-(4-fluorophenylacetyl)-4-[3-(4-fluorobenzyl)-1,2,4-thiadiazol-5-yl]-2-methylpiperazine | 75 | |
| 7 | 1-[chloro(phenyl)acetyl]-4-[3-(4-fluorobenzyl)-1,2,4-thiadiazol-5-yl]-2-methylpiperazine | 69 | |
| 17 | N-(2-trifluoromethylphenyl)-4-[3-(4-fluorobenzyl)-1,2,4-thiadiazol-5-yl]piperazine-1-carboxamide | 46 | |
| 18 | N-(2-trifluoromethylphenyl)-4-[3-(4-fluorobenzyl)-1,2,4-thiadiazol-5-yl]-2-methylpiperazine-1-carboxamide | 41 | |
| 26 | N-(3,4-difluorophenyl)-4-[3-(4-fluorobenzyl)-1,2,4-thiadiazol-5-yl]-2-methylpiperazine-1-carboxamide | 70 | |
| 27 | N-(2,4-dimethoxyphenyl)-4-[3-(4-fluorobenzyl)-1,2,4-thiadiazol-5-yl]piperazine-1-carboxamide | 67 | |
| 28 | N-(3,4-difluorophenyl)-4-[3-(4-fluorobenzyl)-1,2,4-thiadiazol-5-yl]piperazine-1-carboxamide | 64 | |
| 29 | N-(3,5-dimethoxyphenyl)-4-[3-(4-fluorobenzyl)-1,2,4-thiadiazol-5-yl]-2-methylpiperazine-1-carboxamide | 51 | |
| 47 | 1-phenylsulfonyl-4-[3-(4-fluorobenzyl)-1,2,4-thiadiazol-5-yl]-2-methylpiperazine | 129 | |
| 50 | 1-[4-methylphenylsulfonyl]-4-[3-(4-methylbenzyl)-1,2,4-thiadiazol-5-yl]-2-methylpiperazine | 105 | |
| 54 | 1-[4-tert-butylphenylsulfonyl]-4-[3-(4-fluorobenzyl)-1,2,4-thiadiazol-5-yl]-2-methylpiperazine | 60 | |
| 56 | 1-[3-trifluoromethylphenylsulfonyl]-4-[3-(4-methylbenzyl)-1,2,4-thiadiazol-5-yl]-2-methylpiperazine | 87 | |
| 59 | 1-[4-fluorophenylsulfonyl]-4-[3-(4-fluorobenzyl)-1,2,4-thiadiazol-5-yl]-2-methylpiperazine | 42 | |
| 61 | 1-[4-ter-butylphenylsulfonyl]-4-[3-(4-fluorobenzyl)-1,2,4-thiadiazol-5-yl]piperazine | 47 | |
| 62 | 1-[3-trifluoromethylphenylsulfonyl]-4-[3-(4-methylbenzyl)-1,2,4-thiadiazol-5-yl]piperazine | 45 | |
| 64 | 1-[4-bromophenylsulfonyl]-4-[3-(4-methylbenzyl)-1,2,4-thiadiazol-5-yl]piperazine | 58 | |

TABLE 2-continued

| No. | Name | % I | EC50 (µg/mL) |
|---|---|---|---|
| 66 | 1-[4-chlorophenylsulfonyl]-4-[3-(4-methyl-benzyl)-1,2,4-thiadiazol-5-yl]piperazine | 81 | |
| 67 | 1-[4-ter-butylphenylsulfonyl]-4-[3-(4-methylbenzyl)-1,2,4-thiadiazol-5-yl]piperazine | 41 | |
| 69 | 1-[4-tert-butylphenylsulfonyl]-4-[3-(4-chlorobenzyl)-1,2,4-thiadiazol-5-yl]piperazine | 31 | |
| 70 | 1-[quinoline-8-sulfonyl]-4-[3-(4-methylbenzyl)-1,2,4-thiadiazol-5-yl]piperazine | 44 | |
| 71 | 1-[4-nitrophenylsulfonyl]-4-[3-(4-methyl-benzyl)-1,2,4-thiadiazol-5-yl]-2-methyl-piperazine | 33 | |
| 72 | 1-[3-nitro-4-chlorophenylsulfonyl]-4-[3-(4-methylbenzyl)-1,2,4-thiadiazol-5-yl]-2-methylpiperazine | | |
| 73 | 1-[4-nitrophenylsulfonyl]-4-[3-(4-fluoro-benzyl)-1,2,4-thiadiazol-5-yl]-2-methyl-piperazine | 33 | |
| 75 | 1-[3-nitro-4-chlorophenylsulfonyl]-4-[3-(4-methylbenzyl)-1,2,4-thiadiazol-5-yl]piperazine | | |
| 76 | 1-(benzylsulfonyl)-4-[3-(4-chlorobenzyl)-1,2,4-thiadiazol-5-yl]piperazine | 40 | |
| 88 | 1-[(2E)-3-phenylprop-2-enoyl]-4-[3-(4-chlorobenzyl)-1,2,4-thiadiazol-5-yl]piperazine | 72 | |
| 105 | 3-fluoro-N-{2-[4-[3-(4-fluorobenzyl)-1,2,4-thiadiazol-5-yl]piperzin-1-yl]ethyl}benzamide | 115 | |
| 106 | 3-fluoro-N-{2-[4-[3-benzyl-1,2,4-thiadiazol-5-yl]piperazin-1-yl]ethyl}benzamide | 49 | |
| 110 | N-benzyl-N'-{2-[4-[3-(4-fluorobenzyl)-1,2,4-thiadiazol-5-yl]piperazin-1-yl]ethyl}urea | 77 | |
| 114 | 1-(1,3-benzodioxol-5-ylmethyl)-4-[3-(4-fluorobenzyl)-1,2,4-thiadiazol-5-yl]piperazine | 86 | |
| 165 | 1-(4-ethylbenzoyl)-4-[3-(4-chlorobenzyl)-1,2,4-thiadiazol-5-yl]piperazine | 133 | |
| 166 | 1-(2-chlorobenzoyl)-4-[3-(4-fluorobenzyl)-1,2,4-thiadiazol-5-yl]-2-methylpiperazine | 123 | |
| 167 | 1-(2-fluorobenzoyl)-4-[3-(4-chlorobenzyl)-1,2,4-thiadiazol-5-yl]-2-methylpiperazine | 117 | |
| 168 | 1-(4-trifluoromethylbenzoyl)-4-[3-(3-methoxybenzyl)-1,2,4-thiadiazol-5-yl]-2-methylpiperazine | 91 | |
| 169 | 1-benzoyl-4-[3-(4-methylbenzyl)-1,2,4-thiadiazol-5-yl]-2-methylpiperazine | 91 | |
| 170 | 1-(4-bromobenzoyl)-4-[3-(3-methoxybenzyl)-1,2,4-thiadiazol-5-yl]-2-methylpiperazine | 89 | |
| 171 | 1-(4-trifluoromethylbenzoyl)-4-[3-(4-methylbenzyl)-1,2,4-thiadiazol-5-yl]piperazine | 86 | |
| 172 | 1-(3-nitro-4-methylbenzoyl)-4-[3-(4-fluoro-benzyl)-1,2,4-thiadiazol-5-yl]-2-methyl-piperazine | 86 | |
| 173 | 1-benzoyl-4-[3-(3-methoxybenzyl)-1,2,4-thiadiazol-5-yl]-2-methylpiperazine | 85 | |
| 174 | 1-(4-chlorobenzoyl)-4-[3-(3-methoxybenzyl)-1,2,4-thiadiazol-5-yl]-2-methylpiperazine | 83 | |
| 175 | 1-(2-fluorobenzoyl)-4-[3-(4-methylbenzyl)-1,2,4-thiadiazol-5-yl]-2-methylpiperazine | 78 | |
| 176 | 1-(4-hexylbenzoyl)-4-[3-(4-methylbenzyl)-1,2,4-thiadiazol-5-yl]piperazine | 77 | |
| 177 | 1-(2-chloro-4-nitrobenzoyl)-4-[3-(4-fluoro-benzyl)-1,2,4-thiadiazol-5-yl]-2-methyl-piperazine | 77 | |
| 178 | 1-(1,3-benzodioxol-5-ylcarbonyl)-4-[3-(4-fluorobenzyl)-1,2,4-thiadiazol-5-yl]-2-methylpiperazine | 68 | |
| 179 | 1-(3-fluorobenzoyl)-4-[3-(4-fluorobenzyl)-1,2,4-thiadiazol-5-yl]-2-methylpiperazine | 68 | |
| 180 | 1-(4-tert-butylbenzoyl)-4-[3-(4-fluorobenzyl)-1,2,4-thiadiazol-5-yl]piperazine | 62 | |
| 181 | 1-benzoyl-4-[3-(4-fluorobenzyl)-1,2,4-thia-diazol-5-yl]piperazine | 60 | |
| 182 | 1-(4-butylbenzoyl)-4-[3-(4-methylbenzyl)-1,2,4-thiadiazol-5-yl]piperazine | 57 | |
| 183 | 1-(4-tert-butylbenzoyl)-4-[3-(4-methylbenzyl)-1,2,4-thiadiazol-5-yl]piperazine | 52 | |
| 184 | 1-(4-nitrobenzoyl)-4-[3-(4-fluorobenzyl)-1,2,4-thiadiazol-5-yl]-2-methylpiperazine | 52 | |
| 188 | 1-(3-trifluoromethylphenyl)-4-[3-(4-fluoro-benzyl)-1,2,4-thiadiazol-5-yl]piperazine | 96 | |
| 191 | 1-(1,3-benzodioxol-5-ylcarbonyl)-4-[3-(4-fluorobenzyl)-1,2,4-thiadiazol-5-yl]-1,4-diazepane | 63 | |
| 44 | 1-[3-methoxyphenylsulfonyl]-4-[3-(4-fluorobenzyl)-1,2,4-thiadiazol-5-yl]piperazine | 99 | 0.0571 |
| 53 | 1-[4-methoxyphenylsulfonyl]-4-[3-(3-methoxybenzyl)-1,2,4-thiadiazol-5-yl]piperazine | 83 | 0.00066 |
| 32 | 1-[4-methoxyphenylsulfonyl]-4-[3-(4-fluorobenzyl)-1,2,4-thiadiazol-5-yl]piperazine | 78 | 0.0024 |
| 193 | 1-[4-mthoxyphenylsulfonyl]-4-[3-(4-benzyl)-1,2,4-thiadiazol-5-yl]piperazine | 68 | 0.0048 |
| 194 | 1-[4-methoxyphenylsulfonyl]-4-[3-(2-fluoro-benzyl)-1,2,4-thiadiazol-5-yl]piperazine | 102 | 0.0012 |
| 195 | 1-[2-methoxyphenylsulfonyl]-4-[3-(4-fluoro-benzyl)-1,2,4-thiadiazol-5-yl]piperazine | 99 | 0.025 |
| 196 | 1-[4-ethoxyphenylsulfonyl]-4-[3-(4-fluoro-benzyl)-1,2,4-thiadiazol-5-yl]piperazine | 42 | 0.0081 |
| 197 | 1-[4-ethylphenylsulfonyl]-4-[3-(4-fluoro-benzyl)-1,2,4-thiadiazol-5-yl]piperazine | 84 | 0.239 |
| 198 | 1-phenylsulfonyl-4-[3-(4-fluoro-benzyl)-1,2,4-thiadiazol-5-yl]piperazine | 25 | 0.146 |
| 199 | 1-[4-methoxyphenylsulfonyl]-4-[3-benzyl-1,2,4-thiadiazol-5-yl]piperazine | 38 | 0.0016 |
| 200 | 1-(4-propionyloxy)benzene-sulfonyl-4-[3-(4-fluoro-benzyl)-1,2,4-thiadiazol-5-yl]piperazine | 80 | 0.051 |
| 201 | 1-[4-methoxyphenylsulfonyl]-4-[3-(3-methyl-benzyl-1,2,4-thiadiazol-5-yl]piperazine | 97 | 0.0021 |
| 202 | 1-[4-methoxyphenylsulfonyl]-4-[3-92-methyl-benzyl-1,2,4-thiadiazol-5-yl]piperazine | 63 | 0.0075 |
| 203 | 1-[4-methoxyphenylsulfonyl]-4-[3-(2-methoxy-benzyl-1,2,4-thiadiazol-5-yl]piperazine | 61 | 0.0062 |
| 204 | 1-[4-methoxyphenylsulfonyl]-4-[3-(3-methyl-4-fluoro-benzyl-1,2,4-thiadiazol-5-yl]piperazine | 90 | 0.0010 |
| 205 | 1-[4-methoxyphenylsulfonyl]-4-[3-(4-methoxy-benzyl-1,2,4-thiadiazol-5-yl]piperazine | 53 | 0.0011 |
| 207 | 1-[4-bromophenylsulfonyl]-4-[3-(3-methoxy-benzyl-1,2,4-thiadiazol-5-yl]piperazine | 83 | 0.028 |
| 208 | 1-[4-methoxyphenylsulfonyl]-4-[3-(3-methoxybenzyl)-1,2,4-thia-diazol-5-yl]-2-methyl-piperazine | 92 | 0.0034 |
| 217 | 1-(4-hydroxybenzenesulfonyl)-4-[3-(4-fluoro-benzyl)-1,2,4-thiadiazol-5-yl]piperazine | 77 | 0.033 |

EXAMPLES 16 TO 20

Amidine Hydrochloride Salts

According to the method of example 1, the following intermediate amidine compounds are obtained:
4-oxo-1-phenylcyclohexanecarboximidamide hydrochloride (example 16),
2-(4-aminophenyl)-3-[4-(dimethylamino)phenyl]propan-imidamide hydrochloride (example 17),
2-[4-(4-methylphenoxy)phenyl]ethanimidamide hydrochloride (example 18),
2-hydroxy-2-(4-phenoxyphenyl)ethanimidamide hydrochloride (example 19), and
2-nitrobenzyl amidine hydrochloride (example 20).

EXAMPLES 21 TO 25

Synthesis of 3-(substituted benzyl)-5-chloro-1,2,4-thiadiazole derivatives

According to the procedure of example 2, the following 3-(substituted benzyl)-5-chloro-1,2,4-thiadiazole compounds are obtained:
(5-chloro-1,2,4-thiadiazol-3-yl)(4-phenoxyphenyl)methanol (example 21), 5-chloro-3-[4-(4-methylphenoxy)benzyl]-1,2,4-thiadiazole (example 22),
4-(5-chloro-1,2,4-thiadiazol-3-yl)-4-phenylcyclohexanone (example 23),
4-[2-(4-aminophenyl)-2-(5-chloro-1,2,4-thiadiazol-3-yl) ethyl]-N,N-dimethylaniline (example 24), and
5-chloro-3-(2-nitrobenzyl)-1,2,4-thiadiazole (example 25).

EXAMPLES 26 TO 40

Nucleophilic replacement of 5-chloro-3-(substituted benzyl)1,2,4-thiadiazole derivatives with cyclic diamines The following intermediate compounds are synthesised using these experimental conditions of example 3, but changing the cyclic diamine and/or the 3-(substituted benzyl)-5-chloro-1,2,4-thiadiazole derivative:
[3-[4-(4-methylphenoxy)benzyl]-1,2,4-thiadiazol-5-yl]-piperazine (example 26),
[3-[4-(4-methylphenoxy)benzyl]-1,2,4-thiadiazol-5-yl]-homopiperazine (example 27),
3-methyl-1-[3-[4-(4-methylphenoxy)benzyl]-1,2,4-thiadiazol-5-yl]-piperazine (example 28),
[3-[(4-phenoxyphenyl)(hydroxy)methyl]-1,2,4-thiadiazol-5-yl]-piperazine (example 29),
[3-[(4-phenoxyphenyl)(hydroxy)methyl]-1,2,4-thiadiazol-5-yl]-homopiperazine (example 30),
3-methyl-[3-[(4-phenoxyphenyl)(hydroxy)methyl]-1,2,4-thiadiazol-5-yl]-piperazine (example 31),
4-[5-(piperazin-1-yl)-1,2,4-thiadiazol-3-yl]-4-phenylcyclohexanone (example 32),
4-[5-(homopiperazin-1-yl)-1,2,4-thiadiazol-3-yl]-4-phenylcyclohexanone (example 33),
4-[5-(3-methylpiperazin-1-yl)-1,2,4-thiadiazol-3-yl]-4-phenylcyclohexanone (example 34),
[3-[2-(4-dimethylaminophenyl)-1-(4-aminophenyl)-ethyl]-1,2,4-thiadiazol-5-yl]-homopiperazine (example 35),
[3-[2-(4-dimethylaminophenyl)-1-(4-aminophenyl)-ethyl]-1,2,4-thiadiazol-5-yl]-piperazine (example 36),
3-methyl-1-[3-[2-(4-dimethylaminophenyl)-1-(4-aminophenyl)-ethyl]-1,2,4-thiadiazol-5-yl]-piperazine (example 37),
[3-(2-nitrobenzyl)-1,2,4-thiadiazol-5-yl]-piperazine (example 38),
[3-(2-nitrobenzyl)-1,2,4-thiadiazol-5-yl]-homopiperazine (example 39), and
3-methyl-[3-(2-nitrobenzyl)-1,2,4-thiadiazol-5-yl]-piperazine (example 40).

EXAMPLE 41

N-alkylsulfonylation and N-cycloalkylsulfonylation of 3-(substituted benzyl)-1,2,4-thiadiazol-5-ylpiperazines and analogues thereof

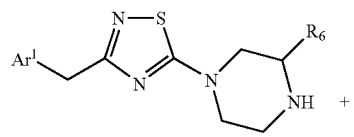

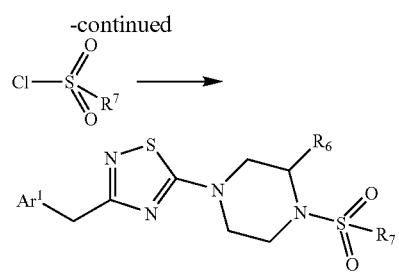

Similarly to the procedure of example 4, a 3-(substituted benzyl)-1,2,4-thiadiazol-5-ylpiperazine derivative, or analogue thereof, obtained according to the procedure of example 3 or examples 26 to 40 is reacted with an appropriate sulfonyl chloride derivative according to the above scheme (wherein $R_7$ is alkyl or cycloalkyl). The following compounds are synthesised using these experimental conditions.

Using N-[3-(4-fluorobenzyl)-1,2,4-thiadiazol-5-yl]-1,4-diazepane as starting material:
1-(3,3,3-trifluoropropane-1-sulfonyl)-4-[3-(4-fluorobenzyl)-1,2,4-thiadiazol-5-yl]-1,4-diazepane.

Using N-[3-(4-fluorobenzyl)-1,2,4-thiadiazol-5-yl]piperazine as starting material:
1-(3,3,3-trifluoropropane-1-sulfonyl)-4-[3-(4-fluorobenzyl)-1,2,4-thiadiazol-5-yl]piperazine,
1-(cyclopropanesulfonyl)-4-[3-(4-fluorobenzyl)-1,2,4-thiadiazol-5-yl]piperazine
1-(nonafluoro-1-butanesulfonyl)-4-[3-(4-chlorobenzyl)-1,2,4-thiadiazol-5-yl]piperazine,
1-(butanesulfonyl)-4-[3-(4-fluorobenzyl)-1,2,4-thiadiazol-5-yl]piperazine,
1-(4-chlorobutanesulfonyl)-4-[3-(4-fluorobenzyl)-1,2,4-thiadiazol-5-yl]piperazine,
1-(cyclopentanesulfonyl)-4-[3-(4-fluorobenzyl)-1,2,4-thiadiazol-5-yl]piperazine,
1-(heptadecafluoro-1-octanesulfonyl)-4-[3-(4-fluorobenzyl)-1,2,4-thiadiazol-5-yl]piperazine,
1-(trichloromethanesulfonyl)-4-[3-(4-fluorobenzyl)-1,2,4-thiadiazol-5-yl]piperazine,
1-(hexanesulfonyl)-4-[3-(4-fluorobenzyl)-1,2,4-thiadiazol-5-yl]piperazine
1-(5,7,7-trimethyl-2-(1,3,3-trimethylbutyl)-1-octanesulfonyl)-4-[3-(4-fluorobenzyl)-1,2,4-thiadiazol-5-yl]piperazine,
1-(isobutanesulfonyl)-4-[3-(4-fluorobenzyl)-1,2,4-thiadiazol-5-yl]piperazine
1-(2,2,2-trifluoroethanesulfonyl)-4-[3-(4-fluorobenzyl)-1,2,4-thiadiazol-5-yl]piperazine, and
1-(cyclohexanesulfonyl)-4-[3-(4-fluorobenzyl)-1,2,4-thiadiazol-5-yl]piperazine.

Using N-[3-(4-chlorobenzyl)-1,2,4-thiadiazol-5-yl]piperazine as starting material:
1-(3,3,3-trifluoropropane-1-sulfonyl)-4-[3-(4-chlorobenzyl)-1,2,4-thiadiazol-5-yl]piperazine,
1-(cyclopropanesulfonyl)-4-[3-(4-chlorobenzyl)-1,2,4-thiadiazol-5-yl]piperazine
1-(nonafluoro-1-butanesulfonyl)-4-[3-(4-chlorobenzyl)-1,2,4-thiadiazol-5-yl]piperazine,
1-(isobutanesulfonyl)-4-[3-(4-chlorobenzyl)-1,2,4-thiadiazol-5-yl]piperazine,
1-(cyclopentanesulfonyl)-4-[3-(4-chlorobenzyl)-1,2,4-thiadiazol-5-yl]piperazine
1-(heptadecafluoro-1-octanesulfonyl)-4-[3-(4-chlorobenzyl)-1,2,4-thiadiazol-5-yl]piperazine, 1-(trichloromethanesulfonyl)-4-[3-(4-chlorobenzyl)-1,2,4-thiadiazol-5-yl]piperazine,
1-(hexanesulfonyl)-4-[3-(4-chlorobenzyl)-1,2,4-thiadiazol-5-yl]piperazine,
1-(5,7,7-trimethyl-2-(1,3,3-trimethylbutyl)-1-octanesulfonyl)-4-[3-(4-chlorobenzyl)-1,2,4-thiadiazol-5-yl]piperazine,
1-(isobutanesulfonyl)-4-[3-(4-chlorobenzyl)-1,2,4-thiadiazol-5-yl]piperazine,
1-(2,2,2-trifluoroethanesulfonyl)-4-[3-(4-chlorobenzyl)-1,2,4-thiadiazol-5-yl]piperazine,
1-(cyclohexanesulfonyl)-4-[3-(4-chlorobenzyl)-1,2,4-thiadiazol-5-yl]piperazine,
1-(1-octanesulfonyl)-4-[3-[4-(4-chlorobenzyl]-1,2,4-thiadiazol-5-yl]piperazine,
1-(1-propanesulfonyl)-4-[3-[4-(4-chlorobenzyl]-1,2,4-thiadiazol-5-yl]piperazine,
1-(1-hexadecanesulfonyl)-4-[3-[4-(4-chlorobenzyl]-1,2,4-thiadiazol-5-yl]piperazine,
1-(3-chloropropanesulfonyl)-4-[3-[4-(4-chlorobenzyl]-1,2,4-thiadiazol-5-yl]-piperazine,
1-(D(+)-10-camphorsulfonyl)-4-[3-[4-(4-chlorobenzyl]-1,2,4-thiadiazol-5-yl]-piperazine,
1-(L(−)-10-camphorsulfonyl)-4-[3-[4-(4-chlorobenzyl]-1,2,4-thiadiazol-5-yl]-piperazine,
1-(ethanesulfonyl)-4-[3-[4-(4-chlorobenzyl]-1,2,4-thiadiazol-5-yl]piperazine,
1-(1-butanesulfonyl)-4-[3-[4-(4-chlorobenzyl]-1,2,4-thiadiazol-5-yl]piperazine,
1-(2-chloroethanesulfonyl)-4-[3-[4-(4-chlorobenzyl]-1,2,4-thiadiazol-5-yl]-piperazine,
1-(chlorosulfonylacetyl)-4-[3-[4-(4-chlorobenzyl]-1,2,4-thiadiazol-5-yl]-piperazine, and
1-(1-decanesulfonyl)-4-[3-[4-(4-chlorobenzyl]-1,2,4-thiadiazol-5-yl]piperazine.

Using N-[3-(4-methylbenzyl)-1,2,4-thiadiazol-5-yl]piperazine as starting material:
1-(3,3,3-trifluoropropane-1-sulfonyl)-4-[3-(4-methylbenzyl)-1,2,4-thiadiazol-5-yl]piperazine,
1-(cyclopropanesulfonyl)-4-[3-(4-methylbenzyl)-1,2,4-thiadiazol-5-yl]piperazine,
1-(nonafluoro-1-butanesulfonyl)-4-[3-(4-methylbenzyl)-1,2,4-thiadiazol-5-yl]piperazine,
1-(isobutanesulfonyl)-4-[3-(4-methylbenzyl)-1,2,4-thiadiazol-5-yl]piperazine
1-(cyclopentanesulfonyl)-4-[3-(4-methylbenzyl)-1,2,4-thiadiazol-5-yl]piperazine
1-(heptadecafluoro-1-octanesulfonyl)-4-[3-(4-methylbenzyl)-1,2,4-thiadiazol-5-yl]piperazine,
1-(trichloromethanesulfonyl)-4-[3-(4-methylbenzyl)-1,2,4-thiadiazol-5-yl]piperazine,
1-(hexanesulfonyl)-4-[3-(4-methylbenzyl)-1,2,4-thiadiazol-5-yl]piperazine
1-(5,7,7-trimethyl-2-(1,3,3-trimethylbutyl)-1-octanesulfonyl)-4-[3-(4-methylbenzyl)-1,2,4-thiadiazol-5-yl]piperazine,
1-(isobutanesulfonyl)-4-[3-(4-methylbenzyl)-1,2,4-thiadiazol-5-yl]piperazine
1-(2,2,2-trifluoroethanesulfonyl)-4-[3-(4-methylbenzyl)-1,2,4-thiadiazol-5-yl]piperazine,
1-(cyclohexanesulfonyl)-4-[3-(4-methylbenzyl)-1,2,4-thiadiazol-5-yl]piperazine,
1-(1-octanesulfonyl)-4-[3-(4-methylbenzyl)-1,2,4-thiadiazol-5-yl]piperazine,
1-(1-propanesulfonyl)-4-[3-[4-(4-methylbenzyl]-1,2,4-thiadiazol-5-yl]piperazine,
1-(1-hexadecanesulfonyl)-4-[3-[4-(4-methylbenzyl]-1,2,4-thiadiazol-5-yl]piperazine,
1-(3-chloropropanesulfonyl)-4-[3-[4-(4-methylbenzyl]-1,2,4-thiadiazol-5-yl]-piperazine,
1-(D(+)-10-camphorsulfonyl)-4-[3-[4-(4-methylbenzyl]-1,2,4-thiadiazol-5-yl]-piperazine,
1-(L(−)-10-camphorsulfonyl)-4-[3-[4-(4-methylbenzyl]-1,2,4-thiadiazol-5-yl]-piperazine,
1-(ethanesulfonyl)-4-[3-[4-(4-methylbenzyl]-1,2,4-thiadiazol-5-yl]piperazine,
1-(1-butanesulfonyl)-4-[3-[4-(4-methylbenzyl]-1,2,4-thiadiazol-5-yl]piperazine,
1-(2-chloroethanesulfonyl)-4-[3-[4-(4-methylbenzyl]-1,2,4-thiadiazol-5-yl]-piperazine,
1-(chlorosulfonylacetyl)-4-[3-[4-(4-methylbenzyl]-1,2,4-thiadiazol-5-yl]-piperazine, and
1-(1-decanesulfonyl)-4-[3-[4-(4-methylbenzyl]-1,2,4-thiadiazol-5-yl]-piperazine.

Using [3-[4-(4-methylphenoxy)benzyl]-1,2,4-thiadiazol-5-yl]-homopiperazine as starting material:
1-(3,3,3-Trifluoropropane-1-sulfonyl)-4-[3-[4-(4-methylphenoxy)benzyl]-1,2,4-thiadiazol-5-yl]-homopiperazine
1-(cyclopropanesulfonyl)-4-[3-[4-(4-methylphenoxy)benzyl]-1,2,4-thiadiazol-5-yl]-homopiperazine
1-(nonafluoro-1-butanesulfonyl)-4-[3-[4-(4-methylphenoxy)benzyl]-1,2,4-thiadiazol-5-yl]-homopiperazine
1-(isobutanesulfonyl)-4-[3-[4-(4-methylphenoxy)benzyl]-1,2,4-thiadiazol-5-yl]-homopiperazine
1-(cyclopentanesulfonyl)-4-[3-[4-(4-methylphenoxy)benzyl]-1,2,4-thiadiazol-5-yl]-homopiperazine
1-(heptadecafluoro-1-octanesulfonyl)-4-[3-[4-(4-methylphenoxy)benzyl]-1,2,4-thiadiazol-5-yl]-homopiperazine
1-(trichloromethanesulfonyl)-4-[3-[4-(4-methylphenoxy)benzyl]-1,2,4-thiadiazol-5-yl]-homopiperazine
1-(hexanesulfonyl)-4-[3-[4-(4-methylphenoxy)benzyl]-1,2,4-thiadiazol-5-yl]-homopiperazine
1-(5,7,7-trimethyl-2-(1,3,3-trimethylbutyl)-1-octanesulfonyl)-4-[3-[4-(4-methylphenoxy)benzyl]-1,2,4-thiadiazol-5-yl]-homopiperazine
1-(isobutanesulfonyl)-4-[3-[4-(4-methylphenoxy)benzyl]-1,2,4-thiadiazol-5-yl]-homopiperazine
1-(2,2,2-trifluoroethanesulfonyl)-4-[3-[4-(4-methylphenoxy)benzyl]-1,2,4-thiadiazol-5-yl]-homopiperazine,
1-(cyclohexanesulfonyl)-4-[3-[4-(4-methylphenoxy)benzyl]-1,2,4-thiadiazol-5-yl]-homopiperazine,
1-(1-octanesulfonyl)-4-[3-[4-(4-methylphenoxy)benzyl]-1,2,4-thiadiazol-5-yl]-homopiperazine,
1-(1-propanesulfonyl)-4-[3-[4-(4-methylphenoxy)benzyl]-1,2,4-thiadiazol-5-yl]-homopiperazine,
1-(1-hexadecanesulfonyl)-4-[3-[4-(4-methylphenoxy)benzyl]-1,2,4-thiadiazol-5-yl]-homopiperazine,
1-(3-chloropropanesulfonyl)-4-[3-[4-(4-methylphenoxy)benzyl]-1,2,4-thiadiazol-5-yl]-homopiperazine,
1-(D(+)-10-camphorsulfonyl)-4-[3-[4-(4-methylphenoxy)benzyl]-1,2,4-thiadiazol-5-yl]-homopiperazine,
1-(L(−)-10-camphorsulfonyl)-4-[3-[4-(4-methylphenoxy)benzyl]-1,2,4-thiadiazol-5-yl]-homopiperazine,
1-(ethanesulfonyl)-4-[3-[4-(4-methylphenoxy)benzyl]-1,2,4-thiadiazol-5-yl]-homopiperazine,
1-(1-butanesulfonyl)-4-[3-[4-(4-methylphenoxy)benzyl]-1,2,4-thiadiazol-5-yl]-homopiperazine,
1-(2-chloroethanesulfonyl)-4-[3-[4-(4-methylphenoxy)benzyl]-1,2,4-thiadiazol-5-yl]-homopiperazine,
1-(chlorosulfonylacetyl)-4-[3-[4-(4-methylphenoxy)benzyl]-1,2,4-thiadiazol-5-yl]-homopiperazine, and 1-(1-decanesulfonyl)-4-[3-(4-(4-methylphenoxy)benzyl]-1,2,4-thiadiazol-5-yl]-homopiperazine.

Using 3-methyl-3-[(4-phenoxyphenyl)(hydroxy)methyl]-1,2,4-thiadiazol-5-yl]-piperazine as starting material:

1-(3,3,3-Trifluoropropane-1-sulfonyl)-3-methyl-4-[3-[(4-phenoxyphenyl)(hydroxy)methyl]-1,2,4-thiadiazol-5-yl]-piperazine 1-(cyclopropanesulfonyl)-3-methyl-4-[3-[(4-phenoxyphenyl)(hydroxy)methyl]-1,2,4-thiadiazol-5-yl]-piperazine 1-(nonafluoro-1-butanesulfonyl)-3-methyl-4-[3-[(4-phenoxyphenyl)(hydroxy)methyl]-1,2,4-thiadiazol-5-yl]-piperazine 1-(butanesulfonyl)-3-methyl-4-[3-[(4-phenoxyphenyl)(hydroxy)methyl]-1,2,4-thiadiazol-5-yl]-piperazine, 1-(cyclopentanesulfonyl)-3-methyl-4-[3-[(4-phenoxyphenyl)(hydroxy)methyl]-1,2,4-thiadiazol-5-yl]-piperazine, 1-(heptadecafluoro-1-octanesulfonyl)-3-methyl-4-[3-[(4-phenoxyphenyl)(hydroxy)methyl]-1,2,4-thiadiazol-5-yl]-piperazine, 1-(trichloromethanesulfonyl)-3-methyl-4-[3-[(4-phenoxyphenyl)(hydroxy)methyl]-1,2,4-thiadiazol-5-yl]-piperazine, 1-(hexanesulfonyl)-3-methyl-4-[3-[(4-phenoxyphenyl)(hydroxy)methyl]-1,2,4-thiadiazol-5-yl]-piperazine, 1-(5,7,7-trimethyl-2-(1,3,3-trimethylbutyl)-1-octanesulfonyl)-3-methyl-4-[3-[(4-phenoxyphenyl)(hydroxy)methyl]-1,2,4-thiadiazol-5-yl]-piperazine, 1-(isobutanesulfonyl)-3-methyl-4-[3-[(4-phenoxyphenyl)(hydroxy)methyl]-1,2,4-thiadiazol-5-yl]-piperazine, 1-(2,2,2-trifluoroethanesultonyl)-3-methyl-4-[3-[(4-phenoxyphenyl)(hydroxy)methyl]-1,2,4-thiadiazol-5-yl]-piperazine, 1-(cyclohexanesulfonyl)-3-methyl-4-[3-[(4-phenoxyphenyl)(hydroxy)methyl]-1,2,4-thiadiazol-5-yl]-piperazine, 1-(1-octanesulfonyl)-3-methyl-4-[3-[(4-phenoxyphenyl)(hydroxy)methyl]-1,2,4-thiadiazol-5-yl]-piperazine, 1-(2-propanesulfonyl)-3-methyl-4-[3-[(4-phenoxyphenyl)(hydroxy)methyl]-1,2,4-thiadiazol-5-yl]-piperazine, 1-(1-hexadecanesulfonyl)-3-methyl-4-[3-[(4-phenoxyphenyl)(hydroxy)methyl]-1,2,4-thiadiazol-5-yl]-piperazine, 1-(3-chloropropanesulfonyl)-3-methyl-4-[3-[(4-phenoxyphenyl)(hydroxy)methyl]-1,2,4-thiadiazol-5-yl]-piperazine, 1-(D(+)-10-camphorsulfonyl)-3-methyl-4-[3-[(4-phenoxyphenyl)(hydroxy)methyl]-1,2,4-thiadiazol-5-yl]-piperazine, 1-(L(−)-10-camphorsulfonyl)-3-methyl-4-[3-[(4-phenoxyphenyl)(hydroxy)methyl]-1,2,4-thiadiazol-5-yl]-piperazine, 1-(ethanesulfonyl)-3-methyl-4-[3-[(4-phenoxyphenyl)(hydroxy)methyl]-1,2,4-thiadiazol-5-yl]-piperazine, 1-(1-butanesulfonyl)-3-methyl-4-[3-[(4-phenoxyphenyl)(hydroxy)methyl]-1,2,4-thiadiazol-5-yl]-piperazine, 1-(2-chloroethanesulfonyl)-4-[3-[4-(4-methylphenoxy)benzyl]-1,2,4-thiadiazol-5-yl]-homopiperazine, 1-(chlorosulfonylacetyl)-3-methyl-4-[3-[(4-phenoxyphenyl)(hydroxy)methyl]-1,2,4-thiadiazol-5-yl]-piperazine, and 1-(1-decanesulfonyl)-3-methyl-4-[3-[(4-phenoxyphenyl)(hydroxy)methyl]-1,2,4-thiadiazol-5-yl]-piperazine.

Using [3-[4-phenylcyclohexan-1-one-4-yl]-1,2,4-thiadiazol-5-yl]-piperazine as starting material:

1-(3,3,3-trifluoropropane-1-sulfonyl)-4-[3-[4-phenylcyclohexan-1-one-4-yl]-1,2,4-thiadiazol-5-yl]-piperazine, 1-(cyclopropanesulfonyl)-4-[3-[4-phenylcyclohexan-1-one-4-yl]-1,2,4-thiadiazol-5-yl]-piperazine, 1-(nonafluoro-1-butanesulfonyl)-4-[3-[4-phenylcyclohexan-1-one-4-yl]-1,2,4-thiadiazol-5-yl]-piperazine, 1-(butanesulfonyl)-4-[3-[4-phenylcyclohexan-1-one-4-yl]-1,2,4-thiadiazol-5-yl]-piperazine, 1-(cyclopentanesulfonyl)-4-[3-[4-phenylcyclohexan-1-one-4-yl]-1,2,4-thiadiazol-5-yl]-piperazine, 1-(heptadecafluoro-1-octanesulfonyl)-4-[3-[4-phenylcyclohexan-1-one-4-yl]-1,2,4-thiadiazol-5-yl]-piperazine, 1-(trichloromethanesulfonyl)-4-[3-[4-phenylcyclohexan-1-one-4-yl]-1,2,4-thiadiazol-5-yl]-piperazine, 1-(hexanesulfonyl)-4-[3-[4-phenylcyclohexan-1-one-4-yl]-1,2,4-thiadiazol-5-yl]-piperazine, 1-(5,7,7-trimethyl-2-(1,3,3-trimethylbutyl)-1-octanesulfonyl)-4-[3-[4-phenylcyclohexan-1-one-4-yl]-1,2,4-thiadiazol-5-yl]-piperazine, 1-(isobutanesulfonyl)-4-[3-[4-phenylcyclohexan-1-one-4-yl]-1,2,4-thiadiazol-5-yl]-piperazine, 1-(2,2,2-trifluoroethanesulfonyl)-4-[3-[4-phenylcyclohexan-1-one-4-yl]-1,2,4-thiadiazol-5-yl]-piperazine, 1-(cyclohexanesulfonyl)-4-[3-[4-phenylcyclohexan-1-one-4-yl]-1,2,4-thiadiazol-5-yl]-piperazine, 1-(1-octanesulfonyl)-4-[3-[4-phenylcyclohexan-1-one-4-yl]-1,2,4-thiadiazol-5-yl]-piperazine, 1-(2-propanesulfonyl)-4-[3-[4-phenylcyclohexan-1-one-4-yl]-1,2,4-thiadiazol-5-yl]-piperazine, 1-(1-hexadecanesulfonyl)-4-[3-[4-phenylcyclohexan-1-one-4-yl]-1,2,4-thiadiazol-5-yl]-piperazine, 1-(3-chloropropanesulfonyl)-4-[3-[4-phenylcyclohexan-1-one-4-yl]-1,2,4-thiadiazol-5-yl]-piperazine, 1-(D(+)-10-camphorsulfonyl)-4-[3-[4-phenylcyclohexan-1-one-4-yl]-1,2,4-thiadiazol-5-yl]-piperazine, 1-(L(−)-10-camphorsulfonyl)-4-[3-[4-phenylcyclohexan-1-one-4-yl]-1,2,4-thiadiazol-5-yl]-piperazine, 1-(ethanesulfonyl)-4-[3-[4-phenylcyclohexan-1-one-4-yl]-1,2,4-thiadiazol-5-yl]-piperazine, 1-(2-chloroethanesulfonyl)-4-[3-[4-phenylcyclohexan-1-one-4-yl]-1,2,4-thiadiazol-5-yl]-piperazine, 1-(chlorosulfonylacetyl)-4-[3-[4-phenylcyclohexan-1-one-4-yl]-1,2,4-thiadiazol-5-yl]-piperazine, and 1-(1-decanesulfonyl)-4-[3-[4-phenylcyclohexan-1-one-4-yl]-1,2,4-thiadiazol-5-yl]-piperazine.

Using [3-[2-(4-dimethylaminophenyl)-1-(4-aminophenyl)-ethyl]-1,2,4-thiadiazol-5-yl]-piperazine as starting material:

1-(3,3,3-trifluoropropane-1-sulfonyl)-4-[3-[2-(4-dimethylaminophenyl)-1-(4-aminophenyl)-ethyl]-1,2,4-thiadiazol-5-yl]-piperazine, 1-(cyclopropanesulfonyl)-4-[3-[2-(4-dimethylaminophenyl)-1-(4-aminophenyl)-ethyl]-1,2,4-thiadiazol-5-yl]-piperazine, 1-(nonafluoro-1-butanesulfonyl)-4-[3-[2-(4-dimethylaminophenyl)-1-(4-aminophenyl)-ethyl]-1,2,4-thiadiazol-5-yl]-piperazine, 1-(butanesulfonyl)-4-[3-[2-(4-dimethylaminophenyl)-1-(4-aminophenyl)-ethyl]-1,2,4-thiadiazol-5-yl]-piperazine, 1-(cyclopentanesulfonyl)-4-[3-[2-(4-dimethylaminophenyl)-1-(4-aminophenyl)-ethyl]-1,2,4-thiadiazol-5-yl]-piperazine, 1-(heptadecafluoro-1-octanesulfonyl)-4-[3-[2-(4-dimethylaminophenyl)-1-(4-aminophenyl)-ethyl]-1,2,4-thiadiazol-5-yl]-piperazine, 1-(trichloromethanesulfonyl)-4-[3-[2-(4-dimethylaminophenyl)-1-(4-aminophenyl)-ethyl]-1,2,4-thiadiazol-5-yl]-piperazine, 1-(hexanesulfonyl)-4-[3-[2-(4-dimethylaminophenyl)-1-(4-aminophenyl)-ethyl]-1,2,4-thiadiazol-5-yl]-piperazine, 1-(5,7,7-trimethyl-2-(1,3,3-trimethylbutyl)-1-octanesulfonyl)-4-[3-[2-(4-dimethylaminophenyl)-1-(4-aminophenyl)-ethyl]-1,2,4-thiadiazol-5-yl]-piperazine, 1-(isobutanesulfonyl)-4-[3-[2-(4-dimethylaminophenyl)-1-(4-aminophenyl)-ethyl]-1,2,4-thiadiazol-5-yl]-piperazine,
1-(2,2,2-trifluoroethanesulfonyl)-4-[3-[2-(4-dimethylaminophenyl)-1-(4-aminophenyl)-ethyl]-1,2,4-thiadiazol-5-yl]-piperazine,
1-(cyclohexanesulfonyl)-4-[3-[2-(4-dimethylaminophenyl)-1-(4-aminophenyl)-ethyl]-1,2,4-thiadiazol-5-yl]-piperazine,
1-(1-octanesulfonyl)-4-[3-[2-(4-dimethylaminophenyl)-1-(4-aminophenyl)-ethyl]-1,2,4-thiadiazol-5-yl]-piperazine,
1-(2-propanesulfonyl)-4-[3-[2-(4-dimethylaminophenyl)-1-(4-aminophenyl)-ethyl]-1,2,4-thiadiazol-5-yl]-piperazine,
1-(1-hexadecanesulfonyl)-4-[3-[2-(4-dimethylaminophenyl)-1-(4-aminophenyl)-ethyl]-1,2,4-thiadiazol-5-yl]-piperazine,
1-(3-chloropropanesulfonyl)-4-[3-[2-(4-dimethylaminophenyl)-1-(4-aminophenyl)-ethyl]-1,2,4-thiadiazol-5-yl]-piperazine,
1-(D(+)-10-camphorsulfonyl)-4-[3-[2-(4-dimethylaminophenyl)-1-(4-aminophenyl)-ethyl]-1,2,4-thiadiazol-5-yl]-piperazine,
1-(L(−)-10-camphorsulfonyl)-4-[3-[2-(4-dimethylaminophenyl)-1-(4-aminophenyl)-ethyl]-1,2,4-thiadiazol-5-yl]-piperazine,
1-(ethanesulfonyl)-4-[3-[2-(4-dimethylaminophenyl)-1-(4-aminophenyl)-ethyl]-1,2,4-thiadiazol-5-yl]-piperazine,
1-(2-chloroethanesulfonyl)-4-[3-[2-(4-dimethylaminophenyl)-1-(4-aminophenyl)-ethyl]-1,2,4-thiadiazol-5-yl]-piperazine,
1-(chlorosulfonylacetyl)-4-[3-[2-(4-dimethylaminophenyl)-1-(4-aminophenyl)-ethyl]-1,2,4-thiadiazol-5-yl]-piperazine, and
1-(1-decanesulfonyl)-4-[3-[2-(4-dimethylaminophenyl)-1-(4-aminophenyl)-ethyl]-1,2,4-thiadiazol-5-yl]-piperazine.

Using 3-methyl-[3-(2-nitrobenzyl)-1,2,4-thiadiazol-5-yl]-piperazine as starting material:
1-(3,3,3-trifluoropropane-1-sulfonyl)-3-methyl-4-[3-(2-nitrobenzyl)-1,2,4-thiadiazol-5-yl]-piperazine,
1-(cyclopropanesulfonyl)-3-methyl-4-[3-(2-nitrobenzyl)-1,2,4-thiadiazol-5-yl]-piperazine,
1-(nonafluoro-1-butanesulfonyl)-3-methyl-4-[3-(2-nitrobenzyl)-1,2,4-thiadiazol-5-yl]-piperazine,
1-(butanesulfonyl)-3-methyl-4-[3-(2-nitrobenzyl)-1,2,4-thiadiazol-5-yl]-piperazine,
1-(cyclopentanesulfonyl)-3-methyl-4-[3-(2-nitrobenzyl)-1,2,4-thiadiazol-5-yl]-piperazine
1-(heptadecafluoro-1-octanesulfonyl)-3-methyl-4-[3-(2-nitrobenzyl)-1,2,4-thiadiazol-5-yl]-piperazine,
1-(trichloromethanesulfonyl)-3-methyl-4-[3-(2-nitrobenzyl)-1,2,4-thiadiazol-5-yl]-piperazine,
1-(hexanesulfonyl)-3-methyl-4-[3-(2-nitrobenzyl)-1,2,4-thiadiazol-5-yl]-piperazine,
1-(5,7,7-trimethyl-2-(1,3,3-trimethylbutyl)-1-octanesulfonyl)-3-methyl-4-[3-(2-nitrobenzyl)-1,2,4-thiadiazol-5-yl]-piperazine,
1-(isobutanesulfonyl)-3-methyl-4-[3-(2-nitrobenzyl)-1,2,4-thiadiazol-5-yl]-piperazine,
1-(2,2,2-trifluoroethanesulfonyl)-3-methyl-4-[3-(2-nitrobenzyl)-1,2,4-thiadiazol-5-yl]-piperazine,
1-(cyclohexanesulfonyl)-3-methyl-4-[3-(2-nitrobenzyl)-1,2,4-thiadiazol-5-yl]-piperazine,
1-(1-octanesulfonyl)-3-methyl-4-[3-(2-nitrobenzyl)-1,2,4-thiadiazol-5-yl]-piperazine,
1-(2-propanesulfonyl)-3-methyl-4-[3-(2-nitrobenzyl)-1,2,4-thiadiazol-5-yl]-piperazine,
1-(1-hexadecanesulfonyl)-3-methyl-4-[3-(2-nitrobenzyl)-1,2,4-thiadiazol-5-yl]-piperazine,
1-(3-chloropropanesulfonyl)-3-methyl-4-[3-(2-nitrobenzyl)-1,2,4-thiadiazol-5-yl]-piperazine,
1-(D(+)-10-camphorsulfonyl)-3-methyl-4-[3-(2-nitrobenzyl)-1,2,4-thiadiazol-5-yl]-piperazine,
1-(L(−)-10-camphorsulfonyl)-3-methyl-4-[3-(2-nitrobenzyl)-1,2,4-thiadiazol-5-yl]-piperazine,
1-(ethanesulfonyl)-3-methyl-4-[3-(2-nitrobenzyl)-1,2,4-thiadiazol-5-yl]-piperazine,
1-(2-chloroethanesulfonyl)-3-methyl-4-[3-(2-nitrobenzyl)-1,2,4-thiadiazol-5-yl]-piperazine,
1-(chlorosulfonylacetyl)-3-methyl-4-[3-(2-nitrobenzyl)-1,2,4-thiadiazol-5-yl]-piperazine, and
1-(1-decanesulfonyl)-3-methyl-4-[3-(2-nitrobenzyl)-1,2,4-thiadiazol-5-yl]-piperazine.

Using 1-[3-(3-methoxybenzyl)-[1,2,4]thiadiazol-5-yl]-piperazine as starting material:
1-(3,3,3-trifluoropropane-1-sulfonyl)-4-[3-(3-methoxybenzyl)-[1,2,4]thiadiazol-5-yl]-piperazine,
1-(cyclopropanesulfonyl)-4-[3-(3-methoxybenzyl)-[1,2,4]thiadiazol-5-yl]-piperazine,
1-(nonafluoro-1-butanesulfonyl)-4-[3-(3-methoxybenzyl)-[1,2,4]thiadiazol-5-yl]-piperazine,
1-(butanesulfonyl)-4-[3-(3-methoxybenzyl)-[1,2,4]thiadiazol-5-yl]-piperazine
1-(cyclopentanesulfonyl)-4-[3-(3-methoxybenzyl)-[1,2,4]thiadiazol-5-yl]-piperazine,
1-(heptadecafluoro-1-octanesulfonyl)-4-[3-(3-methoxybenzyl)-[1,2,4]thiadiazol-5-yl]-piperazine,
1-(trichloromethanesulfonyl)-4-[3-(3-methoxybenzyl)-[1,2,4]thiadiazol-5-yl]-piperazine,
1-(hexanesulfonyl)-4-[3-(3-methoxybenzyl)-[1,2,4]thiadiazol-5-yl]-piperazine
1-(5,7,7-trimethyl-2-(1,3,3-trimethylbutyl)-1-octanesulfonyl)-4-[3-(3-Methoxy-benzyl)-[1,2,4]thiadiazol-5-yl]-piperazine,
1-(isobutanesulfonyl)-4-[3-(3-methoxybenzyl)-[1,2,4]thiadiazol-5-yl]-piperazine
1-(2,2,2-trifluoroethanesulfonyl)-4-[3-(3-methoxybenzyl)-[1,2,4]thiadiazol-5-yl]-piperazine,
1-(cyclohexanesulfonyl)-4-[3-(3-methoxybenzyl)-[1,2,4]thiadiazol-5-yl]-piperazine,
1-(1-octanesulfonyl)-4-[3-(3-methoxybenzyl)-[1,2,4]thiadiazol-5-yl]-piperazine
1-(2-propanesulfonyl)-4-[3-(3-methoxybenzyl)-[1,2,4]thiadiazol-5-yl]-piperazine,
1-(1-hexadecanesulfonyl)-4-[3-(3-methoxybenzyl)-[1,2,4]thiadiazol-5-yl]-piperazine,
1-(3-chloropropanesulfonyl)-4-[3-(3-methoxybenzyl)-[1,2,4]thiadiazol-5-yl]-piperazine,
1-(D(+)-10-camphorsulfonyl)-4-[3-(3-methoxybenzyl)-[1,2,4]thiadiazol-5-yl]-piperazine,
1-(L(−)-10-camphorsulfonyl)-4-[3-(3-methoxybenzyl)-[1,2,4]thiadiazol-5-yl]-piperazine,
1-(ethanesulfonyl)-4-[3-(3-methoxybenzyl)-[1,2,4]thiadiazol-5-yl]-piperazine,
1-(2-chloroethanesulfonyl)-4-[3-(3-methoxybenzyl)-[1,2,4]thiadiazol-5-yl]-piperazine,
1-(chlorosulfonylacetyl)-4-[3-(3-methoxybenzyl)-[1,2,4]thiadiazol-5-yl]-piperazine, and
1-(1-decanesulfonyl)-4-[3-(3-methoxybenzyl)-[1,2,4]thiadiazol-5-yl]-piperazine.

Using 3-methyl-1-[3-(4-methylbenzyl)-1,2,4-thiadiazol-5-yl]piperazine as starting material:
3-methyl-1-(3,3,3-trifluoropropane-1-sulfonyl)-4-[3-(4-methylbenzyl)-1,2,4-thiadiazol-5-yl]piperazine,
3-methyl-1-(cyclopropanesulfonyl)-4-[3-(4-methylbenzyl)-1,2,4-thiadiazol-5-yl]piperazine, 3-methyl-1-(nonafluoro-1-butanesulfonyl)-4-[3-(4-methyl-benzyl)-1,2,4-thiadiazol-5-yl]piperazine,
3-methyl-1-(isobutanesulfonyl)-4-[3-(4-methylbenzyl)-1,2,4-thiadiazol-5-yl]piperazine,
3-methyl-1-(cyclopentanesulfonyl)-4-[3-(4-methylbenzyl)-1,2,4-thiadiazol-5-yl]piperazine,
3-methyl-1-(heptadecafluoro-1-octanesulfonyl)-4-[3-(4-methylbenzyl)-1,2,4-thiadiazol-5-yl]piperazine,
3-methyl-1-(trichloromethanesulfonyl)-4-[3-(4-methylbenzyl)-1,2,4-thiadiazol-5-yl]piperazine,
3-methyl-1-(hexanesulfonyl)-4-[3-(4-methylbenzyl)-1,2,4-thiadiazol-5-yl]piperazine,
3-methyl-1-(5,7,7-trimethyl-2-(1,3,3-trimethylbutyl)-1-octanesulfonyl)-4-[3-(4-methylbenzyl)-1,2,4-thiadiazol-5-yl]piperazine,
3-methyl-1-(isobutanesulfonyl)-4-[3-(4-methylbenzyl)-1,2,4-thiadiazol-5-yl]piperazine,
3-methyl-1-(2,2,2-trifluoroethanesulfonyl)-4-[3-(4-methylbenzyl)-1,2,4-thiadiazol-5-yl]piperazine, and
3-methyl-1-(cyclohexanesulfonyl)-4-[3-(4-methylbenzyl)-1,2,4-thiadiazol-5-yl]piperazine,
3-methyl-1-(1-octanesulfonyl)-4-[3-(4-methylbenzyl)-[1,2,4]thiadiazol-5-yl]-piperazine
3-methyl-1-(2-propanesulfonyl)-4-[3-(4-methylbenzyl)-[1,2,4]thiadiazol-5-yl]-piperazine,
3-methyl-1-(1-hexadecanesulfonyl)-4-[3-(4-methylbenzyl)-[1,2,4]thiadiazol-5-yl]-piperazine,
3-methyl-1-(3-chloropropanesulfonyl)-4-[3-(4-methylbenzyl)-[1,2,4]thiadiazol-5-yl]-piperazine,
3-methyl-1-(D(+)-10-camphorsulfonyl)-4-[3-(4-methylbenzyl)-[1,2,4]thiadiazol-5-yl]-piperazine,
3-methyl-1-(L(−)-10-camphorsulfonyl)-4-[3-(4-methylbenzyl)-[1,2,4]thiadiazol-5-yl]-piperazine,
3-methyl-1-(ethanesulfonyl)-4-[3-(4-methylbenzyl)-[1,2,4]thiadiazol-5-yl]-piperazine,
3-methyl-1-(2-chloroethanesulfonyl)-4-[3-(4-methylbenzyl)-[1,2,4]thiadiazol-5-yl]-piperazine,
3-methyl-1-(chlorosulfonylacetyl)-4-[3-(4-methylbenzyl)-[1,2,4]thiadiazol-5-yl]-piperazine, and
3-methyl-1-(1-decanesulfonyl)-4-[3-(4-methylbenzyl)-[1,2,4]thiadiazol-5-yl]-piperazine.

EXAMPLE 42

N-sulfonylation of a 3-(substituted benzyl)-1,2,4-thiadiazol-5-ylpiperazine derivative, or analogue thereof, with a heterocyclic sulfonyl chloride Similarly to the procedure of example 4, a 3-(substituted benzyl)-1,2,4-thiadiazol-5-ylpiperazine derivative, or analogue thereof, obtained according to the procedure of example 3 or examples 26 to 40 (250 µmole, dissolved in 2-3 ml DCM) is reacted, in the presence of triethylamine (500 µmole), with an appropriate heterocyclyl-substituted sulfonyl chloride derivative (250 µmole) such as listed in the above detailed description. The reaction mixture is stirred at room temperature until total consumption of the starting products (reaction time varies between 3 and 5 hours), the course of reaction being monitored by TLC using dichloroethane (DCE)-EtOH 10:1 as an eluent mixture. When reaction is completed, DCM (2-3 ml) is added and the resulting solution is washed with a 5% aqueous citric acid solution (5 ml), water (5 ml), a 5% aqueous $Na_2CO_3$ solution, and water (5 ml), respectively. The organic phase is then separated, dried over $MgSO_4$, filtered and, evaporated to dryness. The residue is crystallised with diethyl ether to yield the desired compound.

According to this procedure, the following novel 1,2,4-thiadiazole compounds are obtained:
1-[2-(5-chloro-2-propoxyphenyl)-4-methyl-5-thiazolesulfonyl]-2-methyl-4-[3-(4-methylbenzyl)-[1,2,4]thiadiazol-5-yl]-piperazine,
1-[2-(5-bromo-2-ethoxyphenyl)-4-methyl-5-thiazolesulfonyl]-4-[3-(4-fluorobenzyl)-[1,2,4]thiadiazol-5-yl]-piperazine,
1-[2-[2-[2-(dimethylamino)ethoxy]-3-methoxyphenyl]-4-methyl-5-thiazolesulfonyl]-4-[3-(3-methoxy-benzyl)-[1,2,4]thiadiazol-5-yl]-piperazine,
1-[2-methoxycarbonylmethyl)-thiophene-5-sulfonyl]-4-[3-(4-fluorobenzyl)-[1,2,4]thiadiazol-5-yl]-1,4-diazepine,
1-[5-[2-[(2,2,2-trifluoroacetyl)amino]ethyl]-2-thiophenesulfonyl]-3-methyl-4-[3-(4-methylbenzyl)-[1,2,4]thiadiazol-5-yl]-piperazine,
1-[5-formyl-2-thiophenesulfonyl]-4-[3-(3-methoxybenzyl)-[1,2,4]thiadiazol-5-yl]-piperazine,
1-[5-(3-amino-3-oxo-1-propen-1-yl)-2-thiophenesulfonyl]-4-[3-(4-fluorobenzyl)-[1,2,4]thiadiazol-5-yl]-piperazine,
1-[5-(2H-tetrazol-5-yl)-2-thiophenesulfonyl]-2-Methyl-4-[3-(4-fluorobenzyl)-[1,2,4]thiadiazol-5-yl]-piperazine,
1-[3-(1,3-dioxolan-2-yl)-2-furansulfonyl]-2-Methyl-4-[3-(4-chlorobenzyl)-[1,2,4]thiadiazol-5-yl]-piperazine,
1-[4-[2-(methylthio)-4-pyrimidinyl]-2-thiophenesulfonyl]-4-[3-(4-chlorobenzyl)-[1,2,4]thiadiazol-5-yl]piperazine,
1-[5-(acetamidomethyl)-2-thiophenesulfonyl]-4-[3-(4-methylbenzyl)-[1,2,4]-thiadiazol-5-yl]-piperazine,
1-[5-(5-isoxazolyl)-2-furansulfonyl]-2-methyl-4-[3-benzyl-[1,2,4]thiadiazol-5-yl]-piperazine,
1-[5-[5-(chloromethyl)-1,2,4-oxadiazol-3-yl]-2-thiophenesulfonyl]-4-[3-benzyl-[1,2,4]thiadiazol-5-yl]-piperazine,
1-[5-[(3-chloro-5-trifluoromethylpyridin-2-yl)methyl]thiophene-2-sulfonyl]-2-{4-[3-(4-fluorobenzyl)-1,2,4-thiadiazol-5-yl]piperazin-1-yl}ethanamine,
1-[5-methyl-2-trifluoromethylfuran-3-sulfonyl]-2-{4-[3-benzyl-1,2,4-thiadiazol-5-yl]piperazin-1-yl}ethanamine,
1-[5-(2-methyl-5-trifluoromethyl-2H-pyrazol-3-yl)thiophene-2-sulfonyl]-2-{4-[3-(4-chlorobenzyl)-1,2,4-thiadiazol-5-yl]piperazin-1-yl}ethanamine,
1-[3-bromo-5-chloro-2-thiophenesulfonyl]-2-{4-[3-(4-methylbenzyl)-1,2,4-thiadiazol-5-yl]piperazin-1-yl}ethanamine,
1-[3-quinolinesulfonyl]-4-[3-[4-(4-methylphenoxy)benzyl]-1,2,4-thiadiazol-5-yl]-piperazine,
1-[2,5-dimethylthiophene-3-sulfonyl]-4-[3-[4-(4-methylphenoxy)benzyl]-1,2,4-thiadiazol-5-yl]-homopiperazine,
1-[5-phenylthiophene-2-sulfonyl]-2-methyl-4-[3-[4-(4-methylphenoxy)benzyl]-1,2,4-thiadiazol-5-yl]-piperazine,
1-[2,5-dibromo-3-thiophenesulfonyl]-4-[3-[(4-phenoxyphenyl)(hydroxy)methyl]-1,2,4-thiadiazol-5-yl]-piperazine,
1-[2,5-dichloro-4-nitro-3-thiophenesulfonyl]-4-[3-[(4-phenoxyphenyl)(hydroxy)-methyl]-1,2,4-thiadiazol-5-yl]-homopiperazine,
1-[5-chloro-4-nitro-2-thiophenesulfonyl]-2-methyl-3-[(4-phenoxyphenyl)-(hydroxy)methyl]-1,2,4-thiadiazol-5-yl]-piperazine,
1-[2-methyl-1-piperidinesulfonyl]-4-[5-(piperazin-4-yl)-1,2,4-thiadiazol-3-yl]-4-phenylcyclohexanone,
1-[5-chloro-3-cyano-4,6-dimethyl-2-pyridinesulfonyl]-4-[5-(homopiperazin-4-yl)-1,2,4-thiadiazol-3-yl]-4-phenylcyclohexanone,
1-[1-methyl-5-(trichloroacetyl)-1H-pyrrole-3-sulfonyl]-4-[5-(3-methylpiperazin-4-yl)-1,2,4-thiadiazol-3-yl]-4-phenylcyclohexanone, 1-[1,2-dimethyl-1H-imidazole-5-sulfonyl]-4-[3-[2-(4-dimethylaminophenyl)-1-(4-aminophenyl)-ethyl]-1,2,4-thiadiazol-5-yl]-homopiperazine,
1-[3-chloro-1,5-dimethyl-1H-Pyrazole-4-sulfonyl]-4-[3-[2-(4-dimethylaminophenyl)-1-(4-aminophenyl)-ethyl]-1,2,4-thiadiazol-5-yl]-piperazine,
1-[1-methyl-1H-pyrazole-4-sulfonyl]-2-methyl-4-[3-[2-(4-dimethylaminophenyl)-1-(4-aminophenyl)-ethyl]-1,2,4-thiadiazol-5-yl]-piperazine,
1-[5-nitro-2-pyridinesulfonyl]-4-[3-(2-nitrobenzyl)-1,2,4-thiadiazol-5-yl]-piperazine,
1-[5-(trifluoromethyl)pyridine-2-sulfonyl]-4-[3-(2-nitrobenzyl)-1,2,4-thiadiazol-5-yl]-homopiperazine,
1-[5-chloro-1,3-dimethyl-1H-pyrazole-4-sulfonyl]-2-methyl-[3-(2-nitrobenzyl)-1,2,4-thiadiazol-5-yl]-piperazine,
1-[1-Piperidinesulfonyl]-2-methyl-4-[3-(4-methylbenzyl)-[1,2,4]thiadiazol-5-yl]-piperazine,
1-[3,4-dihydro-4-oxo-2H-1-benzopyran-3-sulfonyl]-4-[3-(4-fluoro-benzyl)-[1,2,4]thiadiazol-5-yl]-piperazine,
1-[4-isoxazolesulfonyl]-4-[3-(3-methoxybenzyl)-[1,2,4]thiadiazol-5-yl]-piperazine,
1-[5-formyl-1,3,4-thiadiazole-2-sulfonyl]-4-[3-(4-fluorobenzyl)-[1,2,4]thiadiazol-5-yl]-1,4-diazepine,
1-[1H-indole-3-sulfonyl]-3-Methyl-4-[3-(4-methylbenzyl)-[1,2,4]thiadiazol-5-yl]-piperazine,
1-[1,3,4-thiadiazole-2-sulfonyl]-4-[3-(3-methoxybenzyl)-[1,2,4]thiadiazol-5-yl]-piperazine,
1-[5-methyl-4-isoxazolesulfonyl]-4-[3-(4-fluorobenzyl)-[1,2,4]thiadiazol-5-yl]-piperazine,
1-[3,4-dihydro-1H-isoquinoline-2-sulfonyl]-2-methyl-4-[3-(4-fluorobenzyl)-[1,2,4]-thiadiazol-5-yl]-piperazine,
1-[4-chlorotetrahydro-3-thiophenesulfonyl]-2-methyl-4-[3-(4-chlorobenzyl)-[1,2,4]thiadiazol-5-yl]-piperazine, and
1-[tetrahydro-4-hydroxy-3-thiophenesulfonyl]-4-[3-(4-chlorobenzyl)-[1,2,4]thiadiazol-5-yl]piperazine.

EXAMPLE 43

N-acylation of a 3-(substituted benzyl)-1,2,4-thiadiazol-5-ylpiperazine derivative, or analogue thereof, with a heterocyclic carbonyl chloride Similarly to the procedure of example 5, a 3-(substituted benzyl)-1,2,4-thiadiazol-5-ylpiperazine derivative, or analogue thereof, obtained according to the procedure of example 3 or examples 26 to 40 is reacted with an appropriate heterocyclic acyl chloride derivative such as listed in the above detailed description. According to this procedure, the following novel 1,2,4-thiadiazole compounds are obtained:
1-[4-(5-[(2-bromophenoxy)methyl]-2-furancarbonyl]-2-methyl-4-[3-(4-methylbenzyl)-[1,2,4]thiadiazol-5-yl]-piperazine,
1-[2-bromo-3-Furancarbonyl]-4-[3-(4-fluorobenzyl)-[1,2,4]thiadiazol-5-yl]-piperazine,
1-[5-(1-piperidinylmethyl)-2-furancarbonyl]-4-[3-(3-methoxybenzyl)-[1,2,4]thiadiazol-5-yl]-piperazine,
1-[5-(1-pyrrolidinylmethyl)-2-furancarbonyl]-4-[3-(4-fluorobenzyl)-[1,2,4]thiadiazol-5-yl]-1,4-diazepine,
1-[5-(3-bromophenyl)-2-furancarbonyl]-3-methyl-4-[3-(4-methylbenzyl)-[1,2,4]-thiadiazol-5-yl]-piperazine,
1-[2-methyl-5-(2-thienyl)-3-furancarbonyl]-4-[3-(3-methoxybenzyl)-[1,2,4]thiadiazol-5-yl]-piperazine,
1-[5-(3-pyridinyloxy)-2-Furancarbonyl]-4-[3-(4-fluorobenzyl)-[1,2,4]thiadiazol-5-yl]-piperazine,
1-[5-(methoxymethyl)-2-furancarbonyl]-2-methyl-4-[3-(4-fluorobenzyl)-[1,2,4]-thiadiazol-5-yl]-piperazine,
1-[3,4-dimethoxy-2-Furancarbonyl]-2-Methyl-4-[3-(4-chlorobenzyl)-[1,2,4]thiadiazol-5-yl]-piperazine,
1-[4-bromo-1-methyl-1H-Pyrazole-3-carbonyl]-4-[3-(4-chlorobenzyl)-[1,2,4]thiadiazol-5-yl]-piperazine,
1-[1-ethyl-1H-Pyrazole-4-carbonyl]-4-[3-(4-methyl-benzyl)-[1,2,4]thiadiazol-5-yl]-piperazine,
1-[1-methyl-5-(2-thienyl)-1H-Pyrazole-3-carbonyl]-2-methyl-4-[3-benzyl-[1,2,4]-thiadiazol-5-yl]-piperazine,
1-[3-chloro-1-cyclopropyl-1H-pyrazole-4-carbonyl]-4-[3-benzyl-[1,2,4]thiadiazol-5-yl]-piperazine,
N-[pyrazolo[1,5-a]pyrimidine-3-carbonyl]-2-{4-[3-(4-fluorobenzyl)-[1,2,4]-thiadiazol-5-yl]piperazin-1-yl}ethanamine,
N-[5-methyl-7-(pentafluoroethyl)-pyrazolo[1,5-a]pyrimidine-3-carbonyl]-2-{4-[3-benzyl-1,2,4-thiadiazol-5-yl]piperazin-1-yl}ethanamine,
N-[5-cyclopropyl-7-(trifluoromethyl)-pyrazolo[1,5-a]pyrimidine-2-carbonyl]-2-{4-[3-(4-chlorobenzyl)-1,2,4-thiadiazol-5-yl]piperazin-1-yl}ethanamine,
N-[4-cyano-2-thiophenecarbonyl]-2-{4-[3-(4-methylbenzyl)-1,2,4-thiadiazol-5-yl]piperazin-1-yl}ethanamine,
1-[5-(1,1-dimethylethyl)-2-thiophenecarbonyl]-4-[3-[4-(4-methylphenoxy)benzyl]-[1,2,4]thiadiazol-5-yl]-piperazine,
1-[2-methyl-4-thiazolecarbonyl]-4-[3-[4-(4-methylphenoxy)benzyl]-1,2,4-thiadiazol-5-yl]-homopiperazine,
1-[3-(4-methoxyphenyl)-5-Isoxazolecarbonyl]-2-methyl-4-[3-[4-(4-methylphenoxy)benzyl]-1,2,4-thiadiazol-5-yl]-piperazine,
1-[2-[4-(trifluoromethyl)phenyl]-4-Thiazolecarbonyl]-4-[3-[(4-phenoxyphenyl)-(hydroxy)methyl]-1,2,4-thiadiazol-5-yl]-piperazine,
1-[5-(2-methylpropyl)-3-Isoxazolecarbonyl]-4-[3-[(4-phenoxyphenyl)(hydroxy)-methyl]-1,2,4-thiadiazol-5-yl]-homopiperazine,
1-[5-(difluoromethyl)-2-methyl-4-thiazolecarbonyl]-2-methyl-4-[3-[(4-phenoxyphenyl)(hydroxy)methyl]-1,2,4-thiadiazol-5-yl]-piperazine,
1-[3-methyl-5-(4-methyl-1,2,3-thiadiazol-5-yl)-4-Isoxazolecarbonyl]-4-[5-(piperazin-4-yl)-1,2,4-thiadiazol-3-yl]-4-phenylcyclohexanone,
4-[5-[1-(5-(2-methyl-4-thiazolyl)-3-isoxazolecarbonyl)-homopiperazin-4-yl]-1,2,4-thiadiazol-3-yl]-4-phenylcyclohexanone,
4-[5-[1-(5-cyano-3-(1-methylethyl)-4-isoxazolecarbonyl)-2-methylpiperazin-4-yl]-1,2,4-thiadiazol-3-yl]-4-phenylcyclohexanone,
1-[2-(dimethylamino)-4-methyl-5-Thiazolecarbonyl]-4-[3-[2-(4-dimethylaminophenyl)-1-(4-aminophenyl)-ethyl]-1,2,4-thiadiazol-5-yl]-homopiperazine,
1-[2-cyclopropyl-4-(trifluoromethyl)-5-Pyrimidinecarbonyl]-4-[3-[2-(4-dimethylaminophenyl)-1-(4-aminophenyl)-ethyl]-1,2,4-thiadiazol-5-yl]-piperazine,
1-[1-methoxy-1H-Indole-3-carbonyl]-2-methyl-4-[3-[2-(4-dimethylaminophenyl)-1-(4-aminophenyl)-ethyl]-1,2,4-thiadiazol-5-yl]-piperazine,
1-[5-fluoro-1-methyl-1H-Indole-2-carbonyl]-4-[3-(2-nitrobenzyl)-1,2,4-thiadiazol-5-yl]-piperazine,
1-[4-acetyl-1-Piperidinecarbonyl]-4-[3-(2-nitrobenzyl)-1,2,4-thiadiazol-5-yl]-homopiperazine, and
1-[6-fluoro-benzo[b]thiophene-2-carbonyl]-2-methyl-4-[3-(2-nitrobenzyl)-1,2,4-thiadiazol-5-yl]-piperazine.

EXAMPLE 44

N-alkylation of a 3-(substituted benzyl)-1,2,4-thiadiazol-5-ylpiperazine derivative, or analogue thereof, with a heterocyclyl chloride Similarly to the procedure of example 6, a 3-(substituted benzyl)-1,2,4-thiadiazol-5-ylpiperazine derivative, or analogue thereof, obtained according to the procedure of example 3 or examples 26 to 40 is reacted with an appropriate heterocyclyl chloride derivative (1.0 molar equivalent) such as listed in the above detailed description, in the presence of triethylamine (2.0 molar equivalents).

EXAMPLE 45

Urea-linkage formation onto a 3-(substituted benzyl)-1,2,4-thiadiazol-5-ylpiperazine derivative, or analogue thereof, by means of a heterocyclic isocyanate Similarly to the procedure of example 7, a 3-(substituted benzyl)-1,2,4-thiadiazol-5-ylpiperazine derivative, or analogue thereof, obtained according to the procedure of example 3 or examples 26 to 40 is reacted with an appropriate heterocyclic isocyanate derivative such as listed in the above detailed description. According to this procedure, the following novel 1,2,4-thiadiazole compounds are obtained:

N-[3-cyclopropyl-isoxazol-5-yl]-4-[3-(4-methyl-benzyl)-[1,2,4]thiadiazol-5-yl]-piperazine-1-carboxamide,
N-[5-fluoro-benzothiazol-2-yl]-2-methyl-4-[3-benzyl-[1,2,4]thiadiazol-5-yl]-piperazine-1-carboxamide,
N-[pyridin-4-yl]-4-[3-benzyl-[1,2,4]thiadiazol-5-yl]-piperazine-1-carboxamide,
N-[thiazol-2-yl]-2-{4-[3-(4-fluorobenzyl)-1,2,4-thiadiazol-5-yl]piperazin-1-yl}ethanamine-1-carboxamide,
N-[3,4-dimethylisoxazol-5-yl]-2-{4-[3-benzyl-1,2,4-thiadiazol-5-yl]piperazin-1-yl}ethanamine-1-carboxamide,
N-[2,6-dimethylpyrimidin-4-yl]-2-{4-[3-(4-chlorobenzyl)-1,2,4-thiadiazol-5-yl]piperazin-1-yl}ethanamine-1-carboxamide,
N-[pyrimidin-2-yl]-2-{4-[3-(4-methylbenzyl)-1,2,4-thiadiazol-5-yl]piperazin-1-yl}ethanamine-1-carboxamide,
N-[thiophen-3-yl]-4-[3-[4-(4-methylphenoxy)benzyl]-1,2,4-thiadiazol-5-yl]-piperazine-1-carboxamide,
N-[furan-2-yl]-4-[3-[4-(4-methylphenoxy)benzyl]-1,2,4-thiadiazol-5-yl]-homopiperazine-1-carboxamide,
N-[2-pyridin5-ylcarbonitrile]-2-methyl-4-[3-[4-(4-methylphenoxy)benzyl]-1,2,4-thiadiazol-5-yl]-piperazine-1-carboxamide,
N-[5-chloro-2-(trifluoromethyl)-1,3-benzodioxol-2-yl]-4-[3-[(4-phenoxyphenyl)-(hydroxy)methyl]-1,2,4-thiadiazol-5-yl]-piperazine-1-carboxamide,
N-[3,5-dimethyl-Isoxazol-4-yl]-4-[3-[(4-phenoxyphenyl)(hydroxy)methyl]-1,2,4-thiadiazol-5-yl]-homopiperazine-1-carboxamide,
N-[4,6-dimethylpyrimidin-2-yl]-2-methyl-[3-[(4-phenoxyphenyl)(hydroxy)-methyl]-1,2,4-thiadiazol-5-yl]-piperazine-1-carboxamide,
N-[1-methyl-1H-pyrrol-2-yl]-4-[5-(piperazin-4-yl)-1,2,4-thiadiazol-3-yl]-4-phenylcyclohexanone-1-carboxamide,
N-[3-bromopyridin-5-yl]-4-[5-(homopiperazin-4-yl)-1,2,4-thiadiazol-3-yl]-4-phenylcyclohexanone-1-carboxamide,
N-[1-carboxaldehydro-piperidin-4-yl]-4-[5-(3-methylpiperazin-4-yl)-1,2,4-thiadiazol-3-yl]-4-phenylcyclohexanone-1-carboxamide,
N-[1,3,4-thiadiazol-2-yl]-4-[3-[2-(4-dimethylaminophenyl)-1-(4-aminophenyl)-ethyl]-1,2,4-thiadiazol-5-yl]-homopiperazine-1-carboxamide,
N-[1,3,5-trimethyl-1H-Pyrazol-4-yl]-4-[3-[2-(4-dimethylaminophenyl)-1-(4-aminophenyl)-ethyl]-1,2,4-thiadiazol-5-yl]-piperazine-1-carboxamide,
N-[5-methyl-3-phenyl-isoxazol-4-yl]-2-methyl-4-[3-[2-(4-dimethylaminophenyl)-1-(4-aminophenyl)-ethyl]-1,2,4-thiadiazol-5-yl]-piperazine-1-carboxamide,
N-[5-methyl-2-(trifluoromethyl)-furan-3-yl]-4-[3-(2-nitrobenzyl)-1,2,4-thiadiazol-5-yl]-piperazine-1-carboxamide,
N-[5-phenyl-thien-2-yl]-4-[3-(2-nitrobenzyl)-1,2,4-thiadiazol-5-yl]-homopiperazine-1-carboxamide,
N-[benzo[b]thiophen-3-yl]-2-methyl-[3-(2-nitrobenzyl)-1,2,4-thiadiazol-5-yl]-piperazine-1-carboxamide,
N-[3-methyl-5-phenyl-isoxazol-4-yl]-2-methyl-4-[3-(4-methylbenzyl)-[1,2,4]thiadiazol-5-yl]-piperazine-1-carboxamide,
N-[6-methoxy-2H-1-benzopyran-2-one-3-yl]-4-[3-(4-fluorobenzyl)-[1,2,4]thiadiazol-5-yl]-piperazine-1-carboxamide,
N-[1-methyl-1H-imidazol-5-yl]-4-[3-(3-methoxybenzyl)-[1,2,4]thiadiazol-5-yl]-piperazine-1-carboxamide,
N-[1-ethynyl-2(1H)-azeton-4-yl]-4-[3-(4-fluorobenzyl)-[1,2,4]thiadiazol-5-yl]-1,4-diazepine-1-carboxamide,
N-[2(1H)-pyridinone-3-yl]-3-methyl-4-[3-(4-methylbenzyl)-[1,2,4]thiadiazol-5-yl]-piperazine-1-carboxamide,
N-[1-oxo-Pyridin-4-yl]-4-[3-(3-Methoxy-benzyl)-[1,2,4]thiadiazol-5-yl]-piperazine-1-carboxamide,
N-[2-methylpyridin-5-yl]-4-[3-(4-fluorobenzyl)-[1,2,4]thiadiazol-5-yl]-piperazine-1-carboxamide,
N-[2-ethyl-1,3,4-thiadiazol-5-yl]-2-Methyl-4-[3-(4-fluorobenzyl)-[1,2,4]thiadiazol-5-yl]-piperazine-1-carboxamide,
N-[1-propyl-1H-pyrazol-3-yl]-2-Methyl-4-[3-(4-chlorobenzyl)-[1,2,4]thiadiazol-5-yl]-piperazine-1-carboxamide,
N-[1,3-dimethyl-1H-pyrazol-5-yl]-4-[3-(4-chlorobenzyl)-[1,2,4]thiadiazol-5-yl]piperazine-1-carboxamide,
N-[1-ethyl-1H-pyrrol-3-yl]-4-[3-(4-methylbenzyl)-[1,2,4]thiadiazol-5-yl]-piperazine-1-carboxamide,
N-[1-(1-methylethyl)-1H-pyrrol-3-yl]-2-methyl-4-[3-benzyl-[1,2,4]thiadiazol-5-yl]-piperazine-1-carboxamide,
N-[1-propyl-1H-pyrrol-3-yl]-4-[3-benzyl-[1,2,4]thiadiazol-5-yl]-piperazine-1-carboxamide,
N-[1-(trifluoroacetyl)-piperidin-3-yl]-2-{4-[3-(4-fluorobenzyl)-1,2,4-thiadiazol-5-yl]piperazin-1-yl}ethanamine-1-carboxamide,
N-[(4-methyl-thien-2-yl)aminocarbonyl]-2-{4-[3-benzyl-1,2,4-thiadiazol-5-yl]piperazin-1-yl}ethanamine,
N-[(4-methyl-2-phenyl-thiazol-5-yl)aminocarbonyl]-2-{4-[3-(4-chlorobenzyl)-1,2,4-thiadiazol-5-yl]piperazin-1-yl}ethanamine,
N-[(2-[4-(trifluoromethyl)phenyl]-thiazole-4-yl)aminocarbonyl]-2-{4-[3-(4-methylbenzyl)-1,2,4-thiadiazol-5-yl]piperazin-1-yl}ethanamine,
N-[2-(3-chlorophenyl)-thiazol-4-yl]-4-[3-[4-(4-methylphenoxy)benzyl]-1,2,4-thiadiazol-5-yl]-piperazine-1-carboxamide,
N-[5-methyl-2-phenyl-Furan-3-yl]-4-[3-[4-(4-methylphenoxy)benzyl]-1,2,4-thiadiazol-5-yl]-homopiperazine-1-carboxamide,
N-[2-bromo-thien-3-yl]-2-methyl-4-[3-[4-(4-methylphenoxy)benzyl]-1,2,4-thiadiazol-5-yl]-piperazine-1-carboxamide, N-[2-[(tetrahydro-2H-pyran-4-yl)oxy]-pyridin5-yl]-4-[3-[(4-phenoxyphenyl)-(hydroxy)methyl]-1,2,4-thiadiazol-5-yl]-piperazine-1-carboxamide,
N-[2-methyl-furan-3-yl]-4-[3-[(4-phenoxyphenyl)(hydroxy)methyl]-1,2,4-thiadiazol-5-yl]-homopiperazine-1-carboxamide, and
N-[2-(trifluoromethyl)-pyridin-4-yl]-2-methyl-[3-[(4-phenoxyphenyl)(hydroxy)methyl]-1,2,4-thiadiazol-5-yl]-piperazine-1-carboxamide.

EXAMPLE 46

N-sulfonylation of 3-(substituted benzyl)-1,2,4-thiadiazol-5-ylpiperazines and analogues thereof

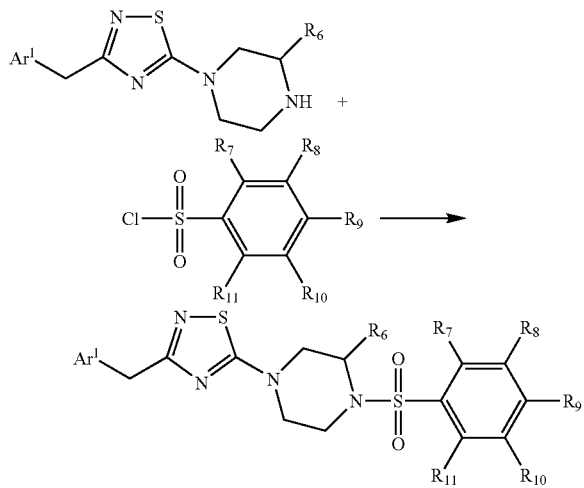

Similarly to the procedure of example 4, a 3-(substituted benzyl)-1,2,4-thiadiazol-5-ylpiperazine derivative, or analogue thereof, obtained according to the procedure of example 3 or examples 26 to 40 (250 µmole, dissolved in 2-3 ml DCM) is reacted, in the presence of triethylamine (500 µmole), with an appropriate sulfonyl chloride derivative (250 µmole).

The following compounds are synthesised using these experimental conditions:
Using 3-methyl-1-[3-(4-methyl-benzyl)-[1,2,4]thiadiazol-5-yl]-piperazine as starting material:
4-(N-acetylsulfanilyl)-3-methyl-1-[3-(4-methylbenzyl)-[1,2,4]thiadiazol-5-yl]-piperazine,
4-[(2-methyloxycarbonyl-phenyl)sulfonyl]-3-methyl-1-[3-(4-methylbenzyl)-[1,2,4]thiadiazol-5-yl]-piperazine,
4-[(2-methylsulfonyl-benzene)sulfonyl]-3-methyl-1-[3-(4-methylbenzyl)-[1,2,4]thiadiazol-5-yl]-piperazine,
4-[(4-methylsulfonyl-benzene)sulfonyl]-3-methyl-1-[3-(4-methylbenzyl)-[1,2,4]thiadiazol-5-yl]-piperazine,
3-{[4-(3-(4-methylbenzyl)-1,2,4-thiadiazol-5-yl)piperazin-1-yl]sulfonyl}benzoic acid,
4-[4-(1,2,3-thiadiazol-4-yl)benzenesulfonyl]-3-methyl-1-[3-(4-methylbenzyl)-[1,2,4]thiadiazol-5-yl]-piperazine,
4-[4-(1H-pyrazol-1-yl)benzenesulfonyl]-3-methyl-1-[3-(4-methylbenzyl)-[1,2,4]thiadiazol-5-yl]-piperazine,
2-hydroxy-4-{[4-(3-(4-methylbenzyl)-1,2,4-thiadiazol-5-yl)piperazin-1-yl]-sulfonyl}benzoic acid,
4-[(4-acetylamino)-3-chlorobenzene-1-sulfonyl]-3-methyl-1-[3-(4-methylbenzyl)-[1,2,4]thiadiazol-5-yl]-piperazine,
4-[3-(5-methyl-1,3,4-oxadiazol-2-yl)benzenesulfonyl]-3-methyl-1-[3-(4-methylbenzyl)-[1,2,4]thiadiazol-5-yl]-piperazine,
methyl 4-methoxy-3-{[4-(3-(4-methylbenzyl)-1,2,4-thiadiazol-5-yl)piperazin-1-yl]sulfonyl}benzoate,
4-[2-cyano-5-methylbenzenesulfonyl]-3-methyl-1-[3-(4-methylbenzyl)-[1,2,4]thiadiazol-5-yl]-piperazine,
4-[2-chloro-4-cyanobenzene-1-sulfonyl]-3-methyl-1-[3-(4-methylbenzyl)-[1,2,4]thiadiazol-5-yl]-piperazine,
4-(4-cyanobenzene-1-sulfonyl)-3-methyl-1-[3-(4-methylbenzyl)-[1,2,4]thiadiazol-5-yl]-piperazine,
4-(3-cyanobenzene-1-sulfonyl)-3-methyl-1-[3-(4-methylbenzyl)-[1,2,4]thiadiazol-5-yl]-piperazine,
4-[4-(2-oxo-1-pyrrolidinyl)benzene sulfonyl]-3-methyl-1-[3-(4-methylbenzyl)-[1,2,4]thiadiazol-5-yl]-piperazine,
4-[4'-methyl-(1,1'-biphenyl)-4-sulfonyl]-3-methyl-1-[3-(4-methylbenzyl)-[1,2,4]thiadiazol-5-yl]-piperazine,
4-[3',4'-dichloro-(1,1'-biphenyl)-4-sulfonyl]-3-methyl-1-[3-(4-methylbenzyl)-[1,2,4]thiadiazol-5-yl]-piperazine,
4-(4-phenoxybenzenesulfonyl)-3-methyl-1-[3-(4-methylbenzyl)-[1,2,4]thiadiazol-5-yl]-piperazine,
4-[4-(2-methyl-1,3-thiazol-4-yl)benzenesulfonyl]-3-methyl-1-[3-(4-methylbenzyl)-[1,2,4]thiadiazol-5-yl]-piperazine,
4-(1-acetyl-5-indolinesulfonyl)-3-methyl-1-[3-(4-methylbenzyl)-[1,2,4]thiadiazol-5-yl]-piperazine,
4-(1-formyl-5-indolinesulfonyl)-3-methyl-1-[3-(4-methylbenzyl)-[1,2,4]thiadiazol-5-yl]-piperazine, and
4-[3-(2-methyl-1,3-thiazol-4-yl)benzenesulfonyl]-3-methyl-1-[3-(4-methylbenzyl)-[1,2,4]thiadiazol-5-yl]-piperazine.
Using [3-[4-(4-methylphenoxy)benzyl]-1,2,4-thiadiazol-5-yl]-piperazine as starting material:
4-(N-acetylsulfanilyl)-1-[3-[4-(4-methylphenoxy)benzyl]-1,2,4-thiadiazol-5-yl]-piperazine,
4-[(2-methyloxycarbonyl-phenyl)sulfonyl]-1-[3-[4-(4-methylphenoxy)benzyl]-1,2,4-thiadiazol-5-yl]-piperazine,
4-[(2-methylsulfonyl-benzene)sulfonyl]-1-[3-[4-(4-methylphenoxy)benzyl]-1,2,4-thiadiazol-5-yl]-piperazine,
4-[(4-methylsulfonyl-benzene)sulfonyl]-1-[3-[4-(4-methylphenoxy)benzyl]-1,2,4-thiadiazol-5-yl]-piperazine,
3-{[4-(3-[4-(4-methylphenoxy)benzyl]-1,2,4-thiadiazol-5-yl)piperazin-1-yl]-sulfonyl}benzoic acid,
4-[4-(1,2,3-thiadiazol-4-yl)benzenesulfonyl]-1-[3-[4-(4-methylphenoxy)benzyl]-1,2,4-thiadiazol-5-yl]-piperazine,
4-[4-(1H-pyrazol-1-yl)benzenesulfonyl]-1-[3-[4-(4-methylphenoxy)benzyl]-1,2,4-thiadiazol-5-yl]-piperazine,
2-hydroxy-4-{[4-(3-[4-(4-methylphenoxy)benzyl]-1,2,4-thiadiazol-5-yl)-piperazin-1-yl]sulfonyl}benzoic acid,
4-[(acetylamino)-3-chlorobenzene-1-sulfonyl]-1-[3-[4-(4-methylphenoxy)-benzyl]-1,2,4-thiadiazol-5-yl]-piperazine,
4-[3-(5-methyl-1,3,4-oxadiazol-2-yl)benzenesulfonyl]-1-[3-[4-(4-methylphenoxy)benzyl]-1,2,4-thiadiazol-5-yl]-piperazine,
methyl 4-methoxy-3-{[4-[3-(4-(4-methylphenoxy)benzyl)-1,2,4-thiadiazol-5-yl]piperazin-1-yl]sulfonyl}benzoate,
4-[2-cyano-5-methylbenzenesulfonyl]-1-[3-[4-(4-methylphenoxy)benzyl]-1,2,4-thiadiazol-5-yl]-piperazine,
4-[2-chloro-4-cyanobenzene-1-sulfonyl]-1-[3-[4-(4-methylphenoxy)benzyl]-1,2,4-thiadiazol-5-yl]-piperazine,
4-(4-cyanobenzene-1-sulfonyl)-1-[3-[4-(4-methylphenoxy)benzyl]-1,2,4-thiadiazol-5-yl]-piperazine,
4-(3-cyanobenzene-1-sulfonyl)-1-[3-[4-(4-methylphenoxy)benzyl]-1,2,4-thiadiazol-5-yl]-piperazine,
4-[4-(2-oxo-1-pyrrolidinyl)benzene sulfonyl]-1-[3-[4-(4-methylphenoxy)benzyl]-1,2,4-thiadiazol-5-yl]-piperazine, 4-[4'-methyl-(1,1'-biphenyl)-4-sulfonyl]-1-[3-[4-(4-methylphenoxy)benzyl]-1,2,4-thiadiazol-5-yl]-piperazine, 4-[3',4'-dichloro-(1,1'-biphenyl)-4-sulfonyl]-1-[3-[4-(4-methylphenoxy)benzyl]-1,2,4-thiadiazol-5-yl]-piperazine, 4-(4-phenoxybenzenesulfonyl)-1-[3-[4-(4-methylphenoxy)benzyl]-1,2,4-thiadiazol-5-yl]-piperazine, 4-[4-(2-methyl-1,3-thiazol-4-yl)benzenesulfonyl]-1-[3-[4-(4-methylphenoxy)-benzyl]-1,2,4-thiadiazol-5-yl]-piperazine, 4-(1-acetyl-5-indolinesulfonyl)-1-[3-[4-(4-methylphenoxy)benzyl]-1,2,4-thiadiazol-5-yl]-piperazine, 4-(1-formyl-5-indolinesulfonyl)-1-[3-[4-(4-methylphenoxy)benzyl]-1,2,4-thiadiazol-5-yl]-piperazine, and 4-[3-(2-methyl-1,3-thiazol-4-yl)benzenesulfonyl]-1-[3-[4-(4-methylphenoxy)-benzyl]-1,2,4-thiadiazol-5-yl]-piperazine.

Using [3-[(4-phenoxyphenyl)(hydroxy)methyl]-1,2,4-thiadiazol-5-yl]-homopiperazine as starting material:

4-(N-acetylsulfanilyl)-1-[3-[(4-phenoxyphenyl)(hydroxy)methyl]-1,2,4-thiadiazol-5-yl]-homopiperazine, 4-[(2-methoxycarbonyl-phenyl)sulfonyl]-1-[3-[(4-phenoxyphenyl)(hydroxy)-methyl]-1,2,4-thiadiazol-5-yl]-homopiperazine, 4-[(2-methylsulfonylbenzene)sulfonyl]-1-[3-[(4-phenoxyphenyl)(hydroxy)-methyl]-1,2,4-thiadiazol-5-yl]-homopiperazine, 4-[(4-methylsulfonyl-benzene)sulfonyl]-1-[3-[(4-phenoxyphenyl)(hydroxy)-methyl]-1,2,4-thiadiazol-5-yl]-homopiperazine, 3-{[4-(3-[(4-phenoxyphenyl)(hydroxy)methyl]-1,2,4-thiadiazol-5-yl)piperazin-1-yl]sulfonyl}benzoic acid, 4-[4-(1,2,3-thiadiazol-4-yl)benzenesulfonyl]-1-[3-[(4-phenoxyphenyl)(hydroxy)-methyl]-1,2,4-thiadiazol-5-yl]-homopiperazine, 4-[4-(1H-pyrazol-1-yl)benzenesulfonyl]-1-[3-[(4-phenoxyphenyl)(hydroxy)-methyl]-1,2,4-thiadiazol-5-yl]-homopiperazine, 2-hydroxy-4-{[4-(3-[(4-phenoxyphenyl)(hydroxy)methyl]-1,2,4-thiadiazol-5-yl)piperazin-1-yl]sulfonyl}benzoic acid, 4-[4-(acetylamino)-3-chlorobenzene-1-sulfonyl]-1-[3-[(4-phenoxyphenyl)-(hydroxy)methyl]-1,2,4-thiadiazol-5-yl]-homopiperazine, 4-[3-(5-methyl-1,3,4-oxadiazol-2-yl)benzenesulfonyl]-1-[3-[(4-phenoxyphenyl)(hydroxy)methyl]-1,2,4-thiadiazol-5-yl]-homopiperazine, methyl 4-methoxy-3-{[4-[3-[(4-phenoxyphenyl)(hydroxy)methyl]-1,2,4-thiadiazol-5-yl]piperazin-1-yl]sulfonyl}benzoate, 4-[2-cyano-5-methylbenzenesulfonyl]-1-[3-[(4-phenoxyphenyl)(hydroxy)-methyl]-1,2,4-thiadiazol-5-yl]-homopiperazine, 4-[2-chloro-4-cyanobenzene-1-sulfonyl]-1-[3-[(4-phenoxyphenyl)(hydroxy)-methyl]-1,2,4-thiadiazol-5-yl]-homopiperazine, 4-(4-cyanobenzene-1-sulfonyl)-1-[3-[(4-phenoxyphenyl)(hydroxy)methyl]-1,2,4-thiadiazol-5-yl]-homopiperazine, 4-(3-cyanobenzene-1-sulfonyl)-1-[3-[(4-phenoxyphenyl)(hydroxy)methyl]-1,2,4-thiadiazol-5-yl]-homopiperazine, 4-[4-(2-oxo-1-pyrrolidinyl)benzenesulfonyl]-1-[3-[(4-phenoxyphenyl)(hydroxy)-methyl]-1,2,4-thiadiazol-5-yl]-homopiperazine, 4-[4'-methyl-(1,1'-biphenyl)-4-sulfonyl]-1-[3-[(4-phenoxyphenyl)(hydroxy)methyl]-1,2,4-thiadiazol-5-yl]-homopiperazine, 4-[3',4'-dichloro-(1,1'-biphenyl)-4-sulfonyl]-1-[3-[(4-phenoxyphenyl)(hydroxy)-methyl]-1,2,4-thiadiazol-5-yl]-homopiperazine, 4-(4-phenoxybenzenesulfonyl)-1-[3-[(4-phenoxyphenyl)(hydroxy)methyl]-1,2,4-thiadiazol-5-yl]-homopiperazine, 4-[4-(2-methyl-1,3-thiazol-4-yl)benzenesulfonyl]-1-[3-[(4-phenoxyphenyl)-(hydroxy)methyl]-1,2,4-thiadiazol-5-yl]-homopiperazine, 4-(1-acetyl-5-indolinesulfonyl)-1-[3-[(4-phenoxyphenyl)(hydroxy)methyl]-1,2,4-thiadiazol-5-yl]-homopiperazine, 4-(1-formyl-5-indolinesulfonyl)-1-[3-[(4-phenoxyphenyl)(hydroxy)methyl]-1,2,4-thiadiazol-5-yl]-homopiperazine, and 4-[3-(2-methyl-1,3-thiazol-4-yl)benzenesulfonyl]-1-[3-[(4-phenoxyphenyl)-(hydroxy)methyl]-1,2,4-thiadiazol-5-yl]-homopiperazine.

Using 4-[5-(3-methylpiperazin-1-yl)-1,2,4-thiadiazol-3-yl]-4-phenylcyclohexanone as starting material:

4-(N-acetylsulfanilyl)-3-methyl-1-[3-(4-phenylcyclohex-4-yl-1-one)-1,2,4-thiadiazol-5-yl]-piperazine, 4-[(2-methyloxycarbonyl-phenyl)sulfonyl]-3-methyl-1-[3-(4-phenylcyclohex-4-yl-1-one)-1,2,4-thiadiazol-5-yl]-piperazine, 4-[(2-methylsulfonyl-benzene)sulfonyl]-3-methyl-1-[3-(4-phenylcyclohex-4-yl-1-one)-1,2,4-thiadiazol-5-yl]-piperazine, 4-[(4-methylsulfonyl-benzene)sulfonyl]-3-methyl-1-[3-(4-phenylcyclohex-4-yl-1-one)-1,2,4-thiadiazol-5-yl]-piperazine, 3-{[4-(3-(4-phenylcyclohex-4-yl-1-one)-1,2,4-thiadiazol-5-yl)piperazin-1-yl]sulfonyl}benzoic acid, 4-[4-(1,2,3-thiadiazol-4-yl)benzenesulfonyl]-3-methyl-1-[3-(4-phenylcyclohex-4-yl-1-one)-1,2,4-thiadiazol-5-yl]-piperazine, 4-[4-(1H-pyrazol-1-yl)benzenesulfonyl]-3-methyl-1-[3-(4-phenylcyclohex-4-yl-1-one)-1,2,4-thiadiazol-5-yl]-piperazine, 2-hydroxy-4-{[4-(3-(4-phenylcyclohex-4-yl-1-one)-1,2,4-thiadiazol-5-yl)-piperazin-1-yl]sulfonyl}benzoic acid, 4-[4-(acetylamino)-3-chlorobenzene-1-sulfonyl]-3-methyl-1-[3-(4-phenylcyclohex-4-yl-1-one)-1,2,4-thiadiazol-5-yl]-piperazine, 4-[3-(5-methyl-1,3,4-oxadiazol-2-yl)benzenesulfonyl]-3-methyl-1-[3-(4-phenylcyclohex-4-yl-1-one)-1,2,4-thiadiazol-5-yl]-piperazine, methyl 4-methoxy-3-{[4-[3-(4-phenylcyclohex-4-yl-1-one)-1,2,4-thiadiazol-5-yl]piperazin-1-yl]sulfonyl}benzoate, 4-[2-cyano-5-methylbenzenesulfonyl]-3-methyl-1-[3-(4-phenylcyclohex-4-yl-1-one)-1,2,4-thiadiazol-5-yl]-piperazine, 4-[2-chloro-4-cyanobenzene-1-sulfonyl]-3-methyl-1-[3-(4-phenylcyclohex-4-yl-1-one)-1,2,4-thiadiazol-5-yl]-piperazine, 4-(4-cyanobenzene-1-sulfonyl)-3-methyl-1-[3-(4-phenylcyclohex-4-yl-1-one)-1,2,4-thiadiazol-5-yl]-piperazine, 4-(3-cyanobenzene-1-sulfonyl)-3-methyl-1-[3-(4-phenylcyclohex-4-yl-1-one)-1,2,4-thiadiazol-5-yl]-piperazine, 4-[4-(2-oxo-1-pyrrolidinyl)benzene sulfonyl]-3-methyl-1-[3-(4-phenylcyclohex-4-yl-1-one)-1,2,4-thiadiazol-5-yl]-piperazine, 4-[4'-methyl-(1,1'-biphenyl)-4-sulfonyl]-3-methyl-1-[3-(4-phenylcyclohex-4-yl-1-one)-1,2,4-thiadiazol-5-yl]-piperazine, 4-[3',4'-dichloro-(1,1'-biphenyl)-4-sulfonyl]-3-methyl-1-[3-(4-phenylcyclohex-4-yl-1-one)-1,2,4-thiadiazol-5-yl]-piperazine, 4-(4-phenoxybenzenesulfonyl)-3-methyl-1-[3-(4-phenylcyclohex-4-yl-1-one)-1,2,4-thiadiazol-5-yl]-piperazine, 4-[4-(2-methyl-1,3-thiazol-4-yl)benzenesulfonyl]-3-methyl-1-[3-(4-phenylcyclohex-4-yl-1-one)-1,2,4-thiadiazol-5-yl]-piperazine, 4-(1-acetyl-5-indolinesulfonyl)-3-methyl-1-[3-(4-phenylcyclohex-4-yl-1-one)-1,2,4-thiadiazol-5-yl]-piperazine, 4-(1-formyl-5-indolinesulfonyl)-3-methyl-1-[3-(4-phenylcyclohex-4-yl-1-one)-1,2,4-thiadiazol-5-yl]-piperazine, and 4-[3-(2-methyl-1,3-thiazol-4-yl)benzenesulfonyl]-3-methyl-1-[3-(4-phenylcyclohex-4-yl-1-one)-1,2,4-thiadiazol-5-yl]-piperazine.

Using [3-[2-(4-dimethylaminophenyl)-1-(4-aminophenyl)-ethyl]-1,2,4-thiadiazol-5-yl]-piperazine as starting material:

4-(N-acetylsulfanilyl)-1-[3-[2-(4-dimethylaminophenyl)-1-(4-aminophenyl)-ethyl]-1,2,4-thiadiazol-5-yl]-piperazine, 4-[(2-methyloxycarbonyl-phenyl)sulfonyl]-1-[3-[2-(4-dimethylaminophenyl)-1-(4-aminophenyl)-ethyl]-1,2,4-thiadiazol-5-yl]-piperazine, 4-[(2-methylsulfonyl-benzene)sulfonyl]-1-[3-[2-(4-dimethylaminophenyl)-1-(4-aminophenyl)-ethyl]-1,2,4-thiadiazol-5-yl]-piperazine, 4-[(4-methylsulfonyl-benzene)sulfonyl]-1-[3-[2-(4-dimethylaminophenyl)-1-(4-aminophenyl)-ethyl]-1,2,4-thiadiazol-5-yl]-piperazine, 3-{[4-(3-[2-(4-dimethylaminophenyl)-1-(4-aminophenyl)-ethyl]-1,2,4-thiadiazol-5-yl)piperazin-1-yl]sulfonyl}benzoic acid, 4-[4-(1,2,3-thiadiazol-4-yl)benzenesulfonyl]-1-[3-[2-(4-dimethylaminophenyl)-1-(4-aminophenyl)-ethyl]-1,2,4-thiadiazol-5-yl]-piperazine, 4-[4-(1H-pyrazol-1-yl)benzenesulfonyl]-1-[3-[2-(4-dimethylaminophenyl)-1-(4-aminophenyl)-ethyl]-1,2,4-thiadiazol-5-yl]-piperazine, 2-hydroxy-4-{[4-(3-[2-(4-dimethylaminophenyl)-1-(4-aminophenyl)-ethyl]-1,2,4-thiadiazol-5-yl)piperazin-1-yl]sulfonyl}benzoic acid, 4-[4-(acetylamino)-3-chlorobenzene-1-sulfonyl]-1-[3-[2-(4-dimethylaminophenyl)-1-(4-aminophenyl)-ethyl]-1,2,4-thiadiazol-5-yl]-piperazine, 4-[3-(5-methyl-1,3,4-oxadiazol-2-yl)benzenesulfonyl]-1-[3-[2-(4-dimethylaminophenyl)-1-(4-aminophenyl)-ethyl]-1,2,4-thiadiazol-5-yl]-piperazine, methyl 4-methoxy-3-{[4-[3-[2-(4-dimethylaminophenyl)-1-(4-aminophenyl)-ethyl]-1,2,4-thiadiazol-5-yl]piperazin-1-yl]sulfonyl}benzoate, 4-[2-cyano-5-methylbenzenesulfonyl]-1-[3-[2-(4-dimethylaminophenyl)-1-(4-aminophenyl)-ethyl]-1,2,4-thiadiazol-5-yl]-piperazine, 4-[2-chloro-4-cyanobenzene-1-sulfonyl]-1-[3-[2-(4-dimethylaminophenyl)-1-(4-aminophenyl)-ethyl]-1,2,4-thiadiazol-5-yl]-piperazine 4-(4-cyanobenzene-1-sulfonyl)-1-[3-[2-(4-dimethylaminophenyl)-1-(4-aminophenyl)-ethyl]-1,2,4-thiadiazol-5-yl]-piperazine, 4-(3-cyanobenzene-1-sulfonyl)-1-[3-[2-(4-dimethylaminophenyl)-1-(4-aminophenyl)-ethyl]-1,2,4-thiadiazol-5-yl]-piperazine, 4-[4-(2-oxo-1-pyrrolidinyl)benzene sulfonyl]-1-[3-[2-(4-dimethylaminophenyl)-1-(4-aminophenyl)-ethyl]-1,2,4-thiadiazol-5-yl]-piperazine, 4-[4'-methyl-(1,1'-biphenyl)-4-sulfonyl]-1-[3-[2-(4-dimethylaminophenyl)-1-(4-aminophenyl)-ethyl]-1,2,4-thiadiazol-5-yl]-piperazine, 4-[3',4'-dichloro-(1,1'-biphenyl)-4-sulfonyl]-1-[3-[2-(4-dimethylaminophenyl)-1-(4-aminophenyl)-ethyl]-1,2,4-thiadiazol-5-yl]-piperazine, 4-(4-phenoxybenzenesulfonyl)-1-[3-[2-(4-dimethylaminophenyl)-1-(4-aminophenyl)-ethyl]-1,2,4-thiadiazol-5-yl]-piperazine, 4-[4-(2-methyl-1,3-thiazol-4-yl)benzenesulfonyl]-1-[3-[2-(4-dimethylaminophenyl)-1-(4-aminophenyl)-ethyl]-1,2,4-thiadiazol-5-yl]-piperazine, 4-(1-acetyl-5-indolinesulfonyl)-1-[3-[2-(4-dimethylaminophenyl)-1-(4-aminophenyl)-ethyl]-1,2,4-thiadiazol-5-yl]-piperazine, 4-(1-formyl-5-indolinesulfonyl)-1-[3-[2-(4-dimethylaminophenyl)-1-(4-aminophenyl)-ethyl]-1,2,4-thiadiazol-5-yl]-piperazine, and 4-[3-(2-methyl-1,3-thiazol-4-yl)benzenesulfonyl]-1-[3-[2-(4-dimethylaminophenyl)-1-(4-aminophenyl)-ethyl]-1,2,4-thiadiazol-5-yl]-piperazine.

Using [3-(2-nitrobenzyl)-1,2,4-thiadiazol-5-yl]-homopiperazine as starting material:

4-(N-acetylsulfanilyl)-1-[3-(2-nitrobenzyl)-1,2,4-thiadiazol-5-yl]-homopiperazine, 4-[(2-methyloxycarbonyl-phenyl)sulfonyl]-1-[3-(2-nitrobenzyl)-1,2,4-thiadiazol-5-yl]-homopiperazine, 4-[(2-methylsulfonyl-benzene)sulfonyl]-1-[3-(2-nitrobenzyl)-1,2,4-thiadiazol-5-yl]-homopiperazine, 4-[(4-methylsulfonyl-benzene)sulfonyl]-1-[3-(2-nitrobenzyl)-1,2,4-thiadiazol-5-yl]-homopiperazine, 3-{[4-(3-(2-nitrobenzyl)-1,2,4-thiadiazol-5-yl)piperazin-1-yl]sulfonyl}benzoic acid, 4-[4-(1,2,3-thiadiazol-4-yl)benzenesulfonyl]-1-[3-(2-nitrobenzyl)-1,2,4-thiadiazol-5-yl]-homopiperazine, 4-[4-(1H-pyrazol-1-yl)benzenesulfonyl]-1-[3-(2-nitrobenzyl)-1,2,4-thiadiazol-5-yl]-homopiperazine, 2-hydroxy-4-{[4-(3-(2-nitrobenzyl)-1,2,4-thiadiazol-5-yl)piperazin-1-yl]-sulfonyl}benzoic acid, 4-[4-(acetylamino)-3-chlorobenzene-1-sulfonyl]-1-[3-(2-nitrobenzyl)-1,2,4-thiadiazol-5-yl]-homopiperazine, 4-[3-(5-methyl-1,3,4-oxadiazol-2-yl)benzenesulfonyl]-1-[3-(2-nitrobenzyl)-1,2,4-thiadiazol-5-yl]-homopiperazine, methyl 4-methoxy-3-{[4-[3-(2-nitrobenzyl)-1,2,4-thiadiazol-5-yl]piperazin-1-yl]sulfonyl}benzoate, 4-[2-cyano-5-methylbenzenesulfonyl]-1-[3-(2-nitrobenzyl)-1,2,4-thiadiazol-5-yl]-homopiperazine, 4-[2-chloro-4-cyanobenzene-1-sulfonyl]-1-[3-(2-nitrobenzyl)-1,2,4-thiadiazol-5-yl]-homopiperazine, 4-(4-cyanobenzene-1-sulfonyl)-1-[3-(2-nitrobenzyl)-1,2,4-thiadiazol-5-yl]-homopiperazine, 4-(3-cyanobenzene-1-sulfonyl)-1-[3-(2-nitrobenzyl)-1,2,4-thiadiazol-5-yl]-homopiperazine, 4-[4-(2-oxo-1-pyrrolidinyl)benzene sulfonyl]-1-[3-(2-nitrobenzyl)-1,2,4-thiadiazol-5-yl]-homopiperazine, 4-[4'-methyl-(1,1'-biphenyl)-4-sulfonyl]-1-[3-(2-nitrobenzyl)-1,2,4-thiadiazol-5-yl]-homopiperazine, 4-[3',4'-dichloro-(1,1'-biphenyl)-4-sulfonyl]-1-[3-(2-nitrobenzyl)-1,2,4-thiadiazol-5-yl]-homopiperazine, 4-(4-phenoxybenzenesulfonyl)-1-[3-(2-nitrobenzyl)-1,2,4-thiadiazol-5-yl]-homopiperazine, 4-[4-(2-methyl-1,3-thiazol-4-yl)benzenesulfonyl]-1-[3-(2-nitrobenzyl)-1,2,4-thiadiazol-5-yl]-homopiperazine, 4-(1-acetyl-5-indolinesulfonyl)-1-[3-(2-nitrobenzyl)-1,2,4-thiadiazol-5-yl]-homopiperazine, 4-(1-formyl-5-indolinesulfonyl)-1-[3-(2-nitrobenzyl)-1,2,4-thiadiazol-5-yl]-homopiperazine, and 4-[3-(2-methyl-1,3-thiazol-4-yl)benzenesulfonyl]-1-[3-(2-nitrobenzyl)-1,2,4-thiadiazol-5-yl]-homopiperazine.

EXAMPLE 47

N-acylation of a 3-(substituted benzyl)-1,2,4-thiadiazol-5-ylpiperazine derivative, or analogue thereof Similarly to the procedure of example 5, a 3-(substituted benzyl)-1,2,4-thiadiazol-5-ylpiperazine derivative, or analogue thereof, obtained according to the procedure of example 3 or examples 26 to 40 is reacted with an appropriate acyl chloride derivative.

The following compounds are synthesised using these experimental conditions:

Using 1-[3-(4-fluorobenzyl)-1,2,4-thiadiazol-5-yl]piperazine as starting material:

4-(4-cyanobenzoyl)-1-[3-(4-fluorobenzyl)-1,2,4-thiadiazol-5-yl]piperazine,
4-(4-methyloxycarbonylbenzoyl)-1-[3-(4-fluorobenzyl)-1,2,4-thiadiazol-5-yl]piperazine,
4-(4-(2-thienyl)-benzoyl)-1-[3-(4-fluorobenzyl)-1,2,4-thiadiazol-5-yl]piperazine,
4-(4-(1H-pyrazol-1-yl)benzoyl)-1-[3-(4-fluorobenzyl)-1,2,4-thiadiazol-5-yl]-piperazine,
4-(1-methyl-1H-1,2,3-benzotriazole-5-carbonyl)-1-[3-(4-fluorobenzyl)-1,2,4-thiadiazol-5-yl]piperazine,
4-(4-[3-(trifluoromethyl)-1H-pyrazol-1-yl]-benzoyl)-1-[3-(4-fluorobenzyl)-1,2,4-thiadiazol-5-yl]piperazine,
4-(4-[3-(trifluoromethyl)-1H-pyrazol-1-yl]-benzoyl)-1-[3-(4-fluorobenzyl)-1,2,4-thiadiazol-5-yl]piperazine,
4-(3-(cyclopentyloxy)-4-methoxybenzoyl)-1-[3-(4-fluorobenzyl)-1,2,4-thiadiazol-5-yl]piperazine,
4-(3-(2-methyl-thiazol-4-yl)-benzoyl)-1-[3-(4-fluorobenzyl)-1,2,4-thiadiazol-5-yl]piperazine,
4-(2-(2-thienyl)-benzoyl)-1-[3-(4-fluorobenzyl)-1,2,4-thiadiazol-5-yl]piperazine,
4-(3-cyanobenzoyl)-1-[3-(4-fluorobenzyl)-1,2,4-thiadiazol-5-yl]piperazine,
4-(acetylsalicyloyl)-1-[3-(4-fluorobenzyl)-1,2,4-thiadiazol-5-yl]piperazine, and
4-(4-(5-methyl-1,2,4-oxadiazol-3-yl)-benzoyl)-1-[3-(4-fluorobenzyl)-1,2,4-thiadiazol-5-yl]piperazine.

Using [3-[4-(4-methylphenoxy)benzyl]-1,2,4-thiadiazol-5-yl]-homopiperazine as starting material:

4-(4-cyanobenzoyl)-1-[3-[4-(4-methylphenoxy)benzyl]-1,2,4-thiadiazol-5-yl]-homopiperazine,
4-(4-methyloxycarbonylbenzoyl)-1-[3-[4-(4-methylphenoxy)benzyl]-1,2,4-thiadiazol-5-yl]-homopiperazine,
4-(4-(2-thienyl)-benzoyl)-1-[3-[4-(4-methylphenoxy)benzyl]-1,2,4-thiadiazol-5-yl]-homopiperazine,
4-(4-(1H-pyrazol-1-yl)benzoyl)-1-[3-[4-(4-methylphenoxy)benzyl]-1,2,4-thiadiazol-5-yl]-homopiperazine,
4-(1-methyl-1H-1,2,3-benzotriazole-5-carbonyl)-1-[3-[4-(4-methylphenoxy)-benzyl]-1,2,4-thiadiazol-5-yl]-homopiperazine,
4-(4-[3-(trifluoromethyl)-1H-pyrazol-1-yl]-benzoyl-1-[3-[4-(4-methylphenoxy)-benzyl]-1,2,4-thiadiazol-5-yl]-homopiperazine,
4-(4-[3-(trifluoromethyl)-1H-pyrazol-1-yl]-benzoyl)-1-[3-[4-(4-methylphenoxy)-benzyl]-1,2,4-thiadiazol-5-yl]-homopiperazine,
4-(3-(cyclopentyloxy)-4-methoxybenzoyl)-1-[3-[4-(4-methylphenoxy)benzyl]-1,2,4-thiadiazol-5-yl]-homopiperazine,
4-(3-(2-methyl-thiazol-4-yl)-benzoyl)-1-[3-[4-(4-methylphenoxy)benzyl]-1,2,4-thiadiazol-5-yl]-homopiperazine,
4-(2-(2-thienyl)-benzoyl)-1-[3-[4-(4-methylphenoxy)benzyl]-1,2,4-thiadiazol-5-yl]-homopiperazine,
4-(3-cyanobenzoyl)-1-[3-[4-(4-methylphenoxy)benzyl]-1,2,4-thiadiazol-5-yl]-homopiperazine,
4-(acetylsalicyloyl)-1-[3-[4-(4-methylphenoxy)benzyl]-1,2,4-thiadiazol-5-yl]-homopiperazine, and
4-(4-(5-methyl-1,2,4-oxadiazol-3-yl)-benzoyl)-1-[3-[4-(4-methylphenoxy)-benzyl]-1,2,4-thiadiazol-5-yl]-homopiperazine.

Using 3-methyl-[3-[(4-phenoxyphenyl)(hydroxy)methyl]-1,2,4-thiadiazol-5-yl]-piperazine as starting material:

4-(4-cyanobenzoyl)-3-methyl-1-[3-[(4-phenoxyphenyl)(hydroxy)methyl]-1,2,4-thiadiazol-5-yl]-piperazine,
4-(4-methyloxycarbonylbenzoyl)-3-methyl-1-[3-[(4-phenoxyphenyl)(hydroxy)-methyl]-1,2,4-thiadiazol-5-yl]-piperazine,
4-(4-(2-thienyl)-benzoyl)-3-methyl-1-[3-[(4-phenoxyphenyl)(hydroxy)methyl]-1,2,4-thiadiazol-5-yl]-piperazine,
4-(4-(1H-pyrazol-1-yl)benzoyl)-3-methyl-1-[3-[(4-phenoxyphenyl)(hydroxy)-methyl]-1,2,4-thiadiazol-5-yl]-piperazine,
4-(1-methyl-1H-1,2,3-benzotriazole-5-carbonyl)-3-methyl-1-[3-[(4-phenoxyphenyl)(hydroxy)methyl]-1,2,4-thiadiazol-5-yl]-piperazine,
4-(4-[3-(trifluoromethyl)-1H-pyrazol-1-yl]-benzoyl)-3-methyl-1-[3-[(4-phenoxyphenyl)(hydroxy)methyl]-1,2,4-thiadiazol-5-yl]-piperazine,
4-(4-[3-(trifluoromethyl)-1H-pyrazol-1-yl]-benzoyl)-3-methyl-1-[3-[(4-phenoxyphenyl)(hydroxy)methyl]-1,2,4-thiadiazol-5-yl]-piperazine,
4-(3-(cyclopentyloxy)-4-methoxybenzoyl)-3-methyl-1-[3-[(4-phenoxyphenyl)-(hydroxy)methyl]-1,2,4-thiadiazol-5-yl]-piperazine,
4-(3-(2-methyl-thiazol-4-yl)-benzoyl)-3-methyl-1-[3-[(4-phenoxyphenyl)-(hydroxy)methyl]-1,2,4-thiadiazol-5-yl]-piperazine,
4-(2-(2-thienyl)-benzoyl)-3-methyl-1-[3-[(4-phenoxyphenyl)(hydroxy)methyl]-1,2,4-thiadiazol-5-yl]-piperazine,
4-(3-cyanobenzoyl)-3-methyl-1-[3-[(4-phenoxyphenyl)(hydroxy)methyl]-1,2,4-thiadiazol-5-yl]-piperazine,
4-(acetylsalicyloyl)-3-methyl-1-[3-[(4-phenoxyphenyl)(hydroxy)methyl]-1,2,4-thiadiazol-5-yl]-piperazine, and
4-(4-(5-methyl-1,2,4-oxadiazol-3-yl)-benzoyl)-3-methyl-1-[3-[(4-phenoxyphenyl)(hydroxy)methyl]-1,2,4-thiadiazol-5-yl]-piperazine.

Using 4-[5-(piperazin-1-yl)-1,2,4-thiadiazol-3-yl]-4-phenyl-cyclohexanone as starting material:

4-(4-cyanobenzoyl)-1-[3-(4-phenylcyclohex-4-yl-1-one)-1,2,4-thiadiazol-5-yl]-piperazine,
4-(4-methyloxycarbonylbenzoyl)-1-[3-(4-phenylcyclohex-4-yl-1-one)-1,2,4-thiadiazol-5-yl]-piperazine,
4-(4-(2-thienyl)-benzoyl)-1-[3-(4-phenylcyclohex-4-yl-1-one)-1,2,4-thiadiazol-5-yl]-piperazine,
4-(4-(1H-pyrazol-1-yl)benzoyl)-1-[3-(4-phenylcyclohex-4-yl-1-one)-1,2,4-thiadiazol-5-yl]-piperazine,
4-(1-methyl-1H-1,2,3-benzotriazole-5-carbonyl)-1-[3-(4-phenylcyclohex-4-yl-1-one)-1,2,4-thiadiazol-5-yl]-piperazine,
4-(4-[3-(trifluoromethyl)-1H-pyrazol-1-yl]-benzoyl)-1-[3-(4-phenylcyclohex-4-yl-1-one)-1,2,4-thiadiazol-5-yl]-piperazine,
4-(4-[3-(trifluoromethyl)-1H-pyrazol-1-yl]-benzoyl)-1-[3-(4-phenylcyclohex-4-yl-1-one)-1,2,4-thiadiazol-5-yl]-piperazine, 4-(3-(cyclopentyloxy)-4-methoxybenzoyl)-1-[3-(4-phenyl-cyclohex-4-yl-1-one)-1,2,4-thiadiazol-5-yl]-piperazine,
4-(3-(2-methyl-thiazol-4-yl)-benzoyl)-1-[3-(4-phenylcyclo-hex-4-yl-1-one)-1,2,4-thiadiazol-5-yl]-piperazine,
4-(2-(2-thienyl)-benzoyl)-1-[3-(4-phenylcyclohex-4-yl-1-one)-1,2,4-thiadiazol-5-yl]-piperazine,
4-(3-cyanobenzoyl)-1-[3-(4-phenylcyclohex-4-yl-1-one)-1,2,4-thiadiazol-5-yl]-piperazine,
4-(acetylsalicyloyl)-1-[3-(4-phenylcyclohex-4-yl-1-one)-1,2,4-thiadiazol-5-yl]-piperazine, and
4-(4-(5-methyl-1,2,4-oxadiazol-3-yl)-benzoyl)-1-[3-(4-phenylcyclohex-4-yl-1-one)-1,2,4-thiadiazol-5-yl]-piperazine.

Using [3-[2-(4-dimethylaminophenyl)-1-(4-aminophenyl)-ethyl]-1,2,4-thiadiazol-5-yl]-homopiperazine as starting material:
4-(4-cyanobenzoyl)-1-[3-[2-(4-dimethylaminophenyl)-1-(4-aminophenyl)-ethyl]-1,2,4-thiadiazol-5-yl]-homopiperazine,
4-(4-methyloxycarbonylbenzoyl)-1-[3-[2-(4-dimethylaminophenyl)-1-(4-aminophenyl)-ethyl]-1,2,4-thiadiazol-5-yl]-homopiperazine,
4-(4-(2-thienyl)-benzoyl)-1-[3-[2-(4-dimethylaminophenyl)-1-(4-aminophenyl)-ethyl]-1,2,4-thiadiazol-5-yl]-homopiperazine,
4-(4-(1H-pyrazol-1-yl)benzoyl)-1-[3-[2-(4-dimethylaminophenyl)-1-(4-aminophenyl)-ethyl]-1,2,4-thiadiazol-5-yl]-homopiperazine,
4-(1-methyl-1H-1,2,3-benzotriazole-5-carbonyl)-1-[3-[2-(4-dimethylaminophenyl)-1-(4-aminophenyl)-ethyl]-1,2,4-thiadiazol-5-yl]-homopiperazine,
4-(4-[3-(trifluoromethyl)-1H-pyrazol-1-yl]-benzoyl)-1-[3-[2-(4-dimethylaminophenyl)-1-(4-aminophenyl)-ethyl]-1,2,4-thiadiazol-5-yl]-homopiperazine,
4-(4-[3-(trifluoromethyl)-1H-pyrazol-1-yl]-benzoyl)-1-[3-[2-(4-dimethylaminophenyl)-1-(4-aminophenyl)-ethyl]-1,2,4-thiadiazol-5-yl]-homopiperazine,
4-(3-(cyclopentyloxy)-4-methoxybenzoyl)-1-[3-[2-(4-dimethylaminophenyl)-1-(4-aminophenyl)-ethyl]-1,2,4-thiadiazol-5-yl]-homopiperazine,
4-(3-(2-methyl-thiazol-4-yl)-benzoyl)-1-[3-[2-(4-dimethylaminophenyl)-1-(4-aminophenyl)-ethyl]-1,2,4-thiadiazol-5-yl]-homopiperazine,
4-(2-(2-thienyl)-benzoyl)-1-[3-[2-(4-dimethylaminophenyl)-1-(4-aminophenyl)-ethyl]-1,2,4-thiadiazol-5-yl]-homopiperazine,
4-(3-cyanobenzoyl)-1-[3-[2-(4-dimethylaminophenyl)-1-(4-aminophenyl)-ethyl]-1,2,4-thiadiazol-5-yl]-homopiperazine,
4-(acetylsalicyloyl)-1-[3-[2-(4-dimethylaminophenyl)-1-(4-aminophenyl)-ethyl]-1,2,4-thiadiazol-5-yl]-homopiperazine, and
4-(4-(5-methyl-1,2,4-oxadiazol-3-yl)-benzoyl)-1-[3-[2-(4-dimethylaminophenyl)-1-(4-aminophenyl)-ethyl]-1,2,4-thiadiazol-5-yl]-homopiperazine.

Using 3-methyl-[3-(2-nitrobenzyl)-1,2,4-thiadiazol-5-yl]-piperazine as starting material:
4-(4-cyanobenzoyl)-3-methyl-1-[3-(2-nitrobenzyl)-1,2,4-thiadiazol-5-yl]-piperazine,
4-(4-methyloxycarbonylbenzoyl)-3-methyl-1-[3-(2-nitrobenzyl)-1,2,4-thiadiazol-5-yl]-piperazine,
4-(4-(2-thienyl)-benzoyl)-3-methyl-1-[3-(2-nitrobenzyl)-1,2,4-thiadiazol-5-yl]-piperazine,
4-(4-(1H-pyrazol-1-yl)benzoyl)-3-methyl-1-[3-(2-nitrobenzyl)-1,2,4-thiadiazol-5-yl]-piperazine,
4-(1-methyl-1H-1,2,3-benzotriazole-5-carbonyl)-3-methyl-1-[3-(2-nitrobenzyl)-1,2,4-thiadiazol-5-yl]-piperazine,
4-(4-[3-(trifluoromethyl)-1H-pyrazol-1-yl]-benzoyl)-3-methyl-1-[3-(2-nitrobenzyl)-1,2,4-thiadiazol-5-yl]-piperazine,
4-(4-[3-(trifluoromethyl)-1H-pyrazol-1-yl]-benzoyl)-3-methyl-1-[3-(2-nitrobenzyl)-1,2,4-thiadiazol-5-yl]-piperazine,
4-(3-(cyclopentyloxy)-4-methoxybenzoyl)-3-methyl-1-[3-(2-nitrobenzyl)-1,2,4-thiadiazol-5-yl]-piperazine,
4-(3-(2-methyl-thiazol-4-yl)-benzoyl)-3-methyl-1-[3-(2-nitrobenzyl)-1,2,4-thiadiazol-5-yl]-piperazine,
4-(2-(2-thienyl)-benzoyl)-3-methyl-1-[3-(2-nitrobenzyl)-1,2,4-thiadiazol-5-yl]-piperazine,
4-(3-cyanobenzoyl)-3-methyl-1-[3-(2-nitrobenzyl)-1,2,4-thiadiazol-5-yl]-piperazine,
4-(acetylsalicyloyl)-3-methyl-1-[3-(2-nitrobenzyl)-1,2,4-thiadiazol-5-yl]-piperazine, and
4-(4-(5-methyl-1,2,4-oxadiazol-3-yl)-benzoyl)-3-methyl-1-[3-(2-nitrobenzyl)-1,2,4-thiadiazol-5-yl]-piperazine.

EXAMPLE 48

Urea-linkage formation onto a 3-(substituted benzyl)-1,2,4-thiadiazol-5-ylpiperazine derivative, or analogue thereof Similarly to the procedure of example 7, a 3-(substituted benzyl)-1,2,4-thiadiazol-5-ylpiperazine derivative, or analogue thereof, obtained according to the procedure of example 3 or examples 26 to 40 is reacted with an appropriate isocyanate derivative.

The following compounds are synthesized according to this method:
Using 1-[3-(3-methoxy-benzyl)-[1,2,4]thiadiazol-5-yl]-piperazine as starting material:
N-(3-cyanophenyl)-4-[3-(3-methoxybenzyl)-[1,2,4]thiadiazol-5-yl]-piperazine-1-carboxamide,
N-(4-(methylthio)-phenyl)-4-[3-(3-methoxybenzyl)-[1,2,4]thiadiazol-5-yl]-piperazine-1-carboxamide,
N-(4-(Dimethylamino)phenyl)-4-[3-(3-methoxybenzyl)-[1,2,4]thiadiazol-5-yl]-piperazine-1-carboxamide,
N-(2-(Methylthio)phenyl)-4-[3-(3-methoxybenzyl)-[1,2,4]thiadiazol-5-yl]-piperazine-1-carboxamide,
N-[3-[2-methyl-1,3-thiazol-4-yl]-phenyl]-4-[3-(3-methoxybenzyl)-[1,2,4]thiadiazol-5-yl]-piperazine-1-carboxamide,
N-(3-[5-methyl-1,2,4-oxadiazol-3-yl]phenyl)-4-[3-(3-methoxybenzyl)-[1,2,4]-thiadiazol-5-yl]-piperazine-1-carboxamide, and
N-[4-(1H-pyrrol-1-yl)phenyl]-4-[3-(3-methoxybenzyl)-[1,2,4]thiadiazol-5-yl]-piperazine-1-carboxamide.

Using 3-methyl-1-[3-[4-(4-methylphenoxy)benzyl]-1,2,4-thiadiazol-5-yl]-piperazine as starting material:
N-(3-cyanophenyl)-3-methyl-4-[3-[4-(4-methylphenoxy)benzyl]-1,2,4-thiadiazol-5-yl]-piperazine-1-carboxamide,
N-(4-(methylthio)-phenyl)-3-methyl-4-[3-[4-(4-methylphenoxy)benzyl]-1,2,4-thiadiazol-5-yl]-piperazine-1-1-carboxamide,
N-(4-(Dimethylamino)phenyl)-3-methyl-4-[3-[4-(4-methylphenoxy)benzyl]-1,2,4-thiadiazol-5-yl]-piperazine-1-1-carboxamide,
N-(2-(Methylthio)phenyl)-3-methyl-4-[3-[4-(4-methylphenoxy)benzyl]-1,2,4-thiadiazol-5-yl]-piperazine-1-1-carboxamide,
N-[3-[2-methyl-1,3-thiazol-4-yl]-phenyl]-3-methyl-4-[3-[4-(4-methylphenoxy)-benzyl]-1,2,4-thiadiazol-5-yl]-piperazine-1-1-carboxamide, N-(3-[5-methyl-1,2,4-oxadiazol-3-yl]phenyl)-3-methyl-4-[3-[4-(4-methylphenoxy)benzyl]-1,2,4-thiadiazol-5-yl]-piperazine-1-1-carboxamide, and N-[4-(1H-pyrrol-1-yl)phenyl]-3-methyl-4-[3-[4-(4-methylphenoxy)benzyl]-1,2,4-thiadiazol-5-yl]-piperazine-1-1-carboxamide.

Using [3-[(4-phenoxyphenyl)(hydroxy)methyl]-1,2,4-thiadiazol-5-yl]-piperazine as starting material:

N-(3-cyanophenyl)-4-[3-[(4-phenoxyphenyl)(hydroxy)methyl]-1,2,4-thiadiazol-5-yl]-piperazine-1-carboxamide, N-(4-(methylthio)-phenyl)-4-[3-[(4-phenoxyphenyl)(hydroxy)methyl]-1,2,4-thiadiazol-5-yl]-piperazine-1-carboxamide, N-(4-(Dimethylamino)phenyl)-4-[3-[(4-phenoxyphenyl)(hydroxy)methyl]-1,2,4-thiadiazol-5-yl]-piperazine-1-carboxamide, N-(2-(Methylthio)phenyl)-4-[3-[(4-phenoxyphenyl)(hydroxy)methyl]-1,2,4-thiadiazol-5-yl]-piperazine-1-carboxamide, N-[3-[2-methyl-1,3-thiazol-4-yl]-phenyl]-4-[3-[(4-phenoxyphenyl)(hydroxy)-methyl]-1,2,4-thiadiazol-5-yl]-piperazine-1-carboxamide, N-(3-[5-methyl-1,2,4-oxadiazol-3-yl]phenyl)-4-[3-[(4-phenoxyphenyl)(hydroxy)-methyl]-1,2,4-thiadiazol-5-yl]-piperazine-1-carboxamide, and N-[4-(1H-pyrrol-1-yl)phenyl]-4-[3-[(4-phenoxyphenyl)(hydroxy)methyl]-1,2,4-thiadiazol-5-yl]-piperazine-1-carboxamide.

Using 4-[5-(homopiperazin-1-yl)-1,2,4-thiadiazol-3-yl]-4-phenylcyclohexanone as starting material:

N-(3-cyanophenyl)-4-[3-(4-phenylcyclohex-4-yl-1-one)-1,2,4-thiadiazol-5-yl]-homopiperazine-1-carboxamide, N-(4-(methylthio)-phenyl)-4-[3-(4-phenylcyclohex-4-yl-1-one)-1,2,4-thiadiazol-5-yl]-homopiperazine-1-carboxamide, N-(4-(Dimethylamino)phenyl)-4-[3-(4-phenylcyclohex-4-yl-1-one)-1,2,4-thiadiazol-5-yl]-homopiperazine-1-carboxamide, N-(2-(Methylthio)phenyl)-4-[3-(4-phenylcyclohex-4-yl-1-one)-1,2,4-thiadiazol-5-yl]-homopiperazine-1-carboxamide, N-[3-[2-methyl-1,3-thiazol-4-yl]-phenyl]-4-[3-(4-phenylcyclohex-4-yl-1-one)-1,2,4-thiadiazol-5-yl]-homopiperazine-1-carboxamide, N-(3-[5-methyl-1,2,4-oxadiazol-3-yl]phenyl)-4-[3-(4-phenylcyclohex-4-yl-1-one)-1,2,4-thiadiazol-5-yl]-homopiperazine-1-carboxamide, and N-[4-(1H-pyrrol-1-yl)phenyl]-4-[3-(4-phenylcyclohex-4-yl-1-one)-1,2,4-thiadiazol-5-yl]-homopiperazine-1-carboxamide.

Using 3-methyl-1-[3-[2-(4-dimethylaminophenyl)-1-(4-aminophenyl)-ethyl]-1,2,4-thiadiazol-5-yl]-piperazine as starting material:

N-(3-cyanophenyl)-3-methyl-4-[3-[2-(4-dimethylaminophenyl)-1-(4-aminophenyl)-ethyl]-1,2,4-thiadiazol-5-yl]-piperazine-1-carboxamide, N-(4-(methylthio)-phenyl)-3-methyl-4-[3-[2-(4-dimethylaminophenyl)-1-(4-aminophenyl)-ethyl]-1,2,4-thiadiazol-5-yl]-piperazine-1-carboxamide, N-(4-(dimethylamino)phenyl)-3-methyl-4-[3-[2-(4-dimethylaminophenyl)-1-(4-aminophenyl)-ethyl]-1,2,4-thiadiazol-5-yl]-piperazine-1-carboxamide, N-(2-(methylthio)phenyl)-3-methyl-4-[3-[2-(4-dimethylaminophenyl)-1-(4-aminophenyl)-ethyl]-1,2,4-thiadiazol-5-yl]-piperazine-1-carboxamide, N-[3-[2-methyl-1,3-thiazol-4-yl]-phenyl]-3-methyl-4-[3-[2-(4-dimethylaminophenyl)-1-(4-aminophenyl)-ethyl]-1,2,4-thiadiazol-5-yl]-piperazine-1-carboxamide, N-(3-[5-methyl-1,2,4-oxadiazol-3-yl]phenyl)-3-methyl-4-[3-[2-(4-dimethylaminophenyl)-1-(4-aminophenyl)-ethyl]-1,2,4-thiadiazol-5-yl]-piperazine-1-carboxamide, and N-[4-(1H-pyrrol-1-yl)phenyl]-3-methyl-4-[3-[2-(4-dimethylaminophenyl)-1-(4-aminophenyl)-ethyl]-1,2,4-thiadiazol-5-yl]-piperazine-1-carboxamide.

Using [3-(2-nitrobenzyl)-1,2,4-thiadiazol-5-yl]-piperazine as starting material:

N-(3-cyanophenyl)-4-[3-(2-nitrobenzyl)-1,2,4-thiadiazol-5-yl]-piperazine-1-carboxamide, N-(4-(methylthio)-phenyl)-4-[3-(2-nitrobenzyl)-1,2,4-thiadiazol-5-yl]-piperazine-1-carboxamide, N-(4-(Dimethylamino)phenyl)-4-[3-(2-nitrobenzyl)-1,2,4-thiadiazol-5-yl]-piperazine-1-carboxamide, N-(2-(Methylthio)phenyl)-4-[3-(2-nitrobenzyl)-1,2,4-thiadiazol-5-yl]-piperazine-1-carboxamide, N-[3-[2-methyl-1,3-thiazol-4-yl]-phenyl]-4-[3-(2-nitrobenzyl)-1,2,4-thiadiazol-5-yl]-piperazine-1-carboxamide, N-(3-[5-methyl-1,2,4-oxadiazol-3-yl]phenyl)-4-[3-(2-nitrobenzyl)-1,2,4-thiadiazol-5-yl]-piperazine-1-carboxamide, and N-[4-(1H-pyrrol-1-yl)phenyl]-4-[3-(2-nitrobenzyl)-1,2,4-thiadiazol-5-yl]-piperazine-1-carboxamide.

EXAMPLE 49

Preparation and biological activity of 1-[4-methoxyphenylsulfonyl]-4-[3-(3-methoxy-benzyl-1,2,4-thiadiazol-5-yl]-2-methylpiperazine The synthesis of this compound was performed according to the general principles of example 4, and more specifically according to the detailed following scheme:

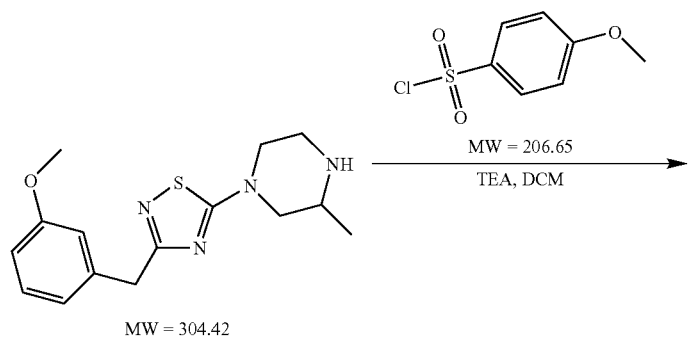

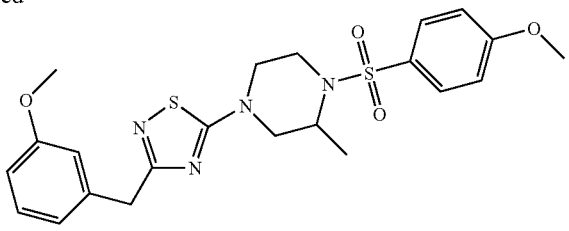

MW = 474.60

141 mg of this compound (yield 90%) were obtained after 2 hours reaction time. The compound was tested according to the procedure of example 12, and the corresponding test results are presented in table 3 below.

EXAMPLE 50

Preparation and biological activity of 1-[thiophen-2-ylsulfonyl]-4-[3-(4-fluoro-benzyl)-1,2,4-thiadiazol-5-yl]piperazine The synthesis of this compound was performed according to the general principles of example 4, and more specifically according to the detailed following scheme:

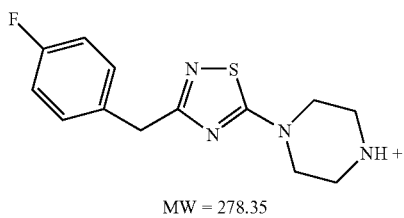

MW = 278.35

-continued

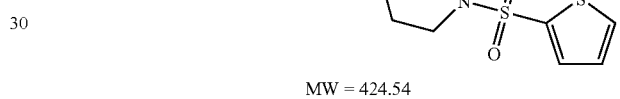

MW = 182.65

MW = 424.54

143 mg of this compound (yield 63%) were obtained after 4 hours reaction time. The compound was tested according to the procedure of example 12, and the corresponding test results are presented in table 3 below.

TABLE 3

| example | Structure | EC$_{50}$ (nM) | % inh. |
|---|---|---|---|
| 49 | 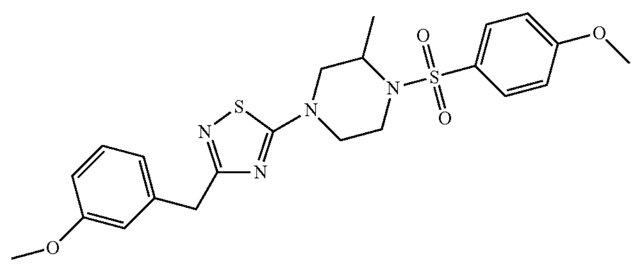 | 7.3 | 92 |
| 50 | 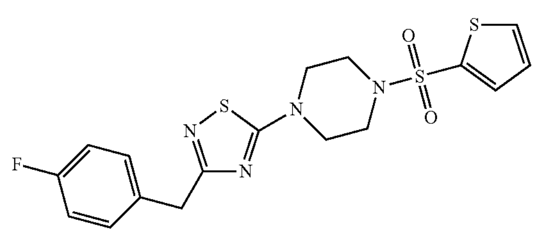 [SMILES: O=S(=O)(c1cccs1)N1CCN(c2nc(Cc3ccc(F)cc3)ns2)CC1] | 468 | 89 |

What is claimed is:

1. A pharmaceutical composition comprising a therapeutically effective amount of a 1,2,4-thiadiazole derivative according to the structural formula (A)

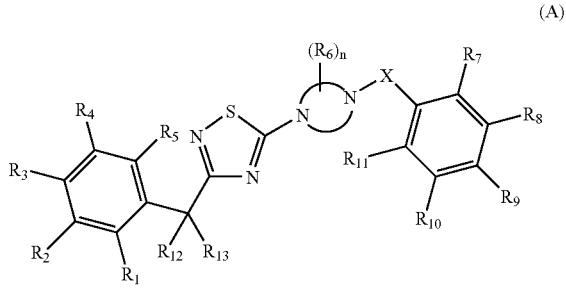

(A)

wherein the divalent group schematically represented by the structural formula (A')

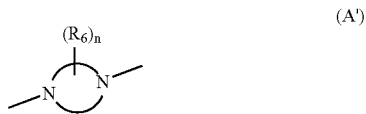

(A')

includes an optionally mono-substituted or poly-substituted, saturated or partly unsaturated heterocyclic ring with at least two nitrogen atoms in the said heterocyclic ring and with a total of 5 to 7 atoms in the said heterocyclic ring, and further wherein:

$R_6$ is a substituent independently selected from the group consisting of oxo and $C_{1-4}$ alkyl;

n is selected from the group consisting of 0, 1, 2 and 3;

$R_1$, $R_2$, $R_3$, $R_4$ and $R_5$ are each independently selected from the group consisting of hydrogen, $C_{1-4}$ alkyl, $C_{1-4}$ alkoxy, aryl, aryloxy, aryl-$C_{1-4}$ alkyloxy, heteroaryloxy, benzenesulfonate, amino, hydroxy, nitro, trifluoromethyl, trifluoromethoxy and halogen, or any two adjacent substituents selected from the group consisting of $R_1$, $R_2$, $R_3$, $R_4$ and $R_5$ form, together with the phenyl ring carbon atoms to which they are attached, a saturated or unsaturated ring fused to said phenyl ring and having from 5 to 7 ring members, said saturated or unsaturated ring optionally having one or two oxygen atoms and being optionally substituted with one or more halogen atoms;

$R_7$, $R_8$, $R_9$, $R_{10}$ and $R_{11}$ are each independently selected from the group consisting of hydrogen, $C_{1-10}$ alkyl, $C_{1-6}$ alkoxy, $C_{1-4}$ alkylthio, $C_{2-4}$ alkenyl, $C_{3-8}$ cycloalkyl, aryl, hydroxy, acetyl, nitro, trifluoromethyl and halogen; or any two adjacent substituents selected from the group consisting of $R_7$, $R_8$, $R_9$, $R_{10}$ and $R_{11}$ form, together with the phenyl ring carbon atoms to which they are attached, a saturated or unsaturated ring fused to said phenyl ring and having from 5 to 7 ring members, said saturated or unsaturated ring optionally having one or two heteroatoms independently selected from the group consisting of oxygen, sulfur and nitrogen; and each of said $C_{1-6}$ alkyl, $C_{1-6}$ alkoxy, aryl or fused ring is optionally substituted with one or more halogen atoms;

$R_{12}$ and $R_{13}$ are each independently selected from the group consisting of hydrogen, $C_{1-6}$ alkyl, aryl-$C_{1-4}$ alkyl, aryl and N-containing heterocyclic rings, or $R_{12}$ and $R_{13}$ together form a $C_{3-6}$ cycloalkyl or heterocyclic group; and X is a linking moiety selected from the group consisting of —C(=O)—; —S(=O)$_2$—; divalent saturated or unsaturated non-cyclic hydrocarbon groups having from 1 to 6 atoms in the main chain, each of said atoms in the main chain being independently selected from the group consisting of carbon, nitrogen and sulfur, each of said carbon atoms in the main chain being optionally substituted with one or more substituents independently selected from the group consisting of oxo, thioxo, $C_{1-4}$ alkyl and halogen, and each of said sulfur atoms in the main chain being optionally substituted with oxo, provided that the number of heteroatoms in the main chain of said divalent saturated or unsaturated non-cyclic hydrocarbon group is 0, 1 or 2, wherein a first terminal atom of the main chain is connected to the structural formula (A') and a second terminal atom of the main chain is connected to the

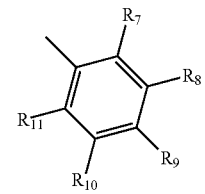

group of structural formula (A); and divalent saturated or unsaturated heterocyclic groups having from 2 to 6 carbon atoms and from 1 to 3 heteroatoms independently selected from the group consisting of oxygen, sulfur and nitrogen in the said heterocyclic group; or X together with one of $R_7$ and $R_{11}$ forms a saturated or unsaturated ring having from 5 to 7 ring members and being fused to the phenyl ring bearing said one of $R_7$ and $R_{11}$, said saturated or unsaturated ring optionally having one or two heteroatoms independently selected from the group consisting of oxygen, sulfur and nitrogen, and said saturated or unsaturated ring optionally having one or more substituents independently selected from the group consisting of $C_{1-4}$ alkyl and trifluoromethyl or is selected from the group consisting of —CO—CH=CH—, —CH$_2$—CH=CH— and —SO$_2$—CH=CH—;

or a stereoisomer or solvate thereof, or a pharmaceutically acceptable salt thereof, in combination with one or more pharmaceutically acceptable excipients.

2. The pharmaceutical composition according to claim 1, wherein the divalent group represented by the structural formula (A') includes one or more further heteroatoms in the heterocyclic ring or attached to one or more carbon atoms of the heterocyclic ring.

3. The pharmaceutical composition according to claim 1, wherein the divalent group represented by the structural formula (A') is selected from the group consisting of piperazinyl, 2,3-dioxopiperazinyl, 2,5-dioxopiperazinyl, 2-methylpiperazinyl, trans-2,5-dimethylpiperazinyl, 3,6-dimethyl-2,5-dioxopiperazinyl, 3-isopropyl-2,5-dioxo-piperazinyl, 3-tert-butyl-2,5-dioxopiperazinyl, 2,4-dioxoimidazolidinyl, 2,4,5-trioxoimidazolidinyl and homopiperazinyl.

4. The pharmaceutical composition according to claim 1, wherein the 1,2,4-thiadiazole derivative is represented by the structural formula ($A_1$)

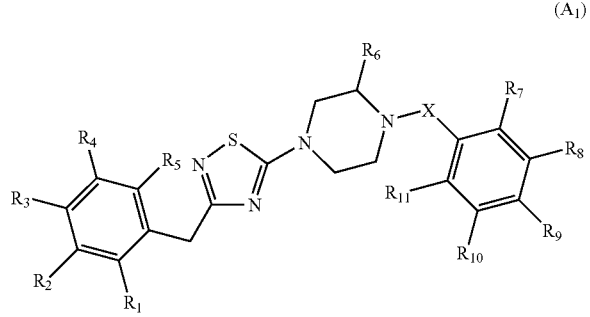

(A₁)

wherein X, $R_1$, $R_2$, $R_3$, $R_4$, $R_5$, $R_7$, $R_8$, $R_9$, $R_{10}$ and $R_{11}$ are as defined in claim 1, $R_6$ is hydrogen or is as defined in claim 1, or a stereoisomer or a solvate thereof, or a pharmaceutically acceptable salt thereof.

5. The pharmaceutical composition according to claim 1, wherein X is a divalent saturated or unsaturated non-cyclic hydrocarbon group having from 1 to 3 carbon atoms but no heteroatom in the main chain, and wherein each of said carbon atoms in the main chain is optionally substituted with one or more substituents independently selected from the group consisting of oxo, thioxo, $C_{1-4}$ alkyl and halogen.

6. The pharmaceutical composition according to claim 1, wherein X is selected from the group consisting of $C_{1-6}$ alkylene, —CO—CH₂—, —CO—(CH₂)₂—, —CO—CHR₁₄— and —CO—CHX'—, wherein $R_{14}$ is $C_{1-4}$ alkyl and wherein X' is halogen.

7. The pharmaceutical composition according to claim 1, wherein X is a divalent saturated or unsaturated non-cyclic hydrocarbon group having from 1 to 5 carbon atoms and one single nitrogen, oxygen or sulfur atom in the main chain, wherein each of said carbon atoms in the main chain is optionally substituted with one or more substituents independently selected from the group consisting of oxo, thioxo and $C_{1-4}$ alkyl, and wherein a sulfur atom in the main chain is optionally substituted with oxo.

8. The pharmaceutical composition according to claim 7, wherein X is selected from the group consisting of —CO—NH—, —(CH₂)₂—NH—CO—, —(CH₂)₂—NH—CO—CH₂—, —(CH₂)₂—NH—CO—(CH₂)₂—, —(CH₂)₂—NH—CO—CHR₁₄—, and —SO₂—CH₂—, wherein $R_{14}$ is $C_{1-4}$ alkyl.

9. The pharmaceutical composition according to claim 1, wherein X is a divalent saturated or unsaturated non-cyclic hydrocarbon group having from 1 to 5 carbon atoms and one single oxygen atom in the main chain, wherein said oxygen atom is not adjacent to the nitrogen atom of the divalent group (A').

10. The pharmaceutical composition according to claim 9, wherein X is —C(=O)—O—CH₂—.

11. The pharmaceutical composition according to claim 1, wherein X is a divalent saturated or unsaturated non-cyclic hydrocarbon group having from 1 to 4 carbon atoms and two non-adjacent nitrogen atoms in the main chain, wherein none of said nitrogen atoms is adjacent to the nitrogen atom of the divalent group (A').

12. The pharmaceutical composition according to claim 11, wherein X is —(CH₂)₂—NH—CO—NH—CH₂—.

13. The pharmaceutical composition according to claim 1, wherein X is 1,2,4-thiadiazolyl.

14. The pharmaceutical composition according to claim 1, wherein each of $R_1$, $R_2$, $R_3$, $R_4$ and $R_5$ is fluoro.

15. The pharmaceutical composition according to claim 1, wherein at least two of $R_1$, $R_2$, $R_3$, $R_4$ and $R_5$ are hydrogen.

16. The pharmaceutical composition according to claim 1, wherein three of $R_1$, $R_2$, $R_3$, $R_4$ and $R_5$ are methoxy.

17. The pharmaceutical composition according to claim 1, wherein three of $R_1$, $R_2$, $R_3$, $R_4$ and $R_5$ are hydrogen, and wherein two of $R_1$, $R_2$, $R_3$, $R_4$ and $R_5$ are identical and are selected from the group consisting of halogen, $C_{1-4}$ alkoxy and trifluoromethyl.

18. The pharmaceutical composition according to claim 1, wherein three of $R_1$, $R_2$, $R_3$, $R_4$ and $R_5$ are hydrogen, and wherein two of $R_1$, $R_2$, $R_3$, $R_4$ and $R_5$ are halogen and are independently selected from the group consisting of fluoro, chloro and bromo.

19. The pharmaceutical composition according to claim 1, wherein three of $R_1$, $R_2$, $R_3$, $R_4$ and $R_5$ are hydrogen, and wherein two adjacent substituents selected from the group consisting of $R_1$, $R_2$, $R_3$, $R_4$ and $R_5$ form, together with the phenyl ring carbon atoms to which they are attached, a phenyl or methylenedioxy ring fused to said phenyl ring.

20. The pharmaceutical composition according to claim 1, wherein four of $R_1$, $R_2$, $R_3$, $R_4$ and $R_5$ are hydrogen, and wherein one of $R_1$, $R_2$, $R_3$, $R_4$ and $R_5$ is selected from the group consisting of $C_{1-4}$ alkyl, $C_{1-4}$ alkoxy, aryl, aryloxy, aryl-$C_{1-4}$ alkyloxy, heteroaryloxy, benzenesulfonate, amino, hydroxy, nitro, trifluoromethyl, trifluoromethoxy and halogen.

21. The pharmaceutical composition according to claim 1, wherein $R_{12}$ and $R_{13}$ together form a ring selected from the group consisting of cyclopropyl, cyclobutyl, cyclopentyl, cyclohexyl and piperidinyl.

22. The pharmaceutical composition according to claim 1, wherein $R_{12}$ is hydrogen and $R_{13}$ is selected from the group consisting of piperidinyl and morpholinyl.

23. The pharmaceutical composition according to claim 1, wherein two adjacent substituents selected from the group consisting of $R_7$, $R_8$, $R_9$, $R_{10}$ and $R_{11}$ form, together with the phenyl ring carbon atoms to which they are attached, a methylenedioxy group fused to said phenyl ring.

24. The pharmaceutical composition according to claim 1, wherein at least three of $R_7$, $R_8$, $R_9$, $R_{10}$ and $R_{11}$ are hydrogen, and wherein at most two of $R_7$, $R_8$, $R_9$, $R_{10}$ and $R_{11}$ are independently selected from the group consisting of $C_{1-6}$ alkyl, $C_{1-6}$ alkoxy, phenyl, hydroxy, acetyl, nitro, trifluoromethyl and halogen.

25. The pharmaceutical composition according to claim 1, wherein said 1,2,4-thiadiazole derivative is selected from the group consisting of:
4-phenylacetyl-1-[3-(4-fluorobenzyl)-1,2,4-thiadiazol-5-yl]piperazine,
4-(4-fluorophenylacetyl), 1-[3-(4-fluorobenzyl)-1,2,4-thiadiazol-5-yl]piperazine,
1-(4-fluorophenylacetyl)-4-[3-(4-methylbenzyl)-1,2,4-thiadiazol-5-yl]-2-methyl-piperazine,
1-(4-methoxyphenylacetyl)-4-[3-(4-fluorobenzyl)-1,2,4-thiadiazol-5-yl]-2-methyl-piperazine,
1-phenylacetyl-4-[3-(4-fluorobenzyl)-1,2,4-thiadiazol-5-yl]-2-methylpiperazine
1-(4-fluorophenylacetyl)-4-[3-(4-fluorobenzyl)-1,2,4-thiadiazol-5-yl]-2-methyl-piperazine,
1-[chloro(phenyl)acetyl]-4-[3-(4-fluorobenzyl)-1,2,4-thiadiazol-5-yl]-2-methyl-piperazine,
1-(2-phenylbutanoyl)-4-[3-(4-fluorobenzyl)-1,2,4-thiadiazol-5-yl]-2-methyl-piperazine,
N-(3-fluorophenyl)-4-[3-(4-fluorobenzyl)-1,2,4-thiadiazol-5-yl]piperazine-1-carboxamide, N-(2-methylphenyl)-4-[3-(4-fluorobenzyl)-1,2,4-thiadiazol-5-yl]-2-methyl-piperazine-1-carboxamide,
N-(4-ethylphenyl)-4-[3-(4-fluorobenzyl)-1,2,4-thiadiazol-5-yl]-2-methylpiperazine-1-carboxamide,
N-(2-ethylphenyl)-4-[3-(4-fluorobenzyl)-1,2,4-thiadiazol-5-yl]-2-methylpiperazine-1-carboxamide,
N-phenyl-4-[3-(4-fluorobenzyl)-1,2,4-thiadiazol-5-yl]piperazine-1-carboxamide,
N-(4-ethoxyphenyl)-4-[3-(4-fluorobenzyl)-1,2,4-thiadiazol-5-yl]-2-methyl-piperazine-1-carboxamide,
N-(2-methylphenyl)-4-[3-(4-fluorobenzyl)-1,2,4-thiadiazol-5-yl]piperazine-1-carboxamide,
N-(2-fluorophenyl)-4-[3-(4-fluorobenzyl)-1,2,4-thiadiazol-5-yl]piperazine-1-carboxamide,
N-(2-trifluoromethylphenyl)-4-[3-(4-fluorobenzyl)-1,2,4-thiadiazol-5-yl]piperazine-1-carboxamide,
N-(2-trifluoromethylphenyl)-4-[3-(4-fluorobenzyl)-1,2,4-thiadiazol-5-yl]-2-methyl-piperazine-1-carboxamide,
N-(2,6-dimethylphenyl)-4-[3-(4-fluorobenzyl)-1,2,4-thiadiazol-5-yl]-2-methyl-piperazine-1-carboxamide,
N-(2,4-dimethylphenyl)-4-[3-(4-fluorobenzyl)-1,2,4-thiadiazol-5-yl]-2-methyl-piperazine-1-carboxamide,
N-(2,6-dichlorophenyl)-4-[3-(4-fluorobenzyl)-1,2,4-thiadiazol-5-yl]-2-methyl-piperazine-1-carboxamide,
N-(3-cyanophenyl)-4-[3-(4-fluorobenzyl)-1,2,4-thiadiazol-5-yl]-2-methylpiperazine-1-carboxamide,
N-(2,4-difluorophenyl)-4-[3-(4-fluorobenzyl)-1,2,4-thiadiazol-5-yl]-2-methyl-piperazine-1-carboxamide,
N-(2,6-dimethylphenyl)-4-[3-(4-fluorobenzyl)-1,2,4-thiadiazol-5-yl]piperazine-1-carboxamide,
N-1-naphtyl-4-[3-(4-fluorobenzyl)-1,2,4-thiadiazol-5-yl]-2-methylpiperazine-1-carboxamide,
N-(3,4-difluorophenyl)-4-[3-(4-fluorobenzyl)-1,2,4-thiadiazol-5-yl]-2-methyl-piperazine-1-carboxamide,
N-(2,4-dimethoxyphenyl)-4-[3-(4-fluorobenzyl)-1,2,4-thiadiazol-5-yl]piperazine-1-carboxamide,
N-(3,4-difluorophenyl)-4-[3-(4-fluorobenzyl)-1,2,4-thiadiazol-5-yl]piperazine-1-carboxamide,
N-(3,5-dimethoxyphenyl)-4-[3-(4-fluorobenzyl)-1,2,4-thiadiazol-5-yl]-2-methyl-piperazine-1-carboxamide,
1-[4-tert-butylphenylsulfonyl]-4-[3-(4-fluorobenzyl)-1,2,4-thiadiazol-5-yl]piperazine,
1-[4-methoxyphenylsulfonyl]-4-[3-(4-chlorobenzyl)-1,2,4-thiadiazol-5-yl]piperazine,
1-[4-methoxyphenylsulfonyl]-4-[3-(4-fluorobenzyl)-1,2,4-thiadiazol-5-yl]piperazine,
1-[4-fluorophenylsulfonyl]-4-[3-(4-chlorobenzyl)-1,2,4-thiadiazol-5-yl]piperazine,
1-[4-chlorophenylsulfonyl]-4-[3-(4-methylbenzyl)-1,2,4-thiadiazol-5-yl]-2-methyl-piperazine,
1-[1-naphtylsulfonyl]-4-[3-(4-methylbenzyl)-1,2,4-thiadiazol-5-yl]piperazine,
1-[2,5-dichlorophenylsulfonyl]-4-[3-(4-methylbenzyl)-1,2,4-thiadiazol-5-yl]-2-methylpiperazine,
1-[2,4,6-trimethylphenylsulfonyl]-4-[3-(4-methylbenzyl)-1,2,4-thiadiazol-5-yl]-piperazine,
1-[2-naphtylsulfonyl]-4-[3-(4-methylbenzyl)-1,2,4-thiadiazol-5-yl]-2-methyl-piperazine,
1-[2,5-dichlorophenylsulfonyl]-4-[3-(4-chlorobenzyl)-1,2,4-thiadiazol-5-yl]-piperazine,
1-[4-bromophenylsulfonyl]-4-[3-(4-methylbenzyl)-1,2,4-thiadiazol-5-yl]-3-methyl-piperazine,
1-[1-naphtylsulfonyl]-4-[3-(4-methylbenzyl)-1,2,4-thiadiazol-5-yl]-3-methyl-piperazine,
1-[4-tert-butylphenylsulfonyl]-4-[3-(4-methylbenzyl)-1,2,4-thiadiazol-5-yl]-2-methylpiperazine,
1-[1-naphtylsulfonyl]-4-[3-(4-chlorobenzyl)-1,2,4-thiadiazol-5-yl]-2-methyl-piperazine,
1-[3-methoxyphenylsulfonyl]-4-[3-(4-fluorobenzyl)-1,2,4-thiadiazol-5-yl]piperazine,
1-[2,4,6-trimethylphenylsulfonyl]-4-[3-(4-methylbenzyl)-1,2,4-thiadiazol-5-yl]-2-methylpiperazine,
1-[3-trifluorophenylsulfonyl]-4-[3-(4-fluorobenzyl)-1,2,4-thiadiazol-5-yl]-2-methyl-piperazine,
1-phenylsulfonyl-4-[3-(4-fluorobenzyl)-1,2,4-thiadiazol-5-yl]-2-methylpiperazine,
1-[4-acetamidophenylsulfonyl]-4-[3-(4-methylbenzyl)-1,2,4-thiadiazol-5-yl]-2-methylpiperazine,
1-[4-acetamidophenylsulfonyl]-4-[3-(4-methylbenzyl)-1,2,4-thiadiazol-5-yl]-piperazine,
1-[4-methylphenylsulfonyl]-4-[3-(4-methylbenzyl)-1,2,4-thiadiazol-5-yl]-2-methylpiperazine,
1-[4-methoxyphenylsulfonyl]-4-[3-(4-chlorobenzyl)-1,2,4-thiadiazol-5-yl]-2-methyl-piperazine,
1-[2-naphtylsulfonyl]-4-[3-(4-chlorobenzyl)-1,2,4-thiadiazol-5-yl]piperazine,
1-[4-methoxyphenylsulfonyl]-4-[3-(3-methoxybenzyl)-1,2,4-thiadiazol-5-yl]piperazine,
1-[4-tert-butylphenylsulfonyl]-4-[3-(4-fluorobenzyl)-1,2,4-thiadiazol-5-yl]-2-methyl-piperazine,
1-[4-acetamidophenylsulfonyl]-4-[3-(4-fluorobenzyl)-1,2,4-thiadiazol-5-yl]-2-methylpiperazine,
1-[3-trifluoromethylphenylsulfonyl]-4-[3-(4-methylbenzyl)-1,2,4-thiadiazol-5-yl]-2-methylpiperazine,
1-[4-fluorophenylsulfonyl]-4-[3-(4-methylbenzyl)-1,2,4-thiadiazol-5-yl]piperazine,
1-[4-fluorophenylsulfonyl]-4-[3-(4-methylbenzyl)-1,2,4-thiadiazol-5-yl]-2-methyl-piperazine,
1-[4-fluorophenylsulfonyl]-4-[3-(4-fluorobenzyl)-1,2,4-thiadiazol-5-yl]-2-methyl-piperazine,
1-[4-methoxyphenylsulfonyl]-4-[3-(4-methylbenzyl)-1,2,4-thiadiazol-5-yl]-2-methyl-piperazine,
1-[4-ter-butylphenylsulfonyl]-4-[3-(4-fluorobenzyl)-1,2,4-thiadiazol-5-yl]piperazine,
1-[3-trifluoromethylphenylsulfonyl]-4-[3-(4-methylbenzyl)-1,2,4-thiadiazol-5-yl]-piperazine,
1-[4-methylphenylsulfonyl]-4-[3-(4-chlorobenzyl)-1,2,4-thiadiazol-5-yl]piperazine,
1-[4-bromophenylsulfonyl]-4-[3-(4-methylbenzyl)-1,2,4-thiadiazol-5-yl]piperazine,
1-[2-naphtylsulfonyl]-4-[3-(4-methylbenzyl)-1,2,4-thiadiazol-5-yl]piperazine,
1-[4-chlorophenylsulfonyl]-4-[3-(4-methylbenzyl)-1,2,4-thiadiazol-5-yl]piperazine,
1-[4-tert-butylphenylsulfonyl]-4-[3-(4-methylbenzyl)-1,2,4-thiadiazol-5-yl]-piperazine,
1-[4-methoxyphenylsulfonyl]-4-[3-(4-methylbenzyl)-1,2,4-thiadiazol-5-yl]piperazine
1-[4-tert-butylphenylsulfonyl]-4-[3-(4-chlorobenzyl)-1,2,4-thiadiazol-5-yl]piperazine
1-[quinoline-8-sulfonyl]-4-[3-(4-methylbenzyl)-1,2,4-thiadiazol-5-yl]piperazine,
1-[4-nitrophenylsulfonyl]-4-[3-(4-methylbenzyl)-1,2,4-thiadiazol-5-yl]-2-methyl-piperazine,
1-[3-nitro-4-chlorophenylsulfonyl]-4-[3-(4-methylbenzyl)-1,2,4-thiadiazol-5-yl]-2-methylpiperazine,
1-[4-nitrophenylsulfonyl]-4-[3-(4-fluorobenzyl)-1,2,4-thiadiazol-5-yl]-2-methyl-piperazine,
1-[4-methoxyphenylsulfonyl]-4-[3-(4-fluorobenzyl)-1,2,4-thiadiazol-5-yl]piperazine,
1-[3-nitro-4-chlorophenylsulfonyl]-4-[3-(4-methylbenzyl)-1,2,4-thiadiazol-5-yl]-piperazine 1-(benzylsulfonyl)-4-[3-(4-chlorobenzyl)-1,2,4-thiadiazol-5-yl]piperazine,
1-(benzylsulfonyl)-4-[3-(4-methylbenzyl)-1,2,4-thiadiazol-5-yl]piperazine,
1-(phenylprop-2-ensulfonyl)-4-[3-(4-fluorobenzyl)-1,2,4-thiadiazol-5-yl]piperazine,
1-(phenylprop-2-ensulfonyl)-4-[3-(4-methylbenzyl)-1,2,4-thiadiazol-5-yl]-2-methyl-piperazine
1-(phenylprop-2-ensulfonyl)-4-[3-(4-methylbenzyl)-1,2,4-thiadiazol-5-yl]piperazine,
1-(butylsulfonyl)-4-[3-(4-chlorobenzyl)-1,2,4-thiadiazol-5-yl]piperazine,
1-(octylsulfonyl)-4-[3-(4-methylbenzyl)-1,2,4-thiadiazol-5-yl]piperazine,
1-(butylsulfonyl)-4-[3-(4-methylbenzyl)-1,2,4-thiadiazol-5-yl]piperazine,
1-(ethylsulfonyl)-4-[3-(4-chlorobenzyl)-1,2,4-thiadiazol-5-yl]piperazine,
1-(isopropylsulfonyl)-4-[3-(4-methylbenzyl)-1,2,4-thiadiazol-5-yl]piperazine,
1-[(2E)-3-phenylprop-2-enoyl]-4-[3-(4-chlorobenzyl)-1,2,4-thiadiazol-5-yl]-2-methylpiperazine,
1-[(2E)-3-phenylprop-2-enoyl]-4-[3-(4-fluorobenzyl)-1,2,4-thiadiazol-5-yl]-2-methylpiperazine,
1-[(2E)-3-phenylprop-2-enoyl]-4-[3-(4-chlorobenzyl)-1,2,4-thiadiazol-5-yl]-piperazine,
1-(3-phenylpropanoyl)-4-[3-(4-fluorobenzyl)-1,2,4-thiadiazol-5-yl]-2-methyl-piperazine,
1-(3-phenylpropanoyl)-4-[3-(4-fluorobenzyl)-1,2,4-thiadiazol-5-yl]piperazine,
1-[3-phenylprop-2-enyl]-4-[3-(4-methylbenzyl)-1,2,4-thiadiazol-5-yl]piperazine,
1-[3-phenylprop-2-enyl]-4-[3-(4-chlorobenzyl)-1,2,4-thiadiazol-5-yl]piperazine,
1-[3-phenylprop-2-enyl]-4-[3-(4-fluorobenzyl)-1,2,4-thiadiazol-5-yl]piperazine,
4-pentyl-N-{2-[4-[3-(4-fluorobenzyl)-1,2,4-thiadiazol-5-yl]piperazin-1-yl]ethyl}-benzamide,
4-butyl-N-{2-[4-[3-(4-fluorobenzyl)-1,2,4-thiadiazol-5-yl]piperazin-1-yl]ethyl}-benzamide,
4-hexyl-N-{2-[4-[3-(4-fluorobenzyl)-1,2,4-thiadiazol-5-yl]piperazin-1-yl]ethyl}-benzamide,
4-chloro-N-{2-[4-[3-(4-fluorobenzyl)-1,2,4-thiadiazol-5-yl]piperazin-1-yl]ethyl}-benzamide,
3,5-dichloro-N-{2-[4-[3-(4-fluorobenzyl)-1,2,4-thiadiazol-5-yl]piperazin-1-yl]ethyl}-benzamide,
2-methyl-N-{2-[4-[3-(4-fluorobenzyl)-1,2,4-thiadiazol-5-yl]piperazin-1-yl]ethyl}-benzamide,
3-fluoro-N-{2-[4-[3-(4-chlorobenzyl)-1,2,4-thiadiazol-5-yl]piperazin-1-yl]ethyl}-benzamide,
4-methyl-N-{2-[4-[3-(4-fluorobenzyl)-1,2,4-thiadiazol-5-yl]piperazin-1-yl]ethyl}-benzamide,
4-fluoro-N-{2-[4-[3-(4-fluorobenzyl)-1,2,4-thiadiazol-5-yl]piperazin-1-yl]ethyl}-benzamide,
4-ethyl-N-{2-[4-[3-(4-fluorobenzyl)-1,2,4-thiadiazol-5-yl]piperazin-1-yl]ethyl}-benzamide,
N-{2-[4-[3-(4-fluorobenzyl)-1,2,4-thiadiazol-5-yl]piperazin-1-yl]ethyl}benzamide,
3-fluoro-N-{2-[4-[3-(4-fluorobenzyl)-1,2,4-thiadiazol-5-yl]piperazin-1-yl]ethyl}-benzamide,
3-fluoro-N-{2-[4-[3-benzyl-1,2,4-thiadiazol-5-yl]piperazin-1-yl]ethyl}benzamide,
2-(4-fluorophenyl)-N-{2-[4-[3-(4-fluorobenzyl)-1,2,4-thiadiazol-5-yl]piperazin-1-yl]ethyl}acetamide,
2-phenyl-N-{2-[4-[3-(4-fluorobenzyl)-1,2,4-thiadiazol-5-yl]piperazin-1-yl]ethyl}-acetamide,
2-(4-fluorophenyl)-N-{2-[4-[3-(4-methylbenzyl)-1,2,4-thiadiazol-5-yl]piperazin-1-yl]ethyl}acetamide,
N-benzyl-N'-{2-[4-[3-(4-fluorobenzyl)-1,2,4-thiadiazol-5-yl]piperazin-1-yl]ethyl urea
2-phenyl-N-{2-[4-[3-(4-fluorobenzyl)-1,2,4-thiadiazol-5-yl]piperazin-1-yl]ethyl}-butanamide,
3-phenyl-N-{2-[4-[3-(4-fluorobenzyl)-1,2,4-thiadiazol-5-yl]piperazin-1-yl]ethyl}-propanamide,
1-benzyl-4-[3-(4-fluorobenzyl)-1,2,4-thiadiazol-5-yl]piperazine,
1-(1,3-benzodioxol-5-ylmethyl)-4-[3-(4-fluorobenzyl)-1,2,4-thiadiazol-5-yl]-piperazine,
1-(2-fluorobenzoyl)-4-[3-(3-methoxybenzyl)-1,2,4-thiadiazol-5-yl]-2-methyl-piperazine,
1-(4-ethylbenzoyl)-4-[3-(4-fluorobenzyl)-1,2,4-thiadiazol-5-yl]-2-methylpiperazine,
1-(4-butylbenzoyl)-4-[3-(4-methylbenzyl)-1,2,4-thiadiazol-5-yl]-2-methylpiperazine,
1-(4-methoxybenzoyl)-4-[3-(4-fluorobenzyl)-1,2,4-thiadiazol-5-yl]-2-methyl-piperazine,
1-(1,3-benzodioxol-5-ylcarbonyl)-4-[3-(3-methoxybenzyl)-1,2,4-thiadiazol-5-yl]-2-methylpiperazine,
1-(4-butylbenzoyl)-4-[3-(4-fluorobenzyl)-1,2,4-thiadiazol-5-yl]-2-methylpiperazine,
1-(4-hexylbenzoyl)-4-[3-(4-fluorobenzyl)-1,2,4-thiadiazol-5-yl]piperazine,
1-(3-chlorobenzoyl)-4-[3-(4-fluorobenzyl)-1,2,4-thiadiazol-5-yl]-2-methylpiperazine
1-(4-fluorobenzoyl)-4-[3-(3-methoxybenzyl)-1,2,4-thiadiazol-5-yl]-2-methylpiperazine,
1-(4-methylbenzoyl)-4-[3-(3-methoxybenzyl)-1,2,4-thiadiazol-5-yl]-2-methyl-piperazine,
1-(3-fluorobenzoyl)-4-[3-(4-chlorobenzyl)-1,2,4-thiadiazol-5-yl]-2-methylpiperazine
1-benzoyl-4-[3-(4-fluorobenzyl)-1,2,4-thiadiazol-5-yl]-2-methylpiperazine,
1-(4-fluorobenzoyl)-4-[3-(4-fluorobenzyl)-1,2,4-thiadiazol-5-yl]-2-methylpiperazine,
1-(4-tert-butylbenzoyl)-4-[3-(4-fluorobenzyl)-1,2,4-thiadiazol-5-yl]-2-methyl-piperazine,
1-(1,1'-biphenyl-4-ylcarbonyl)-4-[3-(4-fluorobenzyl)-1,2,4-thiadiazol-5-yl]-2-methylpiperazine,
1-(methoxybenzoyl)-4-[3-(4-methylbenzyl)-1,2,4-thiadiazol-5-yl]-2-methylpiperazine,
1-(4-ethylbenzoyl)-4-[3-(4-methylbenzyl)-1,2,4-thiadiazol-5-yl]piperazine,
1-(2-naphthoyl)-4-[3-(4-fluorobenzyl)-1,2,4-thiadiazol-5-yl]-2-methylpiperazine,
1-(2-methoxybenzoyl)-4-[3-(4-fluorobenzyl)-1,2,4-thiadiazol-5-yl]-2-methyl-piperazine,
1-(4-pentylbenzoyl)-4-[3-(4-methylbenzyl)-1,2,4-thiadiazol-5-yl]-2-methyl-piperazine,
1-(4-bromobenzoyl)-4-[3-(4-fluorobenzyl)-1,2,4-thiadiazol-5-yl]-2-methylpiperazine
1-(2,4-dimethoxybenzoyl)-4-[3-(4-fluorobenzyl)-1,2,4-thiadiazol-5-yl]-2-methyl-piperazine,
1-(3,5-dichlorobenzoyl)-4-[3-(4-fluorobenzyl)-1,2,4-thiadiazol-5-yl]piperazine,
1-(3-chlorobenzoyl)-4-[3-(4-fluorobenzyl)-1,2,4-thiadiazol-5-yl]piperazine,
1-(4-methylbenzoyl)-4-[3-(4-fluorobenzyl)-1,2,4-thiadiazol-5-yl]-2-methyl-piperazine,
1-(2-methylbenzoyl)-4-[3-(4-fluorobenzyl)-1,2,4-thiadiazol-5-yl]-2-methylpiperazine,
1-(4-methylbenzoyl)-4-[3-(4-fluorobenzyl)-1,2,4-thiadiazol-5-yl]piperazine, 1-(3-bromobenzoyl)-4-[3-(4-fluorobenzyl)-1,2,4-thiadiazol-5-yl]-2-methylpiperazine
1-(4-ethylbenzoyl)-4-[3-(3-methoxybenzyl)-1,2,4-thiadiazol-5-yl]-2-methyl-piperazine,
1-(3-methylbenzoyl)-4-[3-(4-methylbenzyl)-1,2,4-thiadiazol-5-yl]-2-methyl-piperazine,
1-(3-trifluoromethylbenzoyl)-4-[3-(4-fluorobenzyl)-1,2,4-thiadiazol-5-yl]-2-methyl-piperazine,
1-(4-tert-butylbenzoyl)-4-[3-(3-methoxybenzyl)-1,2,4-thiadiazol-5-yl]-2-methylpiperazine,
1-(4-ethylbenzoyl)-4-[3-(4-methylbenzyl)-1,2,4-thiadiazol-5-yl]-2-methylpiperazine,
1-(2-bromobenzoyl)-4-[3-(4-fluorobenzyl)-1,2,4-thiadiazol-5-yl]-2-methylpiperazine
1-(2-fluorobenzoyl)-4-[3-(4-methylbenzyl)-1,2,4-thiadiazol-5-yl]-2-methyl-piperazine,
1-(3-fluorobenzoyl)-4-[3-benzyl-1,2,4-thiadiazol-5-yl]-2-methylpiperazine,
1-(4-fluorobenzoyl)-4-[3-(4-methylbenzyl)-1,2,4-thiadiazol-5-yl]-2-methyl-piperazine,
1-(2-methylbenzoyl)-4-[3-(4-fluorobenzyl)-1,2,4-thiadiazol-5-yl]piperazine,
1-(4-fluorobenzoyl)-4-[3-(4-chlorobenzyl)-1,2,4-thiadiazol-5-yl]piperazine,
1-(4-fluorobenzoyl)-4-[3-benzyl-1,2,4-thiadiazol-5-yl]-2-methylpiperazine,
1-(4-chlorobenzoyl)-4-[3-(4-methylbenzyl)-1,2,4-thiadiazol-5-yl]piperazine,
1-(3-fluorobenzoyl)-4-[3-(4-methylbenzyl)-1,2,4-thiadiazol-5-yl]-2-methyl-piperazine,
1-(3-fluorobenzoyl)-4-[3-(4-chlorobenzyl)-1,2,4-thiadiazol-5-yl]piperazine,
1-benzoyl-4-[3-(4-methylbenzyl)-1,2,4-thiadiazol-5-yl]piperazine,
1-(2-fluorobenzoyl)-4-[3-(4-chlorobenzyl)-1,2,4-thiadiazol-5-yl]piperazine,
1-(4-fluorobenzoyl)-4-[3-(4-methylbenzyl)-1,2,4-thiadiazol-5-yl]piperazine,
1-(1,3-benzodioxol-5-ylcarbonyl)-4-[3-(4-methylbenzyl)-1,2,4-thiadiazol-5-yl]-2-methylpiperazine,
1-(3-fluororbenzoyl)-4-[3-(4-methylbenzyl)-1,2,4-thiadiazol-5-yl]piperazine,
1-(4-fluorobenzoyl)-4-[3-benzyl-1,2,4-thiadiazol-5-yl]piperazine,
1-(4-bromobenzoyl)-4-[3-(4-methylbenzyl)-1,2,4-thiadiazol-5-yl]piperazine,
1-(4-ethylbenzoyl)-4-[3-(4-chlorobenzyl)-1,2,4-thiadiazol-5-yl]piperazine,
1-(2-chlorobenzoyl)-4-[3-(4-fluorobenzyl)-1,2,4-thiadiazol-5-yl]-2-methylpiperazine
1-(2-fluorobenzoyl)-4-[3-(4-chlorobenzyl)-1,2,4-thiadiazol-5-yl]-2-methylpiperazine
1-(4-trifluoromethylbenzoyl)-4-[3-(3-methoxybenzyl)-1,2,4-thiadiazol-5-yl]-2-methylpiperazine,
1-benzoyl-4-[3-(4-methylbenzyl)-1,2,4-thiadiazol-5-yl]-2-methylpiperazine,
1-(4-bromobenzoyl)-4-[3-(3-methoxybenzyl)-1,2,4-thiadiazol-5-yl]-2-methyl-piperazine,
1-(4-trifluoromethylbenzoyl)-4-[3-(4-methylbenzyl)-1,2,4-thiadiazol-5-yl]piperazine,
1-(3-nitro-4-methylbenzoyl)-4-[3-(4-fluorobenzyl)-1,2,4-thiadiazol-5-yl]-2-methyl-piperazine,
1-benzoyl-4-[3-(3-methoxybenzyl)-1,2,4-thiadiazol-5-yl]-2-methylpiperazine,
1-(4-chlorobenzoyl)-4-[3-(3-methoxybenzyl)-1,2,4-thiadiazol-5-yl]-2-methyl-piperazine,
1-(2-fluorobenzoyl)-4-[3-(4-methylbenzyl)-1,2,4-thiadiazol-5-yl]piperazine,
1-(4-hexylbenzoyl)-4-[3-(4-methylbenzyl)-1,2,4-thiadiazol-5-yl]piperazine,
1-(2-chloro-4-nitrobenzoyl)-4-[3-(4-fluorobenzyl)-1,2,4-thiadiazol-5-yl]-2-methyl-piperazine,
1-(1,3-benzodioxol-5-ylcarbonyl)-4-[3-(4-fluorobenzyl)-1,2,4-thiadiazol-5-yl]-2-methylpiperazine
1-(3-fluorobenzoyl)-4-[3-(4-fluorobenzyl)-1,2,4-thiadiazol-5-yl]-2-methylpiperazine,
1-(4-tert-butylbenzoyl)-4-[3-(4-fluorobenzyl)-1,2,4-thiadiazol-5-yl]piperazine,
1-benzoyl-4-[3-(4-fluorobenzyl)-1,2,4-thiadiazol-5-yl]piperazine,
1-(4-butylbenzoyl)-4-[3-(4-methylbenzyl)-1,2,4-thiadiazol-5-yl]piperazine,
1-(4-tert-butylbenzoyl)-4-[3-(4-methylbenzyl)-1,2,4-thiadiazol-5-yl]piperazine,
1-(4-nitrobenzoyl)-4-[3-(4-fluorobenzyl)-1,2,4-thiadiazol-5-yl]-2-methylpiperazine,
1-(2-methylphenyl)-4-[3-(4-fluorobenzyl)-1,2,4-thiadiazol-5-yl]piperazine,
1-(2-ethoxyphenyl)-4-[3-(4-fluorobenzyl)-1,2,4-thiadiazol-5-yl]piperazine,
1-(2-fluorophenyl)-4-[3-(4-fluorobenzyl)-1,2,4-thiadiazol-5-yl]piperazine,
1-(3-trifluoromethylphenyl)-4-[3-(4-fluorobenzyl)-1,2,4-thiadiazol-5-yl]piperazine,
1-(4-chlorobenzoyl)-4-[3-(4-fluorobenzyl)-1,2,4-thiadiazol-5-yl]-1,4-diazepane,
1-(4-methylbenzoyl)-4-[3-(4-fluorobenzyl)-1,2,4-thiadiazol-5-yl]-1,4-diazepane,
1-(1,3-benzodioxol-5-ylcarbonyl)-4-[3-(4-fluorobenzyl)-1,2,4-thiadiazol-5-yl]-1,4-diazepane,
1-[4-methoxyphenylsulfonyl]-4-[3-(3-fluoro-benzyl)-1,2,4-thiadiazol-5-yl]piperazine;
1-[4-methoxyphenylsulfonyl]-4-[3-(2-fluoro-benzyl)-1,2,4-thiadiazol-5-yl]piperazine;
1-[2-methoxyphenylsulfonyl]-4-[3-(4-fluoro-benzyl)-1,2,4-thiadiazol-5-yl]piperazine;
1-[4-ethoxyphenylsulfonyl]-4-[3-(4-fluoro-benzyl)-1,2,4-thiadiazol-5-yl]piperazine;
1-[4-ethylphenylsulfonyl]-4-[3-(4-fluoro-benzyl)-1,2,4-thiadiazol-5-yl]piperazine;
1-phenylsulfonyl-4-[3-(4-fluoro-benzyl)-1,2,4-thiadiazol-5-yl]piperazine;
1-[4-methoxyphenylsulfonyl]-4-[3-benzyl-1,2,4-thiadiazol-5-yl]piperazine;
1-(4-propionyloxy)benzene-sulfonyl-4-[3-(4-fluoro-benzyl)-1,2,4-thiadiazol-5-yl]-piperazine;
1-[4-methoxyphenylsulfonyl]-4-[3-(3-methyl-benzyl-1,2,4-thiadiazol-5-yl]piperazine;
1-[4-methoxyphenylsulfonyl]-4-[3-(2-methyl-benzyl-1,2,4-thiadiazol-5-yl]piperazine;
1-[4-methoxyphenylsulfonyl]-4-[3-(2-methoxy-benzyl-1,2,4-thiadiazol-5-yl]piperazine;
1-[4-methoxyphenylsulfonyl]-4-[3-(3-methyl-4-fluoro-benzyl-1,2,4-thiadiazol-5-yl]-piperazine;
1-[4-methoxyphenylsulfonyl]-4-[3-(4-methoxy-benzyl-1,2,4-thiadiazol-5-yl]piperazine;
1-[4-bromophenylsulfonyl]-4-[3-(3-methoxy-benzyl-1,2,4-thiadiazol-5-yl]piperazine;
1-[4-methoxyphenylsulfonyl]-4-[3-(3-methoxybenzyl)-1,2,4-thia-diazol-5-yl]-2-methyl-piperazine;

1-(4-hydroxybenzenesulfonyl)-4-[3-(4-fluoro-benzyl)-1,2,4-thiadiazol-5-yl]piperazine; and 1-(thien-2-ylsulfonyl)-4-[3-(4-fluoro-benzyl)-1,2,4-thiadiazol-5-yl]piperazine.

26. A 1,2,4-thiadiazole derivative selected from the group consisting of:
1-[3-methoxyphenylsulfonyl]-4-[3-(4-fluorobenzyl)-1,2,4-thiadiazol-5-yl]piperazine;
1-[4-methoxyphenylsulfonyl]-4-[3-(3-methoxybenzyl)-1,2,4-thiadiazol-5-yl]piperazine;
1-[4-methoxyphenylsulfonyl]-4-[3-(3-fluoro-benzyl)-1,2,4-thiadiazol-5-yl]piperazine;
1-[4-methoxyphenylsulfonyl]-4-[3-(2-fluoro-benzyl)-1,2,4-thiadiazol-5-yl]piperazine;
1-[2-methoxyphenylsulfonyl]-4-[3-(4-fluoro-benzyl)-1,2,4-thiadiazol-5-yl]piperazine;
1-[4-ethoxyphenylsulfonyl]-4-[3-(4-fluoro-benzyl)-1,2,4-thiadiazol-5-yl]piperazine;
1-[4-ethylphenylsulfonyl]-4-[3-(4-fluoro-benzyl)-1,2,4-thiadiazol-5-yl]piperazine;
1-phenylsulfonyl-4-[3-(4-fluoro-benzyl)-1,2,4-thiadiazol-5-yl]piperazine;
1-[4-methoxyphenylsulfonyl]-4-[3-benzyl-1,2,4-thiadiazol-5-yl]piperazine;
1-(4-propionyloxy)benzene-sulfonyl-4-[3-(4-fluoro-benzyl)-1,2,4-thiadiazol-5-yl]-piperazine;
1-[4-methoxyphenylsulfonyl]-4-[3-(3-methyl-benzyl-1,2,4-thiadiazol-5-yl]piperazine;
1-[4-methoxyphenylsulfonyl]-4-[3-(2-methyl-benzyl-1,2,4-thiadiazol-5-yl]piperazine;
1-[4-methoxyphenylsulfonyl]-4-[3-(2-methoxy-benzyl-1,2,4-thiadiazol-5-yl]piperazine;
1-[4-methoxyphenylsulfonyl]-4-[3-(3-methyl-4-fluoro-benzyl-1,2,4-thiadiazol-5-yl]-piperazine;
1-[4-methoxyphenylsulfonyl]-4-[3-(4-methoxy-benzyl-1,2,4-thiadiazol-5-yl]piperazine;
1-[4-bromophenylsulfonyl]-4-[3-(3-methoxy-benzyl-1,2,4-thiadiazol-5-yl]piperazine;
1-[4-methoxyphenylsulfonyl]-4-[3-(3-methoxybenzyl)-1,2,4-thia-diazol-5-yl]-2-methyl-piperazine; and
1-(4-hydroxybenzenesulfonyl)-4-[3-(4-fluoro-benzyl)-1,2,4-thiadiazol-5-yl]piperazine.

27. The pharmaceutical composition according to claim 1, further comprising a therapeutic amount of one or more drugs selected from the group consisting of neuro-protective agents and α-synuclein deposition inhibitors.

28. A method of treating an α-synucleopathy, comprising the administration of a therapeutic effective amount of a 1,2,4-thiadiazole derivative to a patient in need thereof, optionally in combination with one or more pharmaceutically acceptable carriers, and optionally in combination with a therapeutic amount of one or more drugs selected from the group consisting of neuro-protective agents and α-synuclein deposition inhibitors, wherein said α-synucleopathy is selected from the group consisting of Parkinson's disease, diffuse Lewy body disease, traumatic brain injury, amyotrophic lateral sclerosis, Niemann-Pick disease, Hallervorden-Spatz syndrome, Down syndrome, neuroaxonal dystrophy, multiple system atrophy and Alzheimer's disease and wherein said 1,2,4-thiadiazole derivative is according to the structural formula (A)

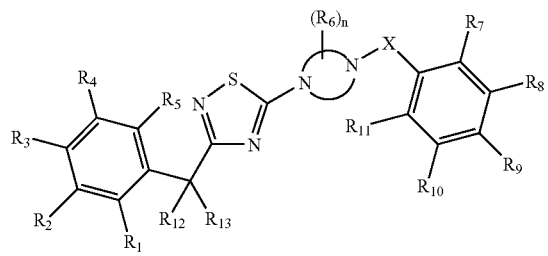

(A)

wherein the divalent group schematically represented by the structural formula (A')

(A')

includes an optionally mono-substituted or poly-substituted, saturated or partly unsaturated heterocyclic ring with at least two nitrogen atoms in the said heterocyclic ring and with a total of 5 to 7 atoms in the said heterocyclic ring, and further wherein:

$R_6$ is a substituent independently selected from the group consisting of oxo and $C_{1-4}$ alkyl;

n is selected from the group consisting of 0, 1, 2 and 3;

$R_1$, $R_2$, $R_3$, $R_4$ and $R_5$ are each independently selected from the group consisting of hydrogen, $C_{1-4}$ alkyl, $C_{1-4}$ alkoxy, aryl, aryloxy, alkyloxy, aryl-$C_{1-4}$ alkloxy, heteroaryloxy, benzenesulfonate, amino, hydroxy, nitro, trifluoromethyl, trifluoromethoxy and halogen, or any two adjacent substituents selected from the group consisting of $R_1$, $R_2$, $R_3$, $R_4$ and $R_5$ form, together with the phenyl ring carbon atoms to which they are attached, a saturated or unsaturated ring fused to said phenyl ring and having from 5 to 7 ring members, said saturated or unsaturated ring optionally having one or two oxygen atoms and being optionally substituted with one or more halogen atoms;

$R_7$, $R_8$, $R_9$, $R_{10}$, and $R_{11}$ are each independently selected from the group consisting of hydrogen, $C_{1-10}$ alkyl, $C_{1-6}$ alkoxy, $C_{1-4}$ alkylthio, $C_{2-4}$ alkenyl, $C_{3-8}$ cycloalkyl, aryl, hydroxy, acetyl, nitro, trifluoromethyl and halogen; or any two adjacent substituents selected from the group consisting of $R_7$, $R_8$, $R_9$, $R_{10}$ and $R_{11}$ form, together with the phenyl ring carbon atoms to which they are attached, a saturated or unsaturated ring fused to said phenyl ring and having from 5 to 7 ring members, said saturated or unsaturated ring optionally having one or two heteroatoms independently selected from the group consisting of oxygen, sulfur and nitrogen; and each of said $C_{1-6}$ alkyl, $C_{1-6}$ alkoxy, aryl or fused ring is optionally substituted with one or more halogen atoms;

$R_{12}$ and $R_{13}$ are each independently selected from the group consisting of hydrogen, $C_{1-6}$ alkyl, aryl-$C_{1-4}$ alkyl, aryl and N-containing heterocyclic rings, or $R_{12}$ and $R_{13}$ together form a $C_{3-6}$ cycloalkyl or heterocyclic group; and X is a linking moiety selected from the group consisting of —C(=O)—; —S(=O)$_2$—; divalent saturated non-cyclic hydrocarbon groups having from 1 to 6 atoms in the main chain, each of said atoms in the main chain being independently selected from the group consisting of carbon, nitrogen and sulfur, each of said carbon atoms in the main chain being optionally substituted with one or more substituents independently selected from the group consisting of oxo, thioxo, $C_{1-4}$ alkyl and halogen, and each of said sulfur atoms in the main chain being optionally substituted with oxo, provided that the number of heteroatoms in the main chain of said divalent saturated or unsaturated non-cyclic hydrocarbon group is 0, 1 or 2, wherein a first terminal atom of the main chain is connected to the structural formula (A') and a second terminal atom of the main chain is connected to the

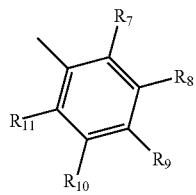

group of structural formula (A): and divalent saturated or unsaturated heterocyclic groups having from 2 to 6 carbon atoms and from 1 to 3 heteroatoms independently selected from the group consisting of oxygen, sulfur and nitrogen in the said heterocyclic group; or X together with one of $R_7$ and $R_{11}$ forms a saturated or unsaturated ring having from 5 to 7 ring members and being fused to the phenyl ring bearing said one of $R_7$ and $R_{11}$, said saturated or unsaturated ring optionally having one or two heteroatoms independently selected from the group consisting of oxygen, sulfur and nitrogen, and said saturated or unsaturated ring optionally having one or more substituents independently selected from the group consisting of $C_{1-4}$ alkyl and trifluoromethyl or is selected from the group consisting of —CO—CH=CH—, —CH$_2$—CH=CH— and —SO$_2$—CH=CH—.

* * * * *